United States Patent
Wang et al.

(10) Patent No.: US 11,090,307 B2
(45) Date of Patent: Aug. 17, 2021

(54) TREATING MALE SENESCENCE

(71) Applicant: National Institute of Biological Sciences, Beijing, Beijing (CN)

(72) Inventors: Xiaodong Wang, Beijing (CN); Dianrong Li, Beijing (CN); Lingjun Meng, Beijing (CN); Zhiyuan Zhang, Beijing (CN)

(73) Assignee: National Institute of Biological Sciences, Beijing, Beijing (CN)

( * ) Notice: Subject to any disclaimer, the term of this patent is extended or adjusted under 35 U.S.C. 154(b) by 62 days.

(21) Appl. No.: 16/656,574

(22) Filed: Oct. 18, 2019

(65) Prior Publication Data
US 2020/0046714 A1    Feb. 13, 2020

Related U.S. Application Data

(63) Continuation of application No. PCT/CN2018/082934, filed on Apr. 13, 2018.

(30) Foreign Application Priority Data

Apr. 17, 2017  (WO) ................ PCT/CN2017/080746

(51) Int. Cl.
| | | |
|---|---|---|
| *A61K 31/52* | (2006.01) | |
| *A61K 31/522* | (2006.01) | |
| *A61P 15/08* | (2006.01) | |
| *A61K 31/165* | (2006.01) | |
| *A61K 31/17* | (2006.01) | |
| *A61K 31/18* | (2006.01) | |
| *A61K 31/341* | (2006.01) | |
| *A61K 31/381* | (2006.01) | |
| *A61K 31/396* | (2006.01) | |
| *A61K 31/397* | (2006.01) | |
| *A61K 31/40* | (2006.01) | |
| *A61K 31/415* | (2006.01) | |
| *A61K 31/426* | (2006.01) | |
| *A61K 31/44* | (2006.01) | |
| *A61K 31/4453* | (2006.01) | |
| *A61K 31/47* | (2006.01) | |
| *A61K 31/5375* | (2006.01) | |

(52) U.S. Cl.
CPC .......... *A61K 31/522* (2013.01); *A61K 31/165* (2013.01); *A61K 31/17* (2013.01); *A61K 31/18* (2013.01); *A61K 31/341* (2013.01); *A61K 31/381* (2013.01); *A61K 31/396* (2013.01); *A61K 31/397* (2013.01); *A61K 31/40* (2013.01); *A61K 31/415* (2013.01); *A61K 31/426* (2013.01); *A61K 31/44* (2013.01); *A61K 31/4453* (2013.01); *A61K 31/47* (2013.01); *A61K 31/5375* (2013.01); *A61P 15/08* (2018.01)

(58) Field of Classification Search
CPC .................................................... A61K 31/522
See application file for complete search history.

(56) References Cited

PUBLICATIONS

Galluzzi, et al. Annu Rev Pathol. Jan. 24, 2017; 12: 103-130.*

* cited by examiner

*Primary Examiner* — Shawquia Jackson
(74) *Attorney, Agent, or Firm* — Richard Aron Osman

(57) ABSTRACT

The invention provides methods of treating male reproductive senescence comprising administering to a male in need thereof a necroptosis inhibitor, including inhibitors of RIP1, RIP3 or MLKL. The invention also provides pharmaceutical compositions comprising a necroptosis inhibitor and a second different drug for treating male senescence.

20 Claims, No Drawings

TREATING MALE SENESCENCE

INTRODUCTION

Necroptosis is a form of programmed necrotic cell death caused by the tumor necrosis factor family of cytokines (Christofferson and Yuan, 2010; Vandenabeele et al., 2010). In response to the activation of TNF receptor family members, receptor-interacting kinase 1 (RIP1) is recruited to the cytosolic side of the receptor and its kinase activity is activated (Holler et al., 2000). RIP1 then interacts with and phosphorylates a related kinase, RIP3, leading to its activation (Cho et al., 2009; Degterev et al., 2008; He et al., 2009; Zhang et al., 2009). If the cells also happen to have their caspase-8 activity inhibited, either through interaction with its cellular inhibitor cFLIP or through the action of viral or chemical inhibitors, RIP3 drives the cell fate towards necroptosis (He et al., 2009; Holler et al., 2000). Necroptosis can be inhibited by RIP1 kinase inhibitor compounds, and can be promoted by small molecule Smac mimetics, which shifts RIP1 function from NF-κB activation to activation of RIP3 (Degterev et al., 2008; Wang et al., 2008). Once active, RIP3 then phosphorylates a pseudokinase called mixed lineage kinase domain-like protein (MLKL) (Sun et al., 2012). MLKL normally exists as an inactive monomer in the cytosol. Upon RIP3 phosphorylation on serine 357 and threonine 358 of human MLKL or the mouse equivalent of serine 345, serine 347, and threonine 349, MLKL forms oligomers and translocates to the plasma membrane, where it disrupts membrane integrity, resulting in necrotic cell death (Cai et al., 2014; Chen et al., 2014; Rodriguez et al., 2016; Sun et al., 2012; Wang et al., 2014).

Necroptosis is known to have important functions under pathological conditions of microbial infections or tissue damage since RIP3 knockout mice show defects in defending microbial infections or manifest less tissue damage in a variety of chemical or ischemic reperfusion induced tissue damage models (Cho et al., 2009; He et al., 2009; Robinson et al., 2012; Upton et al., 2010; Zhou and Yuan, 2014). However, mice with RIP3 or MLKL gene knockout are remarkably normal without any noticeable developmental or fertility defects if not challenged by microbial infections or tissue damaging agents (Murphy et al., 2013; Newton et al., 2004; Wu et al., 2013).

While conducting a study investigating the impact of necroptosis on the progression of atherosclerosis (Meng et al., 2015), we serendipitously found that the male reproductive organ of mice with RIP3 and MLKL knockout looked remarkably young even at advanced ages. Our comprehensive follow up work presented here demonstrates that necroptosis functions in promoting the aging of male reproductive system in mice, providing a target for therapeutic and prophylactic intervention.

SUMMARY OF THE INVENTION

The invention provides methods and compositions for treating male senescence or symptoms or makers thereof. In an aspect the invention provides a method of treating male senescence comprising administering to a male in need thereof a necroptosis inhibitor.

In embodiments:
 the necroptosis inhibitor is a RIP1, RIP3 or MLKL inhibitor.
 the necroptosis inhibitor is a RIP1 inhibitor selected from:
 5-((1H-indol-3-yl)methyl)-3-methyl-2-thioxoimidazolidin-4-one (Nec-1);
 (S)-phenyl(5-phenyl-4,5-dihydro-1H-pyrazol-1-yl)methanone;
 5-((1H-indol-3-yl)methyl)-3-methyl-2-thioxoimidazolidin-4-one (Nec-1s);
 3-methyl-5-((7-methyl-1H-indol-3-yl)methyl)imidazolidine-2,4-dione;
 (R)-5-((7-chloro-1H-indol-3-yl)methyl)-3-methylimidazolidine-2,4-dione;
 (R)-5-((7-chloro-1H-indol-3-yl)methyl)-3-(4-(3-(imidazo[1,2-b]pyridazin-3-ylethynyl)-4-methylphenyl)butyl)imidazolidine-2,4-dione (Ponatinib-Nec1s);
 (S)-2,2-dimethyl-1-(5-phenyl-4,5-dihydro-1H-pyrazol-1-yl)propan-1-on (GSK963);
 (S)-2,2-dimethyl-1-(5-phenyl-4,5-dihydro-1H-pyrazol-1-yl)propan-1-one;
 (S)-1-(4-(5-phenyl-4,5-dihydro-1H-pyrazole-1-carbonyl)piperidin-1-yl)ethanone;
 (S)-2,2-dimethyl-1-(5-(pyridin-2-yl)-4,5-dihydro-1H-pyrazol-1-yl)propan-1-one;
 (S)-1-(4-(5-(3,5-difluorophenyl)-4,5-dihydro-1H-pyrazole-1-carbonyl)piperidin-1-yl)ethanone;
 (S)-5-benzyl-N-(5-methyl-4-oxo-2,3,4,5-tetrahydrobenzo[b][1,4]oxazepin-3-yl)isoxazole-3-carboxamide;
 (S)-5-benzyl-N-(5-methyl-4-oxo-2,3,4,5-tetrahydrobenzo[b][1,4]oxazepin-3-yl)-4H-1,2,4-triazole-3-carboxamide;
 (S)-5-benzyl-N-(8-chloro-4-oxo-2,3,4,5-tetrahydrobenzo[b][1,4]oxazepin-3-yl)-4H-1,2,4-triazole-3-carboxamide;
 (S)-5-benzyl-N-(5-methyl-4-oxo-7-(1H-tetrazol-5-yl)-2,3,4,5-tetrahydrobenzo[b][1,4]oxazepin-3-yl)isoxazole-3-carboxamide;
 8-bromo-4,5-dihydro-1H-benzo[b]azepin-2(3H)-one;
 (S)-5-benzyl-N-(5-methyl-4-oxo-2,3,4,5-tetrahydrobenzo[b][1,4]oxazepin-3-yl)isoxazole-3-carboxamide (GSK481);
 (S)-5-benzyl-N-(5-methyl-4-oxo-2,3,4,5-tetrahydrobenzo[b]-[1,4]oxazepin-3-yl)-1H-1,2,4-triazole-3-carboxamide (GSK2982772);
 1-(4 (4-aminofuro[2,3-d]pyrimidin-5-yl)phenyl)-3-(2-fluoro-5-(trifluoromethyl)phenyl)urea (Cpd27);
 3-methyl-5-((7-methyl-1H-indol-3-yl)methyl)imidazolidine-2,4-dione;
 (R)-5-((7-chloro-1H-indol-3-yl)methyl)-3-methylimidazolidine-2,4-dione;
 3-benzyl-6,7-dihydro-3H-cyclopenta[4,5]thieno[2,3-d]pyrimidin-4(5H)-one;
 N-(3-chloro-2,6-difluorobenzyl)-4-cyclopropyl-1,2,3-thiadiazole-5-carboxamide;
 (S)—N-(1-(2-chloro-6-fluorophenyl)ethyl)-5-cyano-1-methyl-1H-pyrrole-2-carboxamide;
 (S)—N-(1-(2-chloro-6-fluorophenyl)ethyl)-4-cyclopropyl-1,2,3-thiadiazole-5-carboxamide;
 N-Benzyl-N-hydroxy-2,2-dimethylbutanamide;
 N-(4-Fluorobenzyl)-N-hydroxy-2,2-dimethylbutanamide;
 N-(2,4-Difluorobenzyl)-N-hydroxy-2,2-dimethylbutanamide;
 N-(3,4-Difluorobenzyl)-N-hydroxy-2,2-dimethylbutanamide;
 N-Hydroxy-2,2-dimethyl-N-(2,3,4-trifluorobenzyl)butanamide;
 N-Hydroxy-2,2-dimethyl-N-(3,4,5-trifluorobenzyl)butanamide;
 N-Hydroxy-2,2-dimethyl-N-(2,3,5-trifluorobenzyl)butanamide;
 (2-(3-fluorophenyl)pyrrolidin-1-yl)(1-(trifluoromethyl)cyclopentyl)methanone;
 (2-(3-fluorophenyl)pyrrolidin-1-yl)(1-(trifluoromethyl)cyclobutyl)methanone;

(S)-1-(2,2-dimethylbut-3-enoyl)-4-phenylazetidin-2-one;
(S)-2,2-dimethyl-1-(2-phenylazetidin-1-yl)but-3-yn-1-one; and
(S)-1-(2,2-dimethylbutanoyl)-4-phenylazetidin-2-one;
or a RIP1 inhibitor disclosed in WO2016/101885 or WO2016/101887;

the necroptosis inhibitor is a RIP3 inhibitor selected from:
tert-butyl 2-(4-(5-(methylcarbamoyl)-1H-benzo[d]imidazol-1-yl)phenyl)acetate (GSK'840);
3-(benzo[d]thiazol-5-yl)-7-(1,3-dimethyl-1H-pyrazol-5-yl)thieno[3,2-c]pyridin-4-amine (GSK'843);
N-(6-(isopropylsulfonyl)quinolin-4-yl)benzo[d]thiazol-5-amine (GSK'872);
N-[3-[5-(2-amino-4-pyrimidinyl)-2-(1,1-dimethylethyl)-4-thiazolyl]-2-fluorophenyl]-2,6-difluoro-benzenesulfonamide (Dabrafenib);
3-(2-Imidazo[1,2-b]pyridazin-3-ylethynyl)-4-methyl-N-[4-[(4-methyl-1-piperazinyl)methyl]-3-(trifluoromethyl)phenyl]-benzamide (ponatinib); and
5-[[4-[(2,3-dimethyl-2H-indazol-6-yl)methylamino]-2-pyrimidinyl]amino]-2-methyl-benzenesulfonamide (pazopanib);

the necroptosis inhibitor is a MLKL inhibitor selected from:
(2E)-N-[4-[[(3-Methoxy-2-pyrazinyl)amino]sulfonyl]phenyl]-3-(5-nitro-2-thienyl)-2-propenamide (Necrosulfonamide);
1,3,7-trimethyl-8-(methylsulfonyl)-1H-purine-2,6(3H,7H)-dione (TC13-4);
8-(2,5-dimethoxybenzylsulfonyl)-1,3,7-trimethyl-1H-purine-2,6(3H,7H)-dione (TC13-58);
7-ethyl-1,3-dimethyl-8-(methylsulfonyl)-1H-purine-2,6(3H,7H)-dione (TC13-74);
1,7-dimethyl-8-(methylsulfonyl)-3-(prop-2-ynyl)-1H-purine-2,6(3H,7H)-dione (TC13-106);
2-(1,7-dimethyl-8-(methylsulfonyl)-2,6-dioxo-1H-purin-3(2H,6H,7H)-yl)acetonitrile (TC13-107);
3-(3-(3-chlorophenyl)prop-2-yn-1-yl)-8-((cyclopropylmethyl)sulfonyl)-1,7-dimethyl-3,7-dihydro-1H-purine-2,6-dione (TC13-119);
8-((2,5-dimethoxybenzyl)sulfonyl)-1,7-dimethyl-3-(3-(2-(methylamino)pyridin-4-yl)prop-2-yn-1-yl)-3,7-dihydro-1H-purine-2,6-dione (TC13-127);
3-(3-(3-hydroxyphenyl)prop-2-yn-1-yl)-1,7-dimethyl-8-(methylsulfonyl)-3,7-dihydro-1H-purine-2,6-dione (TC13-172); and
3-((4-(methyl(4-(3-(4-(trifluoromethoxy)phenyl)ureido)phenyl)amino)pyrimidin-2-yl) amino)benzenesulfonamide (Compound 1); or
and MLKL inhibitor disclosed in PCT/CN2018/077464 (WO2018/157800);

the male senescence is selected from age-associated low testosterone, low libido, erectile dysfunction, weight gain, reduced muscle mass or tone, and prostate hyperplasia;

the method further comprises administering to the male a second, different drug for treating male senescence; and/or the method further comprises the antecedent step of diagnosis the male senescence, and/or the subsequent step of detecting a resultant diminution or reversal of the male senescence.

In other aspects the invention provides a pharmaceutical composition comprising a necroptosis inhibitor and a second different drug for treating male senescence.

In embodiments:

the different drug is selected from an androgen including exogenous and endogenous anabolic androgenic steroids, endogenous androgen stimulators (e.g. enclomiphene, clomiphene), female hormone inhibitor (e.g. anti-estrogens like clomiphene, zuclomiphene, tamoxifen, raloxifen), growth hormone (e.g. HGH);

the different drug is selected from:
testosterone, prasterone (dehydroepiandrosterone, DHEA), androstenedione (A4), androstenediol (A5), dihydrotestosterone (DHT),
1-Androstenediol, 1-Androstenedione, Bolandiol, Bolasterone, Boldenone, Boldione, Calusterone, Clostebol, Danazol, Dehydrochlormethyltestosterone, Desoxymethyltestosterone, Drostanolone, Ethylestrenol, Fluoxymesterone, Formebolone, Furazabol, Gestrinone, 4-Hydroxytestosterone, Mestanolone, Mesterolone, Metenolone, Methandienone, Methandriol, Methasterone, Methyldienolone, Methyl-1-testosterone, Methylnortestosterone, Methyltestosterone, Metribolone, Mibolerone, Nandrolone, 19-Norandrostenedione, Norboletone, Norclostebol, Norethandrolone, Oxabolone, Oxandrlone, Oxymesterone, Oxymetholone, Prostanozol, Quinbolone, Stanozolol, Stenbolone, 1-Testosterone, Tetrahydrogestrinone, and Trenbolone; and/or the composition is in unit dosage form.

The invention encompasses all combinations of the particular embodiments recited herein.

Description of Particular Embodiments of the Invention

The following descriptions of particular embodiments and examples are provided by way of illustration and not by way of limitation. Those skilled in the art will readily recognize a variety of noncritical parameters that could be changed or modified to yield essentially similar results. The invention provides myriad embodiments.

Unless contraindicated or noted otherwise, in these descriptions and throughout this specification, the terms "a" and "an" mean one or more, the term "or" means and/or and polynucleotide sequences are understood to encompass opposite strands as well as alternative backbones described herein.

The invention provides methods and compositions for treating male senescence, particularly reproductive (fertility and/or virility) senescence, or symptoms or makers thereof, such as age-associated low testosterone, low libido, erectile dysfunction, weight gain, reduced muscle mass or tone, and prostate hyperplasia. In an aspect the invention provides a method of treating male senescence comprising administering to a male in need thereof a necroptosis inhibitor, particularly a RIP1, RIP3 or MLKL inhibitor. Suitable RIP1, RIP3 and MLKL inhibitors are known in the art, as evidenced by the following references and representative inhibitors:

| References | RIP1 inhibitors |
|---|---|
| Nat. Chem. Biol. 2005, 1, 112-119; Bioorg. Med. Chem. Lett. 2005, 15, 5039-5044. U.S. Pat. No. 6,756,394; | 5-((1H-indol-3-yl)methyl)-3-methyl-2-thioxoimidazolidin-4-one (Nec-1) |

| References | |
|---|---|
| WO 2010075561 | (S)-phenyl(5-phenyl-4,5-dihydro-1H-pyrazol-1-yl)methanone |
| Cell Death Dis. 2012, 3, e437; U.S. Pat. No. 8,741,942 | 5-((1H-indol-3-yl)methyl)-3-methyl-2-thioxoimidazolidin-4-one (Nec-1s) |
| Nat. Chem. Biol. 2008, 4, 313-321; U.S. Pat. No. 8,741,942; US2011144169 | 3-methyl-5-((7-methyl-1H-indol-3-yl)methyl)imidazolidine-2,4-dione<br>(R)-5-((7-chloro-1H-indol-3-yl)methyl)-3-methylimidazolidine-2,4-dione |
| Cell Rep. 2015, 10, 1850-1860; WO2014145022; US20140323489 | (R)-5-((7-chloro-1H-indol-3-yl)methyl)-3-(4-(3-(imidazo[1,2-b]pyridazin-3-ylethynyl)-4-methylphenyl)butyl)imidazolidine-2,4-dione (Ponatinib-Nec1s) |
| Cell Death Dis. 2015, 1, 15009; WO2016185423 | (S)-2,2-dimethyl-1-(5-phenyl-4,5-dihydro-1H-pyrazol-1-yl)propan-1-on (GSK963) |
| WO2016185423 | (S)-2,2-dimethyl-1-(5-phenyl-4,5-dihydro-1H-pyrazol-1-yl)propan-1-one<br>(S)-1-(4-(5-phenyl-4,5-dihydro-1H-pyrazole-1-carbonyl)piperidin-1-yl)ethanone<br>(S)-2,2-dimethyl-1-(5-(pyridin-2-yl)-4,5-dihydro-1H-pyrazol-1-yl)propan-1-one<br>(S)-1-(4-(5-(3,5-difluorophenyl)-4,5-dihydro-1H-pyrazole-1-carbonyl)piperidin-1-yl)ethanone |
| US20170008878 | (S)-5-benzyl-N-(5-methyl-4-oxo-2,3,4,5-tetrahydrobenzo[b][1,4]oxazepin-3-yl)isoxazole-3-carboxamide<br>(S)-5-benzyl-N-(5-methyl-4-oxo-2,3,4,5-tetrahydrobenzo[b][1,4]oxazepin-3-yl)-4H-1,2,4-triazole-3-carboxamide<br>(S)-5-benzyl-N-(8-chloro-4-oxo-2,3,4,5-tetrahydrobenzo[b][1,4]oxazepin-3-yl)-4H-1,2,4-triazole-3-carboxamide<br>(S)-5-benzyl-N-(5-methyl-4-oxo-7-(1H-tetrazol-5-yl)-2,3,4,5-tetrahydrobenzo[b][1,4]oxazepin-3-yl)isoxazole-3-carboxamide<br>8-bromo-4,5-dihydro-1H-benzo[b]azepin-2(3H)-one |
| J. Med. Chem. 2016, 59, 2163-2178; WO2014125444 | (S)-5-benzyl-N-(5-methyl-4-oxo-2,3,4,5-tetrahydrobenzo[b][1,4]oxazepin-3-yl)isoxazole-3-carboxamide (GSK481) |
| J Med Chem 2017 23; 60(4): 1247-1261; WO2016027253 | (S)-5-benzyl-N-(5-methyl-4-oxo-2,3,4,5-tetrahydrobenzo[b]-[1,4]oxazepin-3-yl)-1H-1,2,4-triazole-3-carboxamide (GSK2982772) |
| ACS Med. Chem. Lett. 2013, 4, 1238-1243. | 1-(4-(4-aminofuro[2,3-d]pyrimidin-5-yl)phenyl)-3-(2-fluoro-5-(trifluoromethyl)phenyl)urea (Cpd27) |
| U.S. Pat. No. 8,741,942; US2011144169 | 3-methyl-5-((7-methyl-1H-indol-3-yl)methyl)imidazolidine-2,4-dione<br>(R)-5-((7-chloro-1H-indol-3-yl)methyl)-3-methylimidazolidine-2,4-dione |
| US2012122889 | 3-benzyl-6,7-dihydro-3H-cyclopenta[4,5]thieno[2,3-d]pyrimidin-4(5H)-one |
| WO2009023272; US2010317701; | N-(3-chloro-2,6-difluorobenzyl)-4-cyclopropyl-1,2,3-thiadiazole-5-carboxamide |
| US2009099242; US20120309795; | (S)-N-(1-(2-chloro-6-fluorophenyl)ethyl)-5-cyano-1-methyl-1H-pyrrole-2-carboxamide |
| U.S. Pat. No. 8,278,344; U.S. Pat. No. 9,108,955 | (S)-N-(1-(2-chloro-6-fluorophenyl)ethyl)-4-cyclopropyl-1,2,3-thiadiazole-5-carboxamide |
| Ren et al. J Med Chem, J. Med. Chem., 2017, 60 (3), pp 972-986; WO2016/101885 | N-Benzyl-N-hydroxy-2,2-dimethylbutanamide<br>N-(4-Fluorobenzyl)-N-hydroxy-2,2-dimethylbutanamide<br>N-(2,4-Difluorobenzyl)-N-hydroxy-2,2-dimethylbutanamide<br>N-(3,4-Difluorobenzyl)-N-hydroxy-2,2-dimethylbutanamide<br>N-Hydroxy-2,2-dimethyl-N-(2,3,4-trifluorobenzyl)butanamide<br>N-Hydroxy-2,2-dimethyl-N-(3,4,5-trifluorobenzyl)butanamide<br>N-Hydroxy-2,2-dimethyl-N-(2,3,5-trifluorobenzyl)butanamide |
| WO2016/101887 | (2-(3-fluorophenyl)pyrrolidin-1-yl)(1-(trifluoromethyl)cyclopentyl)methanone<br>(2-(3-fluorophenyl)pyrrolidin-1-yl)(1-(trifluoromethyl)cyclobutyl)methanone<br>(S)-1-(2,2-dimethylbut-3-enoyl)-4-phenylazetidin-2-one<br>(S)-2,2-dimethyl-1-(2-phenylazetidin-1-yl)but-3-yn-1-one<br>(S)-1-(2,2-dimethylbutanoyl)-4-phenylazetidin-2-one |
| RIP3 inhibitors | |
| Mol. Cell 2014, 56, 481-495. | tert-butyl 2-(4-(5-(methylcarbamoyl)-1H-benzo[d]imidazol-1-yl)phenyl)acetate (GSK'840)<br>3-(benzo[d]thiazol-5-yl)-7-(1,3-dimethyl-1H-pyrazol-5-yl)thieno[3,2-c]pyridin-4-amine (GSK'843)<br>N-(6-(isopropylsulfonyl)quinolin-4-yl)benzo[d]thiazol-5-amine (GSK'872) |
| Cell Death Dis. 2014, 5; 5: e1278. | N-[3-[5-(2-amino-4-pyrimidinyl)-2-(1,1-dimethylethyl)-4-thiazolyl]-2-fluorophenyl]-2,6-difluoro-benzenesulfonamide (Dabrafenib) |
| Cell Death and Disease (2015) 6, e1767. | 3-(2-Imidazo[1,2-b]pyridazin-3-ylethynyl)-4-methyl-N-[4-[(4-methyl-1-piperazinyl)methyl]-3-(trifluoromethyl)phenyl]-benzamide (ponatinib)<br>5-[[4-[(2,3-dimethyl-2H-indazol-6-yl)methylamino]-2-pyrimidinyl]amino]-2-methyl-benzenesulfonamide (pazopanib) |

| References | MLKL inhibitors |
|---|---|
| Cell, 2012, 148, 213-227; Med. Chem. Comm., 2014, 5, 333-337 | (2E)-N-[4-[[(3-Methoxy-2-pyrazinyl)amino]sulfonyl]phenyl]-3-(5-nitro-2-thienyl)-2-propenamide (Necrosulfonamide) |
| Chem. Comm., 2017, 53, 3637-3640; PCT/CN2017/075248 | 1,3,7-trimethyl-8-(methylsulfonyl)-1H-purine-2,6(3H,7H)-dione(TC13-4) 58-(2,5-dimethoxybenzylsulfonyl)-1,3,7-trimethyl-1H-purine-2,6(3H,7H)-dione (TC13-58) 7-ethyl-1,3-dimethyl-8-(methylsulfonyl)-1H-purine-2,6(3H,7H)-dione (TC13-74) 1,7-dimethyl-8-(methylsulfonyl)-3-(prop-2-ynyl)-1H-purine-2,6(3H,7H)-dione (TC13-106) 2-(1,7-dimethyl-8-(methylsulfonyl)-2,6-dioxo-1H-purin-3(2H,6H,7H)-yl)acetonitrile (TC13-107) 3-(3-(3-chlorophenyl)prop-2-yn-1-yl)-8-((cyclopropylmethyl)sulfonyl)-1,7-dimethyl-3,7-dihydro-1H-purine-2,6-dione (TC13-119) 8-((2,5-dimethoxybenzyl)sulfonyl)-1,7-dimethyl-3-(3-(2-(methylamino)pyridin-4-yl)prop-2-yn-1-yl)-3,7-dihydro-1H-purine-2,6-dione (TC13-127) 3-(3-(3-hydroxyphenyl)prop-2-yn-1-yl)-1,7-dimethyl-8-(methylsulfonyl)-3,7-dihydro-1H-purine-2,6-dione (TC13-172) |
| Proc Natl Acad Sci USA, 2014, 111, 15072-15077; WO2015172203 | 3-((4-(methyl(4-(3-(4-(trifluoromethoxy)phenyl)ureido)phenyl)amino)pyrimidin-2-yl)amino)benzenesulfonamide (Compound 1) |

The methods and compositions may employ the compounds in any suitable form and dosage unit, including salts, prodrugs, stereoisomers, amorphous forms, etc.

The term "pharmaceutically acceptable salts" is meant to include salts of the active compounds which are prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug is a compound of the invention which is administered as an ester (the "prodrug"), but then is metabolically hydrolyzed to the carboxylic acid, the active entity. Additional examples include peptidyl derivatives of a compound of the invention.

Certain compounds of the invention can exist in unsolvated forms as well as solvated forms, including hydrated forms. In general, the solvated forms are equivalent to unsolvated forms and are intended to be encompassed within the scope of the invention. Certain compounds of the invention may exist in multiple crystalline or amorphous forms. In general, all physical forms are equivalent for the uses contemplated by the invention and are intended to be within the scope of the invention.

Certain compounds of the invention possess asymmetric carbon atoms (optical centers) or double bonds; the racemates, diastereomers, geometric isomers and individual isomers are all intended to be encompassed within the scope of the invention.

The term "therapeutically effective amount" refers to the amount of the subject compound that will elicit, to some significant extent, the biological or medical response of a tissue, system, animal or human that is being sought by the researcher, veterinarian, medical doctor or other clinician, such as when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The invention also provides pharmaceutical compositions comprising the subject compounds and a pharmaceutically acceptable excipient, particularly such compositions comprising a unit dosage of the subject compounds, particularly such compositions copackaged with instructions describing use of the composition to treat an applicable disease or condition (herein).

The compositions for administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules, losenges or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

Suitable excipients or carriers and methods for preparing administrable compositions are known or apparent to those skilled in the art and are described in more detail in such publications as *Remington's Pharmaceutical Science*, Mack Publishing Co, NJ (1991). In addition, the compounds may be advantageously used in conjunction with other therapeutic agents as described herein or otherwise known in the art, particularly other anti-necrosis agents. Hence the compositions may be administered separately, jointly, or combined in a single dosage unit.

The amount administered depends on the compound formulation, route of administration, etc. and is generally empirically determined in routine trials, and variations will necessarily occur depending on the target, the host, and the route of administration, etc. Generally, the quantity of active compound in a unit dose of preparation may be varied or adjusted from about 1, 3, 10 or 30 to about 30, 100, 300 or 1000 mg, according to the particular application. In a particular embodiment, unit dosage forms are packaged in a multipack adapted for sequential use, such as blisterpack, comprising sheets of at least 6, 9 or 12 unit dosage forms. The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The compounds can be administered by a variety of methods including, but not limited to, parenteral, topical, oral, or local administration, such as by aerosol or transdermally, for prophylactic and/or therapeutic treatment. Also, in accordance with the knowledge of the skilled clinician, the therapeutic protocols (e.g., dosage amounts and times of administration) can be varied in view of the observed effects of the administered therapeutic agents on the patient, and in view of the observed responses of the disease to the administered therapeutic agents.

The therapeutics of the invention can be administered in a therapeutically effective dosage and amount, in the process of a therapeutically effective protocol for treatment of the patient. For more potent compounds, microgram (ug) amounts per kilogram of patient may be sufficient, for example, in the range of about 1, 10 or 100 ug/kg to about 0.01, 0.1, 1, 10, or 100 mg/kg of patient weight though optimal dosages are compound specific, and generally empirically determined for each compound.

In general, routine experimentation in clinical trials will determine specific ranges for optimal therapeutic effect, for each therapeutic, each administrative protocol, and administration to specific patients will also be adjusted to within effective and safe ranges depending on the patient condition and responsiveness to initial administrations. However, the ultimate administration protocol will be regulated according to the judgment of the attending clinician considering such factors as age, condition and size of the patient as well as compounds potency, severity of the disease being treated. For example, a dosage regimen of the compounds can be oral administration of from 10 mg to 2000 mg/day, preferably 10 to 1000 mg/day, more preferably 50 to 600 mg/day, in two to four (preferably two) divided doses. Intermittent therapy (e.g., one week out of three weeks or three out of four weeks) may also be used.

The subject compounds may be employed alone or in combination with other therapeutic agents. Combination therapies thus comprise the administration of at least one pharmaceutically acceptable crystalline or amorphous form of the compounds and at least one other therapeutically active agent. The subject compounds and the other therapeutically active agent(s) may be administered together in a single pharmaceutical composition or separately and, when administered separately this may occur simultaneously or sequentially in any order. The amounts of the subject compounds and the other therapeutically active agent(s) and the relative timings of administration will be selected in order to achieve the desired combined therapeutic effect. Thus in a further aspect, there is provided a combination comprising a pharmaceutically acceptable crystalline or amorphous form of the compounds together with one or more other therapeutically active agents.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the disease or disorder being treated, the severity of the disease or disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change. Total daily dosages range from 1 mg to 2000 mg.

For use in therapy, the compounds of the invention will be normally, but not necessarily, formulated into a pharmaceutical composition, or administration unit, prior to administration to a patient. Accordingly, the invention also is directed to a pharmaceutical composition comprising a compound of the invention and one or more pharmaceutically acceptable excipients. The invention also is directed to an administration unit comprising a compound of the invention and one or more pharmaceutically acceptable excipients.

The pharmaceutical compositions or administration units of the invention may be prepared and packaged in bulk form wherein an effective amount of a compound of the invention can be extracted and then given to the patient such as with powders, syrups, and solutions for injection. Alternatively, the pharmaceutical compositions or administration units of the invention may be prepared and packaged in unit dosage form. For oral application, for example, one or more tablets or capsules may be administered. A dose of the pharmaceutical composition contains at least a therapeutically effective amount of a compound of the invention. When prepared in unit dosage form, the pharmaceutical compositions or administration units may contain from 1 mg to 1000 mg of a subject compound.

As provided herein, unit dosage forms (pharmaceutical compositions or administration units) containing from 1 mg to 1000 mg of compound may be administered one, two, three, or four times per day, preferably one, two, or three times per day, and more preferably, one or two times per day.

As used herein, "pharmaceutically acceptable excipient" means a material, composition or vehicle involved in giving form or consistency to the composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically acceptable.

The compounds of the invention and the pharmaceutically acceptable excipient or excipients will typically be formulated into a dosage form adapted for administration to the patient by the desired route of administration. Conventional dosage forms include those adapted for (1) oral administration such as tablets, capsules, caplets, pills, troches, powders, syrups, elixirs, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols and solutions; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting the compound or compounds of the invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anti-caking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation. Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The pharmaceutical compositions of the invention are prepared using techniques and methods known to those skilled in the art. Some of the methods commonly used in the art are described in Remington's Pharmaceutical Sciences (supra). Accordingly, another embodiment of this invention is a method of preparing a pharmaceutical composition or administration unit comprising the step of admixing a pharmaceutically acceptable crystalline form of a subject compound with one or more pharmaceutically acceptable excipients.

In one aspect, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

EXAMPLES

Aging of Reproductive Organs is Delayed in RIP3 Knockout Mice

We first noticed that the 18-month old RIP3-knockout (RIP3$^{-/-}$) mice of the C57BL/6 strain looked thinner than the age-matched wild type (WT, RIP3$^{+/+}$) mice of the same strain that were housed under the same conditions. The average weight of 18-month old wild type mice was 46 grams, significantly more than of 37 grams of weight of the age-matched RIP3-knockout mice. The weights of 4-month old wild type and RIP3-knockout mice, on the other hand, were indistinguishable. In addition to differences in whole body weights, the seminal vesicles, an auxiliary gland in the mouse male reproductive system, appeared to be quite different between 18-month old RIP3-knockout and wild type mice. The weights of the seminal vesicles from 18-month old wild type mice (n=33) ranged from ~1,000 mg to 4,500 mg, while the weights of the same organ from the age-matched RIP3-knockout mice (n=30) were mostly below 1,000 mg.

It is known that seminal vesicles become enlarged as mice get old (Finch and Girgis, 1974; Pettan-Brewer and Treuting, 2011). The difference in seminal vesicles from wild type and RIP3-knockout mice become noticeable after one year of life, and become increasingly evident over time. The seminal vesicles from wild type mice continue to grow, whereas the seminal vesicles from the RIP3-knockout mice did not change in size from 4 months to 24 months. There were no obvious differences in the overall anatomical structure of seminal vesicles between wild type and RIP3-knockout mice. Close examination revealed that the epithelium of the seminal vesicles from 18-month old wild type mice showed irregularities, with spaces separating the epithelium and the liquid compartment, whereas the seminal-vesicle epithelial cells from the age-matched RIP3-knockout mice were tightly packed, just as they are in young mice.

The seminal vesicles of mice are anatomically simple, consisting of only an epithelial layer that envelopes a liquid compartment (Gonzales, 2001). Therefore, the difference in seminal vesicles between wild type and RIP3-knockout mice did not offer much mechanistic insight what caused such a phenotype. We further studied the testes of wild type and RIP3-knockout mice. By the time mice reached 18 months of age, the wild type testes started to appear atrophic, and weighed less than RIP3-knockout testes. Consistently, the testosterone level showed a dramatic drop as wild type mice aged from 4 to 18 months, whereas the testosterone levels hardly decreased at all in RIP3-knockout mice over the same period. Moreover, the typical age-related increase in sex hormone-binding globulin (SHBG) (Vermeulen et al., 1996) that is known to occur in wild type mice was not observed in RIP3-knockout mice. Interestingly, the levels of two endocrine factors secreted by the pituitary gland, LH and FSH (Cooke and Saunders, 2002), did not differ between wild type and RIP3-knockout mice; both dropped significantly as mice aged from 4 months to 18 months. This finding indicated that the difference in aging of reproductive system between old wild type and RIP3-knockout mice may result from local changes in testis.

Unlike what often happens in human upon reproductive organ aging, hematoxylin and eosin (H&E) staining of mouse prostates revealed no apparent anatomical differences in the anterior, dorsal, ventral, or lateral prostate (Pettan-Brewer and Treuting, 2011) sections of young (4-month) or old (18-month) mice of either the wild type or RIP3-knockout genotypes.

Knockout of RIP3 Prevents the Depletion of Cells in the Seminiferous Tubules in Aged Testes As a male mouse becomes sexually mature, the central lumens of seminiferous tubules in its testes begin to fill with sperm generated from the surrounding spermatogonial stem cells. The spermatogonial stem cells and spermatocytes are supported by Sertoli cells, which provide trophic factors and structural support for spermatogenesis (Cooke and Saunders, 2002). Sperm are then transferred and stored in the epididymis, from where mature sperm are ejected. After mixing with fluids from the seminal vesicles and prostate, the sperm travel alone the ejaculation track, where semen is formed (Cooke and Saunders, 2002).

When testes from 4-month old and 18-month old wild type and RIP3-knockout mice were dissected and their cross sections were examined under a microscope, cells in many of the seminiferous tubules from the 18-month old wild type mice were lost, given the seminiferous tubules an "empty" appearance. In contrast, the central lumens of the seminiferous tubules of 4-month old wild type and RIP3-knockout mice are fully surrounded with cells, and are filled with sperm. Strikingly, the seminiferous tubules of 18-month old RIP3-knockout mice looked no different than those of 4-month old mice. Even more dramatically, when testis sections from 36-month old mice were examined, close to half of seminiferous tubules of wild type mice were empty, while more than 90% of those from the RIP3-knockout mice still appeared normal.

Sperm from the seminiferous tubules travel to the epididymis, where they mature and are stored prior to ejaculation (Cooke and Saunders, 2002). Similar to the phenotypes observed in the seminiferous tubules, most of the epididymides from 18-month old wild type mice had few sperm, whereas most of the epididymides of age-matched RIP3-knockout mice were full of sperm. The sperm counts in epididymides increased steadily during development and peaked at four months of age, and there was little difference in the sperm counts between wild type and RIP3-knockout mice up to this time. The sperm counts of wild type mice then started to decline, while those of RIP3-knockout mice remained steady until 12 months of age. Even at 24 months, the sperm counts of RIP3-knockout mice were still comparable with those of 4-month old wild type mice.

Knockout of RIP3 Prevents Age-Associated Decline of Reproductive Capacity

To test if the sperm from aged RIP3-knockout mice remain functional, we set up breeding experiments that mated 4-month old, 13-month old, and 18-month old male mice with pairs of 10-week old wild type female mice. Both wild type and RIP3-knockout 4-month old male mice were fully fertile, and both groups sired a similar number of pups. However, for 13-month-old mice, only 9 of the 20 wild type male mice sired pups, while 18 out of 23 RIP3-knockout males remained fertile. The difference was even more obvious with the 18-month old male mice. Only 4 out of 22 wild type male mice were still fertile at this age, whereas 15 out of 22 RIP3-knockout male mice remained fertile. We subsequently measured the reproductive longevity of wild type and RIP3-knockout male mice by pairing a pair of 10-weeks old female mice with each male in a cage and switch out a fresh pair of females every other month (Hofmann et al., 2015). Monitoring of the age at which each male sired its last litter showed that wild type mice on average lost the ability to sire offspring around 16 months, while the RIP3-knockout mice did not lose this ability until 22 months.

RIP3 Expression in Spermatogonia, Spermatocytes and Sertoli Cells in Testis

To investigate the underlining mechanism responsible for the delayed reproductive system aging phenotype, we first examined RIP3 expression using immunohistochemistry methods (IHC). We noted that the cells inside wild type seminiferous tubules were stained positively with anti-RIP3 antibody. In contrast, no staining was seen in the seminiferous tubules of RIP3-knockout mice, confirming the specificity of the antibody.

The specific cell types from testes were further analyzed by co-immunostaining of testis sections from sexually-mature wild type mice (8-weeks) with antibodies against RIP3 and other previously-described cell-type specific markers. RIP3 expression was apparent in germ line spermatogonia expressing UTF1 (Jung et al., 2014; van Bragt et al., 2008) and in Sertoli cells expressing GATA-1 (Tsai et al., 2006). The testosterone-producing Leydig cells (marked by the HSD3B 1 (Chang et al., 2011) located outside of seminiferous tubules, however, did not express RIP3. The RIP3 expression in each of these cell types was further confirmed when testes were dissected and the cells were spread on a slide and analyzed again with co-immunostaining. The cell shapes changed due to spreading with this method, but the individual cells were more clearly visible. Consistent with the IHC staining results, spermatogonia and Sertoli cells were positive for RIP3 staining while Leydig cells were not. Moreover, the primary spermatocytes within seminiferous tubules that were not marked by IHC were now clearly visible when stained with the specific marker SMAD3 (Hentrich et al., 2011), and these cells expressed RIP3. The fact that the cells within seminiferous tubules, the sperm-producing unit of testis, are all positive for RIP3 expression raised a possibility that the age-associated depletion of these cells is through necroptosis.

The RIP3 Substrate MLKL is Phosphorylated in the Seminiferous Tubules of Aged Wild Type Mice Recall that RIP3 transduces the necroptosis signal by phosphorylating the serine 345 of pesudokinase MLKL, we used an antibody against phospho-serine 345 of MLKL to analyze the testes of young and old mice. Phosphorylated MLKL (phospho-MLKL) was detected in seminiferous tubules in cells surrounding the center lumens in testes of 18-month old wild type mice, whereas no phospho-MLKL was detected in the same tissue area of 8-week old wild type mice nor in 18-month old RIP3-knockout mice. A quantitative analysis of the phospho-MLKL staining of each age and genotype group showed that necroptosis-activation marker, i.e. serine-345 phosphorylation, was present abundantly in the seminiferous tubules of old wild type mice but not in young and RIP3-knockout mice, thus suggesting that necroptosis of these RIP3-expressing cells in seminiferous tubules might trigger the aging of male sex organs. Consistently, phospho-MLKL was detected by western blotting in extracts from testes of 18- and 24-month old wild type mice but not in extracts from age-matched RIP3 knockout mice.

To further identify the exact cell type in the aged seminiferous tubules that show positive marker of necroptosis, we did immunohistochemical staining testis sections using fluroresent-conjugated anti-phospho-MLKL antibody and co-stained with antibodies that specifically mark the different cell types in seminiferous tubules. Spermatogonia that specifically expressing UTF1 were co-stained with the anti-phospho-MLKL antibody. On the other hand, Sertoli cells did not show phosphor-MLKL staining even though they do express RIP3. Not surprisingly, Leydig cells that do not have RIP3 expression also did not stain with the phosphor-MLKL antibody.

Activation of Apoptosis in Leydig Cells During Aging

The sex hormone-producing Leydig cells in testes do not express RIP3, yet in old mice testis, the hormone level drops and Leydig cells are also gone. We therefore checked the cleavage status of procaspase-3 (a known marker of apoptosis) and procaspase-8 in the aged testes of wild type and RIP3-knockout mice using IHC. Cleaved procaspase-3 and Cleaved procaspase-8 was detected in the wild type Leydig cells of 18, and 36-month old mice, while no such signal was observed in age-matched RIP3-knockout mice. The cleaved-Caspase-3 was also detected by western blotting using extracts from the aged wild type testes but not in RIP3-knockout testes. It is thus likely that Leydig cells undergo apoptosis, as a secondary response to necroptosis in seminiferous tubules during aging process.

Caspase 8 Levels Decrease During Aging in Empty Seminiferous Tubules

We also used immunohistochemistry methods to examine the caspase8 level in relative to RIP3 in testes of wild type mice of advanced age. In aged wild type mice, caspse8 levels decreased in the seminiferous tubules showing the sign of cell depletion, and increase in the Leydig cells. This reduction in caspase8 may explain how it is that necroptosis, but not apoptosis, occurs in the seminiferous tubules of aged mice.

Knockout of MLKL Also Delays the Aging of Mouse Reproductive Organs

The delayed testis aging phenotype of RIP3 knockout mice and detection of necrptosis activation marker in spermatogonia in aged wild type mice suggest that necroptosis might be the underlying cause of testis aging. To further investigate possibility, we also characterized the aging-associated phenotype of MLKL knockout mice. We first weighed 15-month old wild type, RIP3-knockout, and MLKL-knockout (MLKL$^{-/-}$) mice. There was no significant difference between the weights of MLKL- and RIP3-knockout mice, and mice of both of these knockout genotypes weighed less than wild type mice at this age. We also analyzed seminal vesicles and seminiferous tubules in aged MLKL-knockout mice (15-month old). Compared to the obvious aging that had occurred in wild type mice, the seminal vesicles of MLKL-knockout mice maintained a youthful appearance, exhibiting the same phenotype as RIP3-knockout mice. Furthermore, while the majority of seminal vesicles from 15-month old wild type mice weighed more than 1,000 milligrams, almost all of the seminal vesicles from age-matched MLKL- and RIP3-knockout weighed less than 1,000 milligrams. Consistently, the testosterone levels of both MLKL- and RIP3-knockout mice were also significant higher than those of age-matched wild type mice. Further, very few (<2%) of the seminiferous tubules from MLKL-knockout mice were empty at 15 months of age, similar to the tubules of RIP3-knockout mice, while more than 12% of seminiferous tubules from the age-matched wild type mice were already empty. Finally, the fertility rates of both 16-Month old MLKL- and RIP3-knockout mice were also significant higher than those of age-matched wild type mice.

Induction of Necroptosis in Testis Depleted Cells in Seminiferous Tubules

To directly demonstrate that necroptosis in testes is sufficient to cause the aging of the male reproductive system, we injected a combination of TNF-α, Smac mimetic, and caspase inhibitor z-VAD-FMK (henceforth 'TSZ')(He et al., 2009), a known necroptosis stimulus to the testes of 2-month old mice. Injection of TSZ directly into the testis induced MLKL phosphorylation. Phospho-MLKL was obviously present within the seminiferous tubules of TSZ-injected wild type testes, but not TSZ-treated RIP3-knockout or MLKL-knockout testes, confirming the activation of necroptosis in testes following TSZ injection. Moreover, when the cells were isolated from a wild type testis and then treated with TSZ prior to staining with antibodies against phospho-MLKL and cell-type specific markers, cells in the seminiferous tubules, including spermatogonia, Sertoli cells, and spermatocytes, were stained positive for phospho-MLKL, whereas Leydig cells outside seminiferous tubules were negative. The consequences of necroptosis induction in testes became apparent 72 hours after a single TSZ injection. By this point, about 25% of wild type seminiferous tubules were empty, whereas almost none of the seminiferous tubules from RIP3- and MLKL-knockout mice were affected.

Induction of Necroptosis in Testes Accelerates Aging of the Male Reproductive System In addition to monitoring these short-term effects following TSZ injection of 3-month-old mice, we waited for three additional months following the injection and assessed the long-term effects of induced necroptosis in mouse testes. Interestingly, three months after TSZ injection, the seminal vesicles of wild type recipient mice were as enlarged as those from mice older than 15 months. However, no such enlargement of seminal vesicles was observed in RIP3- and MLKL-knockout mice after the same TSZ treatment of their testes. Additionally, more than 30% of the wild type seminiferous tubules remained empty three months after the injection, while those of RIP3- and MLKL-knockout mice appeared completely normal without any observable loss of cells.

We also tested the fertility rate of TSZ-treated mice 3-month after the TSZ treatment. Control injection of saline into the testes of wild type mice did not affect the fertility rate and the mice remained 100% fertile, but TSZ injection reduced the fertility rate by 87.5% (only 1 of 8 was fertile). In contrast, 6 out of 8 RIP3-knockout mice and 7 out of 8 MLKL-knockout mice were still fertile following TSZ injection.

RIP1 Kinase Inhibitors Block Aging of the Male Reproductive System

The identification of the role of necroptosis in the aging of the mouse male reproductive system suggests the feasibility of a pharmaceutical intervention against the aging process. We therefore evaluated the effects of a newly-identified, highly-potent, and highly-specific RIP1 kinase inhibitor from our laboratory (henceforth 'RIPA-56')(Ren et al., 2017) by incorporating it into mouse food at 150 mg/kg and 300 mg/kg doses. We first tested the effect of RIPA-56 on necroptosis in testes by injecting TSZ into testes of 2-month old mice after feeding the mice with increasing concentrations of RIPA-56-containing chow for one week. RIPA-56 blocked the appearance of TSZ-induced phospho-MLKL in the testes in a dose-dependent manner, and was able to completely block necroptosis at the 300 mg/kg dose.

We subsequently chose the 300 mg/kg dose to continuously feed 13-month old male wild type mice for two months to study the long-term effects of blocking necroptosis on testes. After two months, the mice feed RIPA-56 weighed less than mice fed with control chow diet. The seminal vesicles of the RIPA-56-treated mice retained the mass (mostly around 1,000 milligrams), while the seminal vesicles control mice grew significantly during the same period, with a majority of them weighing more than 2,000 milligrams. Additionally, the testosterone level of RIPA-56-treated mice remained high, while that of control mice decreased. Consistently, more than 12% of the seminiferous tubules of the control mice were empty, whereas hardly any seminiferous vesicles were empty in the RIPA-56-treated mice. Finally, the fertility rates of the RIPA-56-treated mice were much higher than those of control mice with 19 out of 25 mice on the RIPA-56 diet were fertile while only 6 out of 23 mice on normal diet produced progeny. Overall fed mice present more youthful gross male aging metrics including body weight, fat deposition, libido (evidenced by sexual response to co-caged female mice), fertility, muscle mass, and prostate hyperplasia.

Representative RIP1, RIP3 and MLKL Kinase Inhibitors Block Aging of Male Reproductive System Consistent with our genetic knockout results, exemplary inhibitors of necroptosis, including inhibitors of RIP1, RIP3 and MLKL have similar reversal effects on male senescence, including testes necroptosis, testosterone levels, weight gain, loss of muscle mass and prostate hyperplasia.

Experimental protocols for the compounds of Tables 1-3 were based on those used for RIPA-56. Each inhibitor is mixed into mouse food at 100 mg/kg and/or 300 mg/kg doses, and fed to 13-month old male mice continuously for two months. After two months of feeding with the representative inhibitors the seminal vesicles of the fed mice, now 15 months old, retain youthful morphology and mass (mostly around 1,000 mg), while of the seminal vesicles of the mice fed control chow grow significantly during the same period, with a majority of them greater than 2,000 mg. Consistently, the testosterone level of inhibitor fed mice remains high, while that of the mice on normal chow diet decreases. Additionally, when the seminiferous tubules of these mice are examined, more than 12% of those from control mice were empty, whereas the testes from inhibitor fed mice have few seminiferous vesicles that were empty. Overall the treated mice present more youthful gross male aging metrics including body weight, fat deposition, libido (evidenced by sexual response to co-caged female mice), fertility, muscle mass, and prostate hyperplasia.

TABLE 1

RIP1 inhibitors 5-((1H-indol-3-yl)methyl)-3-methyl-2-thioxoimidazolidin-4-one (Nec-1)
(S)-phenyl(5-phenyl-4,5-dihydro-1H-pyrazol-1-yl)methanone
5-((1H-indol-3-yl)methyl)-3-methyl-2-thioxoimidazolidin-4-one (Nec-1s)
3-methyl-5-((7-methyl-1H-indol-3-yl)methyl)imidazolidine-2,4-dione
(R)-5-((7-chloro-1H-indol-3-yl)methyl)-3-methylimidazolidine-2,4-dione
(R)-5-((7-chloro-1H-indol-3-yl)methyl)-3-(4-(3-(imidazo[1,2-b]pyridazin-3-ylethynyl)-4-methylphenyl)butyl)imidazolidine-2,4-dione (Ponatinib-Nec1s)
(S)-2,2-dimethyl-1-(5-phenyl-4,5-dihydro-1H-pyrazol-1-yl)propan-1-on (GSK963)
(S)-2,2-dimethyl-1-(5-phenyl-4,5-dihydro-1H-pyrazol-1-yl)propan-1-one
(S)-1-(4-(5-phenyl-4,5-dihydro-1H-pyrazole-1-carbonyl)piperidin-1-yl)ethanone
(S)-2,2-dimethyl-1-(5-(pyridin-2-yl)-4,5-dihydro-1H-pyrazol-1-yl)propan-1-one
(S)-1-(4-(5-(3,5-difluorophenyl)-4,5-dihydro-1H-pyrazole-1-carbonyl)piperidin-1-yl)ethanone
(S)-5-benzyl-N-(5-methyl-4-oxo-2,3,4,5-tetrahydrobenzo[b][1,4]oxazepin-3-yl)isoxazole-3-carboxamide
(S)-5-benzyl-N-(5-methyl-4-oxo-2,3,4,5-terahydrobenzo[b][1,4]oxazepin-3-yl)-4H-1,2,4-triazole-3-carboxamide
(S)-5-benzyl-N-(8-chloro-4-oxo-2,3,4,5-tetrahydrobenzo[b][1,4]oxazepin-3-yl)-4H-1,2,4-triazole-3-carboxamide
(S)-5-benzyl-N-(5-methyl-4-oxo-7-(1H-tetrazol-5-yl)-2,3,4,5-tetrahydrobenzo[b][1,4]oxazepin-3-yl)isoxazole-3-carboxamide
8-bromo-4,5-dihydro-1H-benzo[b]azepin-2(3H)-one
(S)-5-benzyl-N-(5-methyl-4-oxo-2,3,4,5-tetrahydrobenzo[b][1,4]oxazepin-3-yl)isoxazole-3-carboxamide (GSK481)
(S)-5-benzyl-N-(5-methyl-4-oxo-2,3,4,5-tetrahydrobenzo[b][1,4]oxazepin-3-yl)-1H-1,2,4-triazole-3-carboxamide (GSK2982772)
1-(4-(4-aminofuro[2,3-d]pyrimidin-5-yl)phenyl)-3-(2-fluoro-5-(trifluoromethyl)phenyl)urea (Cpd27)
3-methyl-5-((7-methyl-1H-indol-3-yl)methyl)imidazolidine-2,4-dione
(R)-5-((7-chloro-1H-indol-3-yl)methyl)-3-methylimidazolidine-2,4-dione
3-benzyl-6,7-dihydro-3H-cyclopenta[4,5]thieno[2,3-d]pyrimidin-4(5H)-one
N-(3-chloro-2,6-difluorobenzyl)-4-cyclopropyl-1,2,3-thiadiazole-5-carboxamide
(S)-N-(1-(2-chloro-6-fluorophenyl)ethyl)-5-cyano-1-methyl-1H-pyrrole-2-carboxamide
(S)-N-(1-(2-chloro-6-fluorophenyl)ethyl)-4-cyclopropyl-1,2,3-thiadiazole-5-carboxamide
N-Benzyl-N-hydroxy-2,2-dimethylbutanamide
N-(4-Fluorobenzyl)-N-hydroxy-2,2-dimethylbutanamide
N-(2,4-Difluorobenzyl)-N-hydroxy-2,2-dimethylbutanamide
N-(3,4-Difluorobenzyl)-N-hydroxy-2,2-dimethylbutanamide
N-Hydroxy-2,2-dimethyl-N-(2,3,4-trifluorobenzyl)butanamide
N-Hydroxy-2,2-dimethyl-N-(3,4,5-trifluorobenzyl)butanamide
N-Hydroxy-2,2-dimethyl-N-(2,3,5-trifluorobenzyl)butanamide
(2-(3-fluorophenyl)pyrrolidin-1-yl)(1-(trifluoromethyl)cyclopentyl)methanone
(2-(3-fluorophenyl)pyrrolidin-1-yl)(1-(trifluoromethyl)cyclobutyl)methanone
(S)-1-(2,2-dimethylbut-3-enoyl)-4-phenylazetidin-2-one
(S)-2,2-dimethyl-1-(2-phenylazetidin-1-yl)but-3-yn-1-one
(S)-1-(2,2-dimethylbutanoyl)-4-phenylazetidin-2-one, or a RIP1 inhibitor disclosed in WO2016/101885 including:

TABLE 2

RIP1 inhibitors

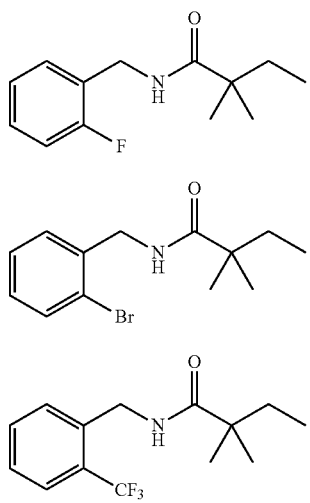

1

3

4

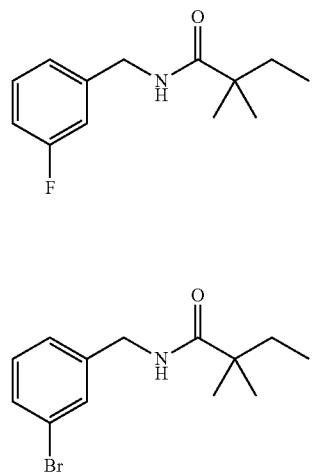

5

6

TABLE 2-continued

RIP1 inhibitors

| No. | Structure |
|---|---|
| 7 | 2,4-difluorobenzyl 2,2-dimethylbutanamide |
| 8 | 3,4-difluorobenzyl 2,2-dimethylbutanamide |
| 9 | pyridin-3-ylmethyl 2,2-dimethylbutanamide |
| 10 | N-(2-fluorobenzyl)-N-ethyl-2,2-dimethylbutanamide |
| 11 | N-(2-fluorobenzyl)-N-(prop-2-yn-1-yl)-2,2-dimethylbutanamide |
| 12 | N-(2-fluorobenzyl)-N-(3-oxobutyl)-2,2-dimethylbutanamide |
| 13 | N-(2-fluorobenzyl)-N-methyl-2,2-dimethylbutanamide |
| 14 | N-(2-chlorobenzyl)-N-methyl-2,2-dimethylbutanamide |
| 15 | N-(2-methoxybenzyl)-N-methyl-2,2-dimethylbutanamide |
| 16 | N-(3-fluorobenzyl)-N-methyl-2,2-dimethylbutanamide |
| 17 | N-(3-cyanobenzyl)-N-methyl-2,2-dimethylbutanamide |
| 18 | N-(3-chlorobenzyl)-N-methyl-2,2-dimethylbutanamide |
| 19 | N-(3-bromobenzyl)-N-methyl-2,2-dimethylbutanamide |
| 20 | N-(3-methoxybenzyl)-N-methyl-2,2-dimethylbutanamide |
| 21 | N-(3-hydroxybenzyl)-N-methyl-2,2-dimethylbutanamide |
| 22 | N-(4-(2-hydroxyethoxy)benzyl)-N-methyl-2,2-dimethylbutanamide |

TABLE 2-continued

RIP1 inhibitors

| # | Structure |
|---|---|
| 23 | 3-(methoxycarbonyl)benzyl-N-methyl-2,2-dimethylbutanamide |
| 24 | 2,4-difluorobenzyl-N-methyl-2,2-dimethylbutanamide |
| 25 | 2,5-difluorobenzyl-N-methyl-2,2-dimethylbutanamide |
| 26 | 3,5-difluorobenzyl-N-methyl-2,2-dimethylbutanamide |
| 27 | 4-chloro-2-fluorobenzyl-N-methyl-2,2-dimethylbutanamide |
| 28 | 2-fluoro-4-methoxybenzyl-N-methyl-2,2-dimethylbutanamide |
| 29 | 2,4-difluorobenzyl-N-ethyl-2,2-dimethylbutanamide |
| 30 | 3-nitro-4-piperidinylbenzyl-N-methyl-2,2-dimethylbutanamide |
| 31 | 2,3-dimethylbenzyl-N-methyl-2,2-dimethylbutanamide |
| 32 | 3,5-dimethylbenzyl-N-methyl-2,2-dimethylbutanamide |
| 33 | 2-fluoro-3-(trifluoromethoxy)benzyl-N-methyl-2,2-dimethylbutanamide |
| 34 | pyridin-4-ylmethyl-N-methyl-2,2-dimethylbutanamide |
| 35 | pyridin-3-ylmethyl-N-methyl-2,2-dimethylbutanamide |
| 36 | (3-fluoropyridin-4-yl)methyl-N-methyl-2,2-dimethylbutanamide |
| 37 | (2-methoxypyridin-3-yl)methyl-N-methyl-2,2-dimethylbutanamide |
| 38 | (6-methoxypyridin-3-yl)methyl-N-methyl-2,2-dimethylbutanamide |

TABLE 2-continued
RIP1 inhibitors
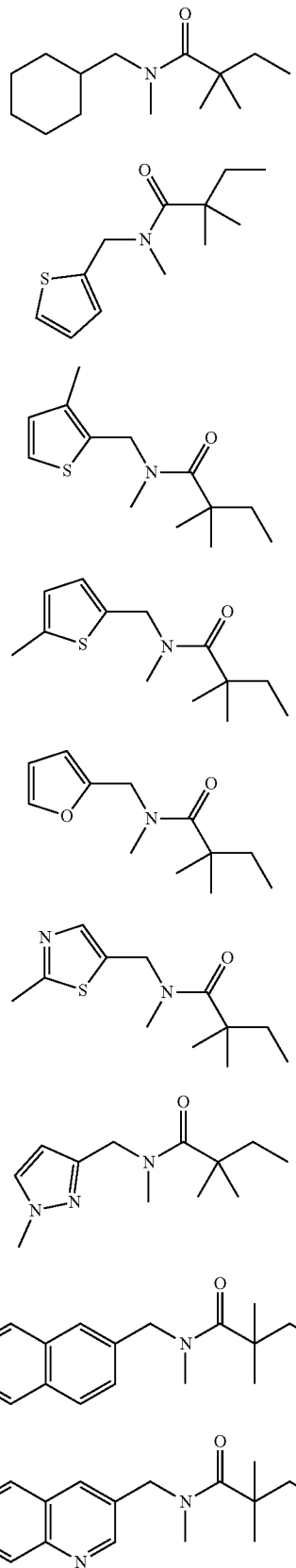
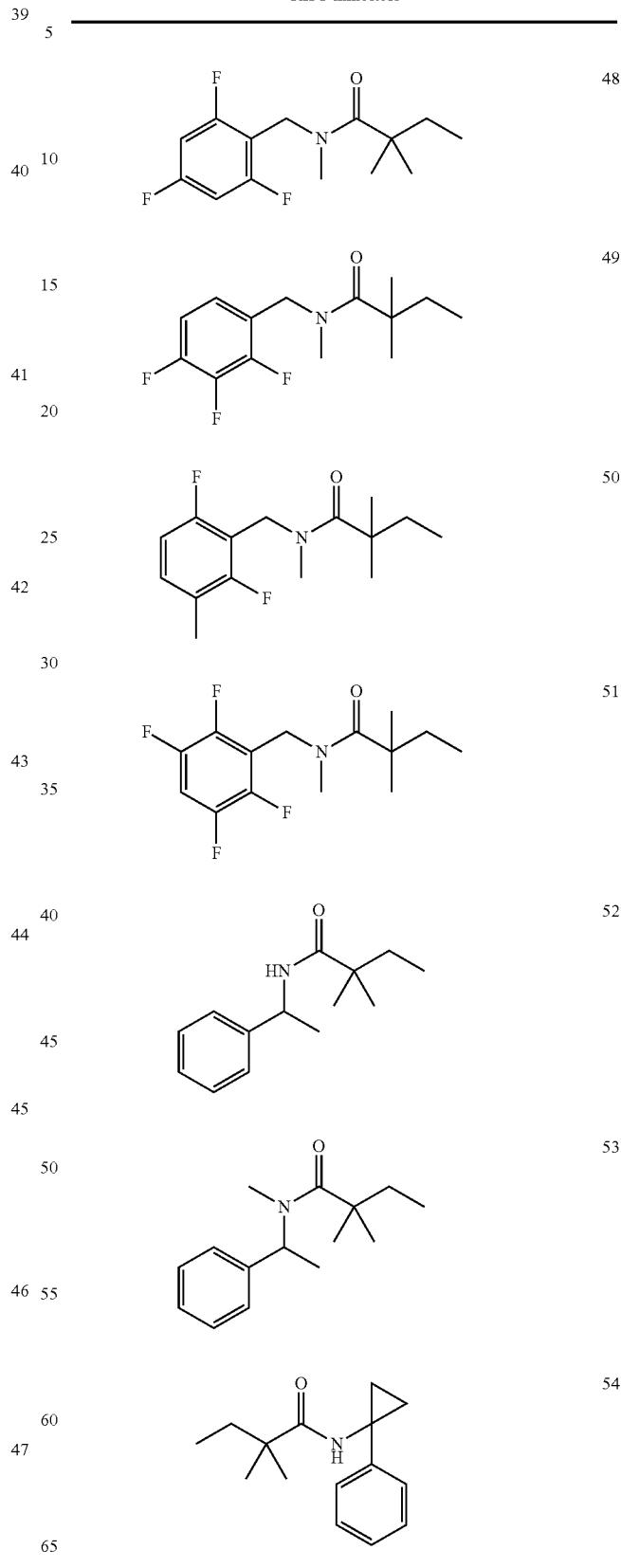

TABLE 2-continued
RIP1 inhibitors
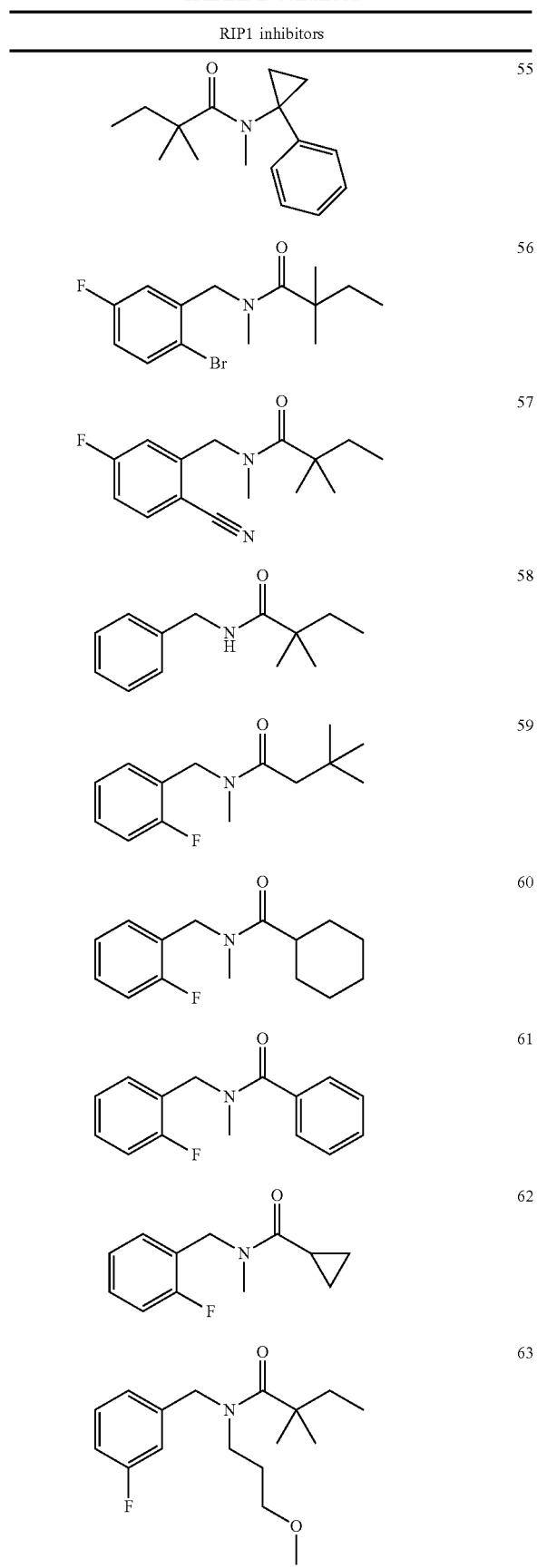
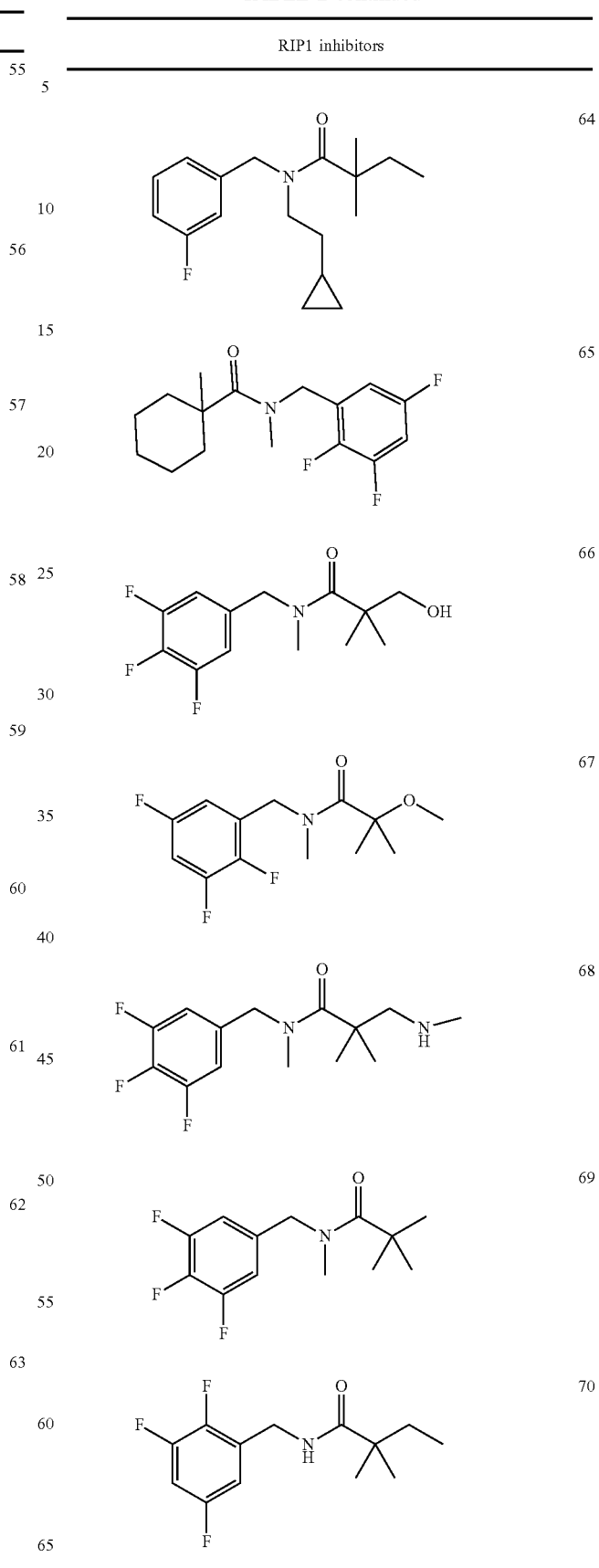

TABLE 2-continued
RIP1 inhibitors
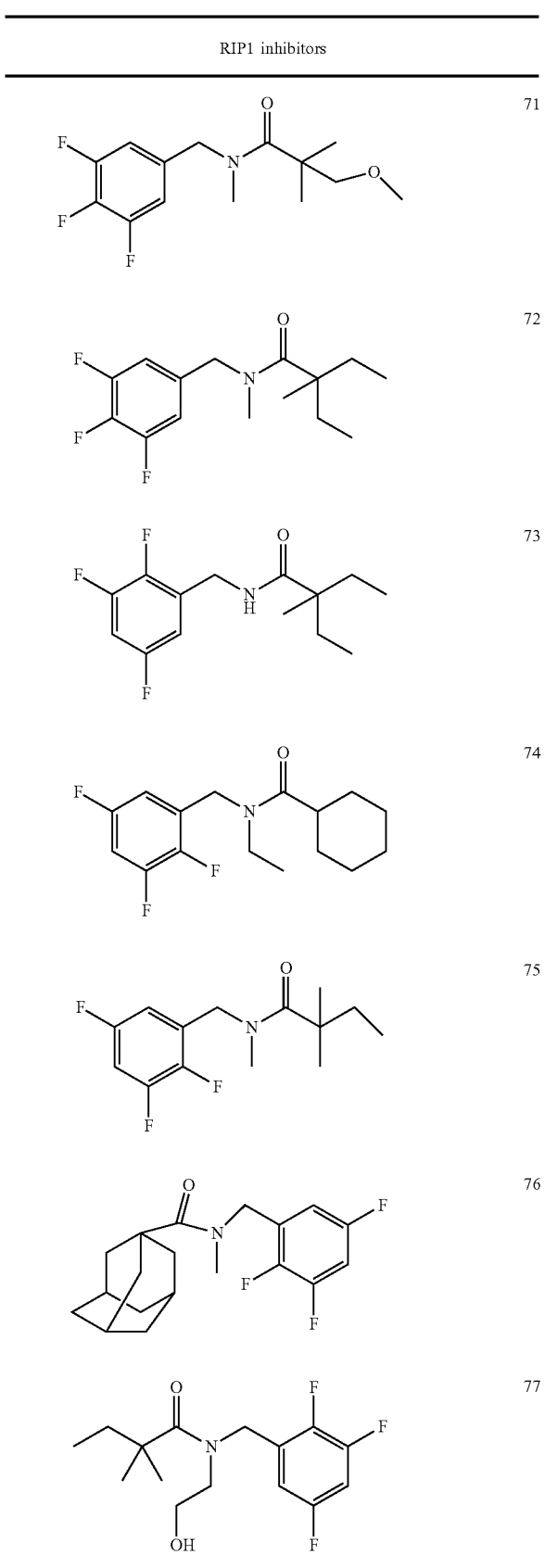
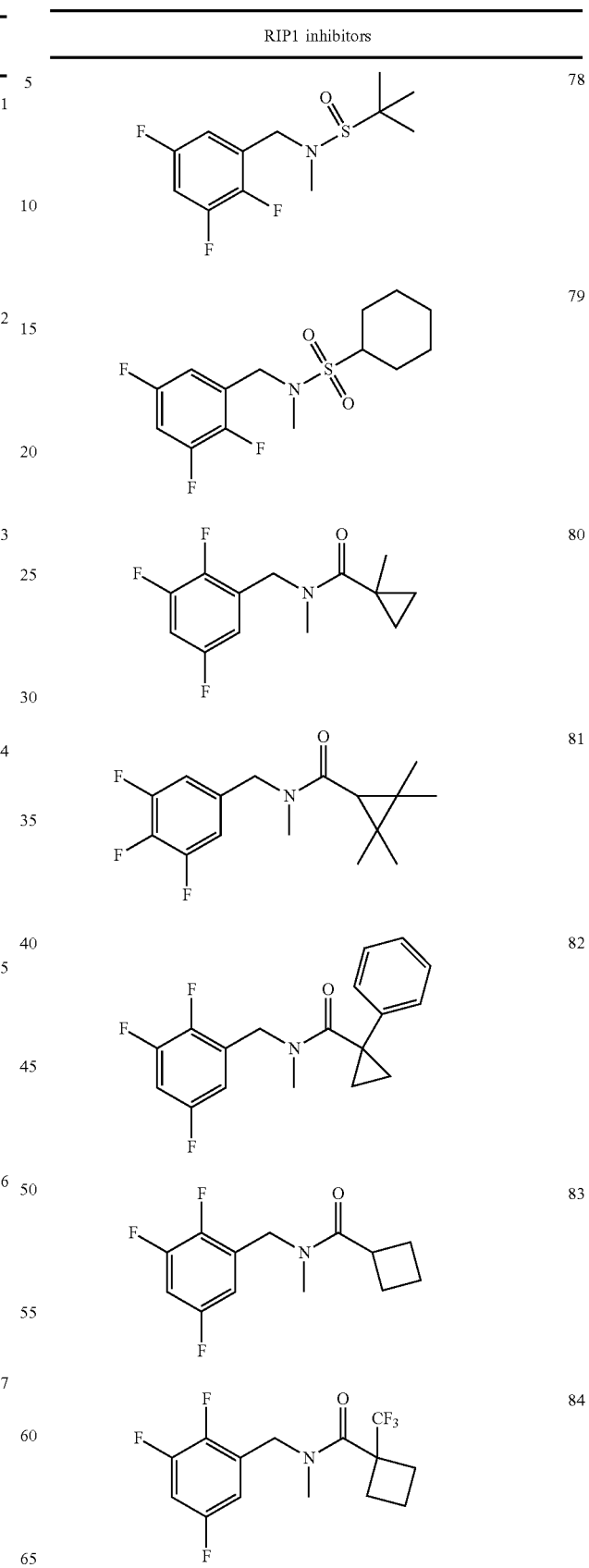

TABLE 2-continued
RIP1 inhibitors
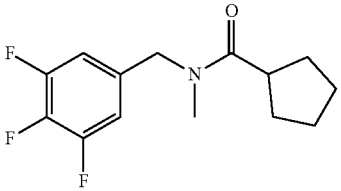 [SMILES: CN(Cc1cc(F)c(F)c(F)c1)C(=O)C1CCCC1] 85
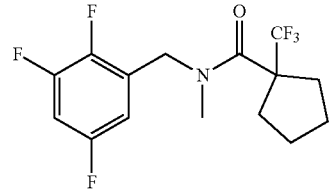 [SMILES: CN(Cc1cc(F)cc(F)c1F)C(=O)C1(C(F)(F)F)CCCC1] 86
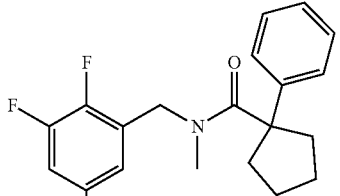 87
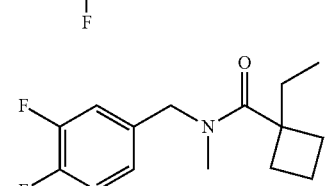 88
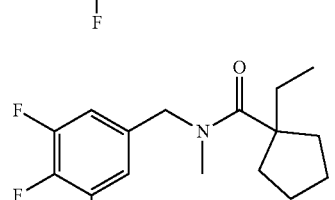 89
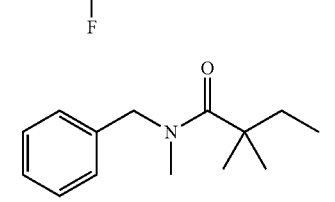 90
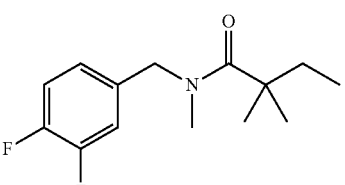 91
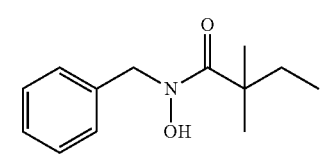 [SMILES: CCC(C)(C)C(=O)N(O)Cc1ccccc1] 92
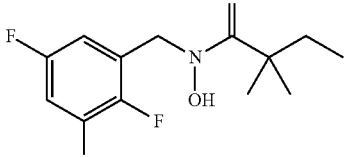 93
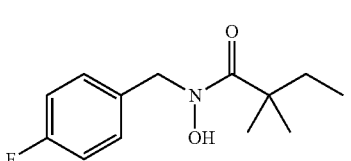 94
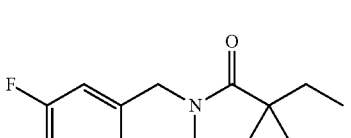 95
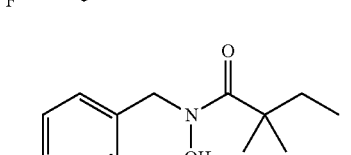 96
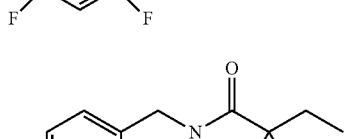 97
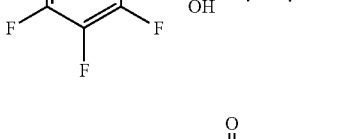 98
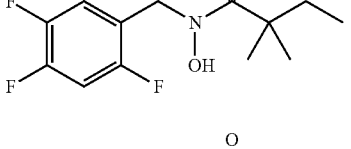 99
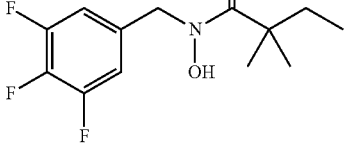 100

TABLE 2-continued
RIP1 inhibitors
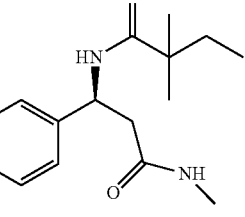 101
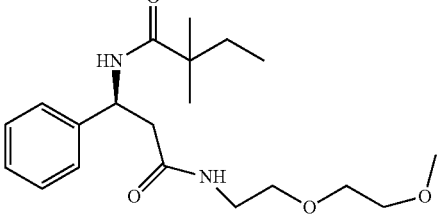 102
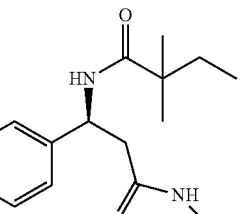 103
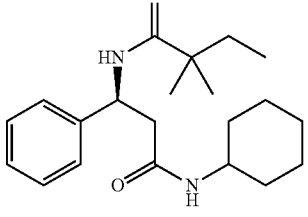 104
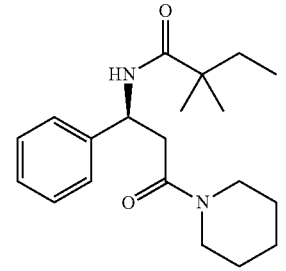 [SMILES: CCC(C)(C)C(=O)N[C@@H](CC(=O)N1CCCCC1)c1ccccc1] 105
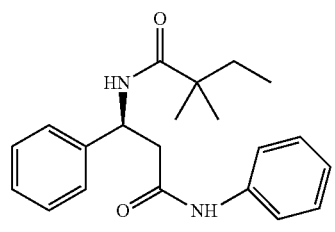 [SMILES: CCC(C)(C)C(=O)N[C@@H](CC(=O)Nc1ccccc1)c1ccccc1] 106
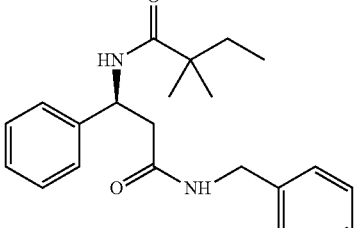 107
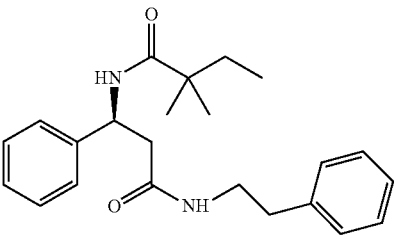 [SMILES: CCC(C)(C)C(=O)N[C@@H](CC(=O)NCCc1ccccc1)c1ccccc1] 108
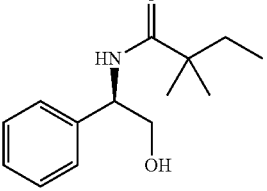 109
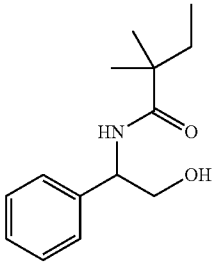 [SMILES: CCC(C)(C)C(=O)NC(CO)c1ccccc1] 110
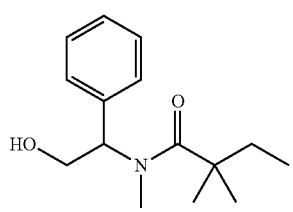 [SMILES: CCC(C)(C)C(=O)N(C)C(CO)c1ccccc1] 111
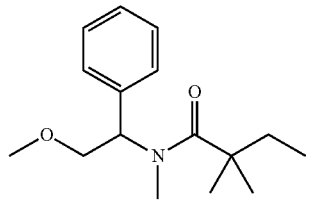 [SMILES: CCC(C)(C)C(=O)N(C)C(COC)c1ccccc1] 112

TABLE 2-continued

RIP1 inhibitors

TABLE 2-continued

RIP1 inhibitors (127) (structure)

(128) (structure)

(129) (structure)

(130) (structure)

(131) (structure)

(132) (structure)

(133) (structure)

(134) (structure)

(135) (structure)

(136) (structure)

(137) (structure)

(138) (structure)

(139) (structure)

(140) (structure)

(141) (structure)

(142) (structure)

TABLE 2-continued
RIP1 inhibitors
| | |
|---|---|
| 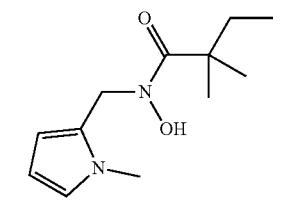 [SMILES: CCC(C)(C)C(=O)N(O)Cc1cccn1C] | 143 |
| 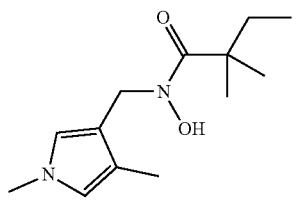 [SMILES: CCC(C)(C)C(=O)N(O)Cc1cn(C)cc1C] | 144 |
| 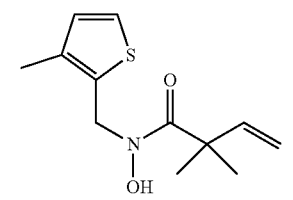 [SMILES: C=CC(C)(C)C(=O)N(O)Cc1sccc1C] | 145 |
| 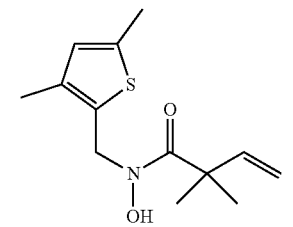 [SMILES: C=CC(C)(C)C(=O)N(O)Cc1sc(C)cc1C] | 146 |
| 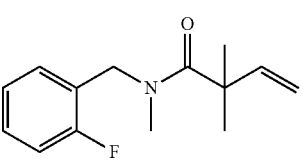 [SMILES: C=CC(C)(C)C(=O)N(C)Cc1ccccc1F] | 147 |
| 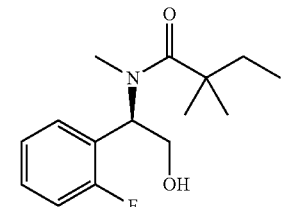 | 148 |
| 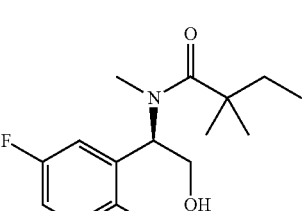 | 149 |
TABLE 2-continued
RIP1 inhibitors
| | |
|---|---|
| 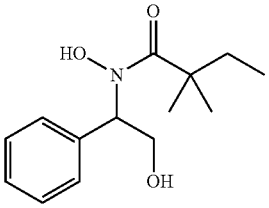 [SMILES: CCC(C)(C)C(=O)N(O)C(CO)c1ccccc1] | 150 |
| 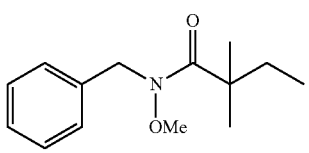 [SMILES: CCC(C)(C)C(=O)N(Cc1ccccc1)OC]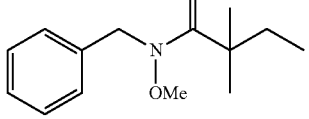 | 151 |
| 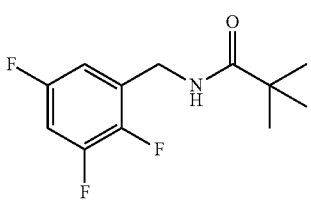 | S1 |
| 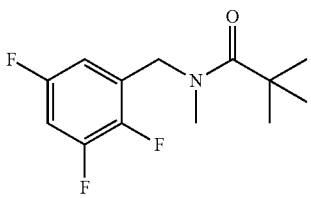 | S2 |
| 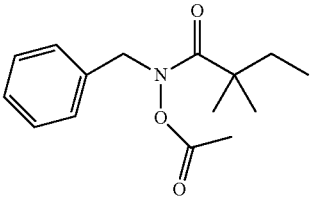 [SMILES: CCC(C)(C)C(=O)N(Cc1ccccc1)OC(C)=O] | S3 |
| 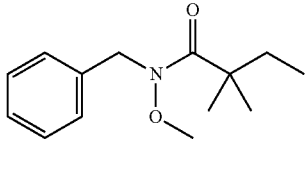 [SMILES: CCC(C)(C)C(=O)N(Cc1ccccc1)OC] | S4 |
| 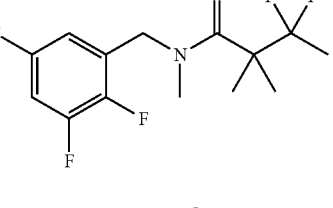 | S5 |
| 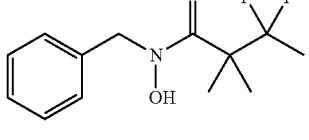 | S6 |

TABLE 2-continued
RIP1 inhibitors
or a RIP1 inhibitor disclosed in WO2016/1011887, including:
TABLE 3
RIP1 inhibitors
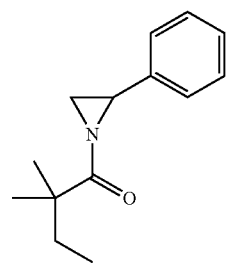 [SMILES: CCC(C)(C)C(=O)N1CC1c1ccccc1]

TABLE 3-continued

RIP1 inhibitors

TABLE 3-continued
RIP1 inhibitors
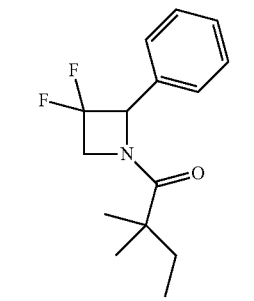 [SMILES: CCC(C)(C)C(=O)N1CC(F)(F)C1c1ccccc1]
14
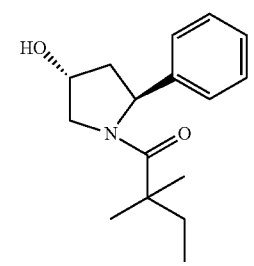 [SMILES: CCC(C)(C)C(=O)N1C[C@H](O)C[C@H]1c1ccccc1]
15
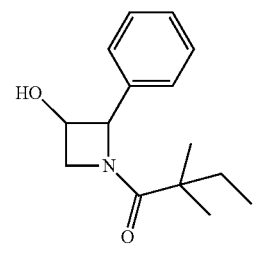 [SMILES: CCC(C)(C)C(=O)N1CC(O)C1c1ccccc1]
16
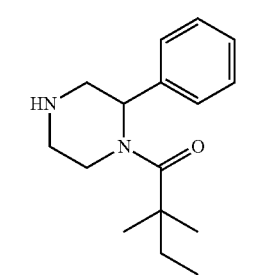 [SMILES: CCC(C)(C)C(=O)N1CCNCC1c1ccccc1]
17
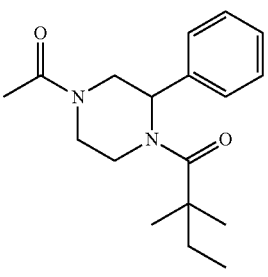 [SMILES: CCC(C)(C)C(=O)N1CCN(C(C)=O)CC1c1ccccc1]
18
TABLE 3-continued
RIP1 inhibitors
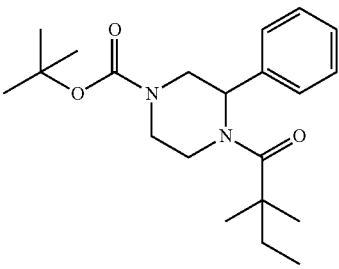 [SMILES: CCC(C)(C)C(=O)N1CCN(C(=O)OC(C)(C)C)CC1c1ccccc1]
19
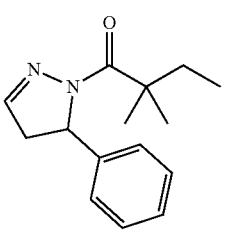 [SMILES: CCC(C)(C)C(=O)N1N=CCC1c1ccccc1]
20
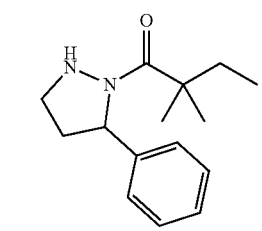 [SMILES: CCC(C)(C)C(=O)N1NCCC1c1ccccc1]
21
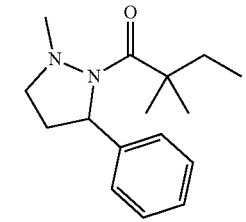 [SMILES: CCC(C)(C)C(=O)N1C(c2ccccc2)CCN1C]
22
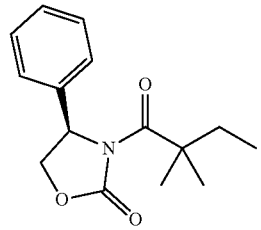 [SMILES: CCC(C)(C)C(=O)N1C(=O)OC[C@H]1c1ccccc1]
23
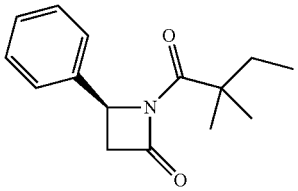 [SMILES: CCC(C)(C)C(=O)N1C(=O)C[C@H]1c1ccccc1]
24

TABLE 3-continued
RIP1 inhibitors
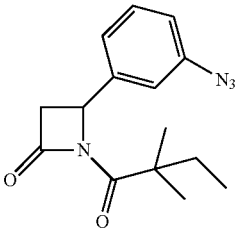 [SMILES: CCC(C)(C)C(=O)N1C(=O)CC1c1cccc(N=[N+]=[N-])c1] 25
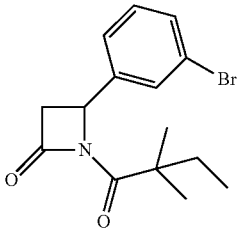 26
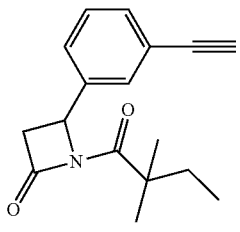 [SMILES: C#Cc1cccc(C2CC(=O)N2C(=O)C(C)(C)CC)c1] 27
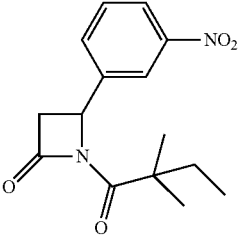 [SMILES: CCC(C)(C)C(=O)N1C(=O)CC1c1cccc([N+](=O)[O-])c1] 28
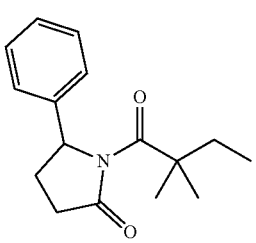 [SMILES: CCC(C)(C)C(=O)N1C(=O)CCC1c1ccccc1] 29
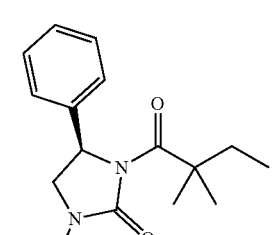 30
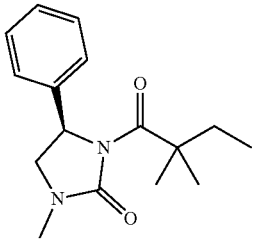 [SMILES: CCC(C)(C)C(=O)N1C(=O)N(C)C[C@H]1c1ccccc1] 31
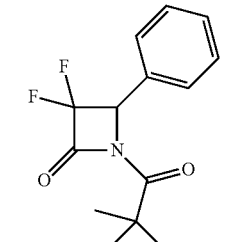 32
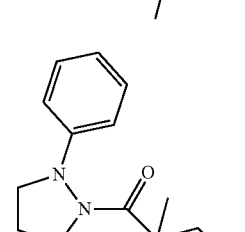 33
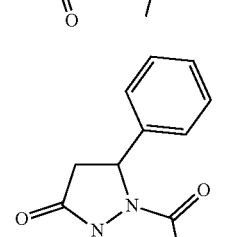 34
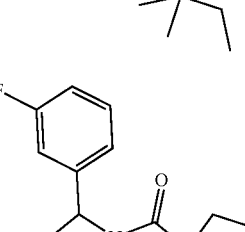 35
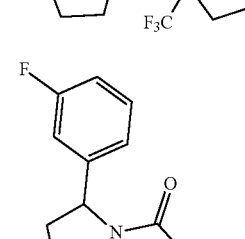 36

TABLE 3-continued
RIP1 inhibitors
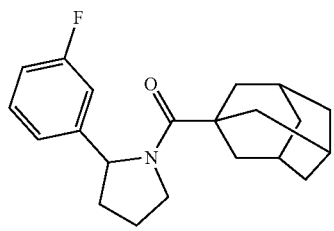 [SMILES: O=C(N1CCCC1c1cccc(F)c1)C12CC3CC(CC(C3)C1)C2] 37
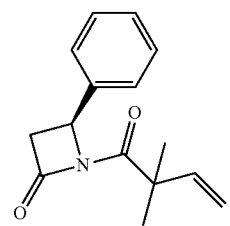 [SMILES: C=CC(C)(C)C(=O)N1C(=O)C[C@H]1c1ccccc1] 38
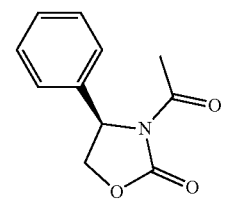 39
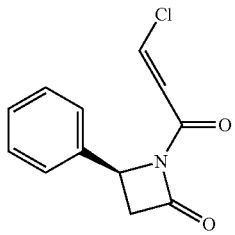 [SMILES: O=C(C=CCl)N1C(=O)C[C@H]1c1ccccc1] 40
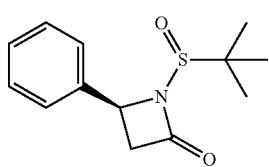 [SMILES: CC(C)(C)S(=O)N1C(=O)C[C@H]1c1ccccc1] 41
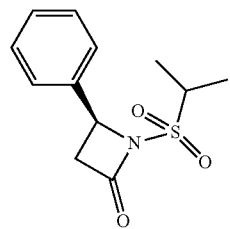 [SMILES: CC(C)S(=O)(=O)N1C(=O)C[C@H]1c1ccccc1] 42
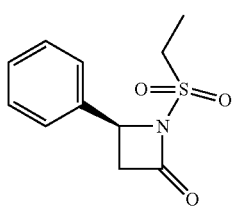 [SMILES: CCS(=O)(=O)N1C(=O)C[C@H]1c1ccccc1] 43
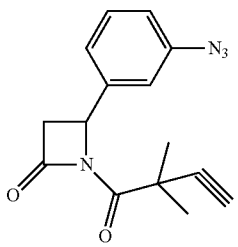 [SMILES: C#CC(C)(C)C(=O)N1C(=O)CC1c1cccc(N=[N+]=[N-])c1] 44
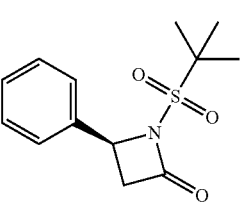 [SMILES: CC(C)(C)S(=O)(=O)N1C(=O)C[C@H]1c1ccccc1] 45
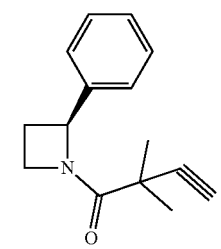 [SMILES: C#CC(C)(C)C(=O)N1CC[C@H]1c1ccccc1] 46
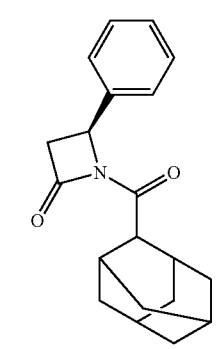 [SMILES: O=C1C[C@@H](c2ccccc2)N1C(=O)C1C2CC3CC(C2)CC1C3] 47
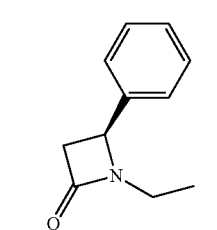 48
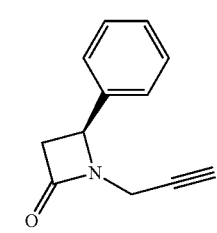 49

TABLE 3-continued
RIP1 inhibitors
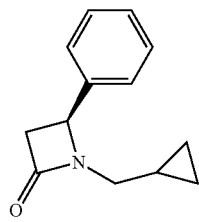 [SMILES: O=C1C[C@@H](c2ccccc2)N1CC1CC1] 50
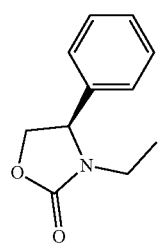 51
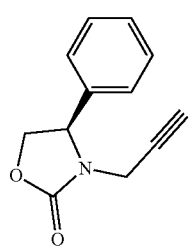 52
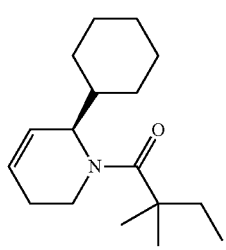 [SMILES: CCC(C)(C)C(=O)N1CCC=C[C@H]1C1CCCCC1] 53
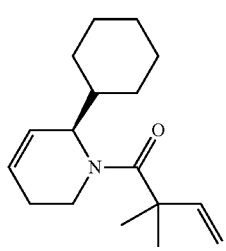 [SMILES: C=CC(C)(C)C(=O)N1CCC=C[C@H]1C1CCCCC1] 54
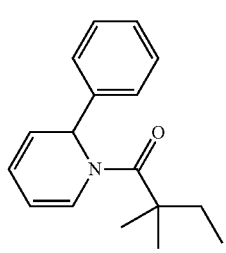 [SMILES: CCC(C)(C)C(=O)N1C=CC=CC1c1ccccc1] 55
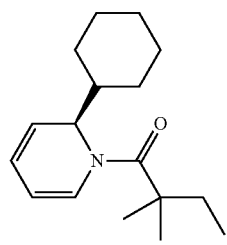 [SMILES: CCC(C)(C)C(=O)N1C=CC=C[C@H]1C1CCCCC1] 56
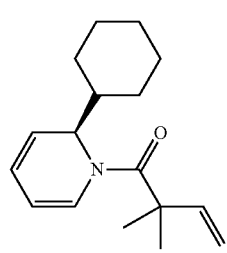 [SMILES: C=CC(C)(C)C(=O)N1C=CC=C[C@H]1C1CCCCC1] 57
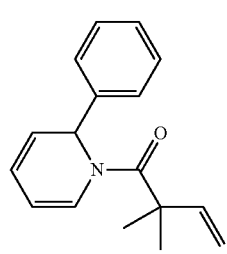 [SMILES: C=CC(C)(C)C(=O)N1C=CC=CC1c1ccccc1] 58
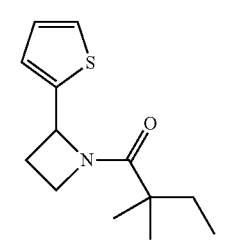 59
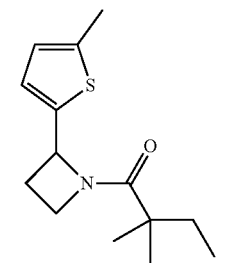 [SMILES: CCC(C)(C)C(=O)N1CCC1c1ccc(C)s1] 60
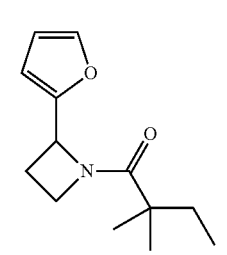 61

TABLE 3-continued

RIP1 inhibitors

TABLE 3-continued
RIP1 inhibitors
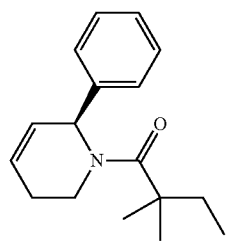 [SMILES: CCC(C)(C)C(=O)N1CCC=C[C@H]1c1ccccc1]
74
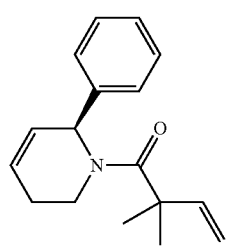 [SMILES: C=CC(C)(C)C(=O)N1CCC=C[C@H]1c1ccccc1]
75
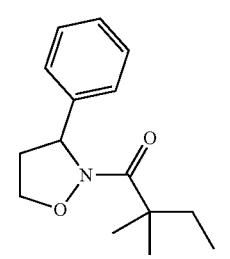 [SMILES: CCC(C)(C)C(=O)N1OCCC1c1ccccc1]
76
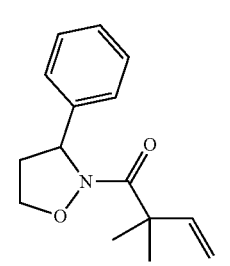 [SMILES: C=CC(C)(C)C(=O)N1OCCC1c1ccccc1]
77
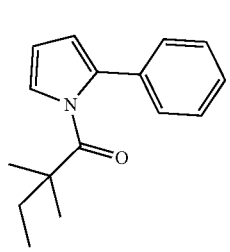 [SMILES: CCC(C)(C)C(=O)n1cccc1-c1ccccc1]
78
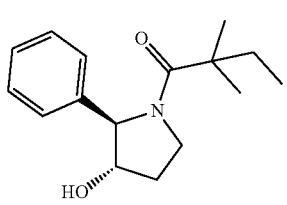 [SMILES: CCC(C)(C)C(=O)N1CC[C@H](O)[C@H]1c1ccccc1]
S1
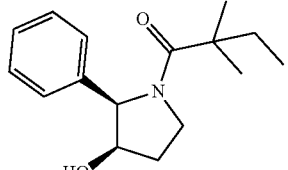
S2
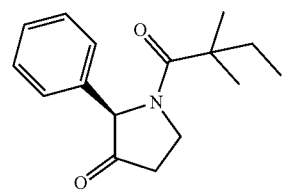 [SMILES: CCC(C)(C)C(=O)N1CCC(=O)[C@H]1c1ccccc1]
S3
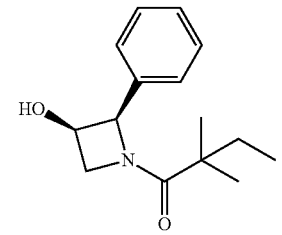 [SMILES: CCC(C)(C)C(=O)N1C[C@@H](O)[C@H]1c1ccccc1]
S4
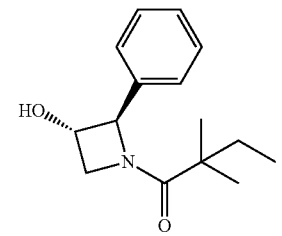 [SMILES: CCC(C)(C)C(=O)N1C[C@H](O)[C@H]1c1ccccc1]
S5
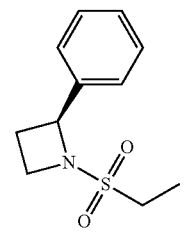
S6
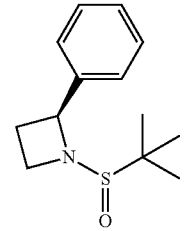 [SMILES: CC(C)(C)S(=O)N1CC[C@H]1c1ccccc1]
S7
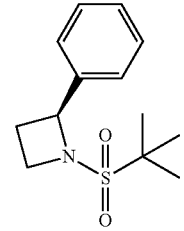 [SMILES: CC(C)(C)S(=O)(=O)N1CC[C@H]1c1ccccc1]
S8

TABLE 3-continued

RIP1 inhibitors

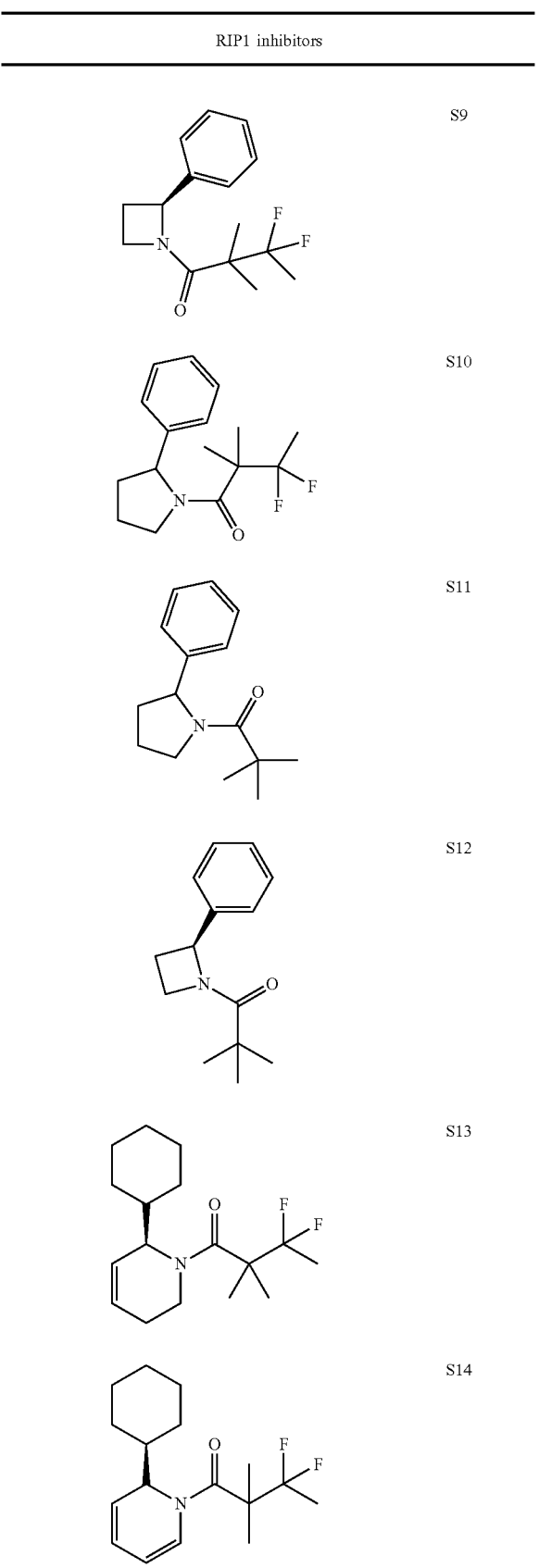

S9

S10

S11

S12

S13

S14

TABLE 3-continued

RIP1 inhibitors

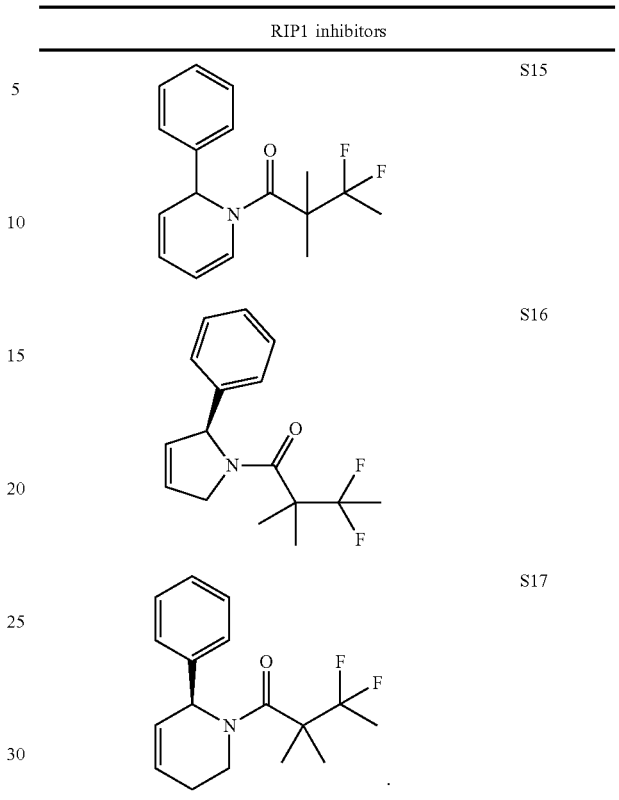

S15

S16

S17

Table 4. RIP3 Inhibitors tert-butyl 2-(4-(5-(methylcarbamoyl)-1H-benzo[d]imidazol-1-yl)phenyl)acetate (GSK'840)

3-(benzo[d]thiazol-5-yl)-7-(1,3-dimethyl-1H-pyrazol-5-yl)thieno[3,2-c]pyridin-4-amine (GSK'843)

N-(6-(isopropylsulfonyl)quinolin-4-yl)benzo[d]thiazol-5-amine (GSK'872)

N-[3-[5-(2-amino-4-pyrimidinyl)-2-(1,1-dimethylethyl)-4-thiazolyl]-2-fluorophenyl]-2,6-difluoro-benzenesulfonamide (Dabrafenib)

3-(2-Imidazo[1,2-b]pyridazin-3-ylethynyl)-4-methyl-N-[4-[(4-methyl-1-piperazinyl)methyl]-3-(trifluoromethyl)phenyl]-benzamide (ponatinib)

5-[[4-[(2,3-dimethyl-2H-indazol-6-yl)methylamino]-2-pyrimidinyl]amino]-2-methyl-benzenesulfonamide (pazopanib)

Table 5. MLKL Inhibitors (2E)-N-[4-[[(3-Methoxy-2-pyrazinyl)amino]sulfonyl]phenyl]-3-(5-nitro-2-thienyl)-2-propenamide (Necrosulfonamide)

1,3,7-trimethyl-8-(methylsulfonyl)-1H-purine-2,6(3H,7H)-dione (TC13-4)

(2,5-dimethoxybenzylsulfonyl)-1,3,7-trimethyl-1H-purine-2,6(3H,7H)-dione (TC13-58)

7-ethyl-1,3-dimethyl-8-(methylsulfonyl)-1H-purine-2,6(3H,7H)-dione (TC13-74)

1,7-dimethyl-8-(methylsulfonyl)-3-(prop-2-ynyl)-1H-purine-2,6(3H,7H)-dione (TC13-106)

2-(1,7-dimethyl-8-(methylsulfonyl)-2,6-dioxo-1H-purin-3(2H,6H,7H)-yl)acetonitrile (TC13-107)

3-(3-(3-chlorophenyl)prop-2-yn-1-yl)-8-((cyclopropylmethyl)sulfonyl)-1,7-dimethyl-3,7-dihydro-1H-purine-2,6-dione (TC13-119)

8-((2,5-dimethoxybenzyl)sulfonyl)-1,7-dimethyl-3-(3-(2-(methylamino)pyridin-4-yl)prop-2-yn-1-yl)-3,7-dihydro-1H-purine-2,6-dione (TC13-127)

3-(3-(3-hydroxyphenyl)prop-2-yn-1-yl)-1,7-dimethyl-8-(methylsulfonyl)-3,7-dihydro-1H-purine-2,6-dione (TC13-172)

3-((4-(methyl(4-(3-(4-(trifluoromethoxy)phenyl)ureido)phenyl)amino)pyrimidin-2-yl) amino)benzenesulfonamide (Compound 1)

Additional active MLKL inhibitors are disclosed in PCT/CN2018/077464 (WO2018/157800), including compounds of Tables 4 and 5.

TABLE 6

MLKL inhibitors

| | |
|---|---|
| 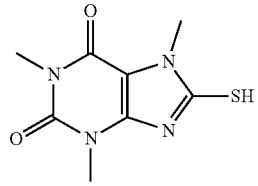 | 1 |
| 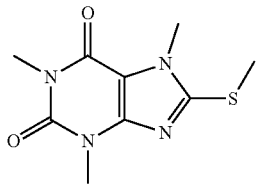 | 2 |
| 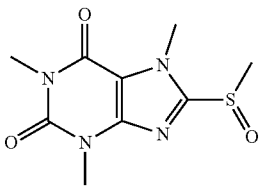 | 3 |
| 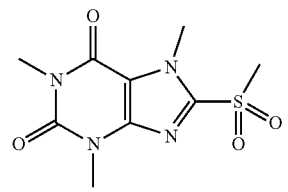 | 4 |
| 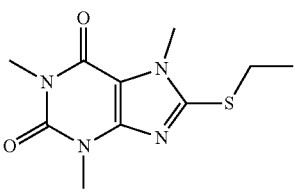 [SMILES: CCSc1nc2c(c(=O)n(C)c(=O)n2C)n1C] | 5 |
| 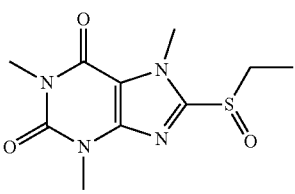 [SMILES: CCS(=O)c1nc2c(c(=O)n(C)c(=O)n2C)n1C] | 6 |

TABLE 6-continued

MLKL inhibitors

| | |
|---|---|
| 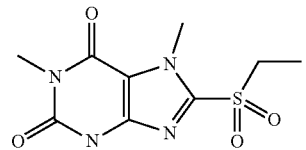 | 7 |
| 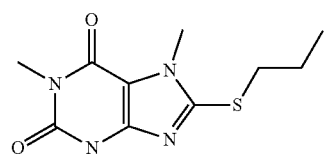 | 8 |
| 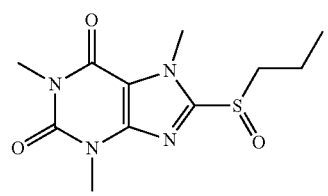 [SMILES: CCCS(=O)c1nc2c(c(=O)n(C)c(=O)n2C)n1C] | 9 |
| 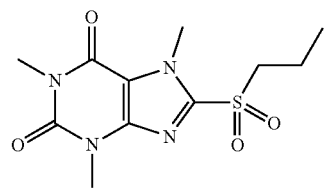 [SMILES: CCCS(=O)(=O)c1nc2c(c(=O)n(C)c(=O)n2C)n1C] | 10 |
| 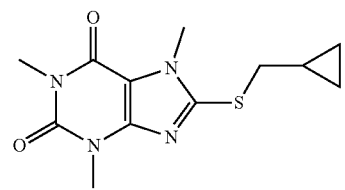 [SMILES: Cn1c(=O)c2c(nc(SCC3CC3)n2C)n(C)c1=O] | 11 |
| 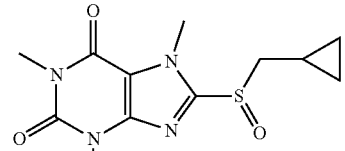 | 12 |
| 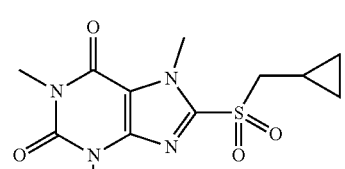 | 13 |
| 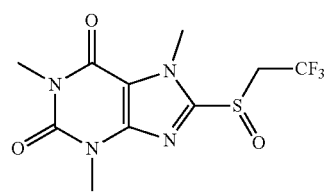 [SMILES: Cn1c(=O)c2c(nc(S(=O)CC(F)(F)F)n2C)n(C)c1=O] | 14 |

TABLE 6-continued

MLKL inhibitors

TABLE 6-continued

MLKL inhibitors

TABLE 6-continued
MLKL inhibitors
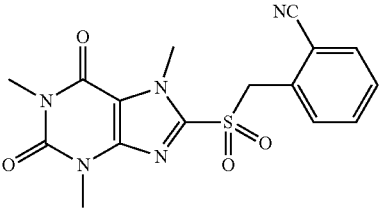 42
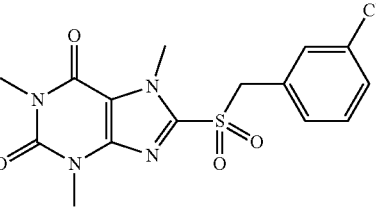 43
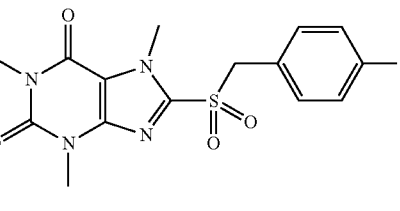 44
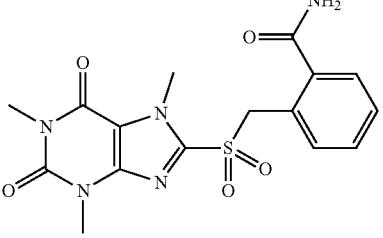 45
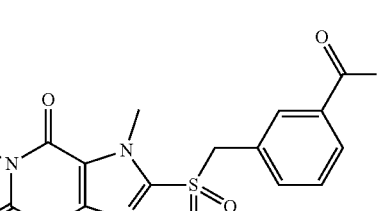 46
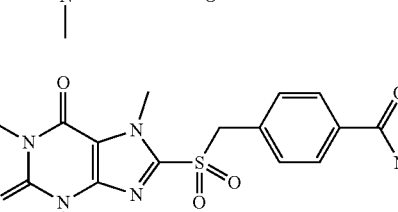 47
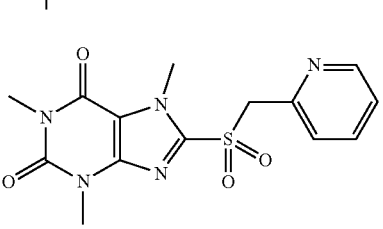 [SMILES: Cn1c(=O)c2c(nc(S(=O)(=O)Cc3cccc[n+]3[O-])n2C)n(C)c1=O] 48
TABLE 6-continued
MLKL inhibitors
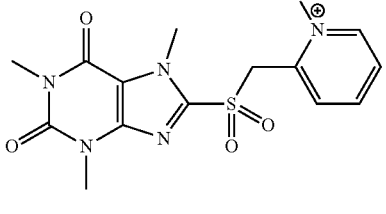 49
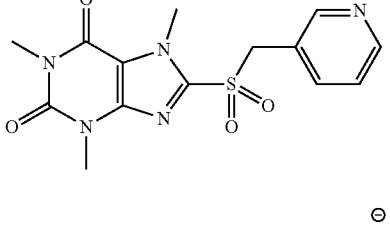 50
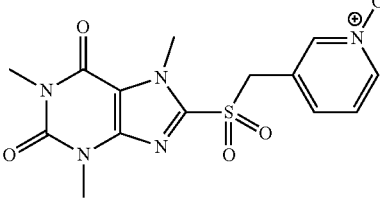 51
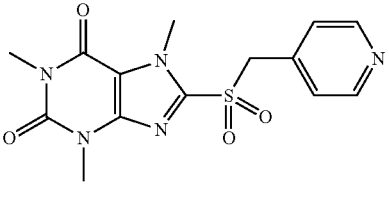 [SMILES: Cn1c(=O)c2c(nc(S(=O)(=O)Cc3ccncc3)n2C)n(C)c1=O] 52
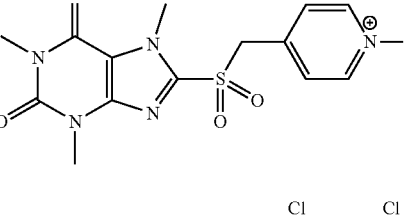 53
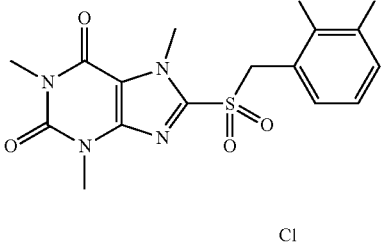 54
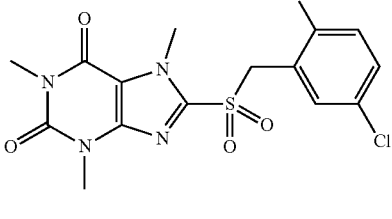 55

TABLE 6-continued

MLKL inhibitors

TABLE 6-continued
MLKL inhibitors
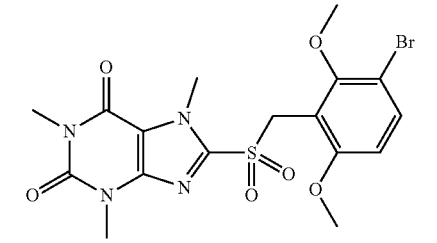 [SMILES: COc1ccc(Br)c(OC)c1CS(=O)(=O)c1nc2c(c(=O)n(C)c(=O)n2C)n1C] 69
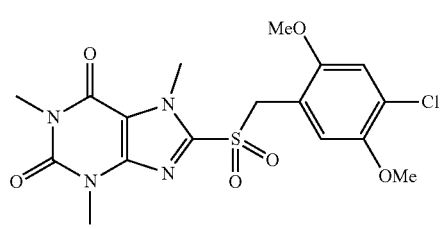 [SMILES: COc1cc(CS(=O)(=O)c2nc3c(c(=O)n(C)c(=O)n3C)n2C)c(OC)cc1Cl] 70
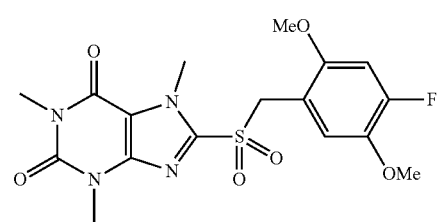 [SMILES: COc1cc(CS(=O)(=O)c2nc3c(c(=O)n(C)c(=O)n3C)n2C)c(OC)cc1F] 71
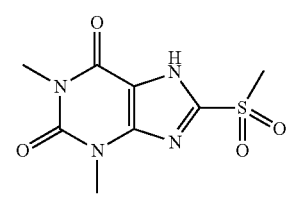 [SMILES: Cn1c(=O)c2[nH]c(S(C)(=O)=O)nc2n(C)c1=O] 72
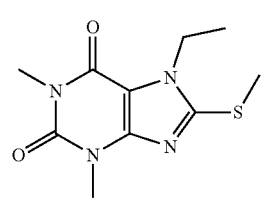 73
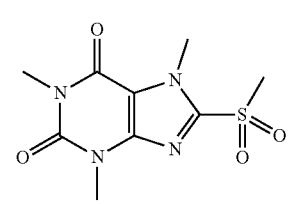 74
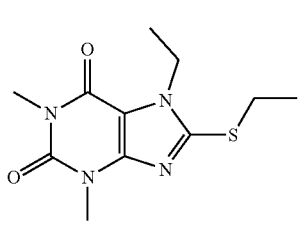 [SMILES: CCSc1nc2c(c(=O)n(C)c(=O)n2C)n1CC] 75
TABLE 6-continued
MLKL inhibitors
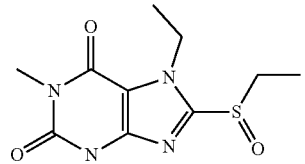 76
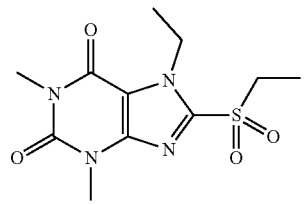 [SMILES: CCn1c(S(=O)(=O)CC)nc2c1c(=O)n(C)c(=O)n2C] 77
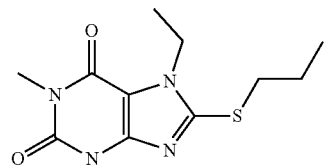 78
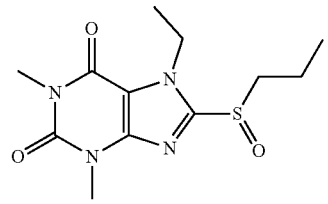 [SMILES: CCCS(=O)c1nc2c(c(=O)n(C)c(=O)n2C)n1CC] 79
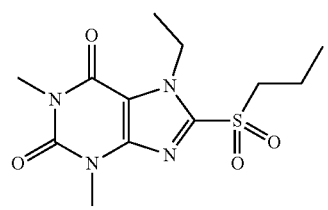 [SMILES: CCCS(=O)(=O)c1nc2c(c(=O)n(C)c(=O)n2C)n1CC] 80
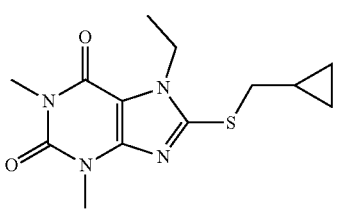 [SMILES: CCn1c(SCC2CC2)nc2c1c(=O)n(C)c(=O)n2C] 81
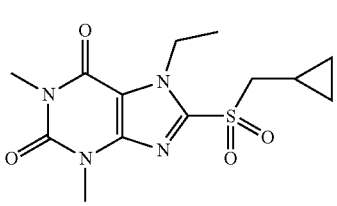 [SMILES: CCn1c(S(=O)(=O)CC2CC2)nc2c1c(=O)n(C)c(=O)n2C] 82

TABLE 6-continued
MLKL inhibitors
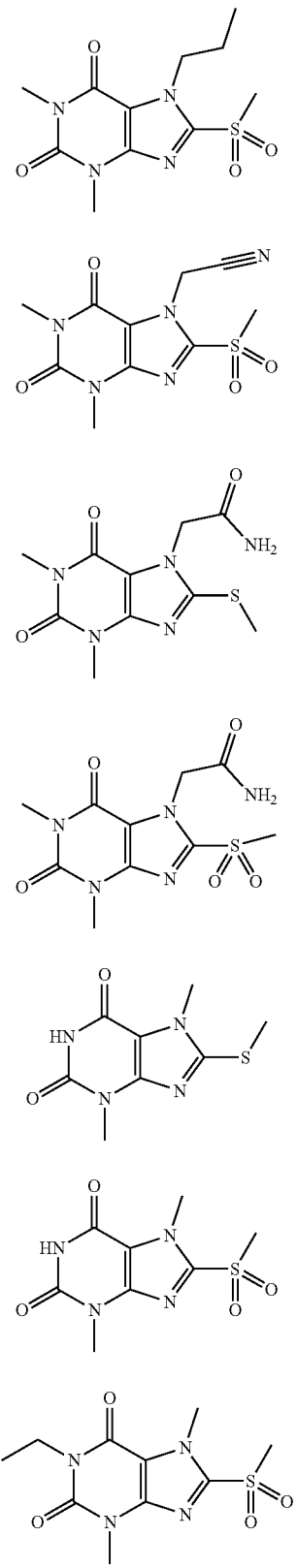
83
84
85
86
87
88
89
TABLE 6-continued
MLKL inhibitors
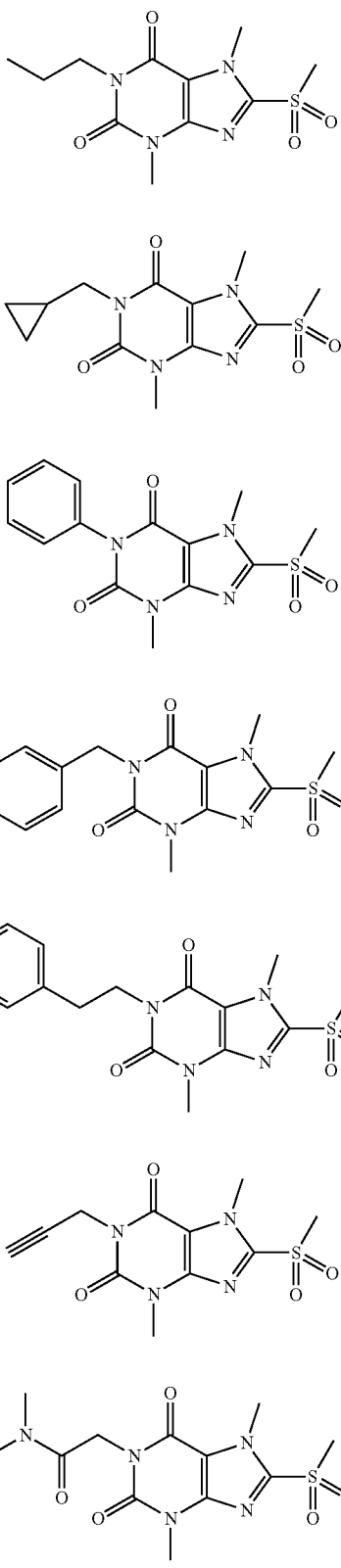
90
91
92
93
94
95
96

TABLE 6-continued

MLKL inhibitors

TABLE 6-continued
MLKL inhibitors
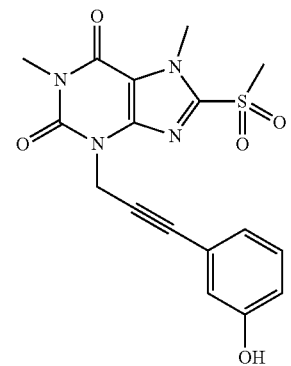 [SMILES: Cn1c(=O)c2c(nc(S(C)(=O)=O)n2C)n(CC#Cc2cccc(O)c2)c1=O]
109
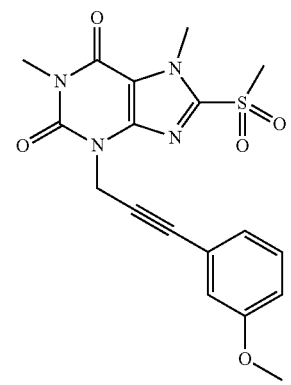
110
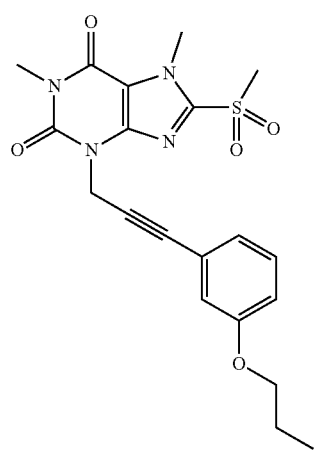 [SMILES: CCCOc1cccc(C#CCn2c(=O)n(C)c(=O)c3c2nc(S(C)(=O)=O)n3C)c1]
111
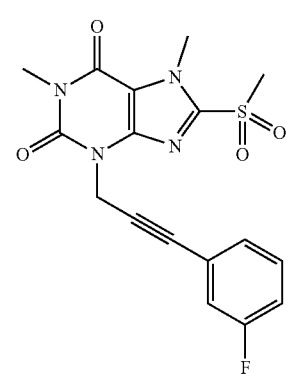 [SMILES: Cn1c(=O)c2c(nc(S(C)(=O)=O)n2C)n(CC#Cc2cccc(F)c2)c1=O]
112
TABLE 6-continued
MLKL inhibitors
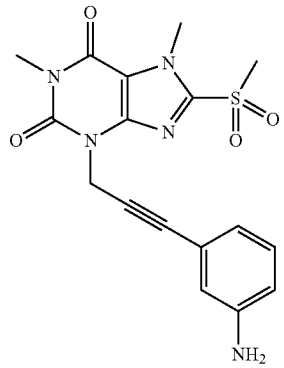 [SMILES: Cn1c(=O)c2c(nc(S(C)(=O)=O)n2C)n(CC#Cc2cccc(N)c2)c1=O]
113
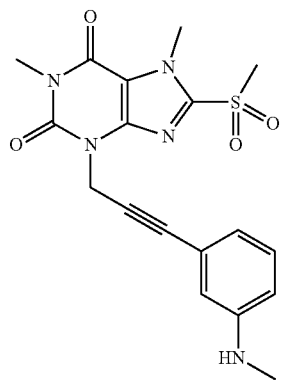
114
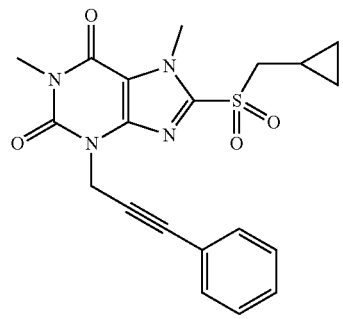 [SMILES: Cn1c(=O)c2c(nc(S(=O)(=O)CC3CC3)n2C)n(CC#Cc2ccccc2)c1=O]
115
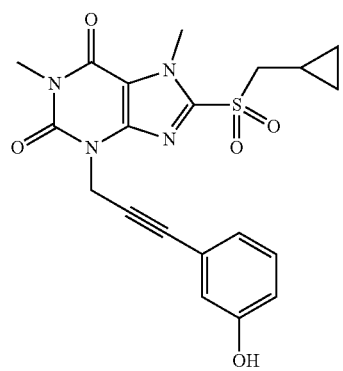
116

TABLE 6-continued
MLKL inhibitors
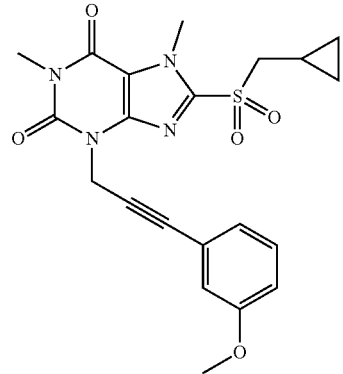 [SMILES: COc1cccc(C#CCn2c(=O)n(C)c(=O)c3c2nc(S(=O)(=O)CC2CC2)n3C)c1]
117
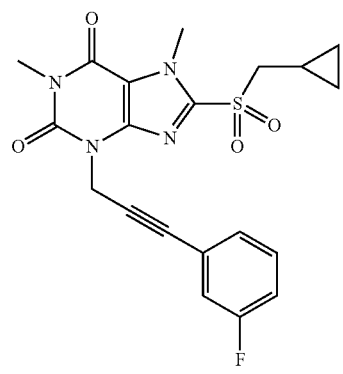
118
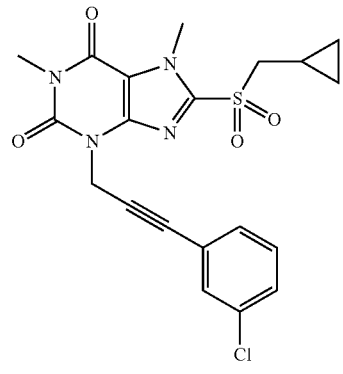
119
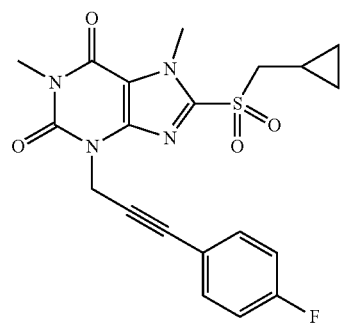 [SMILES: Cn1c(=O)c2c(nc(S(=O)(=O)CC3CC3)n2C)n(CC#Cc2ccc(F)cc2)c1=O]
120
TABLE 6-continued
MLKL inhibitors
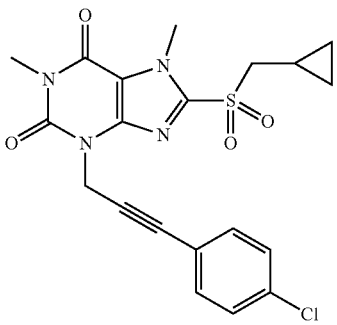 [SMILES: Cn1c(=O)c2c(nc(S(=O)(=O)CC3CC3)n2C)n(CC#Cc2ccc(Cl)cc2)c1=O]
121
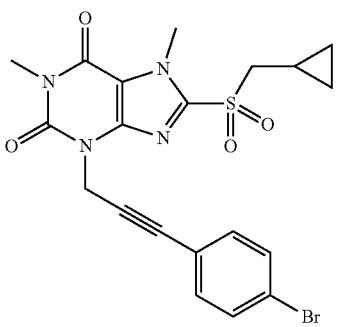 [SMILES: Cn1c(=O)c2c(nc(S(=O)(=O)CC3CC3)n2C)n(CC#Cc2ccc(Br)cc2)c1=O]
122
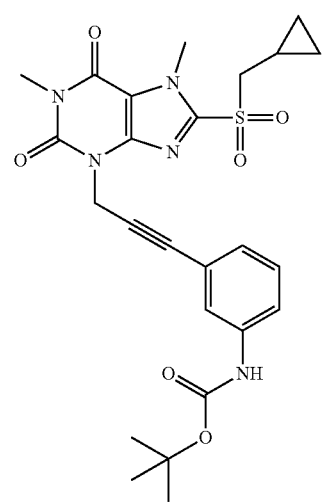 [SMILES: Cn1c(=O)c2c(nc(S(=O)(=O)CC3CC3)n2C)n(CC#Cc2cccc(NC(=O)OC(C)(C)C)c2)c1=O]
123
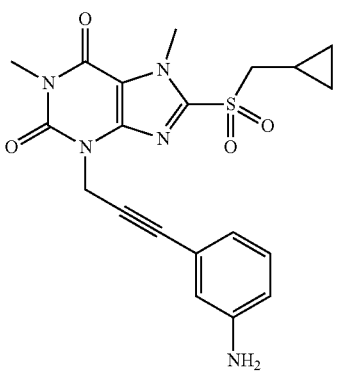
124

TABLE 6-continued
MLKL inhibitors
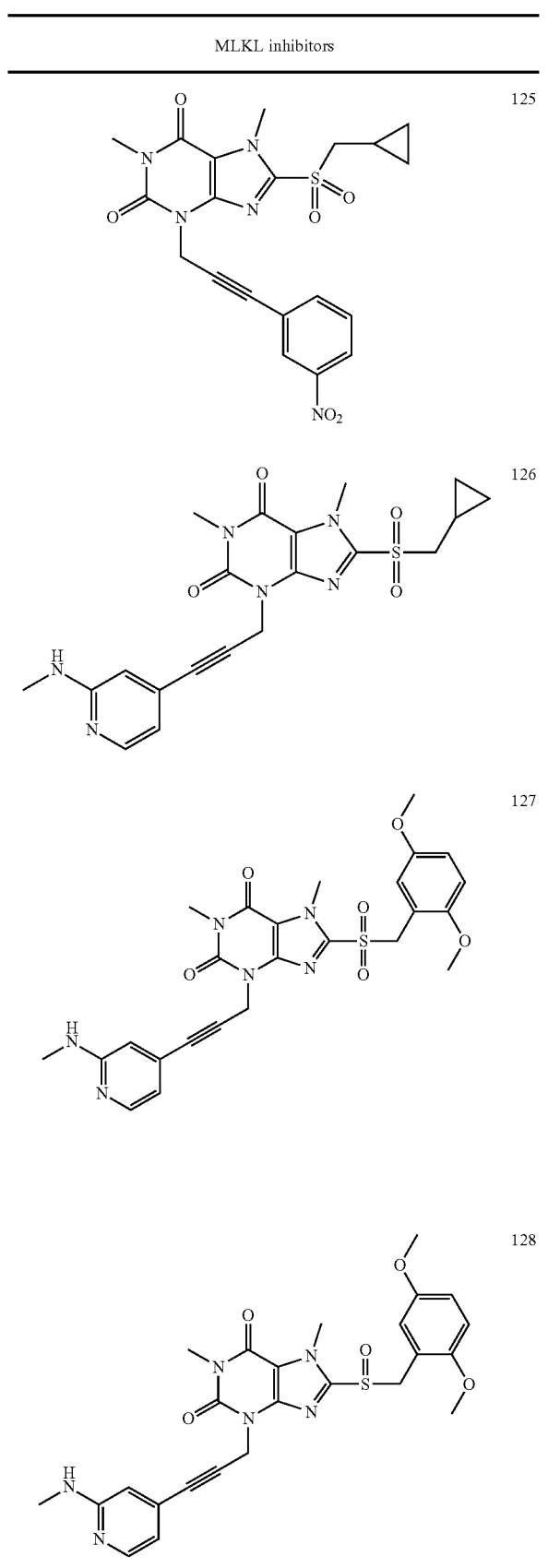
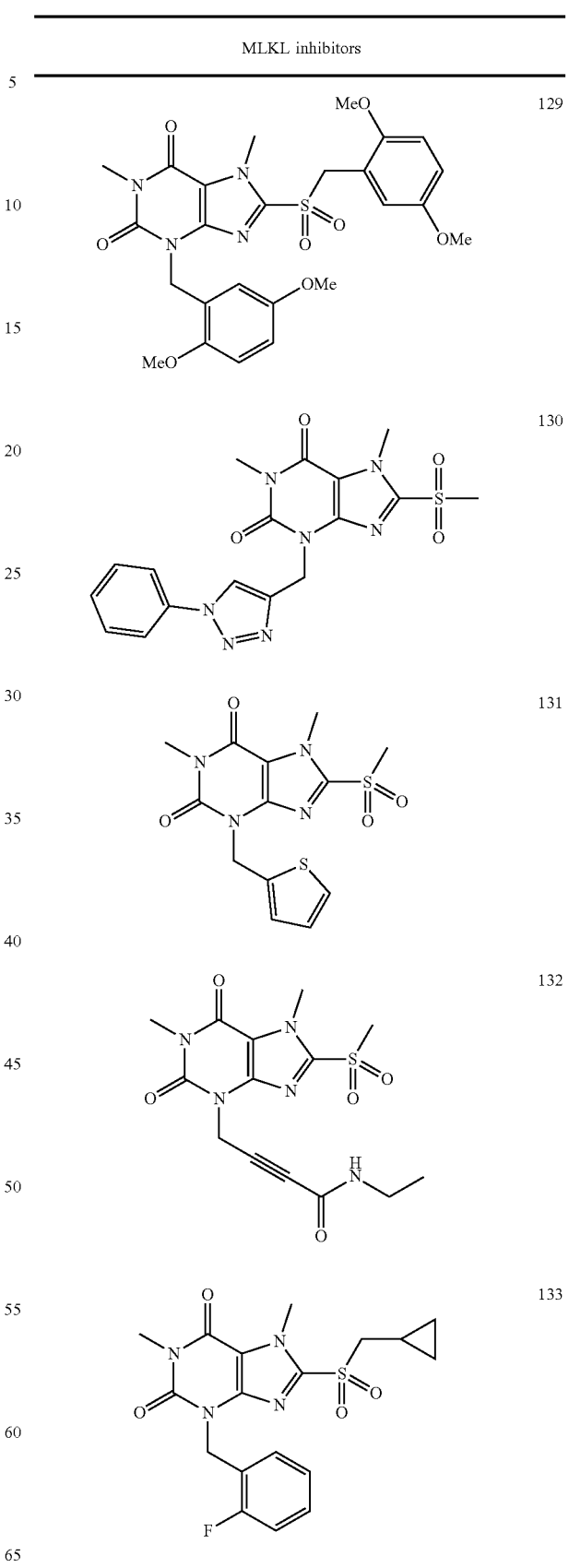

TABLE 6-continued
MLKL inhibitors
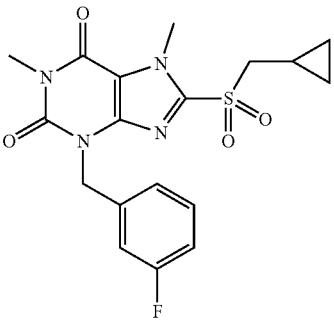 [SMILES: Cn1c(=O)c2c(nc(S(=O)(=O)CC3CC3)n2C)n(Cc2cccc(F)c2)c1=O] 134
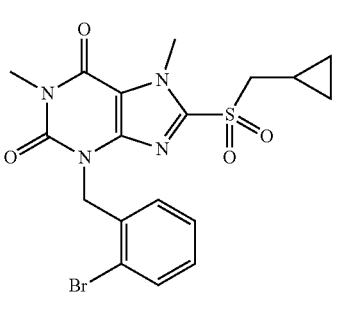 [SMILES: Cn1c(=O)c2c(nc(S(=O)(=O)CC3CC3)n2C)n(Cc2ccccc2Cl)c1=O] 135
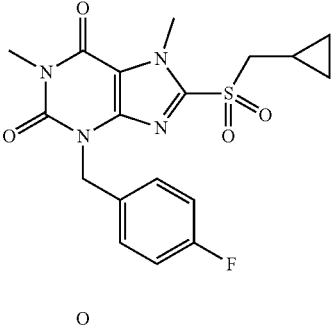 136
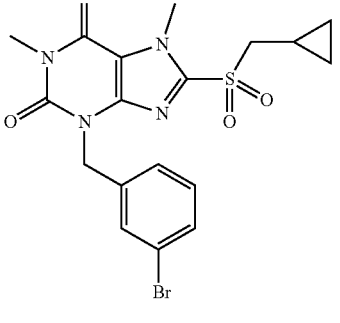 137
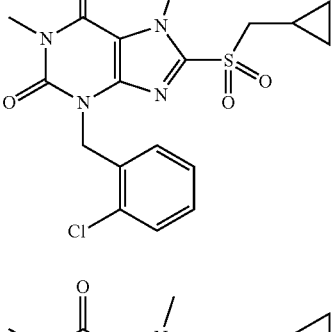 138
TABLE 6-continued
MLKL inhibitors
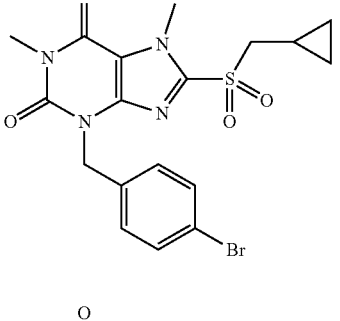 139
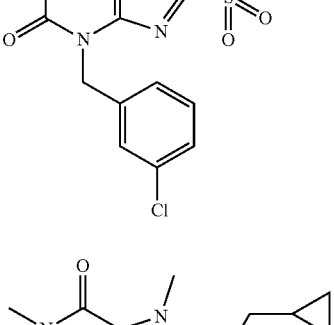 140
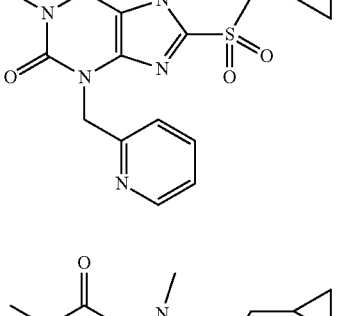 141
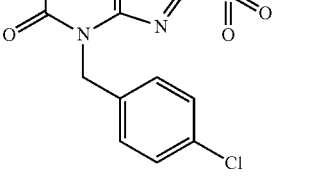 142
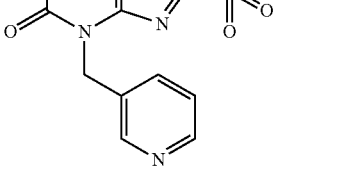 143

TABLE 6-continued
MLKL inhibitors
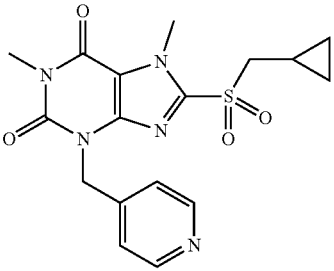 [SMILES: Cn1c(=O)c2c(nc(S(=O)(=O)CC3CC3)n2C)n(Cc2ccncc2)c1=O] 144
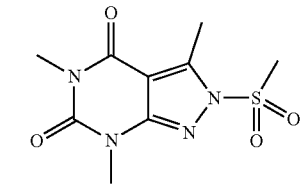 [SMILES: Cc1c2c(=O)n(C)c(=O)n(C)c2nn1S(C)(=O)=O] 145
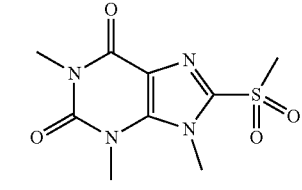 146
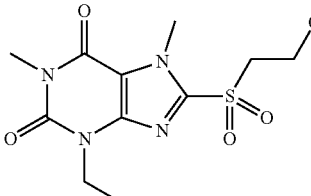 147
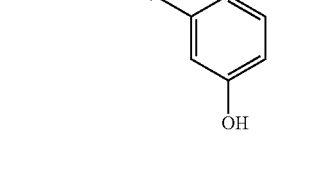 148
TABLE 6-continued
MLKL inhibitors
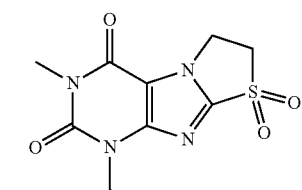 149
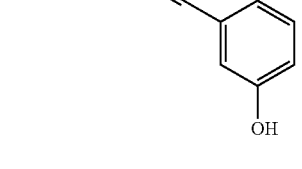 150
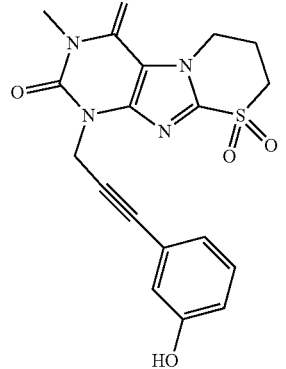 151
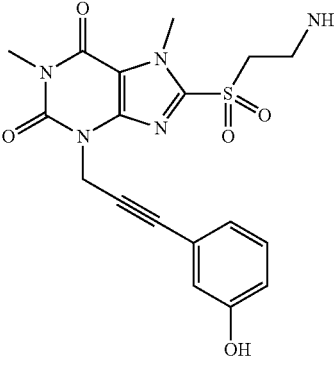 [SMILES: Cn1c(=O)c2c(nc(S(=O)(=O)CCO)n2C)n(CC#Cc2cccc(O)c2)c1=O] 152

TABLE 6-continued
MLKL inhibitors
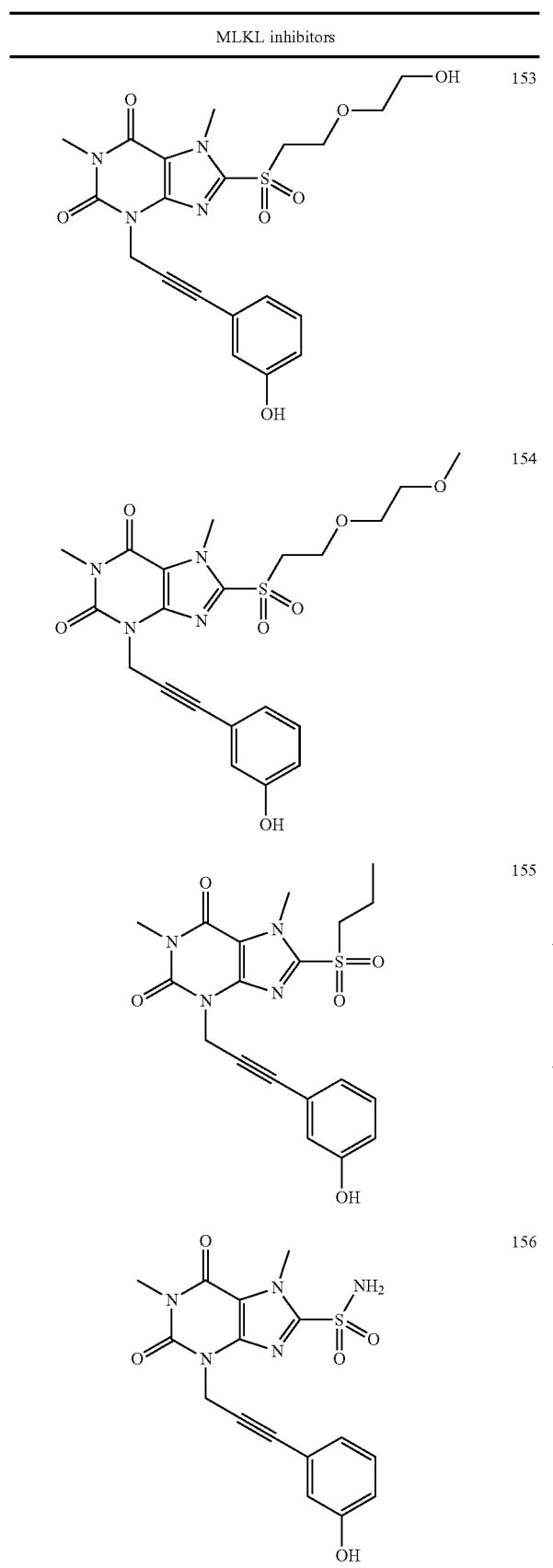
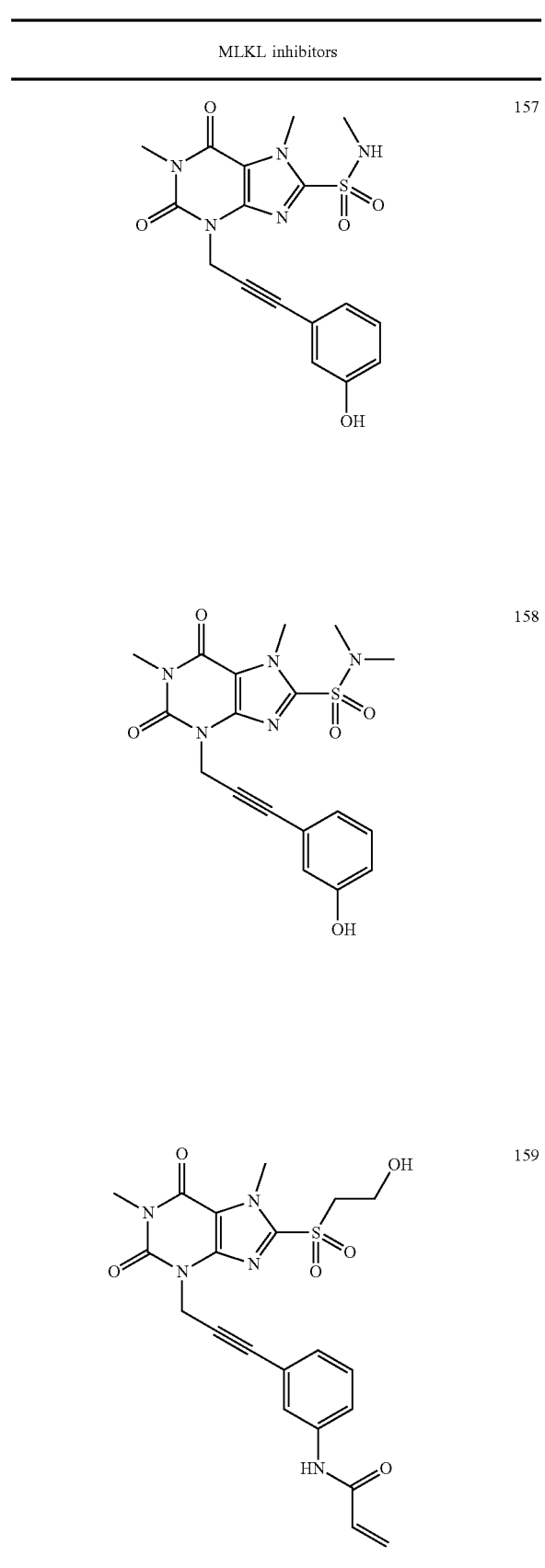

TABLE 6-continued
MLKL inhibitors
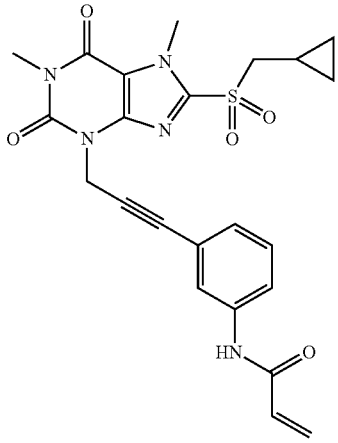 [SMILES: C=CC(=O)Nc1cccc(C#CCn2c(=O)n(C)c(=O)c3c2nc(S(=O)(=O)CC2CC2)n3C)c1]
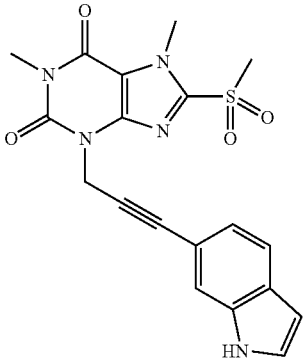 [SMILES: Cn1c(=O)c2c(nc(S(C)(=O)=O)n2C)n(CC#Cc2ccc3cc[nH]c3c2)c1=O]

TABLE 6-continued
MLKL inhibitors
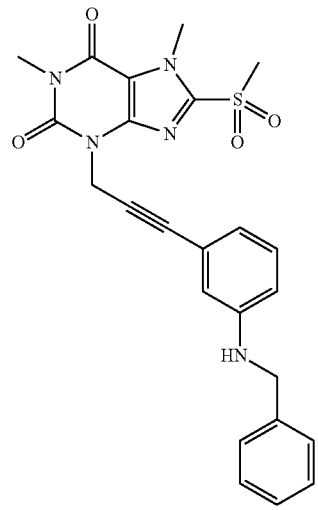 [SMILES: Cn1c(=O)c2c(nc(S(C)(=O)=O)n2C)n(CC#Cc2cccc(NCc3ccccc3)c2)c1=O]
166
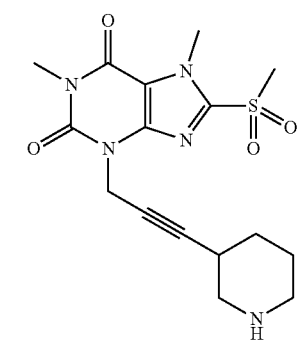 [SMILES: Cn1c(=O)c2c(nc(S(C)(=O)=O)n2C)n(CC#CC2CCCNC2)c1=O]
167
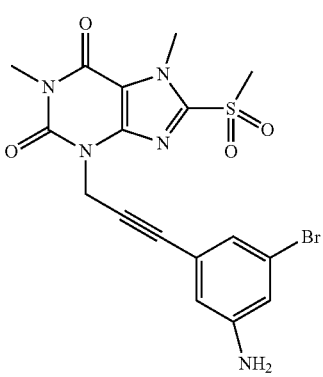 [SMILES: Cn1c(=O)c2c(nc(S(C)(=O)=O)n2C)n(CC#Cc2cc(N)cc(Br)c2)c1=O]
168
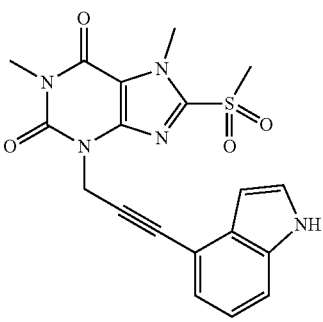 [SMILES: Cn1c(=O)c2c(nc(S(C)(=O)=O)n2C)n(CC#Cc2cccc3[nH]ccc23)c1=O]
169
TABLE 6-continued
MLKL inhibitors
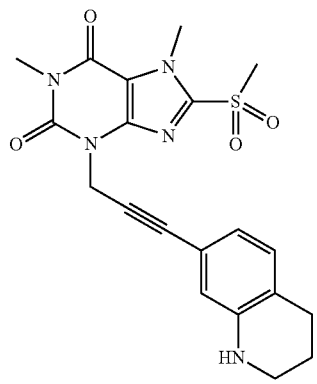 [SMILES: Cn1c(=O)c2c(nc(S(C)(=O)=O)n2C)n(CC#Cc2ccc3c(c2)NCCC3)c1=O]
170
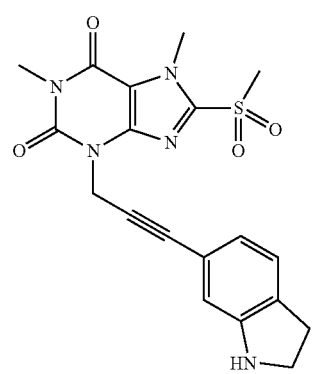 [SMILES: Cn1c(=O)c2c(nc(S(C)(=O)=O)n2C)n(CC#Cc2ccc3c(c2)NCC3)c1=O]
171
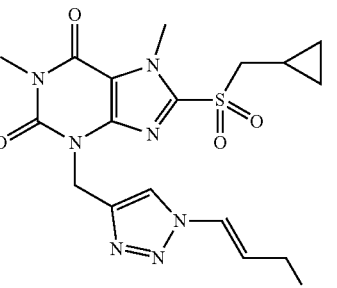
172
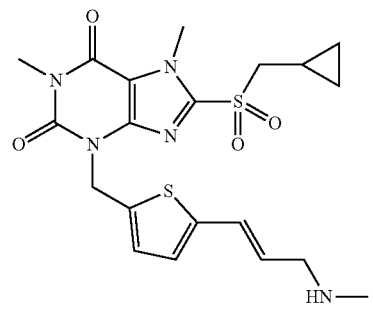
173

TABLE 6-continued
MLKL inhibitors
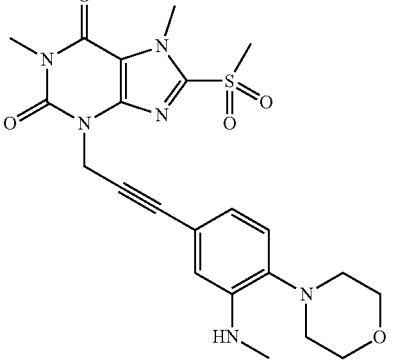
174
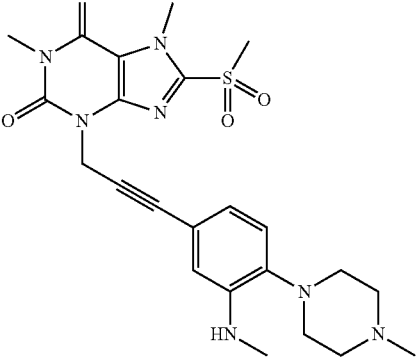
175
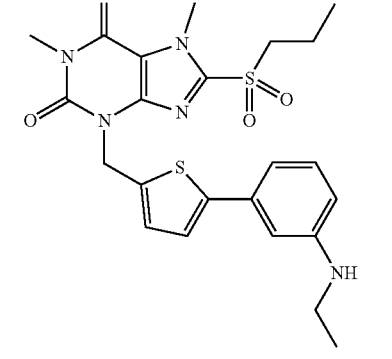
176
TABLE 7
MLKL inhibitors
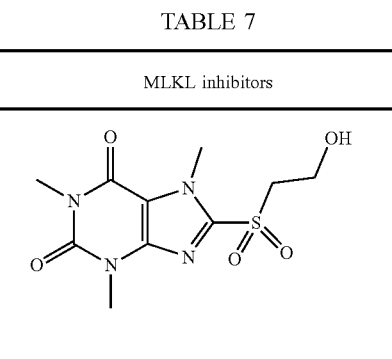
1
TABLE 7-continued
MLKL inhibitors
2
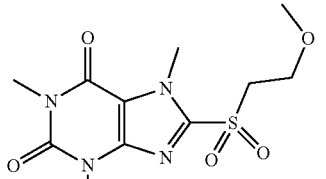
3
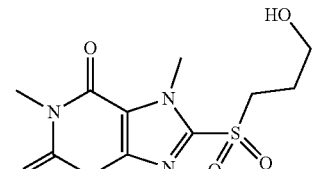
4
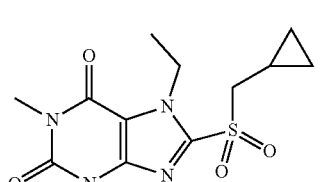
5
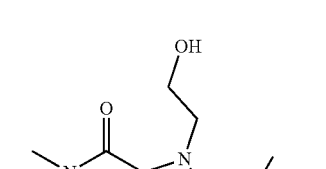
6
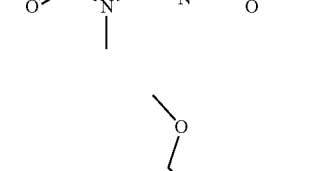
7

TABLE 7-continued
MLKL inhibitors
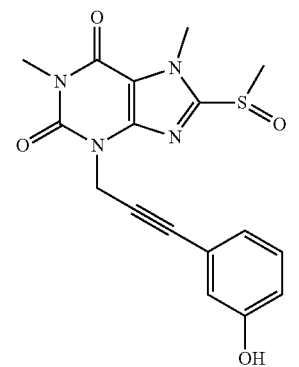 [SMILES: Cn1c(=O)c2c(nc(S(C)=O)n2C)n(CC#Cc2cccc(O)c2)c1=O]
8
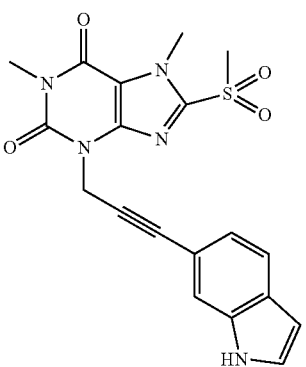 [SMILES: Cn1c(=O)c2c(nc(S(C)(=O)=O)n2C)n(CC#Cc2ccc3cc[nH]c3c2)c1=O]
9
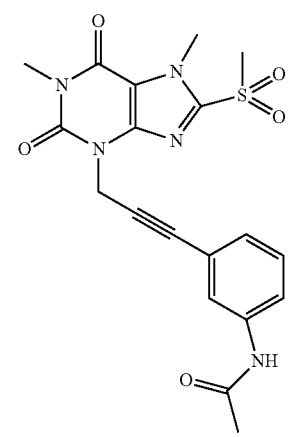 [SMILES: CC(=O)Nc1cccc(C#CCn2c(=O)n(C)c(=O)c3c2nc(S(C)(=O)=O)n3C)c1]
10
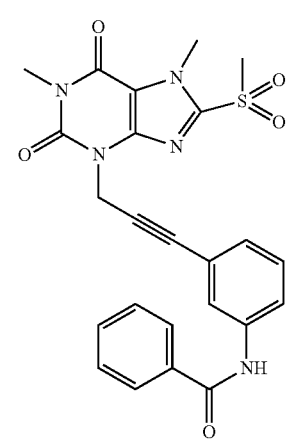 [SMILES: Cn1c(=O)c2c(nc(S(C)(=O)=O)n2C)n(CC#Cc2cccc(NC(=O)c3ccccc3)c2)c1=O]
11
TABLE 7-continued
MLKL inhibitors
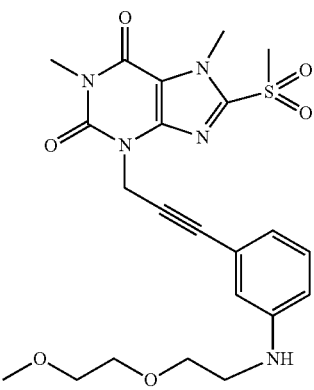 [SMILES: COCCOCCNc1cccc(C#CCn2c(=O)n(C)c(=O)c3c2nc(S(C)(=O)=O)n3C)c1]
12
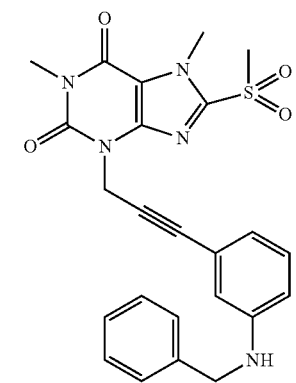 [SMILES: Cn1c(=O)c2c(nc(S(C)(=O)=O)n2C)n(CC#Cc2cccc(NCc3ccccc3)c2)c1=O]
13
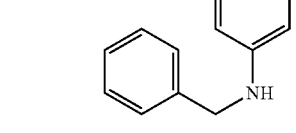
14

TABLE 7-continued
MLKL inhibitors
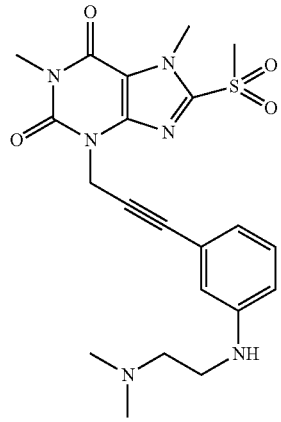 [SMILES: CN(C)CCNc1cccc(C#CCn2c(=O)n(C)c(=O)c3c2nc(S(C)(=O)=O)n3C)c1]
15
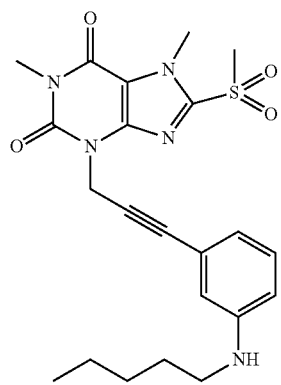 [SMILES: CCCCCNc1cccc(C#CCn2c(=O)n(C)c(=O)c3c2nc(S(C)(=O)=O)n3C)c1]
16
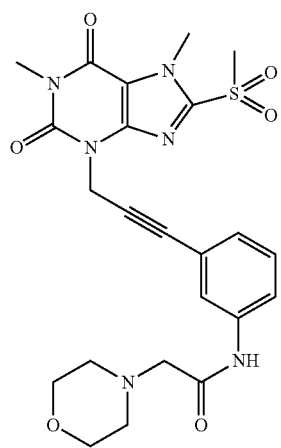 [SMILES: Cn1c(=O)c2c(nc(S(C)(=O)=O)n2C)n(CC#Cc2cccc(NC(=O)CN3CCOCC3)c2)c1=O]
17
TABLE 7-continued
MLKL inhibitors
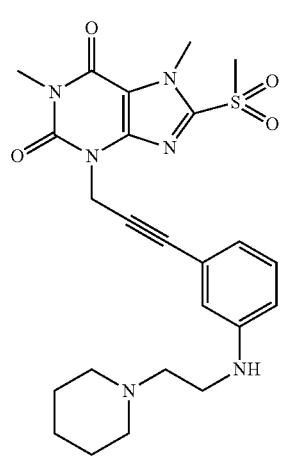 [SMILES: Cn1c(=O)c2c(nc(S(C)(=O)=O)n2C)n(CC#Cc2cccc(NCCN3CCCCC3)c2)c1=O]
18
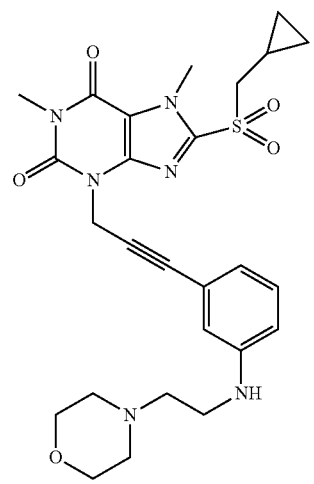 [SMILES: Cn1c(=O)c2c(nc(S(=O)(=O)CC3CC3)n2C)n(CC#Cc2cccc(NCCN3CCOCC3)c2)c1=O]
19
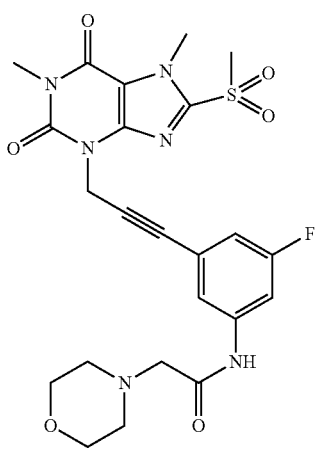 [SMILES: Cn1c(=O)c2c(nc(S(C)(=O)=O)n2C)n(CC#Cc2cc(F)cc(NC(=O)CN3CCOCC3)c2)c1=O]
20

TABLE 7-continued
MLKL inhibitors
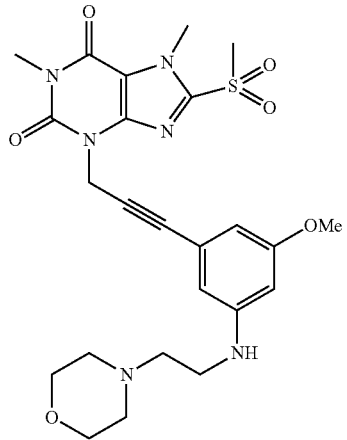 [SMILES: COc1cc(C#CCn2c(=O)n(C)c(=O)c3c2nc(S(C)(=O)=O)n3C)cc(NCCN2CCOCC2)c1]
21
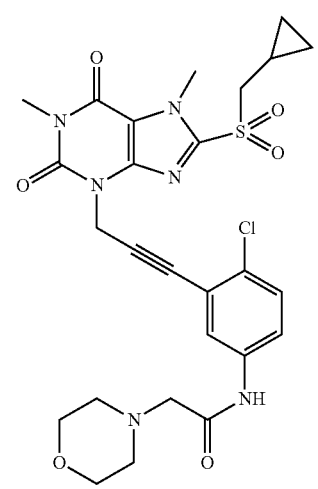 [SMILES: Cn1c(=O)c2c(nc(S(=O)(=O)CC3CC3)n2C)n(CC#Cc2cc(NC(=O)CN3CCOCC3)ccc2Cl)c1=O]
22
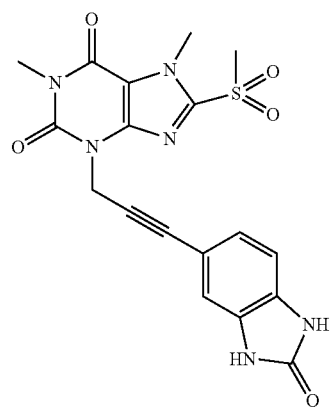 [SMILES: Cn1c(=O)c2c(nc(S(C)(=O)=O)n2C)n(CC#Cc2ccc3[nH]c(=O)[nH]c3c2)c1=O]
23
TABLE 7-continued
MLKL inhibitors
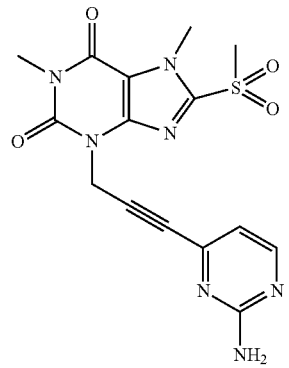 [SMILES: Cn1c(=O)c2c(nc(S(C)(=O)=O)n2C)n(CC#Cc2ccnc(N)n2)c1=O]
24
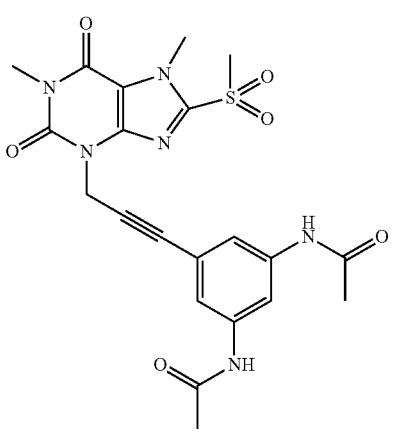 [SMILES: CC(=O)Nc1cc(C#CCn2c(=O)n(C)c(=O)c3c2nc(S(C)(=O)=O)n3C)cc(NC(C)=O)c1]
25
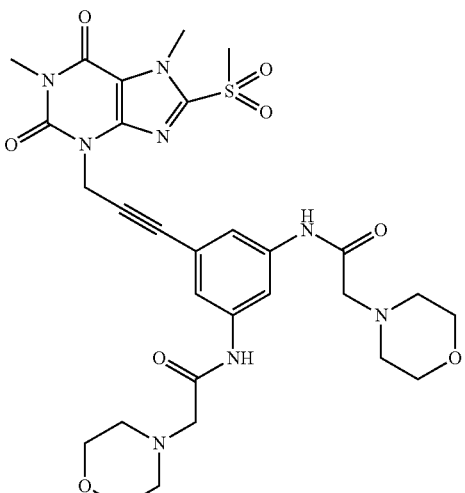
26

TABLE 7-continued
MLKL inhibitors
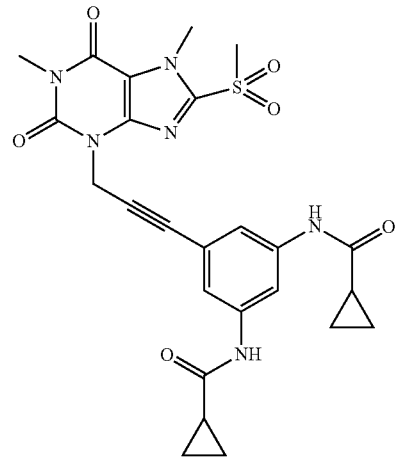 [SMILES: Cn1c(=O)c2c(nc(S(C)(=O)=O)n2C)n(CC#Cc2cc(NC(=O)C3CC3)cc(NC(=O)C3CC3)c2)c1=O]
27
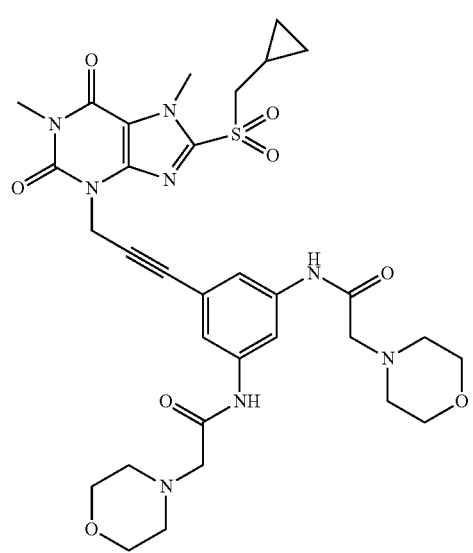 [SMILES: Cn1c(=O)c2c(nc(S(=O)(=O)CC3CC3)n2C)n(CC#Cc2cc(NC(=O)CN3CCOCC3)cc(NC(=O)CN3CCOCC3)c2)c1=O]
28
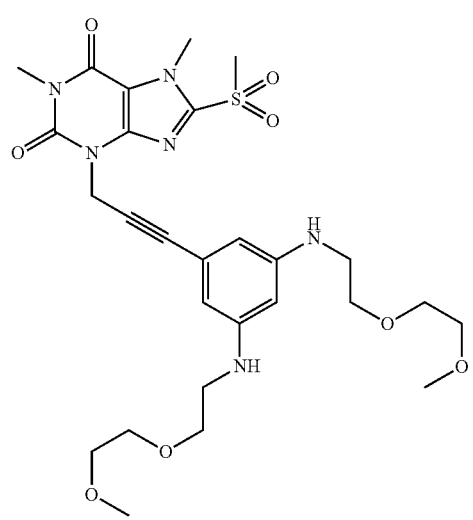 [SMILES: COCCOCCNc1cc(C#CCn2c(=O)n(C)c(=O)c3c2nc(S(C)(=O)=O)n3C)cc(NCCOCCOC)c1]
29
TABLE 7-continued
MLKL inhibitors
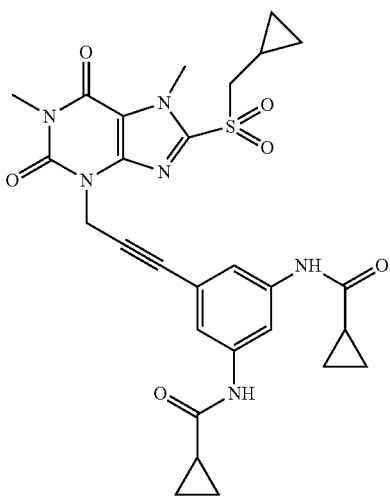 [SMILES: Cn1c(=O)c2c(nc(S(=O)(=O)CC3CC3)n2C)n(CC#Cc2cc(NC(=O)C3CC3)cc(NC(=O)C3CC3)c2)c1=O]
30
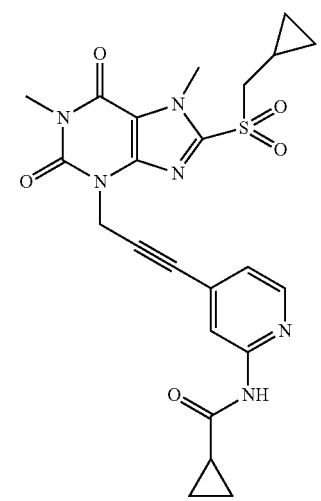 [SMILES: Cn1c(=O)c2c(nc(S(=O)(=O)CC3CC3)n2C)n(CC#Cc2ccnc(NC(=O)C3CC3)c2)c1=O]
31
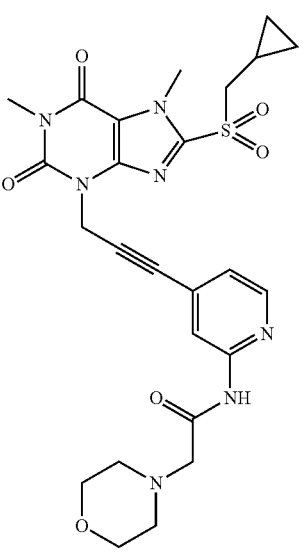 [SMILES: Cn1c(=O)c2c(nc(S(=O)(=O)CC3CC3)n2C)n(CC#Cc2ccnc(NC(=O)CN3CCOCC3)c2)c1=O]
32

TABLE 7-continued
MLKL inhibitors
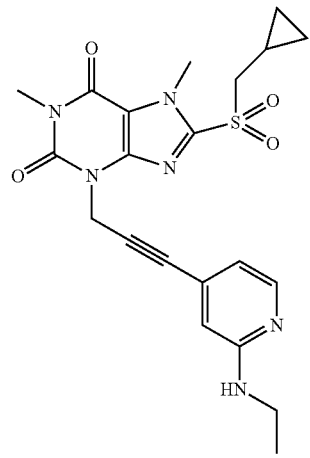 [SMILES: CCNc1cc(C#CCn2c(=O)n(C)c(=O)c3c2nc(S(=O)(=O)CC2CC2)n3C)ccn1] 33
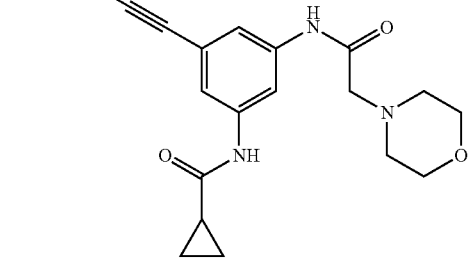 36
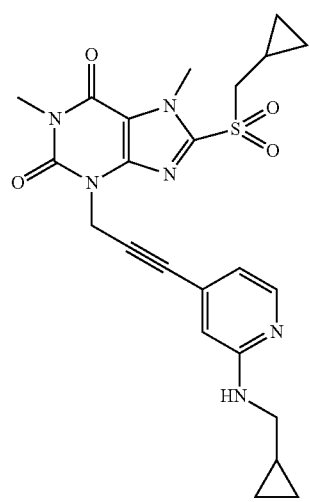 [SMILES: Cn1c(=O)c2c(nc(S(=O)(=O)CC3CC3)n2C)n(CC#Cc2ccnc(NCC3CC3)c2)c1=O] 34
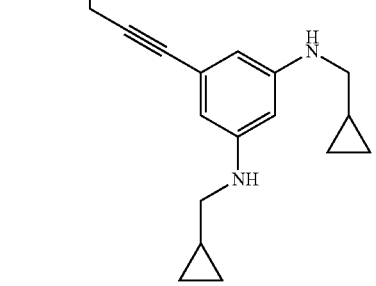 37
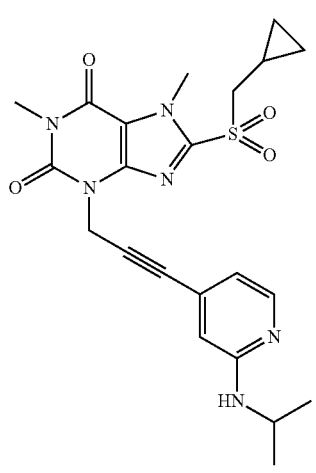 [SMILES: CC(C)Nc1cc(C#CCn2c(=O)n(C)c(=O)c3c2nc(S(=O)(=O)CC2CC2)n3C)ccn1] 35
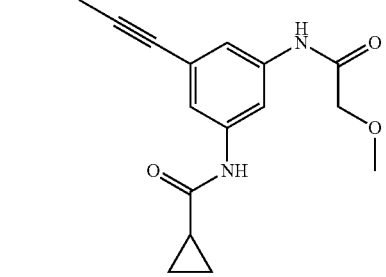 38

TABLE 7-continued
MLKL inhibitors
39
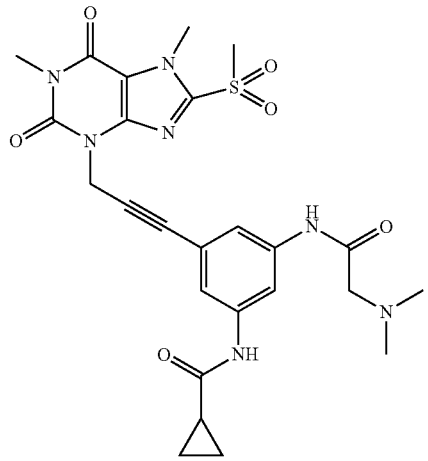
42
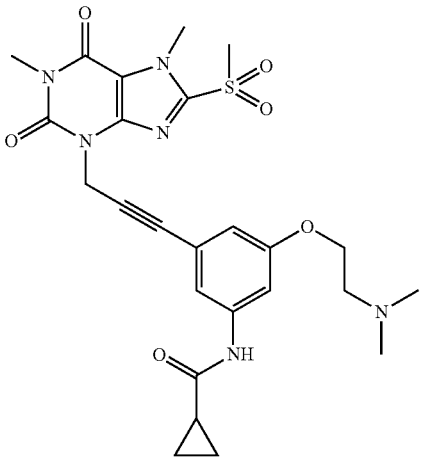
40
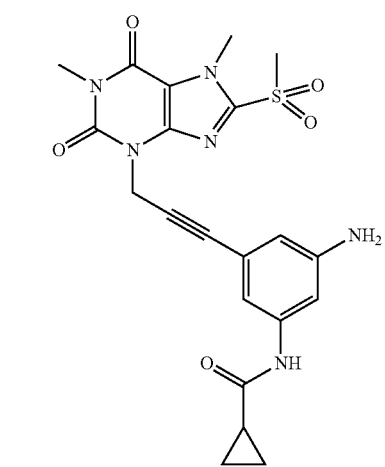 [SMILES: Cn1c(=O)c2c(nc(S(C)(=O)=O)n2C)n(CC#Cc2cc(N)cc(NC(=O)C3CC3)c2)c1=O]
43
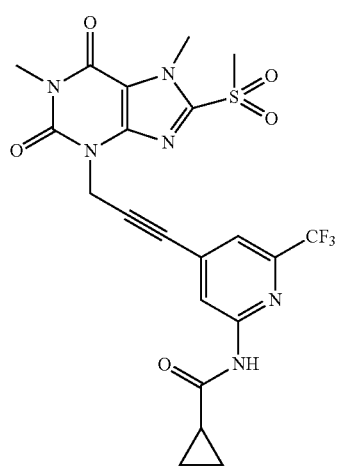
41
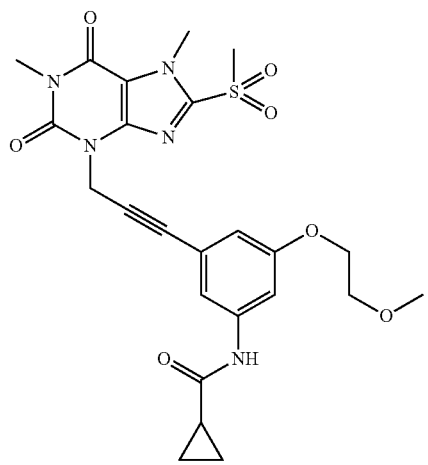
44
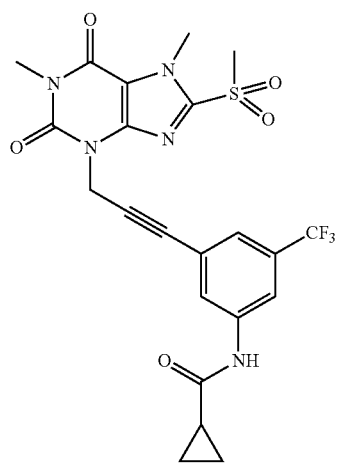 [SMILES: Cn1c(=O)c2c(nc(S(C)(=O)=O)n2C)n(CC#Cc2cc(NC(=O)C3CC3)cc(C(F)(F)F)c2)c1=O]

TABLE 7-continued
MLKL inhibitors
45 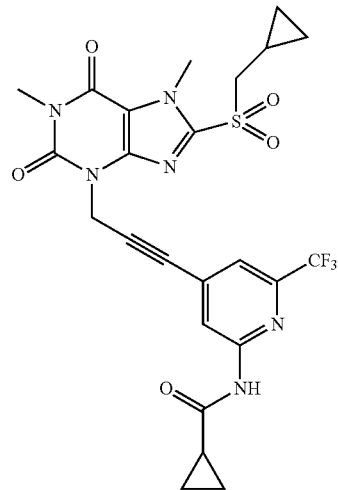 [SMILES: Cn1c(=O)c2c(nc(S(=O)(=O)CC3CC3)n2C)n(CC#Cc2cc(NC(=O)C3CC3)nc(C(F)(F)F)c2)c1=O]
46 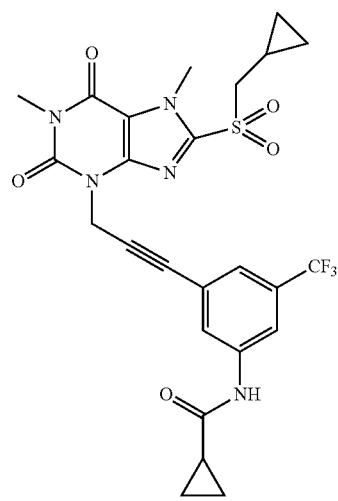 [SMILES: Cn1c(=O)c2c(nc(S(=O)(=O)CC3CC3)n2C)n(CC#Cc2cc(NC(=O)C3CC3)cc(C(F)(F)F)c2)c1=O]
47 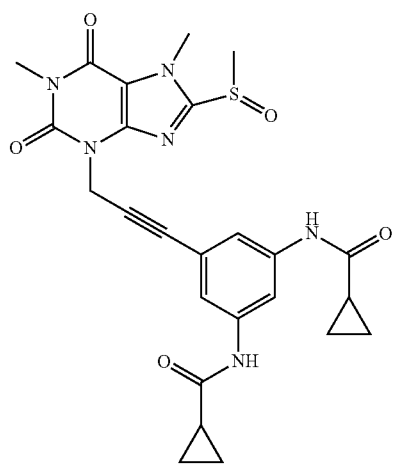 [SMILES: Cn1c(=O)c2c(nc(S(C)=O)n2C)n(CC#Cc2cc(NC(=O)C3CC3)cc(NC(=O)C3CC3)c2)c1=O]
TABLE 7-continued
MLKL inhibitors
48 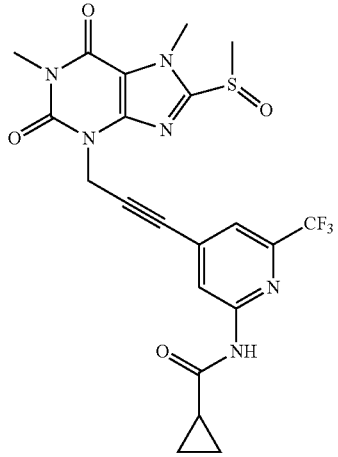 [SMILES: Cn1c(=O)c2c(nc(S(C)=O)n2C)n(CC#Cc2cc(NC(=O)C3CC3)nc(C(F)(F)F)c2)c1=O]
49 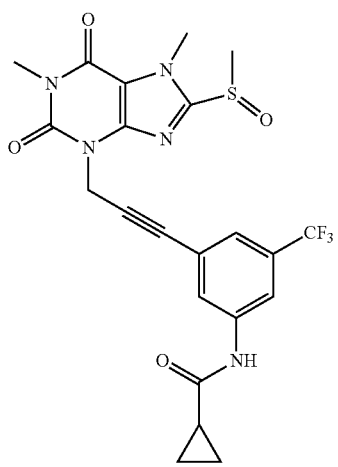 [SMILES: Cn1c(=O)c2c(nc(S(C)=O)n2C)n(CC#Cc2cc(NC(=O)C3CC3)cc(C(F)(F)F)c2)c1=O]
50 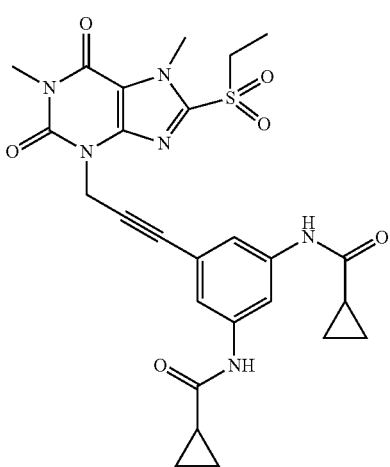 [SMILES: CCS(=O)(=O)c1nc2c(c(=O)n(C)c(=O)n2CC#Cc2cc(NC(=O)C3CC3)cc(NC(=O)C3CC3)c2)n1C]

TABLE 7-continued
MLKL inhibitors
51 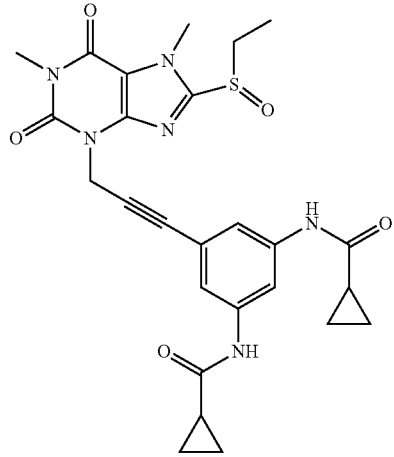 [SMILES: CCS(=O)c1nc2c(c(=O)n(C)c(=O)n2CC#Cc2cc(NC(=O)C3CC3)cc(NC(=O)C3CC3)c2)n1C]
52 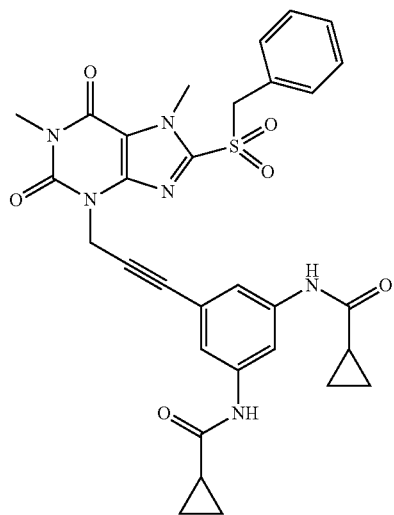 [SMILES: Cn1c(=O)c2c(nc(S(=O)(=O)Cc3ccccc3)n2C)n(CC#Cc2cc(NC(=O)C3CC3)cc(NC(=O)C3CC3)c2)c1=O]
53 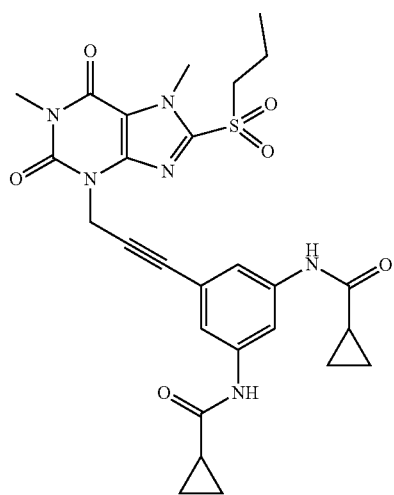 [SMILES: CCCS(=O)(=O)c1nc2c(c(=O)n(C)c(=O)n2CC#Cc2cc(NC(=O)C3CC3)cc(NC(=O)C3CC3)c2)n1C]
TABLE 7-continued
MLKL inhibitors
54 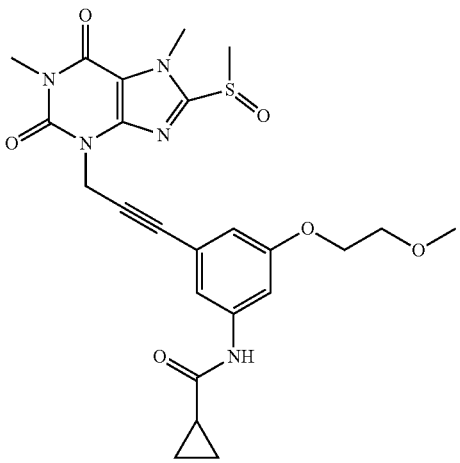
55 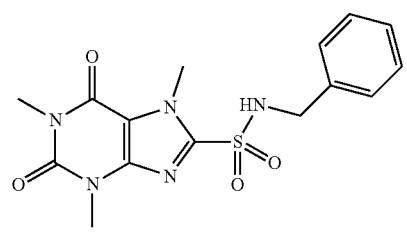 [SMILES: Cn1c(=O)c2c(nc(S(=O)(=O)NCc3ccccc3)n2C)n(C)c1=O]
56 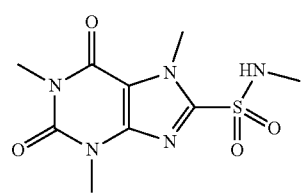
57 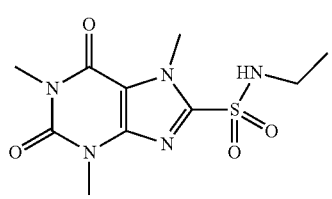 [SMILES: CCNS(=O)(=O)c1nc2c(c(=O)n(C)c(=O)n2C)n1C]
58 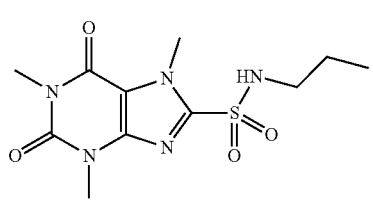 [SMILES: CCCNS(=O)(=O)c1nc2c(c(=O)n(C)c(=O)n2C)n1C]
59 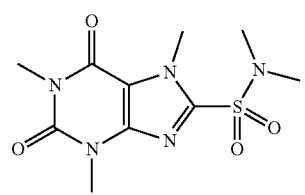

TABLE 7-continued

MLKL inhibitors

TABLE 7-continued
MLKL inhibitors
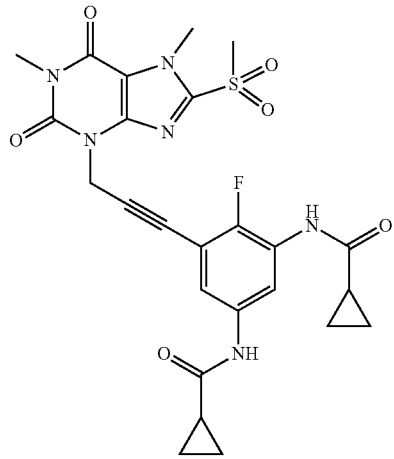 [SMILES: Cn1c(=O)c2c(nc(S(C)(=O)=O)n2C)n(CC#Cc2cc(NC(=O)C3CC3)cc(NC(=O)C3CC3)c2F)c1=O]
70
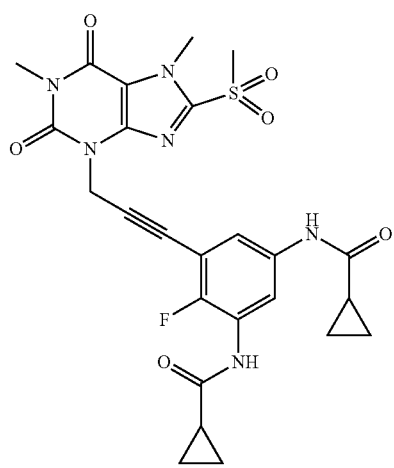 [SMILES: Cn1c(=O)c2c(nc(S(C)(=O)=O)n2C)n(CC#Cc2cc(NC(=O)C3CC3)cc(NC(=O)C3CC3)c2F)c1=O]
71
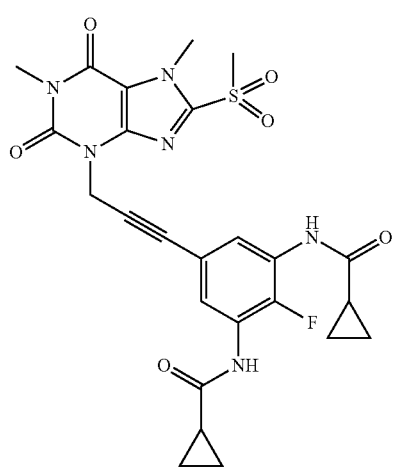 [SMILES: Cn1c(=O)c2c(nc(S(C)(=O)=O)n2C)n(CC#Cc2cc(NC(=O)C3CC3)c(F)c(NC(=O)C3CC3)c2)c1=O]
72
TABLE 7-continued
MLKL inhibitors
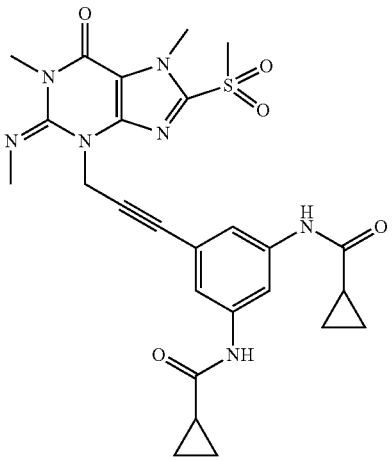 [SMILES: C/N=c1/n(C)c(=O)c2c(nc(S(C)(=O)=O)n2C)n1CC#Cc1cc(NC(=O)C2CC2)cc(NC(=O)C2CC2)c1]
73
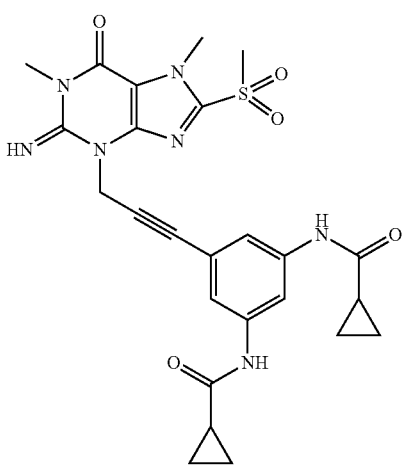 [SMILES: Cn1c(=O)c2c(nc(S(C)(=O)=O)n2C)n(CC#Cc2cc(NC(=O)C3CC3)cc(NC(=O)C3CC3)c2)c1=N]
74
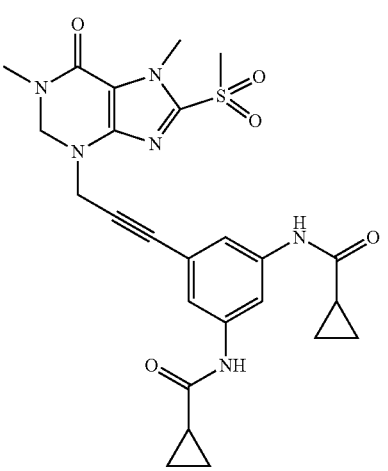 [SMILES: CN1CN(CC#Cc2cc(NC(=O)C3CC3)cc(NC(=O)C3CC3)c2)c2nc(S(C)(=O)=O)n(C)c2C1=O]
75

TABLE 7-continued
MLKL inhibitors
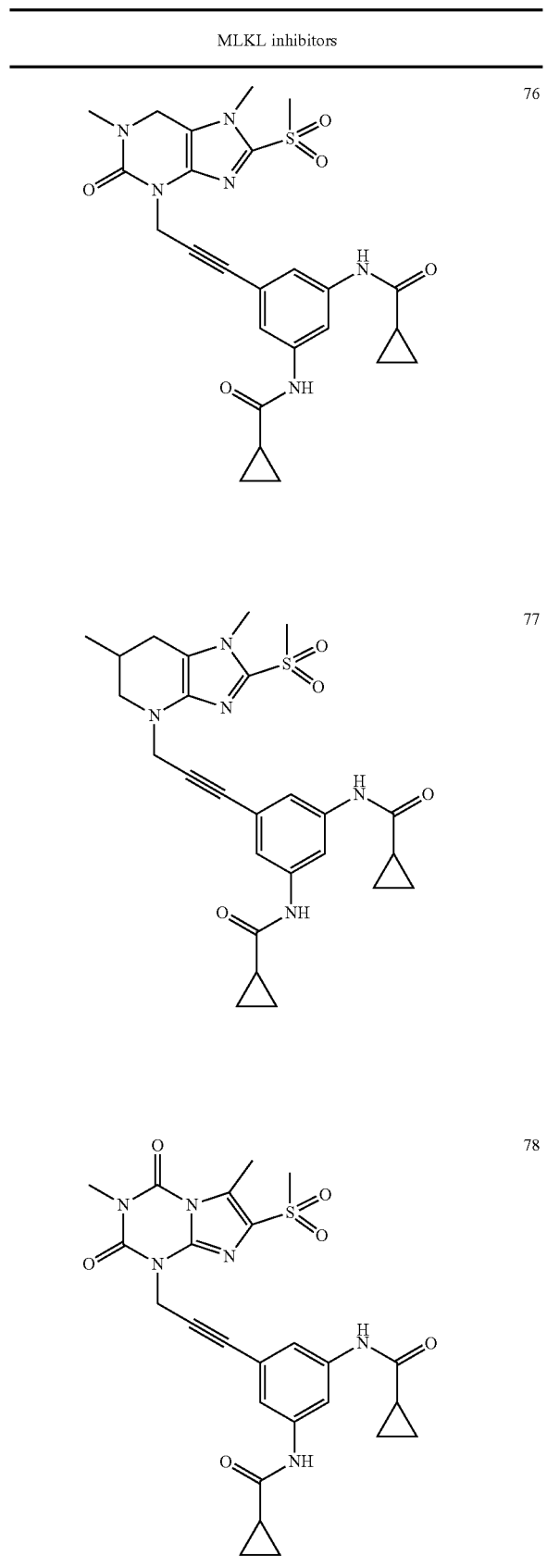
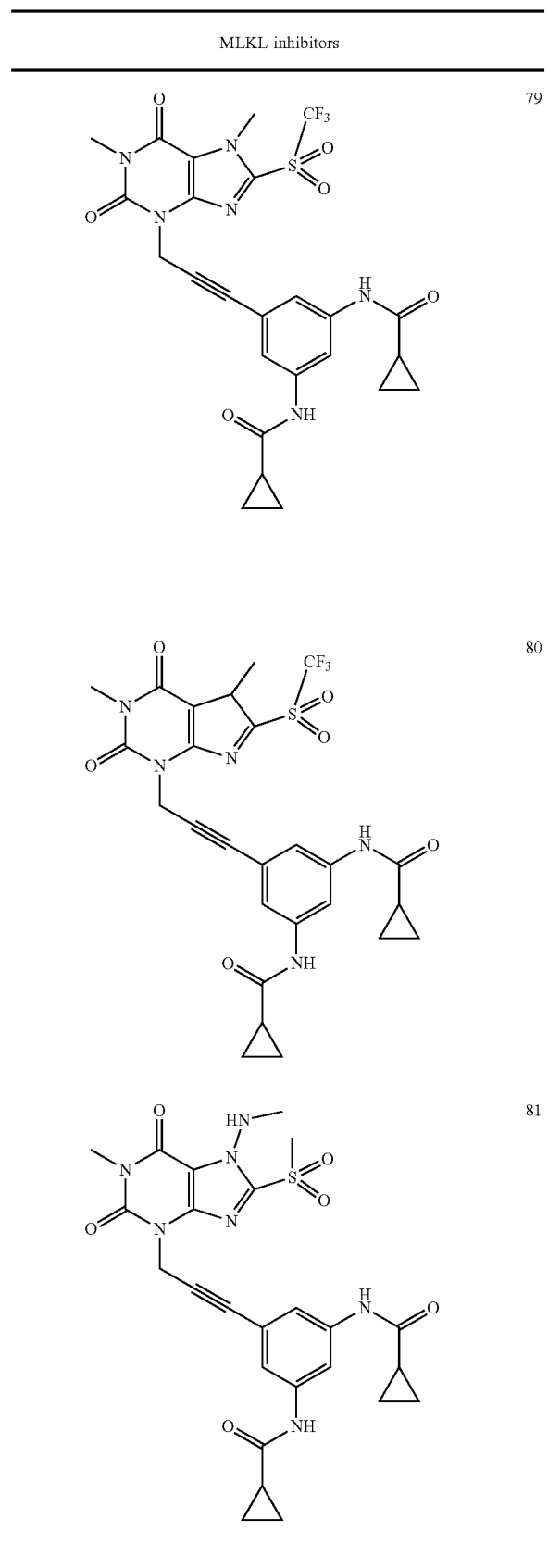

TABLE 7-continued
MLKL inhibitors
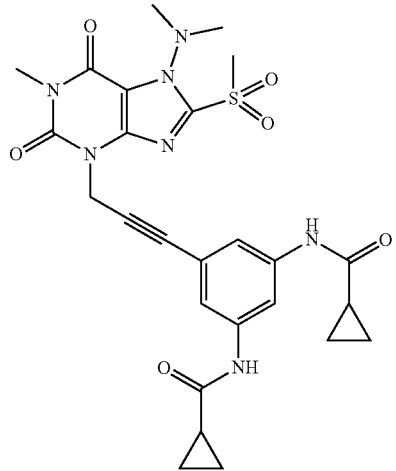 [SMILES: CN(C)n1c(S(C)(=O)=O)nc2c1c(=O)n(C)c(=O)n2CC#Cc1cc(NC(=O)C2CC2)cc(NC(=O)C2CC2)c1]
82
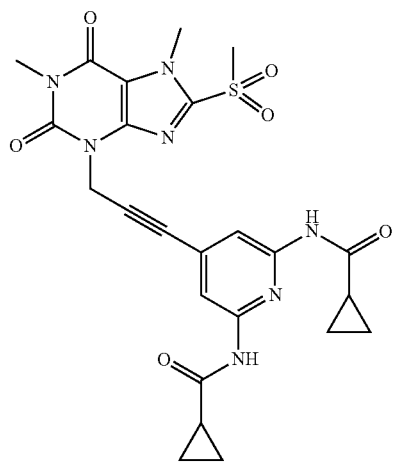 [SMILES: Cn1c(=O)c2c(nc(S(C)(=O)=O)n2C)n(CC#Cc2cc(NC(=O)C3CC3)nc(NC(=O)C3CC3)c2)c1=O]
83
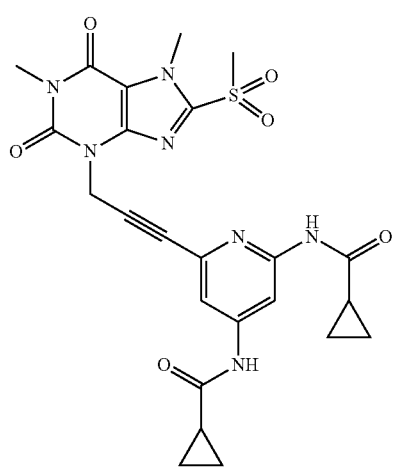 [SMILES: Cn1c(=O)c2c(nc(S(C)(=O)=O)n2C)n(CC#Cc2cc(NC(=O)C3CC3)cc(NC(=O)C3CC3)n2)c1=O]
84
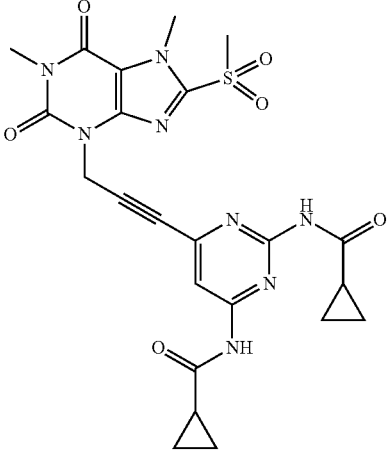 [SMILES: Cn1c(=O)c2c(nc(S(C)(=O)=O)n2C)n(CC#Cc2cc(NC(=O)C3CC3)nc(NC(=O)C3CC3)n2)c1=O]
85
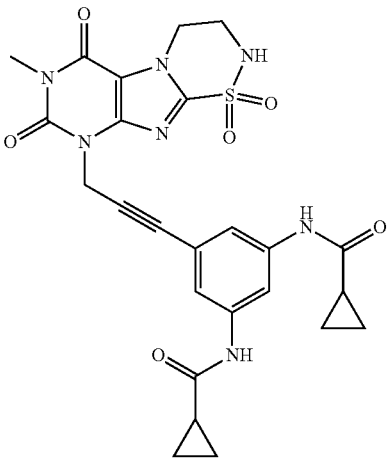 [SMILES: Cn1c(=O)c2c(nc3n2CCNS3(=O)=O)n(CC#Cc2cc(NC(=O)C3CC3)cc(NC(=O)C3CC3)c2)c1=O]
86
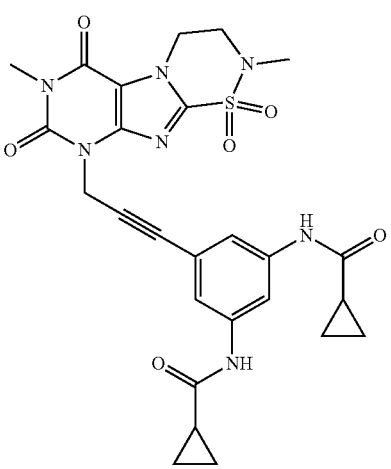 [SMILES: CN1CCn2c(nc3c2c(=O)n(C)c(=O)n3CC#Cc2cc(NC(=O)C3CC3)cc(NC(=O)C3CC3)c2)S1(=O)=O]
87

TABLE 7-continued
MLKL inhibitors
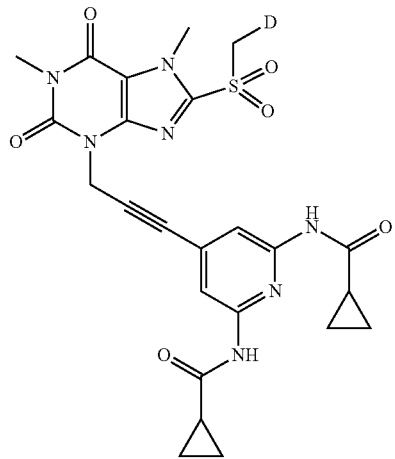 [SMILES: [2H]CS(=O)(=O)c1nc2c(c(=O)n(C)c(=O)n2CC#Cc2cc(NC(=O)C3CC3)nc(NC(=O)C3CC3)c2)n1C] 88
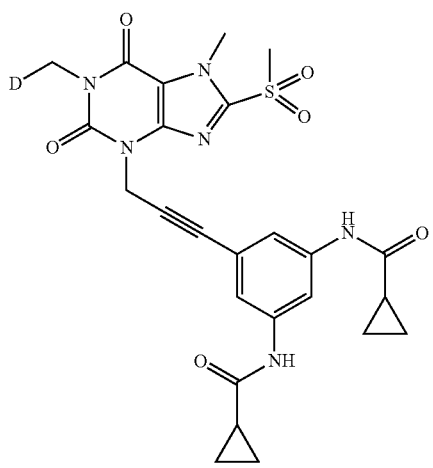 [SMILES: [2H]Cn1c(=O)c2c(nc(S(C)(=O)=O)n2C)n(CC#Cc2cc(NC(=O)C3CC3)cc(NC(=O)C3CC3)c2)c1=O] 89
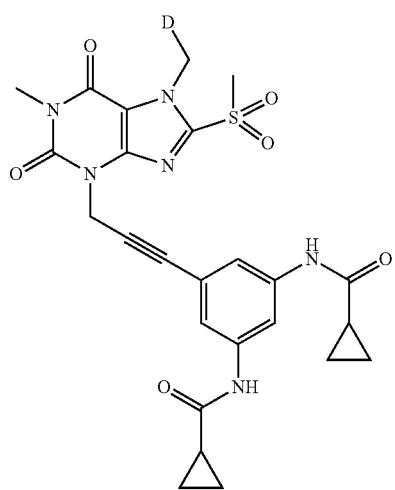 [SMILES: [2H]Cn1c(S(C)(=O)=O)nc2c1c(=O)n(C)c(=O)n2CC#Cc1cc(NC(=O)C2CC2)cc(NC(=O)C2CC2)c1] 90
TABLE 7-continued
MLKL inhibitors
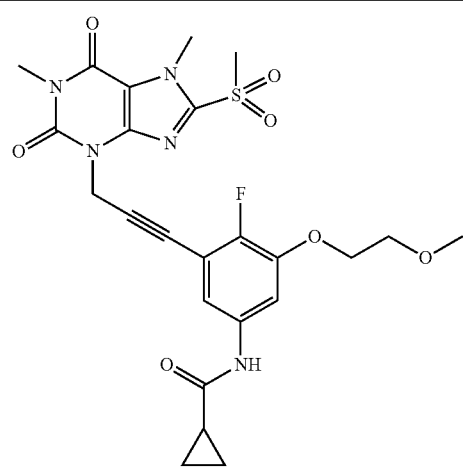 91
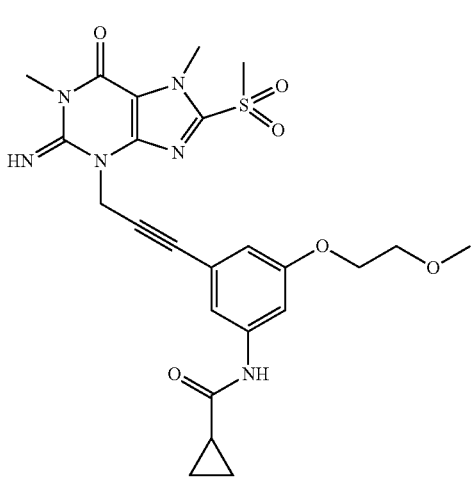 92
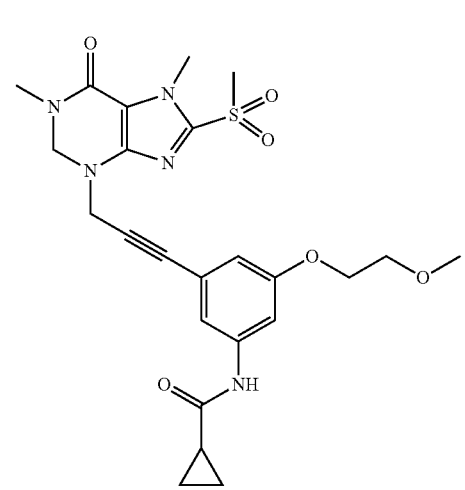 93

TABLE 7-continued
MLKL inhibitors
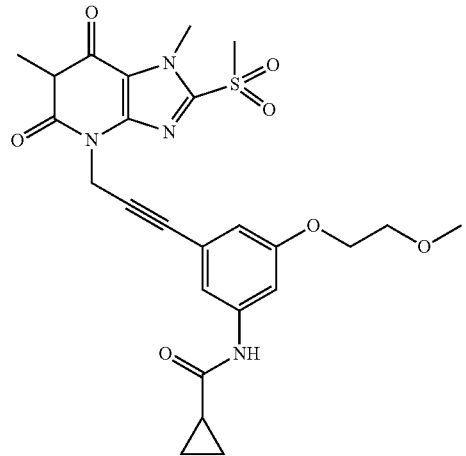
94
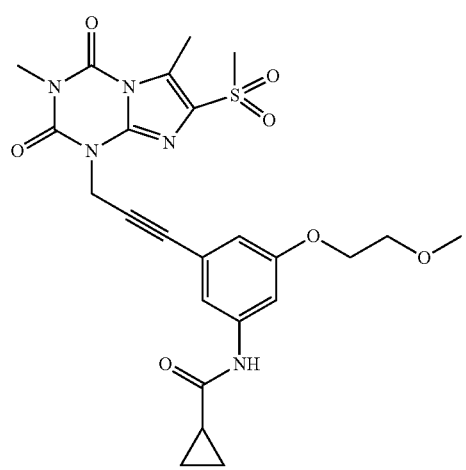
95
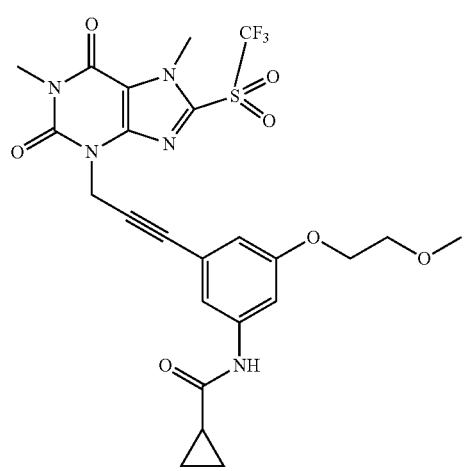
96
TABLE 7-continued
MLKL inhibitors
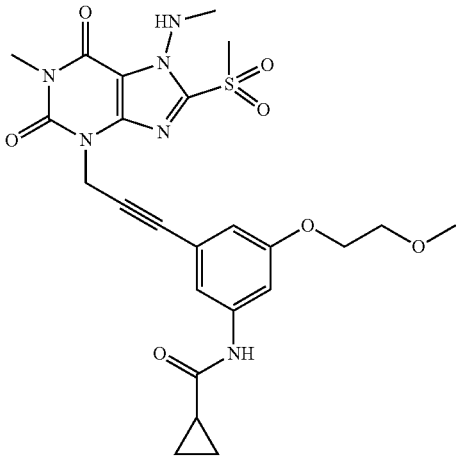
97
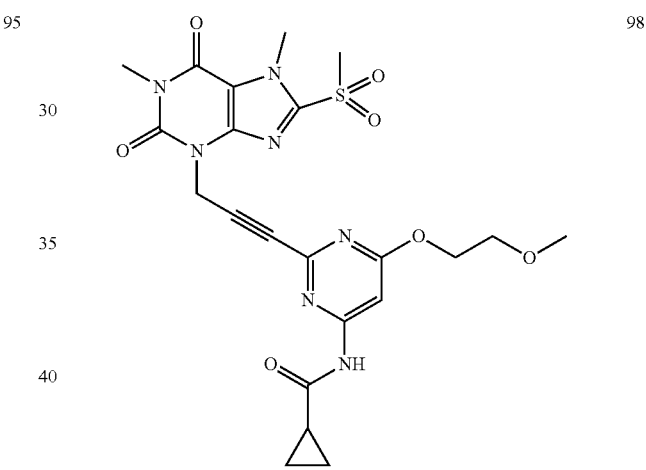
98
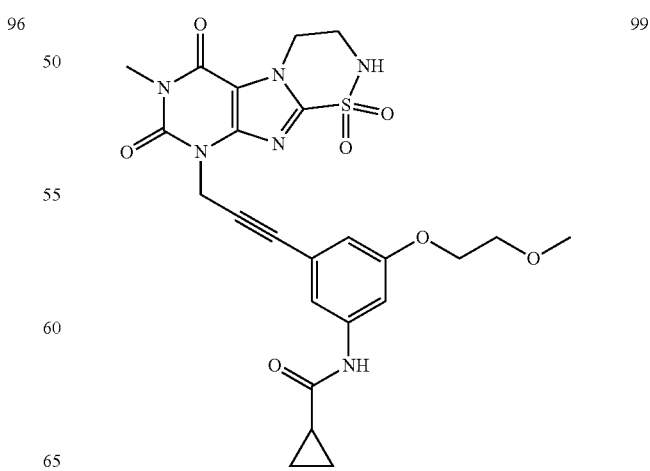
99

TABLE 7-continued
MLKL inhibitors
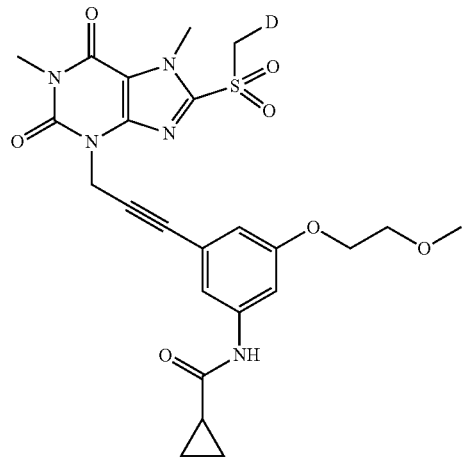
100
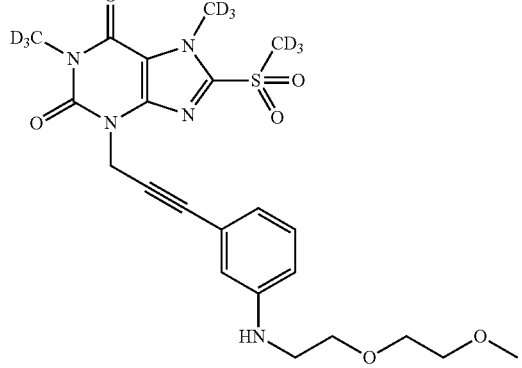
103
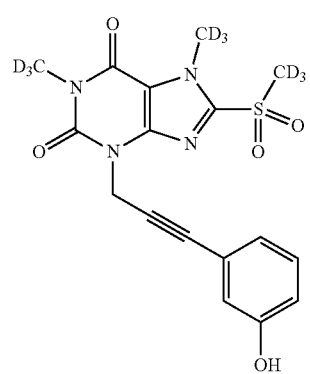 [SMILES: [2H]C([2H])([2H])n1c(=O)c2c(nc(S(=O)(=O)C([2H])([2H])[2H])n2C([2H])([2H])[2H])n(CC#Cc2cccc(O)c2)c1=O]
101
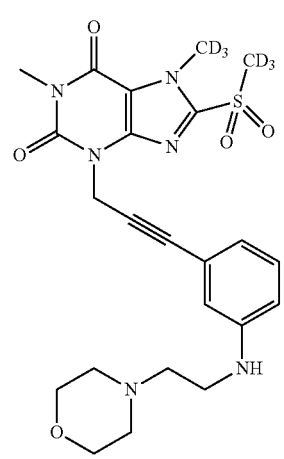
104
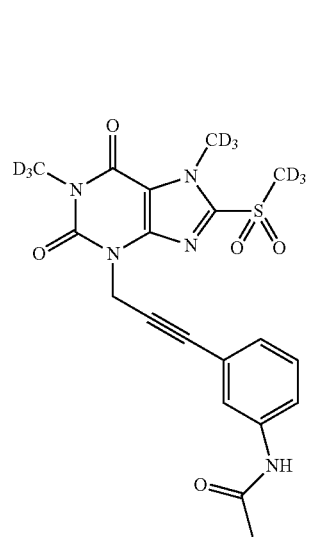 [SMILES: [2H]C([2H])([2H])n1c(=O)c2c(nc(S(=O)(=O)C([2H])([2H])[2H])n2C([2H])([2H])[2H])n(CC#Cc2cccc(NC(C)=O)c2)c1=O]
102
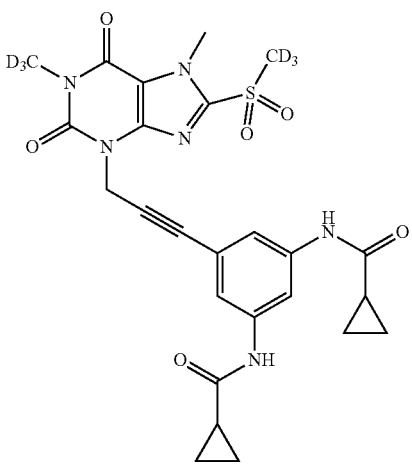 [SMILES: [2H]C([2H])([2H])n1c(=O)c2c(nc(S(=O)(=O)C([2H])([2H])[2H])n2C)n(CC#Cc2cc(NC(=O)C3CC3)cc(NC(=O)C3CC3)c2)c1=O]
105

TABLE 7-continued
MLKL inhibitors
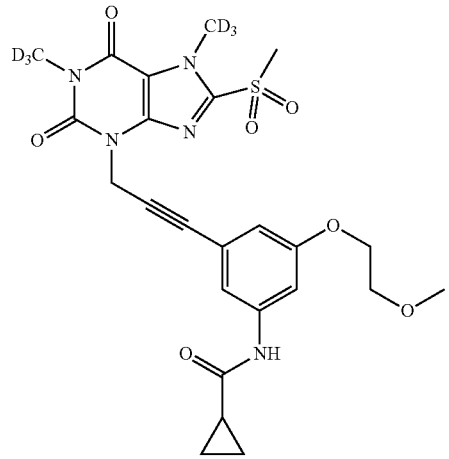 [SMILES: [2H]C([2H])([2H])n1c(=O)c2c(nc(S(C)(=O)=O)n2C([2H])([2H])[2H])n(CC#Cc2cc(NC(=O)C3CC3)cc(OCCOC)c2)c1=O]
106
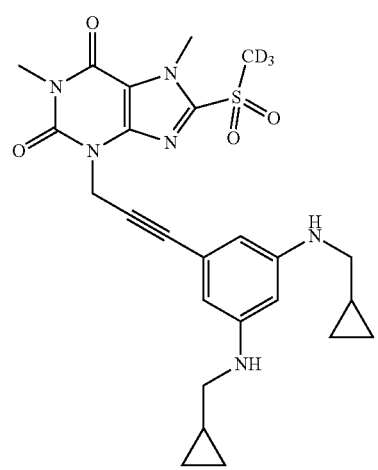 [SMILES: [2H]C([2H])([2H])S(=O)(=O)c1nc2c(c(=O)n(C)c(=O)n2CC#Cc2cc(NCC3CC3)cc(NCC3CC3)c2)n1C]
107
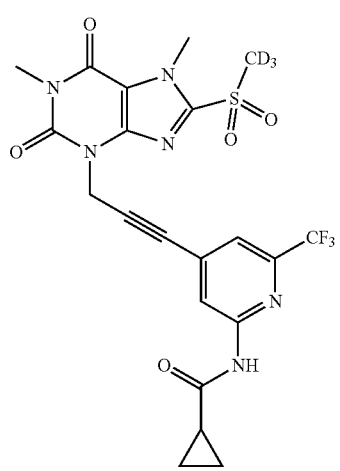 [SMILES: [2H]C([2H])([2H])S(=O)(=O)c1nc2c(c(=O)n(C)c(=O)n2CC#Cc2cc(NC(=O)C3CC3)nc(C(F)(F)F)c2)n1C]
108
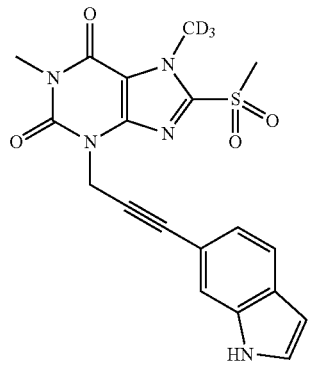 [SMILES: [2H]C([2H])([2H])n1c(S(C)(=O)=O)nc2c1c(=O)n(C)c(=O)n2CC#Cc1ccc2cc[nH]c2c1]
109
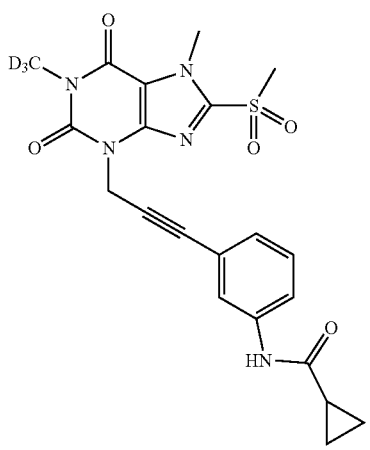 [SMILES: [2H]C([2H])([2H])n1c(=O)c2c(nc(S(C)(=O)=O)n2C)n(CC#Cc2cccc(NC(=O)C3CC3)c2)c1=O]
110
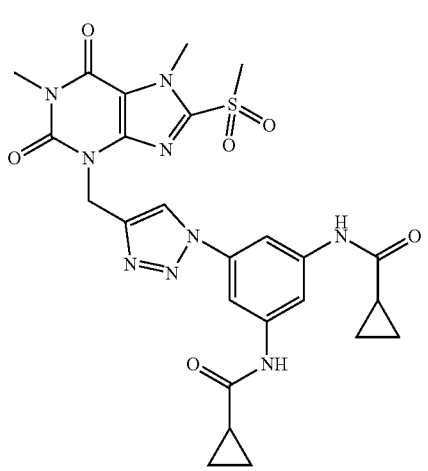 [SMILES: Cn1c(=O)c2c(nc(S(C)(=O)=O)n2C)n(Cc2cn(-c3cc(NC(=O)C4CC4)cc(NC(=O)C4CC4)c3)nn2)c1=O]
111

TABLE 7-continued
MLKL inhibitors
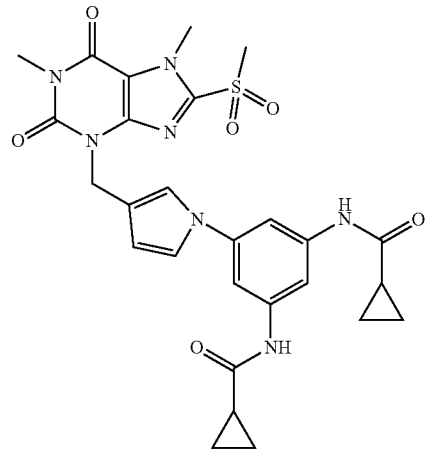 [SMILES: Cn1c(=O)c2c(nc(S(C)(=O)=O)n2C)n(Cc2ccn(-c3cc(NC(=O)C4CC4)cc(NC(=O)C4CC4)c3)c2)c1=O] 112
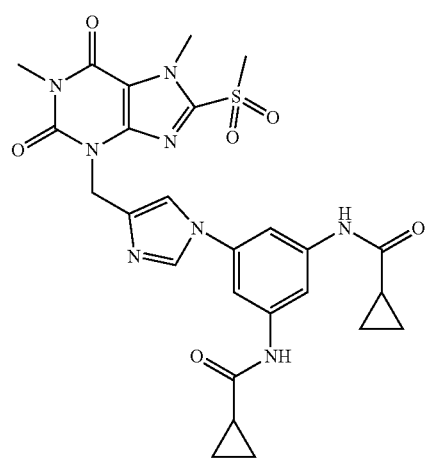 [SMILES: Cn1c(=O)c2c(nc(S(C)(=O)=O)n2C)n(Cc2cn(-c3cc(NC(=O)C4CC4)cc(NC(=O)C4CC4)c3)cn2)c1=O] 113
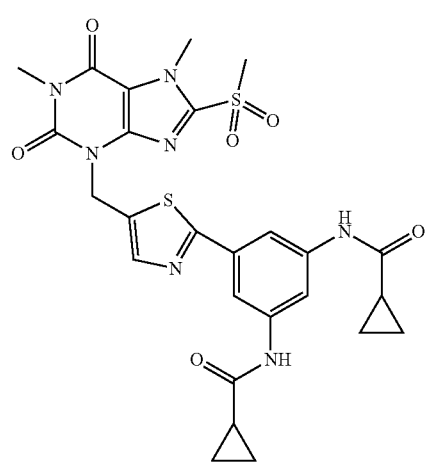 [SMILES: Cn1c(=O)c2c(nc(S(C)(=O)=O)n2C)n(Cc2cnc(-c3cc(NC(=O)C4CC4)cc(NC(=O)C4CC4)c3)s2)c1=O] 114
TABLE 7-continued
MLKL inhibitors
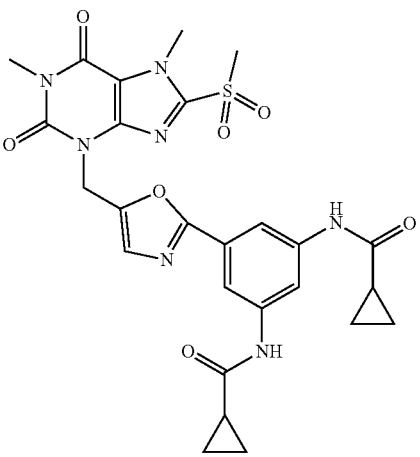 [SMILES: Cn1c(=O)c2c(nc(S(C)(=O)=O)n2C)n(Cc2cnc(-c3cc(NC(=O)C4CC4)cc(NC(=O)C4CC4)c3)o2)c1=O] 115
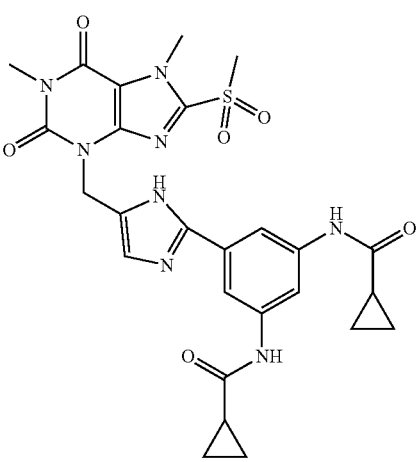 [SMILES: Cn1c(=O)c2c(nc(S(C)(=O)=O)n2C)n(Cc2cnc(-c3cc(NC(=O)C4CC4)cc(NC(=O)C4CC4)c3)[nH]2)c1=O] 116
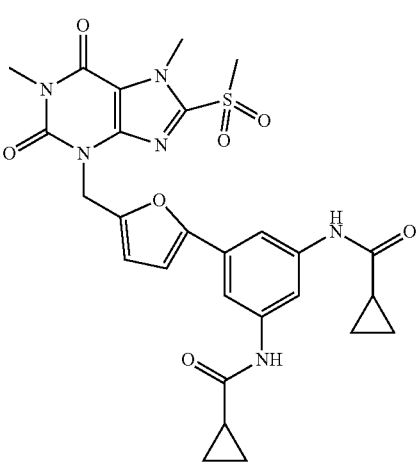 [SMILES: Cn1c(=O)c2c(nc(S(C)(=O)=O)n2C)n(Cc2ccc(-c3cc(NC(=O)C4CC4)cc(NC(=O)C4CC4)c3)o2)c1=O] 117

TABLE 7-continued

MLKL inhibitors

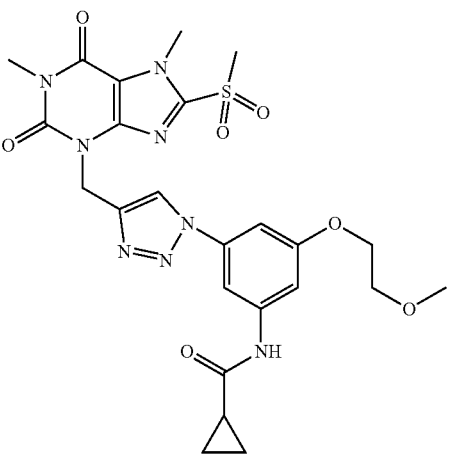

118

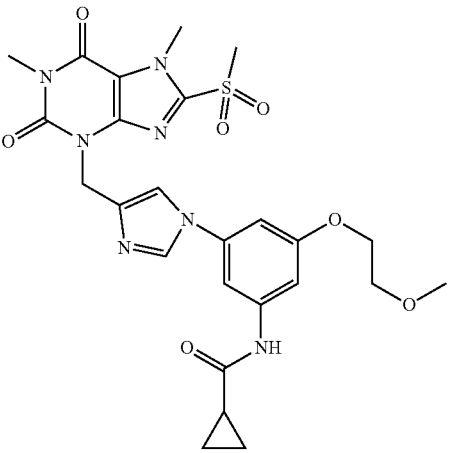

119

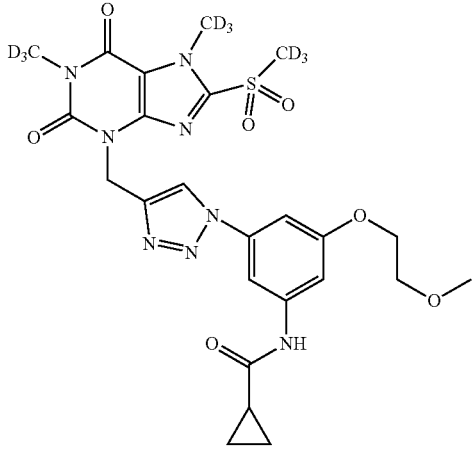 [SMILES: [2H]C([2H])([2H])n1c(=O)c2c(nc(S(=O)(=O)C([2H])([2H])[2H])n2C([2H])([2H])[2H])n(Cc2cn(-c3cc(NC(=O)C4CC4)cc(OCCOC)c3)nn2)c1=O]

120

Necroptosis in Testis is a Gateway for the Programmed Aging of Mouse Male Reproductive System We conducted histological analysis of major organs including small intestines, spleen, lung, liver, large intestines, kidney, heart, and brain of wild type and RIP3 knockout mice at 8 weeks, 4 months, 18 months, and 24 months of age and observed no noticeable differences between wild type and age-matched RIP3 knockout mice during the aging process.

The finding that the testes aging phenotype, including the enlargement of seminal vesicles, empty seminiferous tubules, and decreases in testosterone levels and fertility rates, could all be mimicked in young wild type mice, but not in RIP3 and MLKL knockout mice, following one administered necroptotic stimulus into their testes indicates that necroptosis causes male reproductive system aging. Consistently, the observation that phospho-Serine 345 on MLKL, a necroptotic activation marker, was only present in the seminiferous tubules of old wild type (i.e., not in testes of age-matched RIP3 or MLKL knockout mice) further substantiates this conclusion. Furthermore, mice lacking either of the core components of necroptosis (RIP3 or MLKL) maintained the youthful morphology and function of their male reproductive systems into advanced age.

However, the progenies sired by the old RIP3 knockout mice were less healthy than the progenies sired by young males; the RIP3 knockout progenies had higher rates of prenatal and postnatal death. We sequenced the genomic DNA from the sperm of three 18-month old RIP3 knockout mice and three 4-month old RIP3 knockout mice. The average mutation burden in the sperm of 18-month old knockout mice was not significantly higher than that of 4-month old mice. Thus, as far as could be ascertained via sequencing of genomic DNA, the increased lethality of the pups sired by these old RIP3 knockout mice was not due to significant accumulation of mutations in sperm. A more likely reason for the unhealthy offspring may be accumulated oxidative damage in the sperm DNA of aged RIP3 knockout mice, as the level of 8-hydroxydeoxyguanosine (8-OHdG), which is a biomarker for the oxidative damage of DNA (36), was significantly higher in the sperm of 18-month old RIP3 knockout mice than in 4-month old mice. Also, considering that the pituitary hormones LH and FSH declined in RIP3 knockout mice as they age (just like wild type mice), it is obvious that other age-related changes in DNA in their gametes and other organs occurred normally in these mutant mice. These results indicate that necroptosis in seminiferous tubules is a physiological response to an age-related, locally generated TNF family of cytokines. The necroptosis then triggers the aging of rest of male reproductive organ and other downstream age-related phenotype such as decrease in testosterone and weight gain. Indeed, the mice with their necroptosis blocked, either by genetic deletion of RIP3 and MLKL, or pharmaceutically by RIPA-56, showed much less age-associated wright gain.

The sex hormone-producing Leydig cells in testes do not express RIP3 yet, in aged mouse testis, the hormone level drops and Leydig cells are also gone. We therefore checked the cleavage status of procaspase-3 (a known marker of apoptosis) in the aged testes of wild type and RIP3 knockout mice using IHC. Cleaved procaspase-3 was detected in the wild type Leydig cells of 18-, 24-, and 36-month old mice, while no such signal was observed in RIP3 knockout mice. The cleaved caspase-3 was also detected by western blotting using extracts from the old wild type testes and was not present in RIP3 knockout testes. These results indicate that Leydig cells undergo apoptosis during aging, apparently a consequence of necroptosis.

The aging of the male reproductive system is inhibited when mice are fed with food containing a RIP1, RIP3 or MLKL inhibitor starting immediately at the onset of reproductive system aging phenotype (13 months). This finding not only further confirms that necroptosis is the mechanism underlying aging of the male reproductive system aging, but also provides an effective treatment to delay it.

REFERENCES AND NOTES

Cai, Z., Jitkaew, S., Zhao, J., Chiang, H. C., Choksi, S., Liu, J., Ward, Y., Wu, L. G., and Liu, Z. G. (2014). Plasma membrane translocation of trimerized MLKL protein is required for TNF-induced necroptosis. Nat Cell Biol 16, 55-65.

Chang, Y. F., Lee-Chang, J. S., Panneerdoss, S., MacLean, J. A., 2nd, and Rao, M. K. (2011). Isolation of Sertoli, Leydig, and spermatogenic cells from the mouse testis. Biotechniques 51, 341-342, 344.

Chen, X., Li, W., Ren, J., Huang, D., He, W. T., Song, Y., Yang, C., Li, W., Zheng, X., Chen, P., et al. (2014). Translocation of mixed lineage kinase domain-like protein to plasma membrane leads to necrotic cell death. Cell Res 24, 105-121.

Chigurupati, S., Son, T. G., Hyun, D. H., Lathia, J. D., Mughal, M. R., Savell, J., Li, S. C., Nagaraju, G. P., Chan, S. L., Arumugam, T. V., et al. (2008). Lifelong running reduces oxidative stress and degenerative changes in the testes of mice. J Endocrinol 199, 333-341.

Cho, Y. S., Challa, S., Moquin, D., Genga, R., Ray, T. D., Guildford, M., and Chan, F. K. (2009). Phosphorylation-driven assembly of the RIP1-RIP3 complex regulates programmed necrosis and virus-induced inflammation. Cell 137, 1112-1123.

Christofferson, D. E., and Yuan, J. (2010). Necroptosis as an alternative form of programmed cell death. Curr Opin Cell Biol 22, 263-268.

Cooke, H. J., and Saunders, P. T. (2002). Mouse models of male infertility. Nat Rev Genet 3, 790-801.

Degterev, A., Hitomi, J., Germscheid, M., Ch'en, I. L., Korkina, O., Teng, X., Abbott, D., Cuny, G. D., Yuan, C., Wagner, G., et al. (2008). Identification of RIP1 kinase as a specific cellular target of necrostatins. Nat Chem Biol 4, 313-321.

Finch, C. E., and Girgis, F. G. (1974). Enlarged seminal vesicles of senescent C57BL-6J mice. J Gerontol 29, 134-138.

Gonzales, G. F. (2001). Function of seminal vesicles and their role on male fertility. Asian J Androl 3, 251-258.

He, S., Wang, L., Miao, L., Wang, T., Du, F., Zhao, L., and Wang, X. (2009). Receptor interacting protein kinase-3 determines cellular necrotic response to TNF-alpha. Cell 137, 1100-1111.

Hentrich, A., Wolter, M., Szardening-Kirchner, C., Luers, G. H., Bergmann, M., Kliesch, S., and Konrad, L. (2011). Reduced numbers of Sertoli, germ, and spermatogonial stem cells in impaired spermatogenesis. Mod Pathol 24, 1380-1389.

Hofmann, J. W., Zhao, X., De Cecco, M., Peterson, A. L., Pagliaroli, L., Manivannan, J., Hubbard, G. B., Ikeno, Y., Zhang, Y., Feng, B., et al. (2015). Reduced expression of MYC increases longevity and enhances healthspan. Cell 160, 477-488.

Holler, N., Zaru, R., Micheau, O., Thome, M., Attinger, A., Valitutti, S., Bodmer, J. L., Schneider, P., Seed, B., and Tschopp, J. (2000). Fas triggers an alternative, caspase-8-independent cell death pathway using the kinase RIP as effector molecule. Nat Immunol 1, 489-495.

Hooley, R. P., Paterson, M., Brown, P., Kerr, K., and Saunders, P. T. (2009). Intra-testicular injection of adeno-viral constructs results in Sertoli cell-specific gene expression and disruption of the seminiferous epithelium. Reproduction 137, 361-370.

Johnson, S. L., Dunleavy, J., Gemmell, N. J., and Nakagawa, S. (2015). Consistent age-dependent declines in human semen quality: a systematic review and meta-analysis. Ageing research reviews 19, 22-33.

Jung, H., Roser, J. F., and Yoon, M. (2014). UTF1, a putative marker for spermatogonial stem cells in stallions. PLoS One 9, e108825.

Meng, L., Jin, W., and Wang, X. (2015). RIP3-mediated necrotic cell death accelerates systematic inflammation and mortality. Proc Natl Acad Sci USA 112, 11007-11012.

Murphy, J. M., Czabotar, P. E., Hildebrand, J. M., Lucet, I. S., Zhang, J. G., Alvarez-Diaz, S., Lewis, R., Lalaoui, N., Metcalf, D., Webb, A. I., et al. (2013). The pseudokinase MLKL mediates necroptosis via a molecular switch mechanism. Immunity 39, 443-453.

Newton, K., Sun, X., and Dixit, V. M. (2004). Kinase RIP3 is dispensable for normal NF-kappa Bs, signaling by the B-cell and T-cell receptors, tumor necrosis factor receptor 1, and Toll-like receptors 2 and 4. Molecular and cellular biology 24, 1464-1469.

Paul, C., Nagano, M., and Robaire, B. (2011). Aging results in differential regulation of DNA repair pathways in pachytene spermatocytes in the Brown Norway rat. Biol Reprod 85, 1269-1278.

Pettan-Brewer, C., and Treuting, P. M. (2011). Practical pathology of aging mice. Pathobiol Aging Age Relat Dis 1.

Ren, Y., Su, Y., Sun, L., He, S., Meng, L., Liao, D., Liu, X., Ma, Y., Liu, C., Li, S., et al. (2017). Discovery of a Highly Potent, Selective, and Metabolically Stable Inhibitor of Receptor-Interacting Protein 1 (RIP1) for the Treatment of Systemic Inflammatory Response Syndrome. Journal of medicinal chemistry 60, 972-986.

Robinson, N., McComb, S., Mulligan, R., Dudani, R., Krishnan, L., and Sad, S. (2012). Type I interferon induces necroptosis in macrophages during infection with *Salmonella enterica* serovar Typhimurium. Nature immunology 13, 954-962.

Rodriguez, D. A., Weinlich, R., Brown, S., Guy, C., Fitzgerald, P., Dillon, C. P., Oberst, A., Quarato, G., Low, J., Cripps, J. G., et al. (2016). Characterization of RIPK3-mediated phosphorylation of the activation loop of MLKL during necroptosis. Cell Death Differ 23, 76-88.

Schurmann, A., Koling, S., Jacobs, S., Saftig, P., Krauss, S., Wennemuth, G., Kluge, R., and Joost, H. G. (2002). Reduced sperm count and normal fertility in male mice with targeted disruption of the ADP-ribosylation factor-like 4 (Arl4) gene. Mol Cell Biol 22, 2761-2768.

Sun, L., Wang, H., Wang, Z., He, S., Chen, S., Liao, D., Wang, L., Yan, J., Liu, W., Lei, X., et al. (2012). Mixed lineage kinase domain-like protein mediates necrosis signaling downstream of RIP3 kinase. Cell 148, 213-227.

Tsai, M. Y., Yeh, S. D., Wang, R. S., Yeh, S., Zhang, C., Lin, H. Y., Tzeng, C. R., and Chang, C. (2006). Differential effects of spermatogenesis and fertility in mice lacking androgen receptor in individual testis cells. Proc Natl Acad Sci USA 103, 18975-18980.

Upton, J. W., Kaiser, W. J., and Mocarski, E. S. (2010). Virus inhibition of RIP3-dependent necrosis. Cell host & microbe 7, 302-313.

van Bragt, M. P., Roepers-Gajadien, H. L., Korver, C. M., Bogerd, J., Okuda, A., Eggen, B. J., de Rooij, D. G., and van Pelt, A. M. (2008). Expression of the pluripotency marker UTF1 is restricted to a subpopulation of early A spermatogonia in rat testis. Reproduction 136, 33-40.

Vandenabeele, P., Galluzzi, L., Vanden Berghe, T., and Kroemer, G. (2010). Molecular mechanisms of necroptosis: an ordered cellular explosion. Nat Rev Mol Cell Biol 11, 700-714.

Vermeulen, A., Kaufman, J. M., and Giagulli, V. A. (1996). Influence of some biological indexes on sex hormone-binding globulin and androgen levels in aging or obese males. The Journal of clinical endocrinology and metabolism 81, 1821-1826.

Wang, H., Sun, L., Su, L., Rizo, J., Liu, L., Wang, L. F., Wang, F. S., and Wang, X. (2014). Mixed lineage kinase domain-like protein MLKL causes necrotic membrane disruption upon phosphorylation by RIP3. Molecular cell 54, 133-146.

Wang, L., Du, F., and Wang, X. (2008). TNF-alpha induces two distinct caspase-8 activation pathways. Cell 133, 693-703.

Wu, J., Huang, Z., Ren, J., Zhang, Z., He, P., Li, Y., Ma, J., Chen, W., Zhang, Y., Zhou, X., et al. (2013). Mild knockout mice demonstrate the indispensable role of Mlkl in necroptosis. Cell research 23, 994-1006.

Zhang, D. W., Shao, J., Lin, J., Zhang, N., Lu, B. J., Lin, S. C., Dong, M. Q., and Han, J. (2009). RIP3, an energy metabolism regulator that switches TNF-induced cell death from apoptosis to necrosis. Science 325, 332-336.

Zhou, W., and Yuan, J. (2014). Necroptosis in health and diseases. Seminars in cell & developmental biology 35, 14-23.

What is claimed is:

1. A method of treating male senescence comprising administering to a male in need thereof a necroptosis inhibitor.

2. The method of claim 1 wherein the necroptosis inhibitor is a RIP1, RIP3 or MLKL inhibitor.

3. The method of claim 1 wherein the necroptosis inhibitor is a RIP1 inhibitor.

4. The method of claim 1 wherein the necroptosis inhibitor is a RIP1 inhibitor selected from a compound of Table 1 or Table 2 or Table 3:

Table 1
5-((1H-indol3-yl)methyl)-3-methyl-2-thioxoimidazolidin-4-one (Nec-1)
(S)-phenyl(5-phenyl -4,5-dihydro-1H-pyrazol -1-yl) methanone
5-((1H-indol-3-yl)methyl)-3-methyl-2-thioxoimidazolidin-4-one (Nec-1s)
3-methyl-5-((7-methyl-1H-indol3-yl)methyl)imidazolidine-2,4-dione
(R)-5-((7-chloro-1H-indol3-yl)methyl)-3-methylimidazolidine-2,4-dione
(R)-5-((7-chloro-1H-indol3-yl)methyl)-3-(4-(3-(imidazo[1,2-b]pyridazin-3-ylethynyl)-4-methylphenyl)butyl) imidazolidine-2,4-dione (Ponatinib-Nec1s)
(S)-2,2-dimethyl-1-(5-phenyl-4,5-dihydro-1H-pyrazol-1-yl) propan-1-on (GSK963)
(S)-2,2-dimethyl-1-(5-phenyl-4,5-dihydro-1H-pyrazol-1-yl) propan-1-one
(S)-1-(4-(5-phenyl-4,5-dihydro-1H-pyrazole-1-carbonyl) piperidin-1-yl)ethanone
(S)-2,2-dimethyl-1-(5-(pyridin-2-yl)-4,5-dihydro-1H-pyrazol-1 -yl)propan-1-one
(S)-1-(4-(5-(3 ,5-difluorophenyl)-4,5-dihydro-1H-pyrazol-1 -carbonyl)piperidin-1-yl)ethanone
(S)-5-benzyl-N-(5-methyl-4-oxo-2,3,4,5-tetrahydrobenzo[b][1,4]oxazepin-3-yl)isoxazole-3-carboxamide
5-benzyl-N-(5-methyl-4-oxo-2,3,4,5-tetrahydrobenzo[b][1,4]oxazepin-3-yl)-4H-1,2,4-triazole-3-carboxamide
(S)-5-benzyl-N-(8-chloro-4-oxo-2,3,4,5-tetrahydrobenzo[b][1,4]oxazepin-3-yl)-4H-1,2,4-triazole-3-carboxamide
(S)-5-benzyl-N-(5-methyl-4-oxo-7-(1H-tetrazol-5 -yl)-2,3,4,5-tetrahydrobenzo[b][1,4]oxazepin-3-yl) isoxazole-3-carboxamide
8-bromo-4, 5-dihydro-1H-benzo[b]azepin-2(3H)-one
(S)-5-benzyl-N-(5-methyl-4-oxo-2,3,4,5-tetrahydrobenzo[b][1,4]oxazepin-3 -yl)isoxazole-3 -carboxamide (GSK481)
(S)-5-benzyl-N-(5-methyl-4-oxo-2,3,4,5-tetrahydrobenzo[b]-[1,4]oxazepin-3-yl)-1H-1,2,4-triazole-3-carboxamide (GSK2982772)
1-(4-(4-aminofuro[2,3 -d]pyrimidin-5-yl)phenyl)-3 -(2-fluoro-5-(trifluoromethyl)phenyl)urea (Cpd27)
3-methyl-5-((7-methyl-1H-indol1-3-yl)methyl)imidazolidine-2,4-dione
(R)-5-((7-chloro-1H-indol1-3-yl)methyl)-3-methylimidazolidine-2,4-dione
3 -benzyl-6,7-dihydro-3H-cyclopenta[4,5]thieno[2,3-d] pyrimidin-4(5H)-one
N-(3-chloro-2,6-difluorobenzyl)-4-cyclopropyl-1,2,3-thiadiazole-5 -carboxamide
(S)-N-(1-(2-chloro-6-fluorophenyl)ethyl)-5 -cyano-1-methyl-1H-pyrrole-2-carboxamide
(S)-N-(1-(2-chloro-6-fluorophenyl)ethyl)-4-cyclopropyl -1,2, 3-thiadiazole-5-carboxamide
N-Benzyl -N-hydroxy-2,2-dimethylbutanamide
N-(4-Fluorobenzyl)-N-hydroxy-2,2-dimethylbutanamide
N-(2,4-Difluorobenzyl)-N-hydroxy-2,2-dimethylbutanamide
N-(3,4-Difluorobenzyl)-N-hydroxy-2,2-dimethylbutanamide
N-Hydroxy-2,2-dimethyl -N-(2,3,4-trifluorobenzyl)butanamide
N-Hydroxy-2,2-dimethyl -N-(3,4,5-trifluorobenzyl)butanamide
N-Hydroxy-2,2-dimethyl -N-(2,3,5-trifluorobenzyl)butanamide
(2-(3-fluorophenyl)pyrrolidin-1-yl)(1-(trifluoromethyl) cyclopentyl)methanone
(2-(3-fluorophenyl)pyrrolidin-1-yl)(1-(trifluoromethyl) cyclobutyl)methanone
(S)-1-(2,2-dimethylbut-3-enoyl)-4-phenylazetidin-2-one
(S)-2,2-dimethyl-1-(2-phenylazetidin-1-yl)but-3-yn-1-one
(S)-1-(2,2-dimethylbutanoyl)-4-phenylazetidin-2-one,

TABLE 2

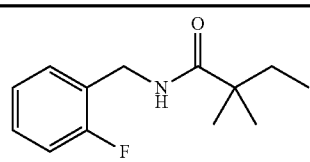

1

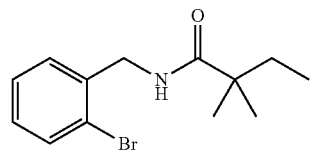

3

TABLE 2-continued
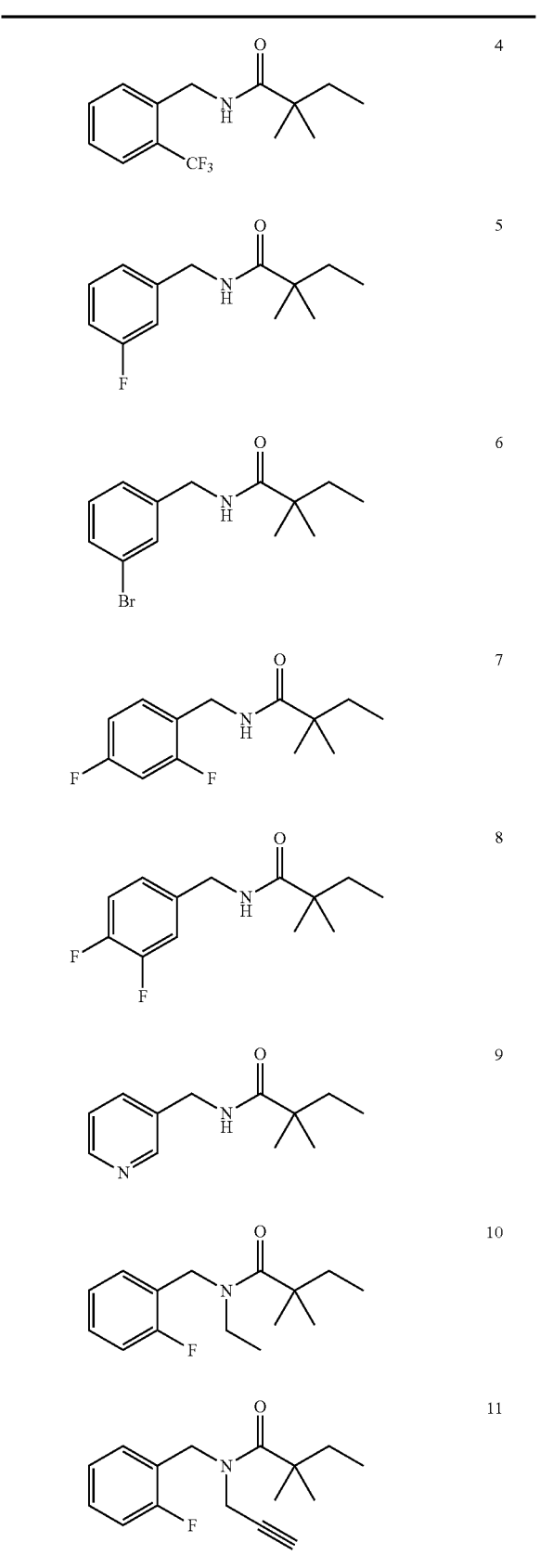
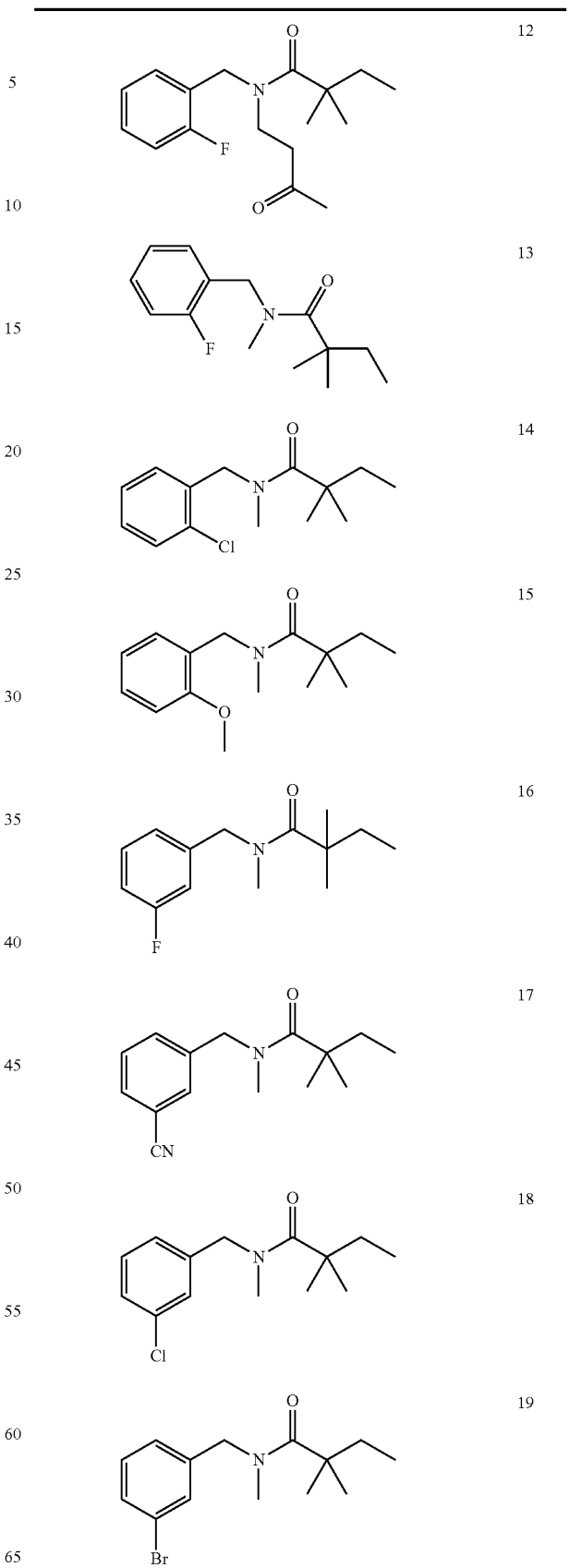

TABLE 2-continued
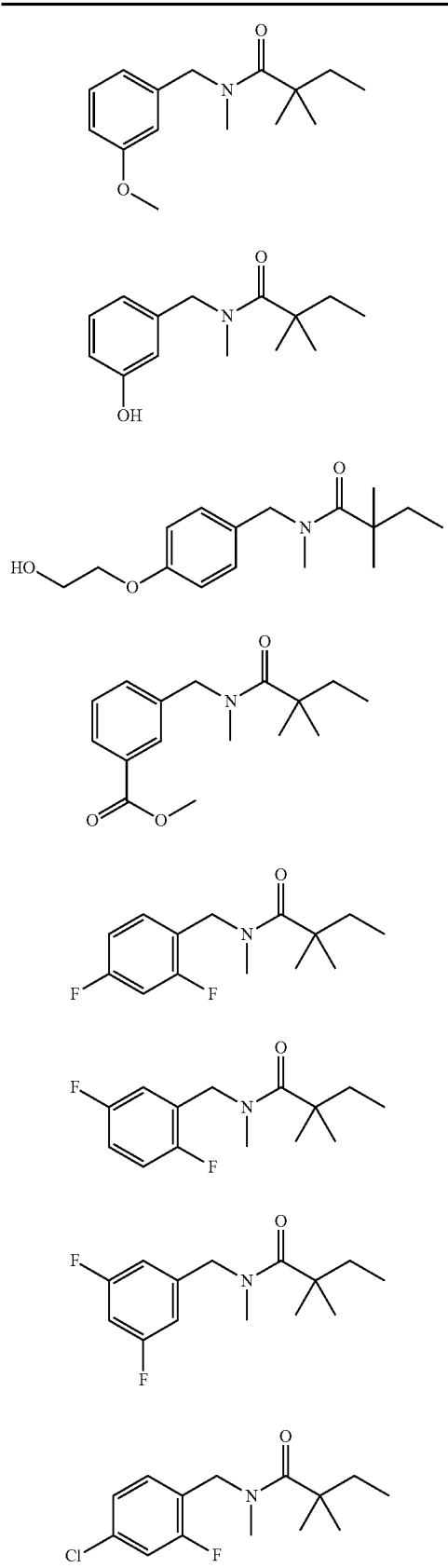
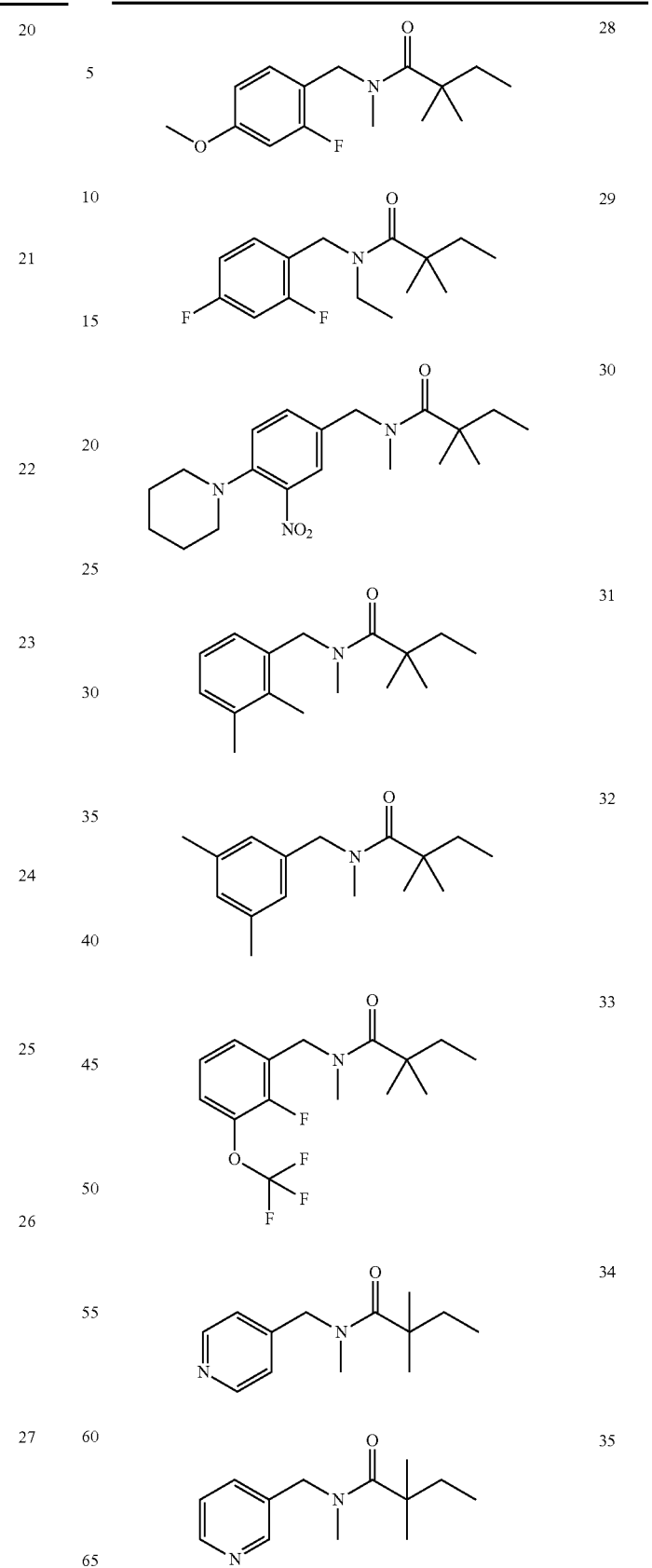

TABLE 2-continued
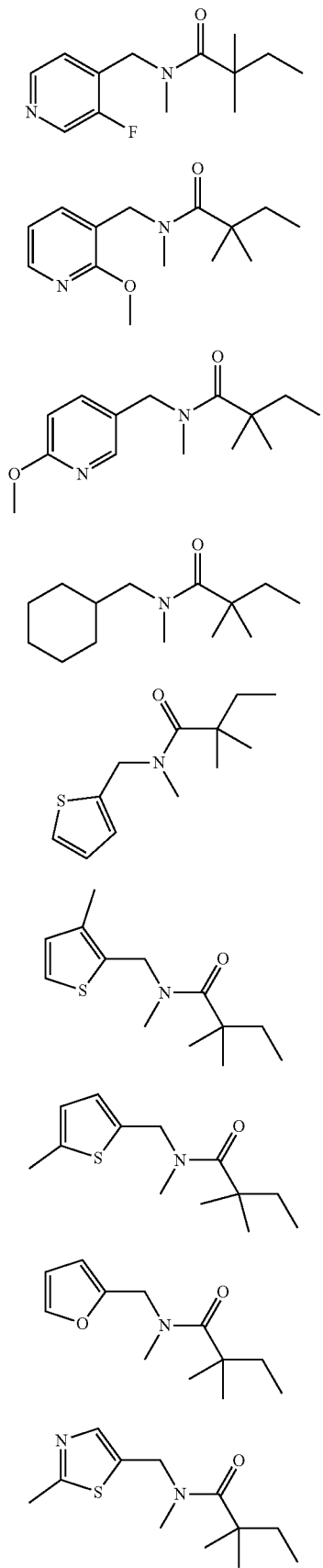
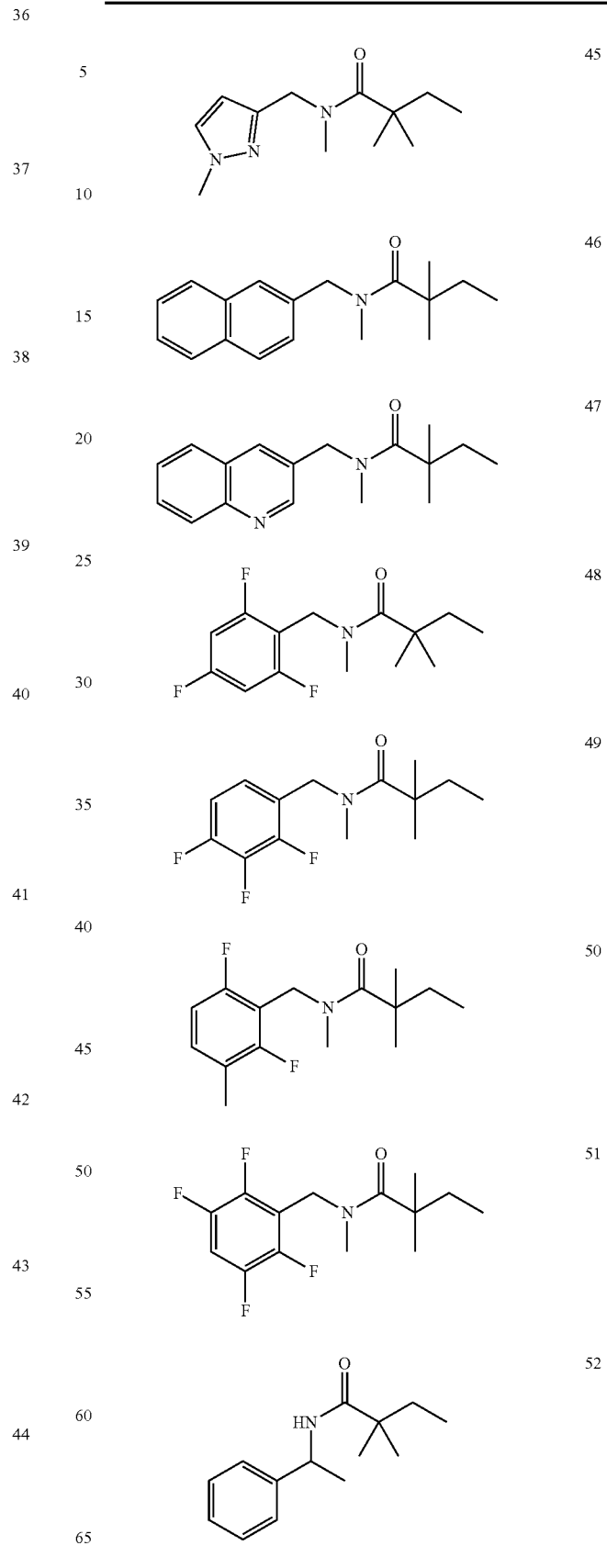

TABLE 2-continued
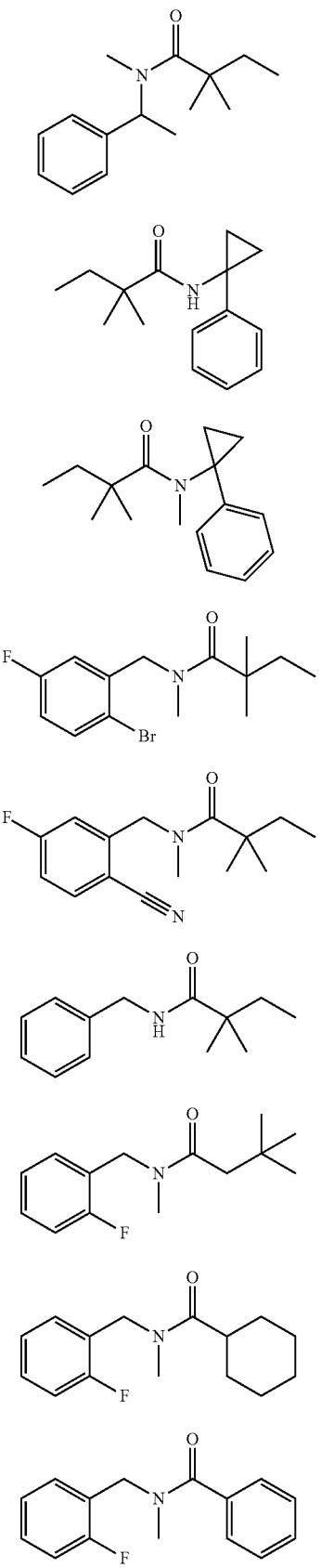
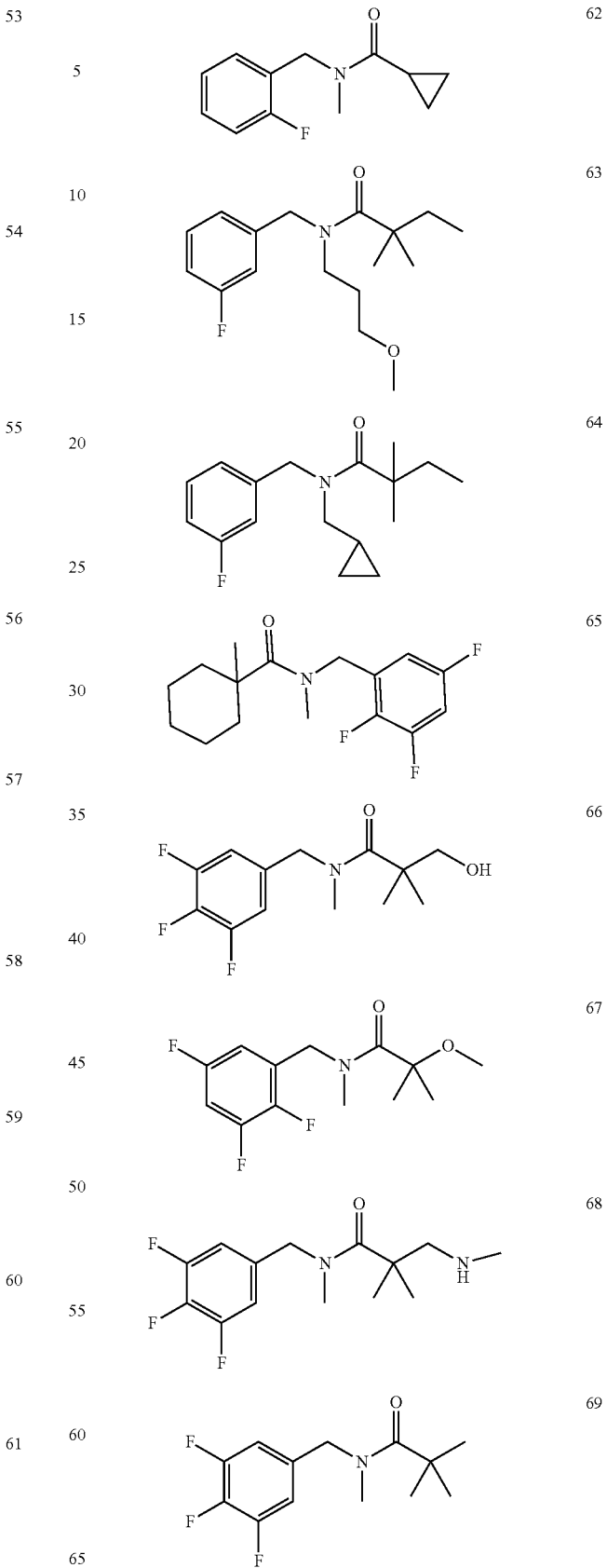

TABLE 2-continued
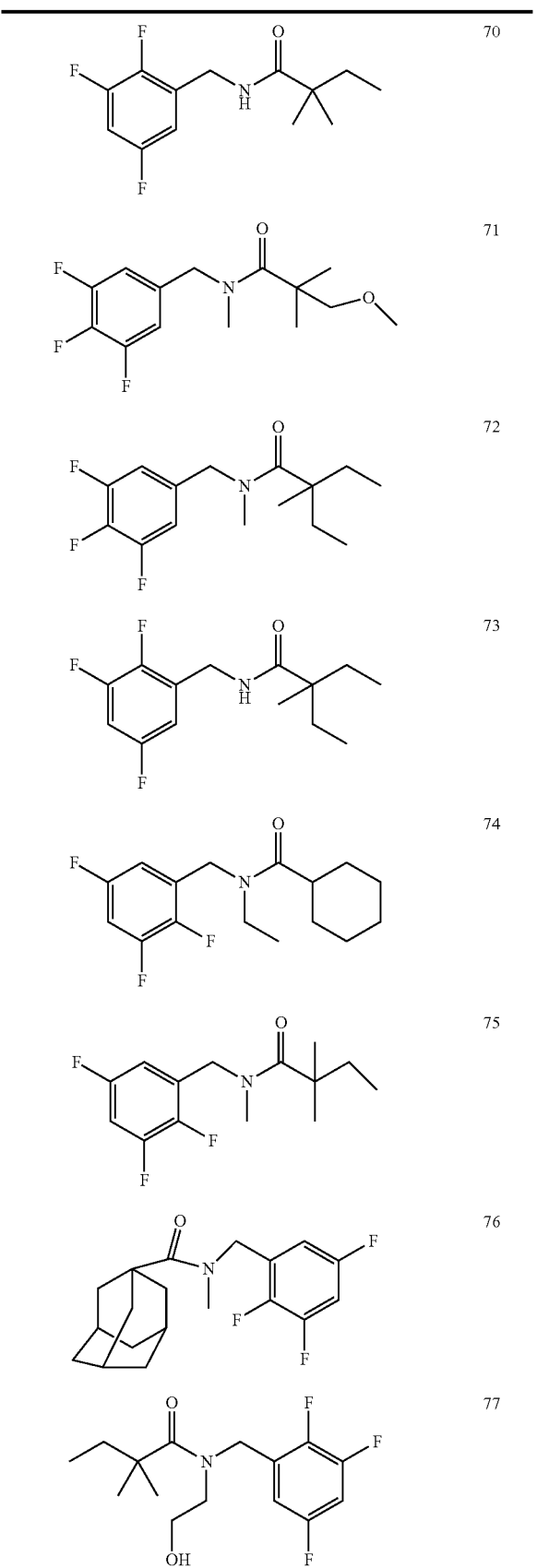
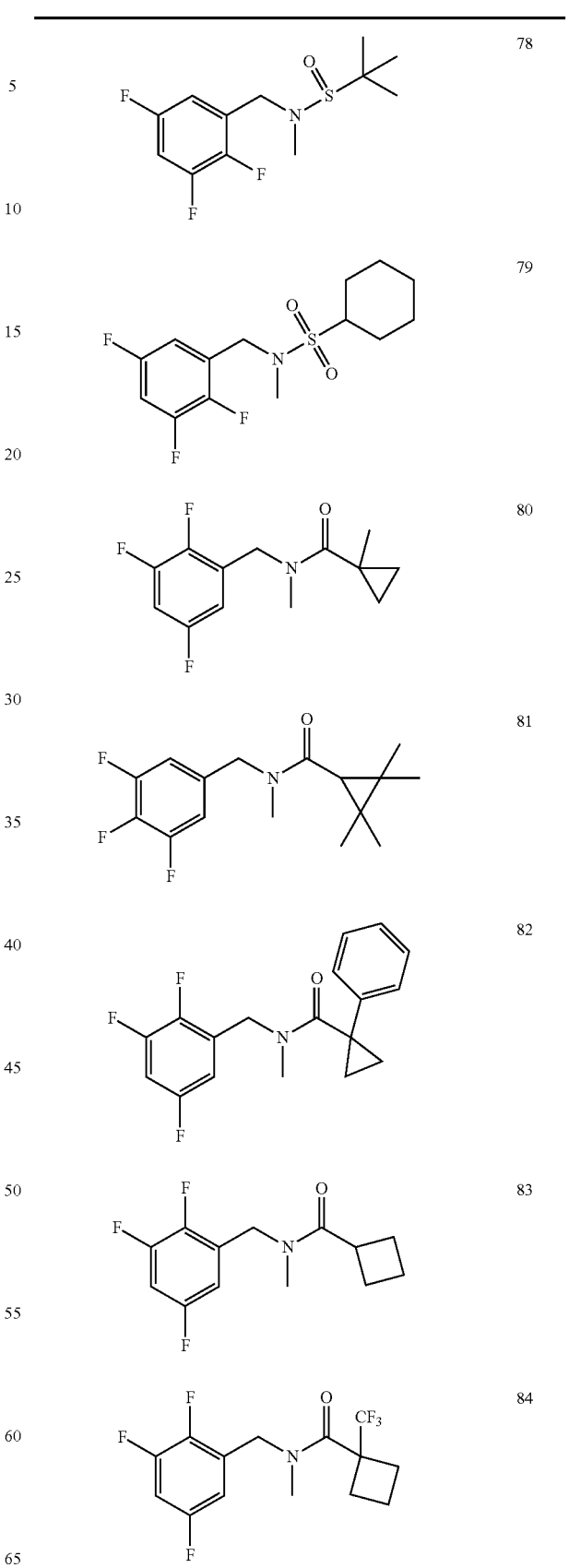

TABLE 2-continued
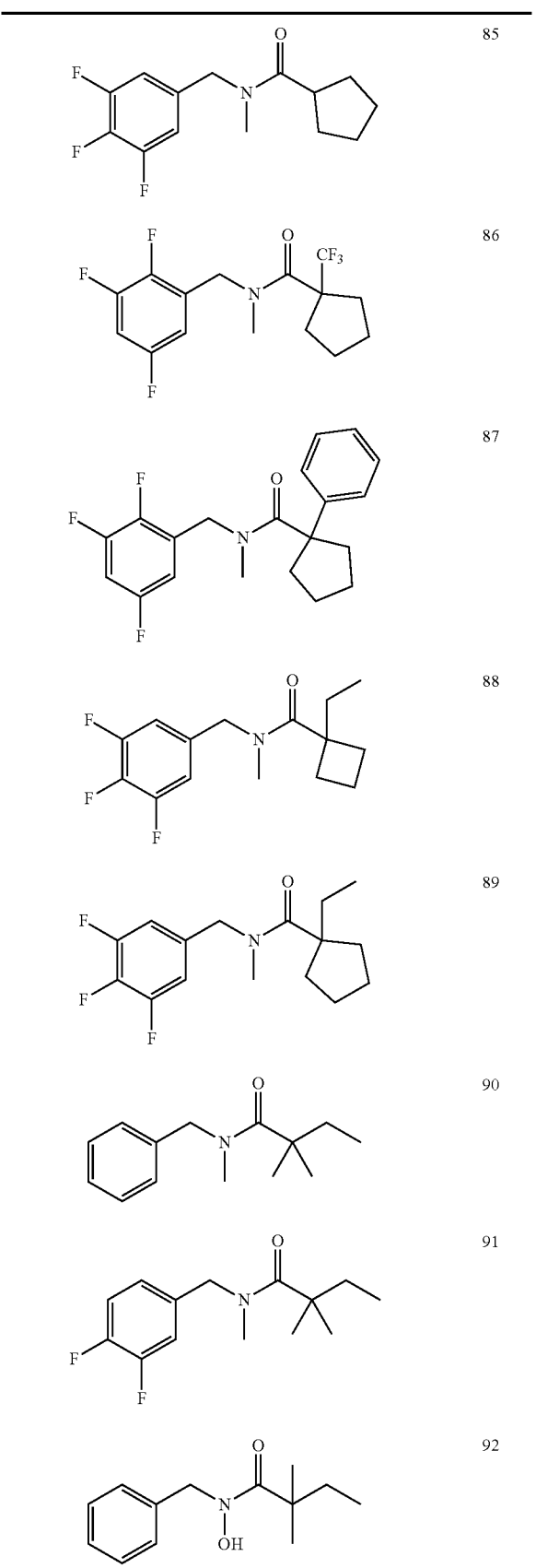
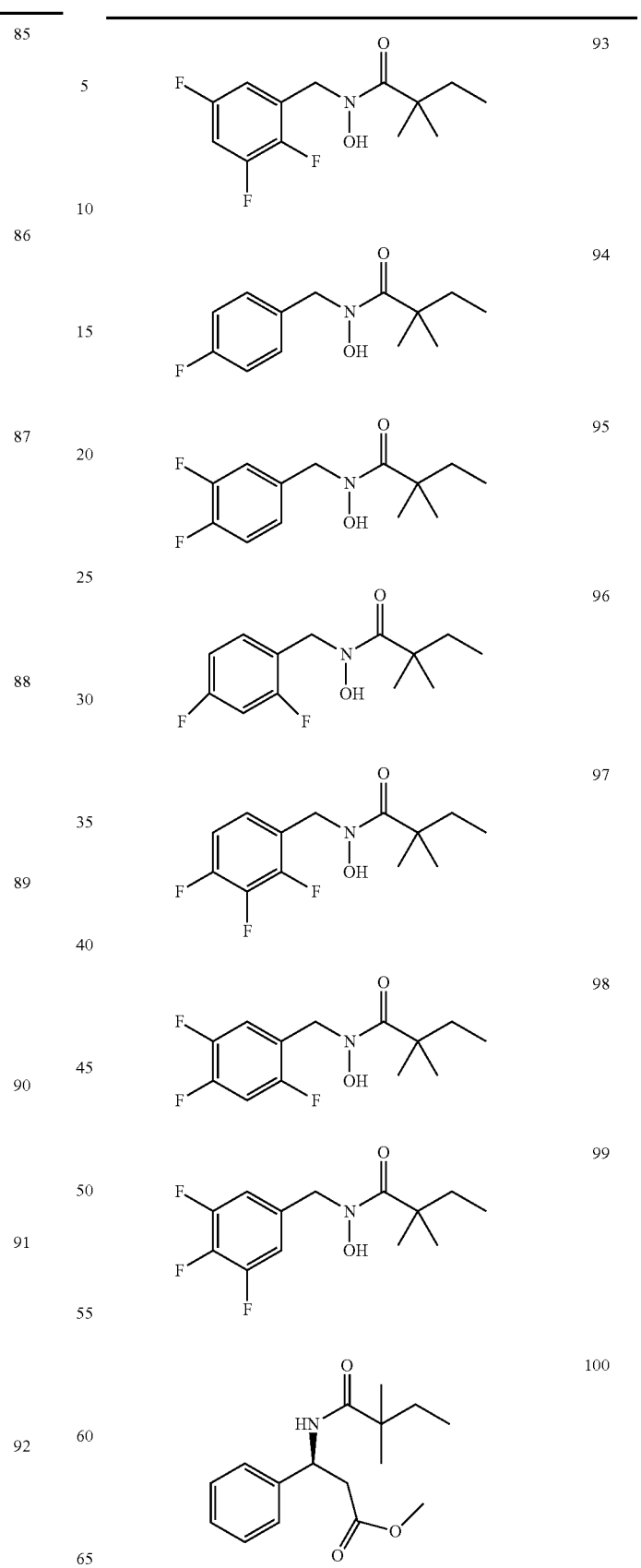

TABLE 2-continued
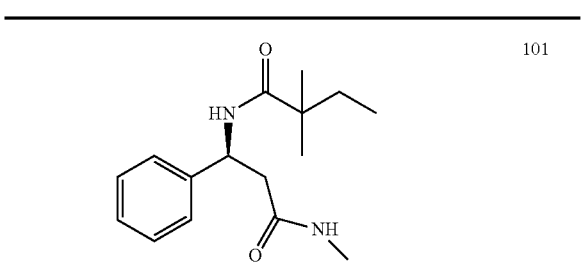 101
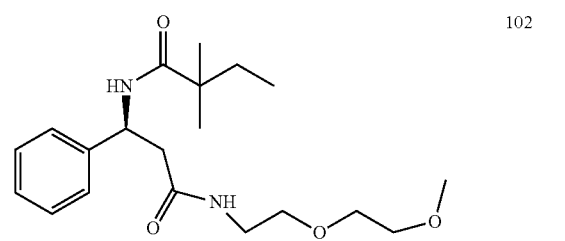 102
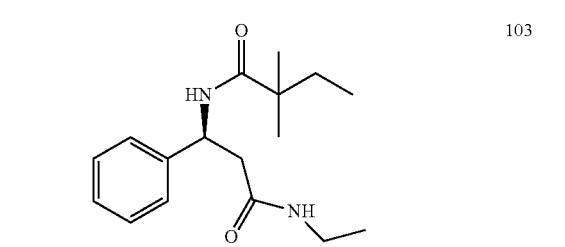 103
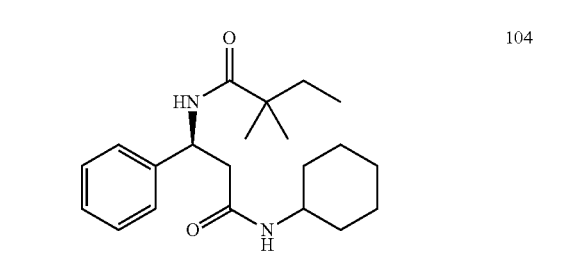 104
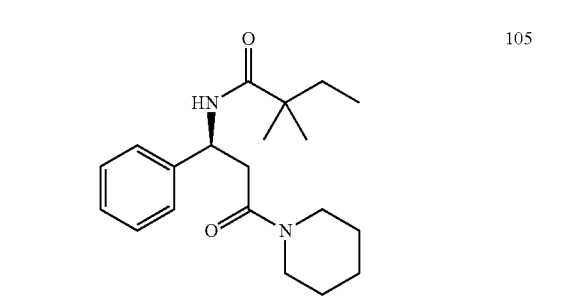 105
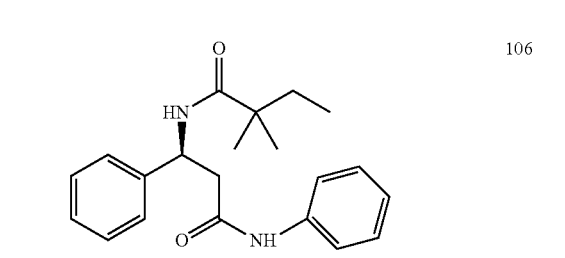 106
TABLE 2-continued
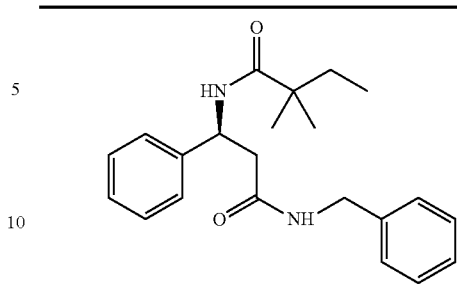 107
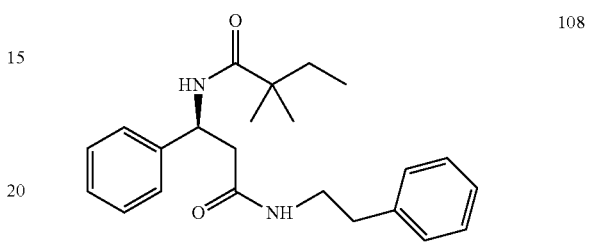 108
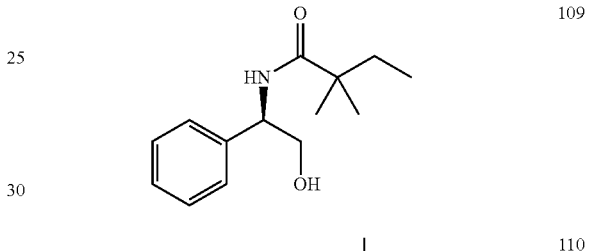 109
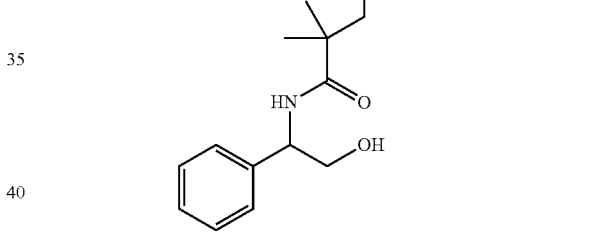 110
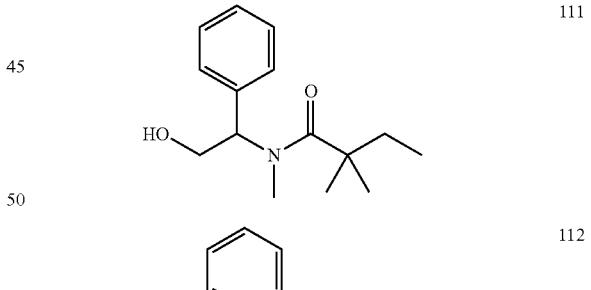 111
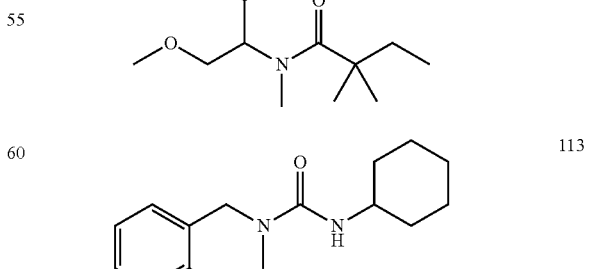 112
113

TABLE 2-continued
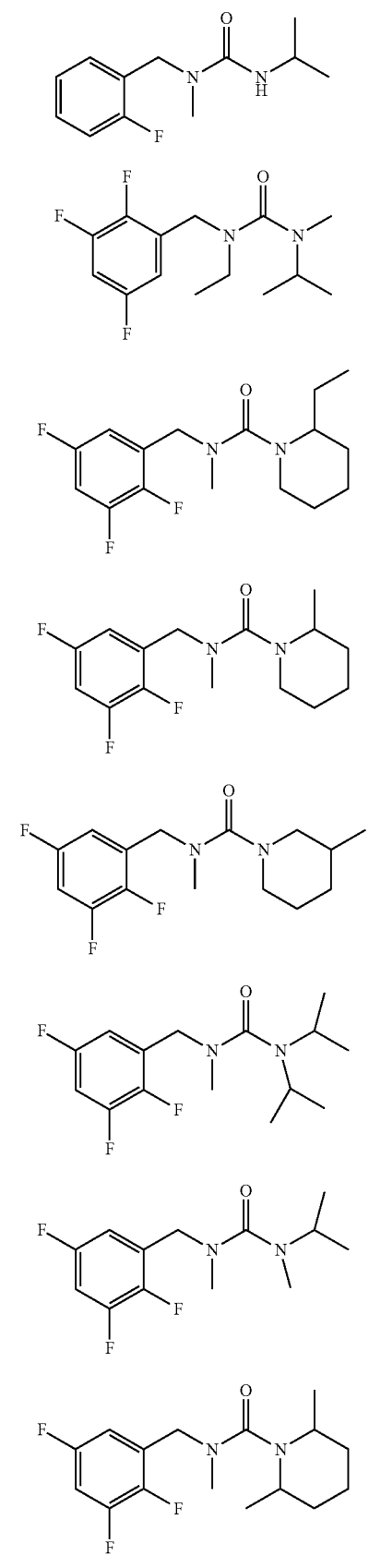
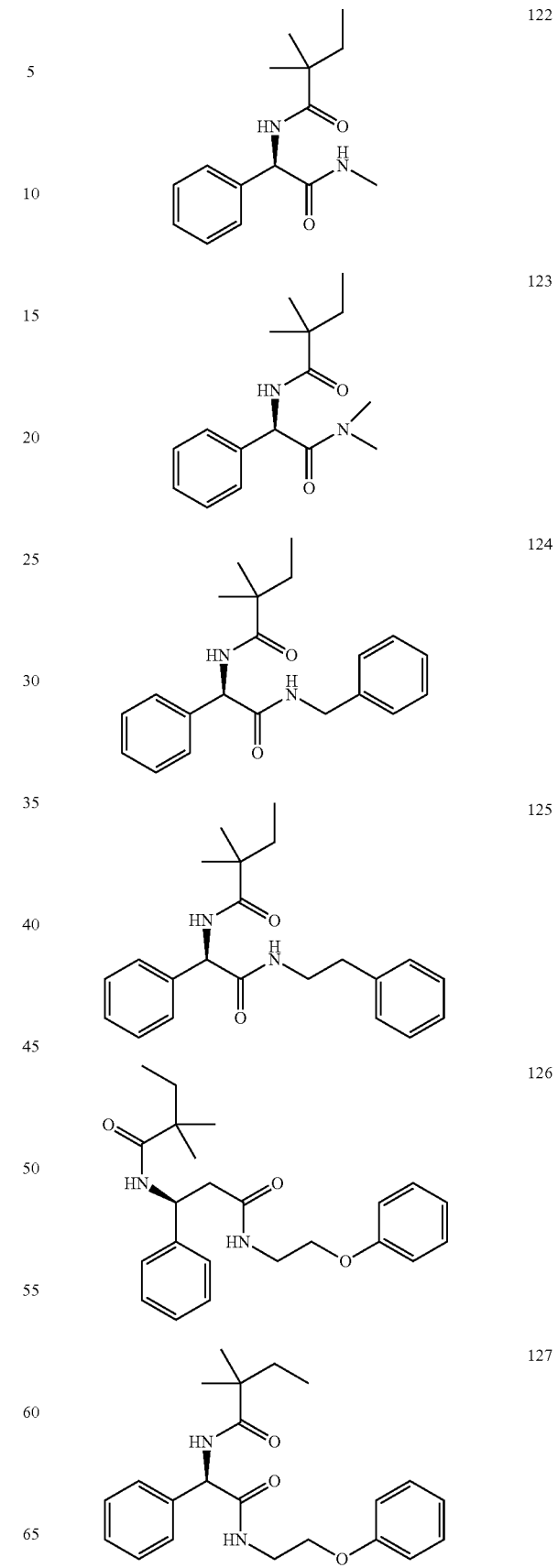

TABLE 2-continued
| | |
|---|---|
| 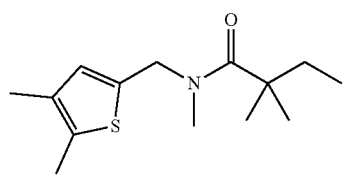 [SMILES: CCC(C)(C)C(=O)N(C)Cc1cc(C)c(C)s1] | 128 |
| 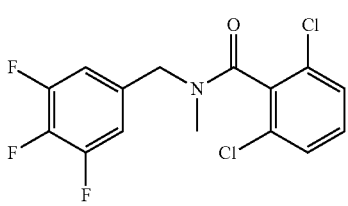 [SMILES: CN(Cc1cc(F)c(F)c(F)c1)C(=O)c1c(Cl)cccc1Cl] | 129 |
| 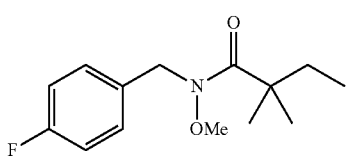 [SMILES: CCC(C)(C)C(=O)N(Cc1ccc(F)cc1)OC] | 130 |
| 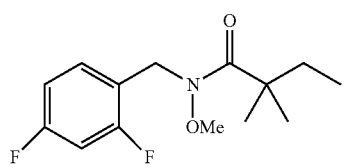 [SMILES: CCC(C)(C)C(=O)N(Cc1ccc(F)cc1F)OC] | 131 |
| 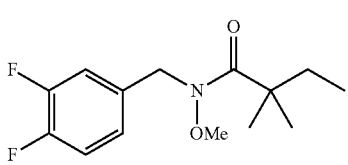 [SMILES: CCC(C)(C)C(=O)N(Cc1ccc(F)c(F)c1)OC] | 132 |
| 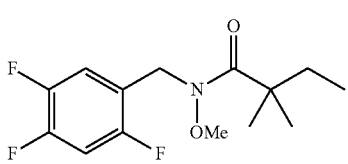 [SMILES: CCC(C)(C)C(=O)N(Cc1cc(F)c(F)cc1F)OC] | 133 |
| 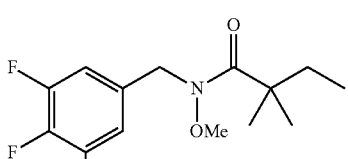 | 134 |
| 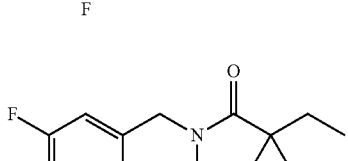 | 135 |
TABLE 2-continued
| | |
|---|---|
| 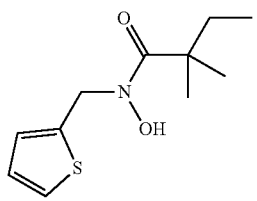 | 136 |
| 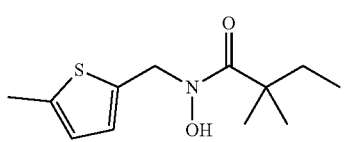 [SMILES: CCC(C)(C)C(=O)N(O)Cc1ccc(C)s1] | 137 |
| 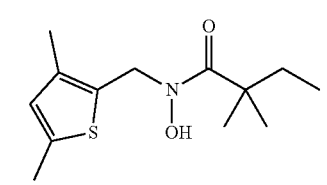 [SMILES: CCC(C)(C)C(=O)N(O)Cc1sc(C)cc1C] | 138 |
| 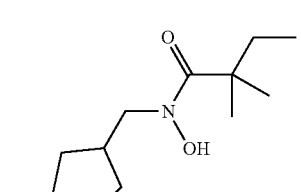 | 139 |
| 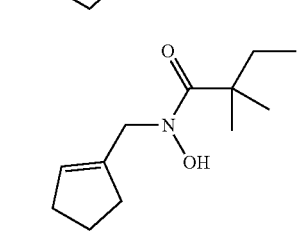 | 140 |
| 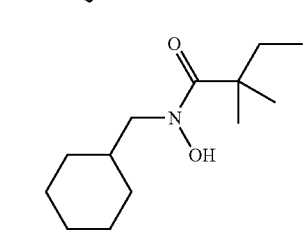 | 141 |
| 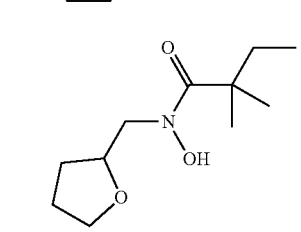 | 142 |
| 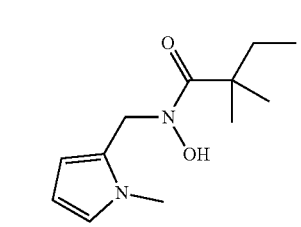 [SMILES: CCC(C)(C)C(=O)N(O)Cc1cccn1C] | 143 |

TABLE 2-continued
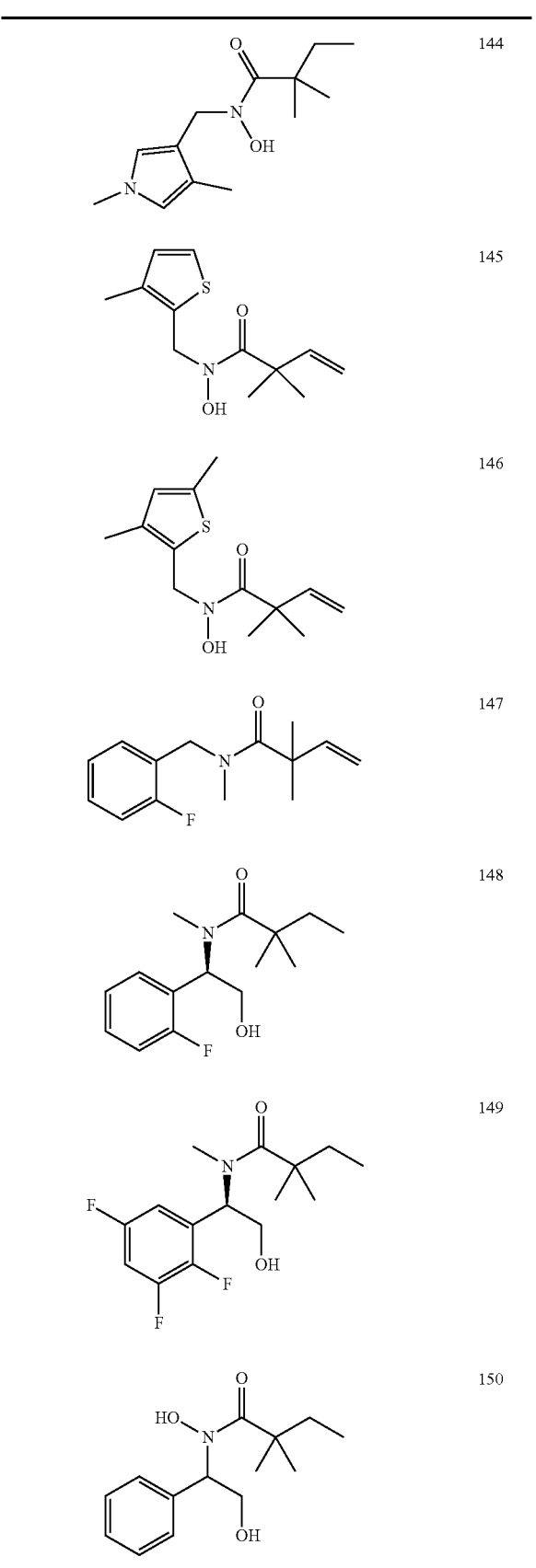
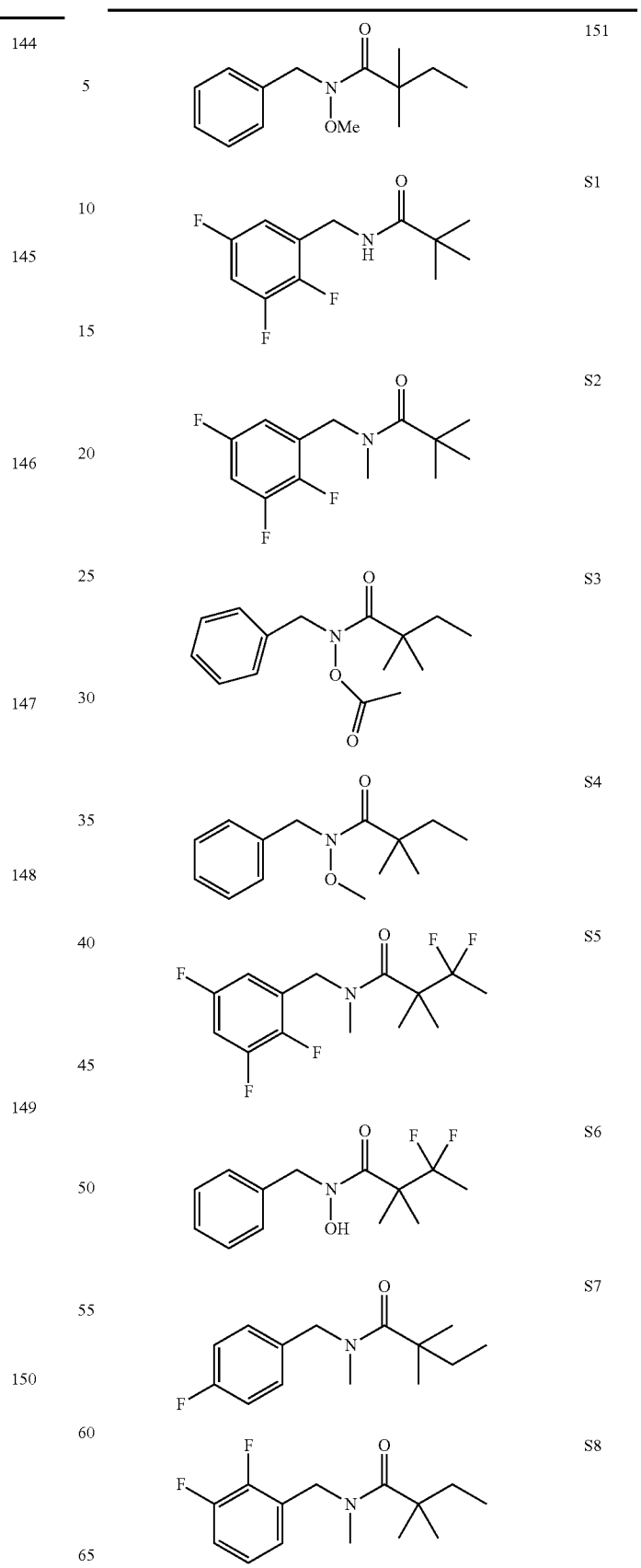

TABLE 2-continued
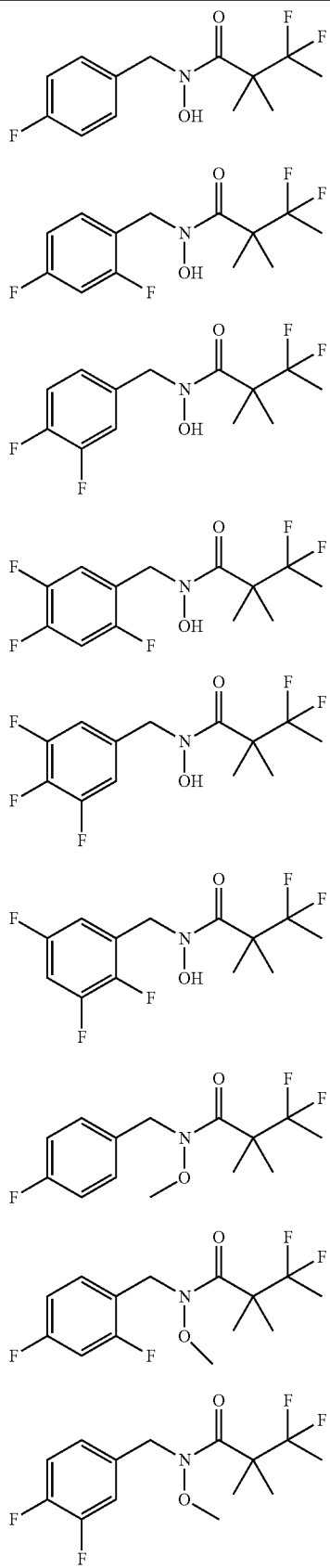
TABLE 2-continued
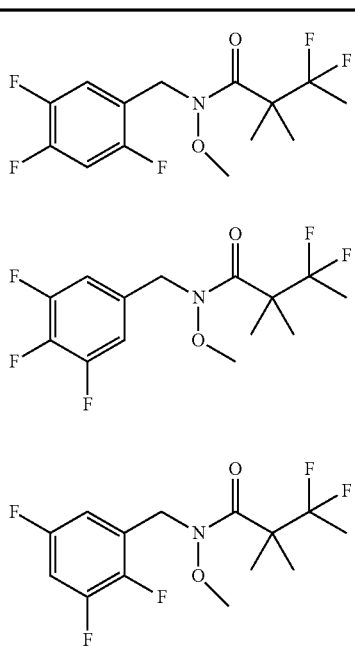
TABLE 3
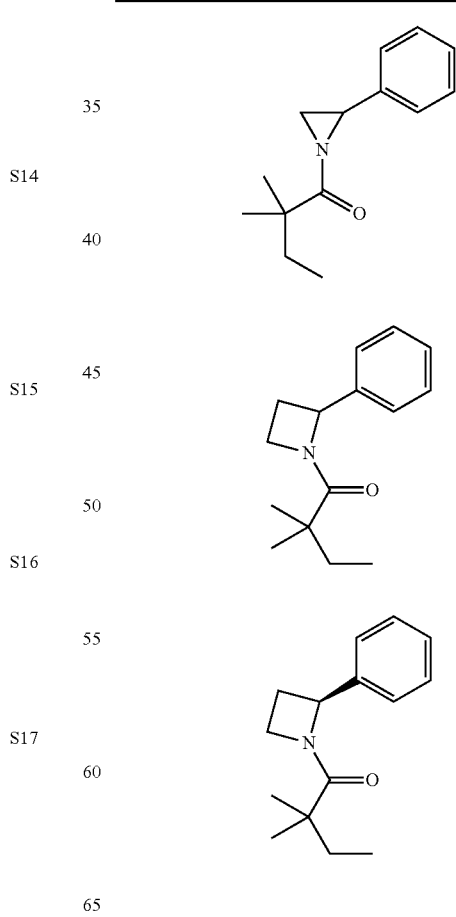

TABLE 3-continued
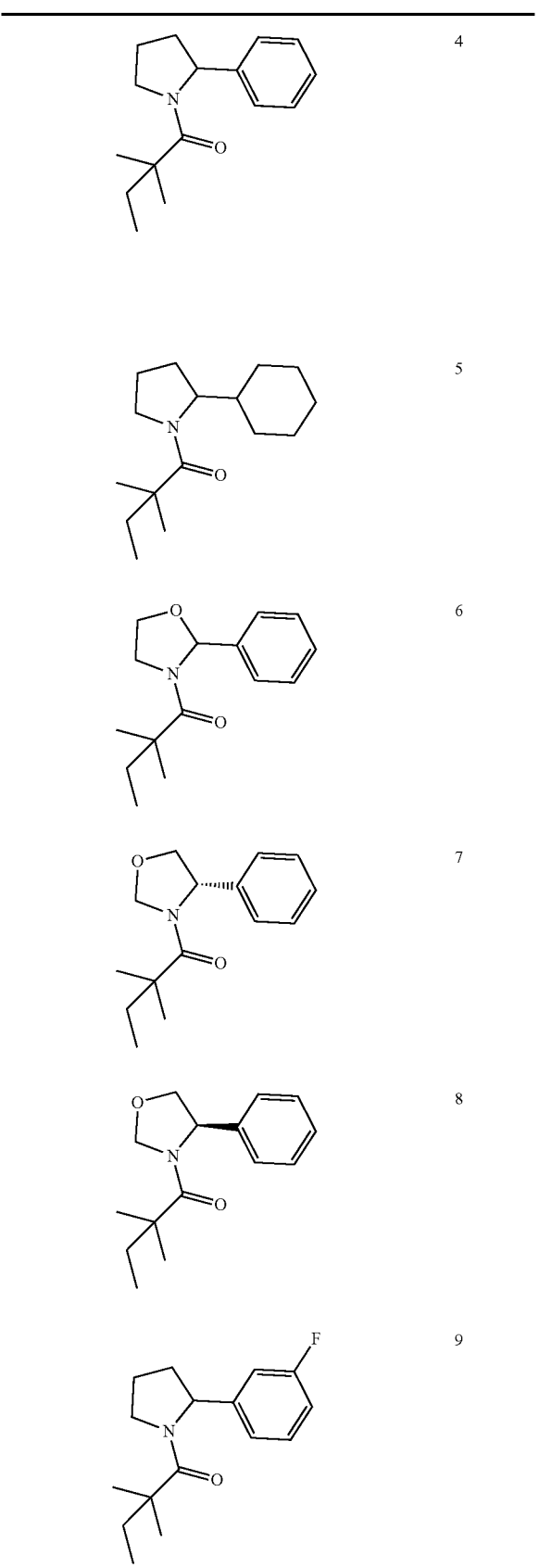
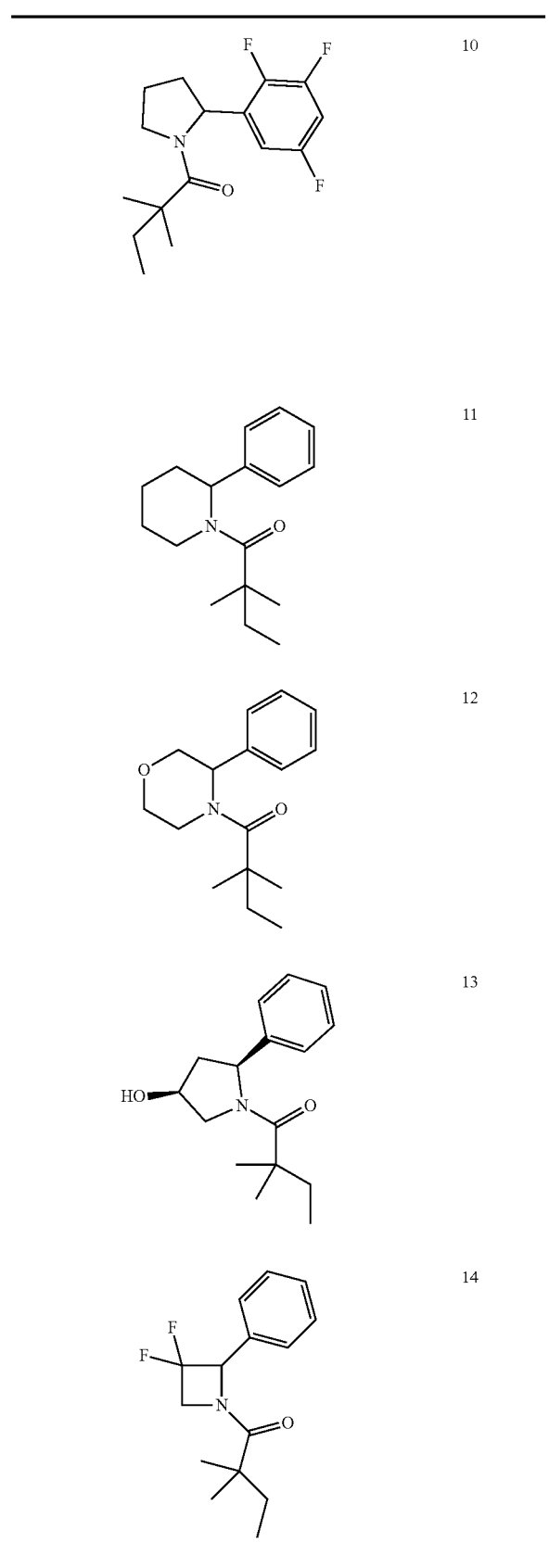

TABLE 3-continued
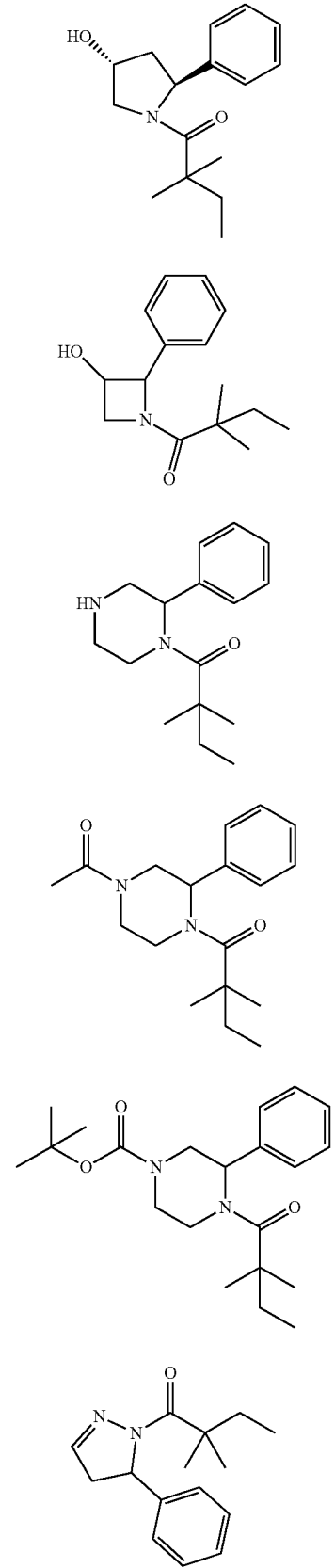
TABLE 3-continued
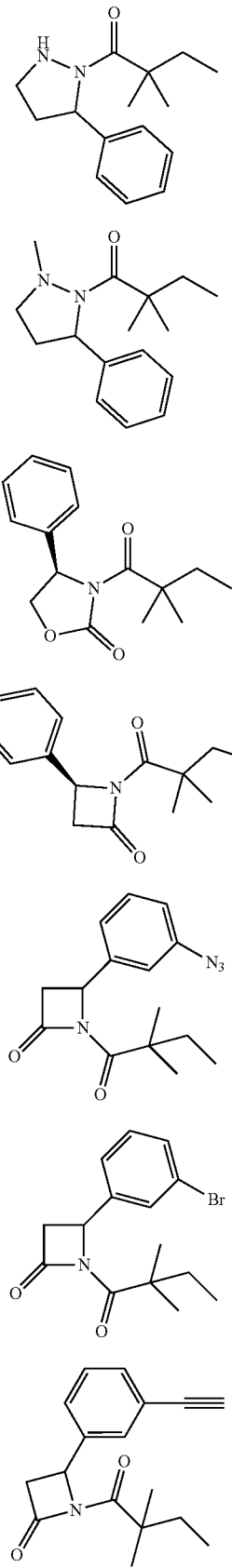

TABLE 3-continued
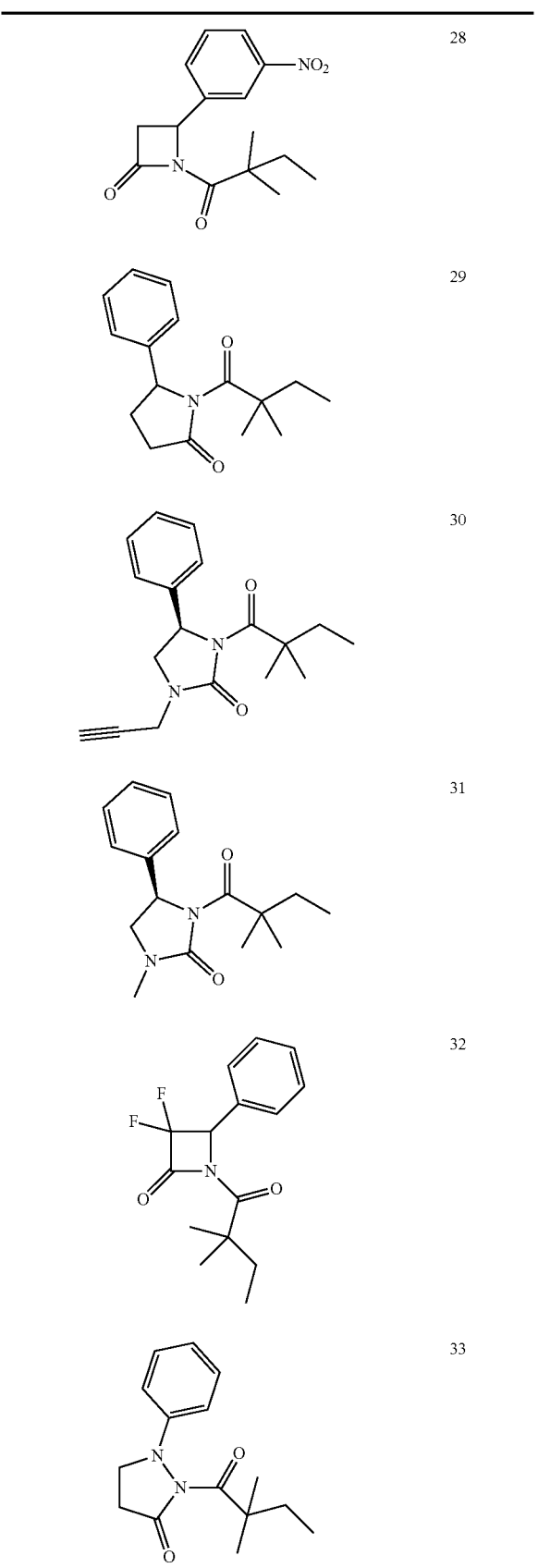
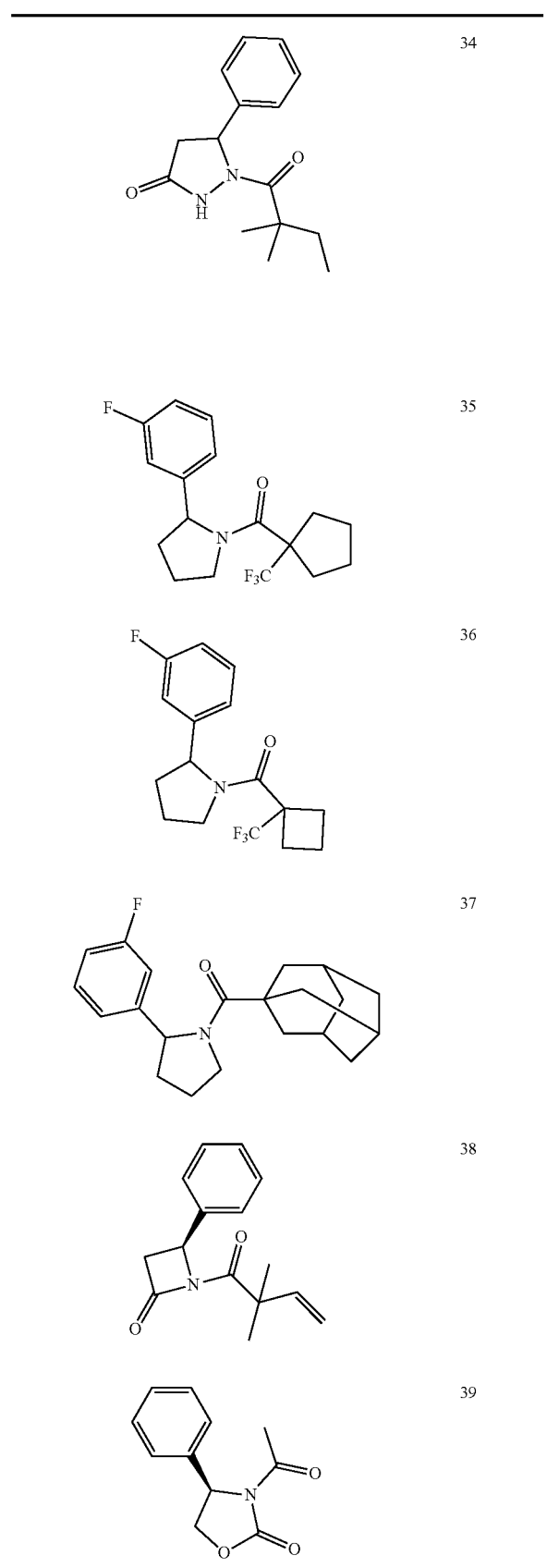

TABLE 3-continued
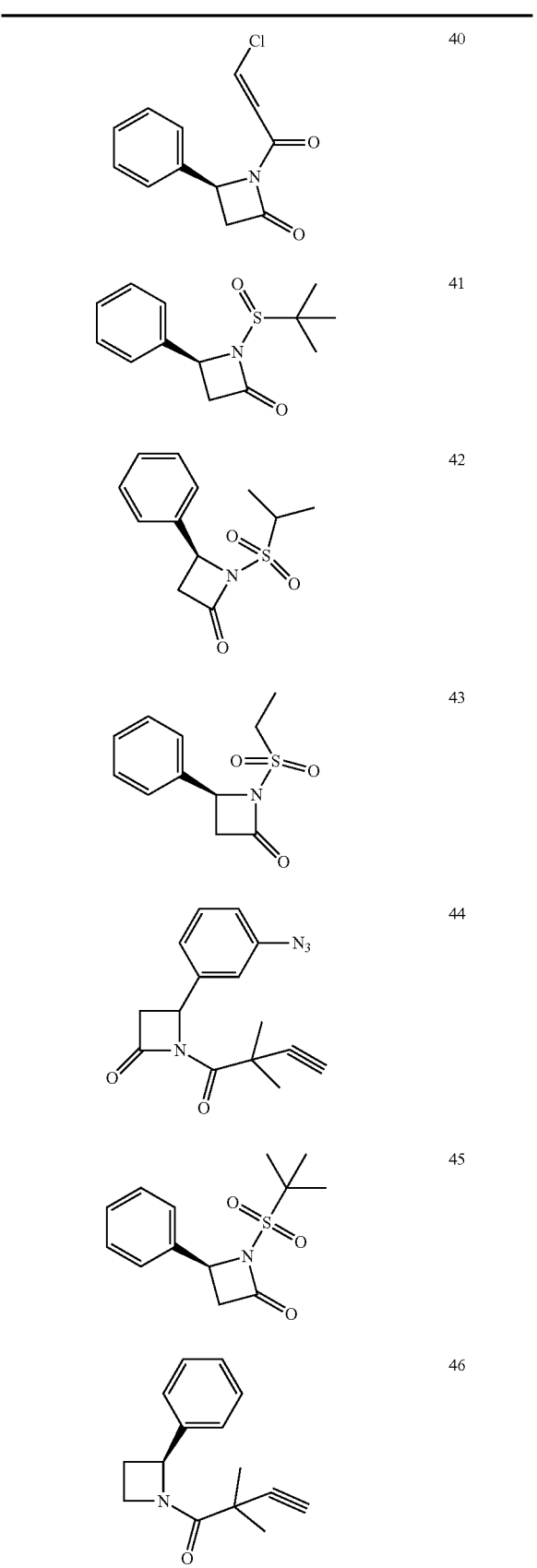
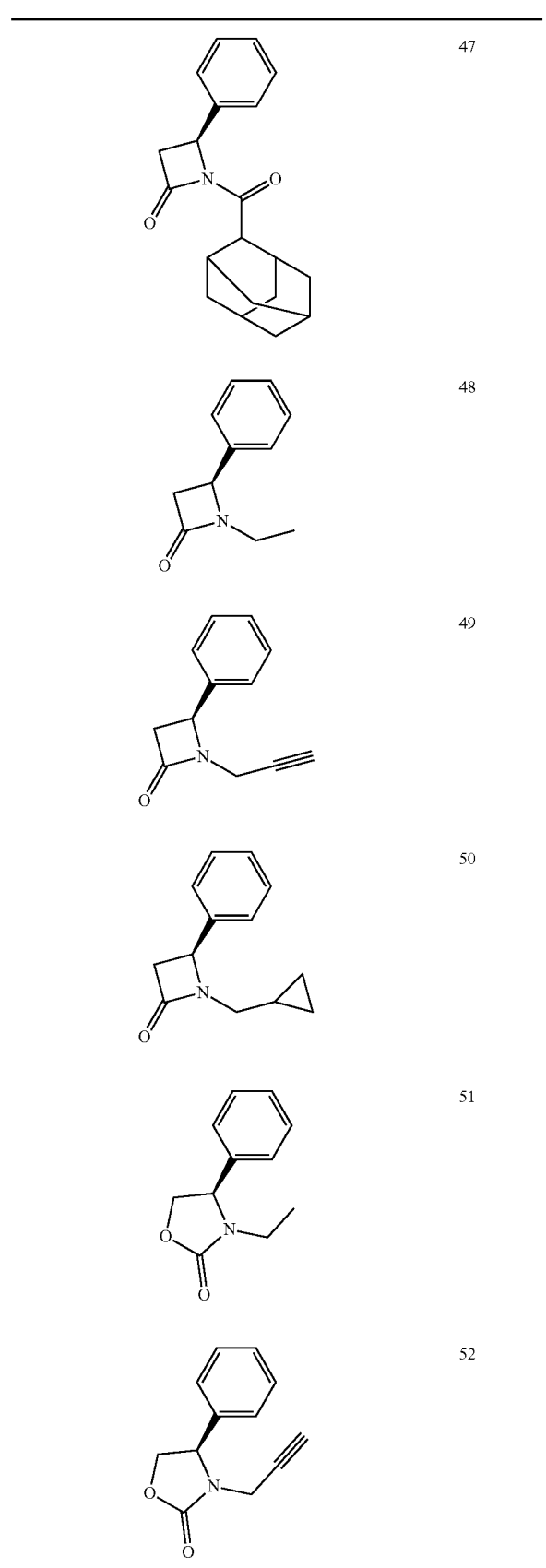

| | |
|---|---|
| 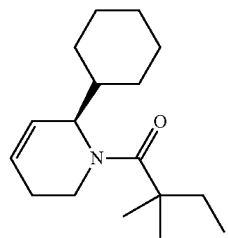 [SMILES: CCC(C)(C)C(=O)N1CCC=C[C@H]1C1CCCCC1] | 53 |
| 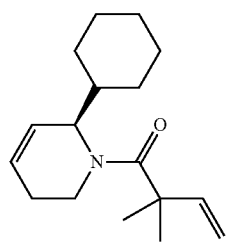 [SMILES: C=CC(C)(C)C(=O)N1CCC=C[C@H]1C1CCCCC1] | 54 |
| 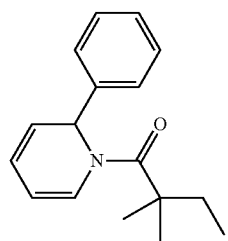 | 55 |
| 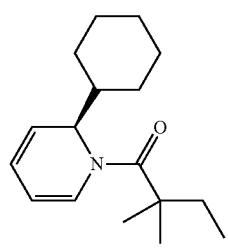 [SMILES: CCC(C)(C)C(=O)N1C=CC=C[C@H]1C1CCCCC1] | 56 |
| 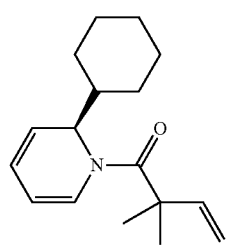 [SMILES: C=CC(C)(C)C(=O)N1C=CC=C[C@H]1C1CCCCC1] | 57 |
| 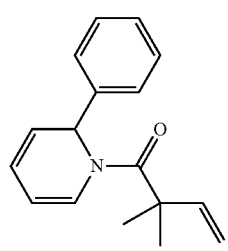 [SMILES: C=CC(C)(C)C(=O)N1C=CC=CC1c1ccccc1] | 58 |
| | |
|---|---|
| 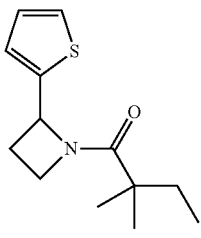 [SMILES: CCC(C)(C)C(=O)N1CCC1c1cccs1] | 59 |
| 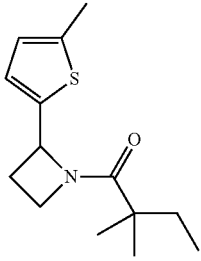 [SMILES: CCC(C)(C)C(=O)N1CCC1c1ccc(C)s1] | 60 |
| 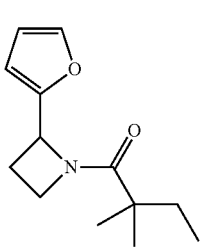 | 61 |
| 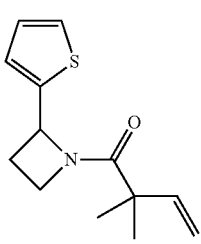 [SMILES: C=CC(C)(C)C(=O)N1CCC1c1cccs1] | 62 |

TABLE 3-continued
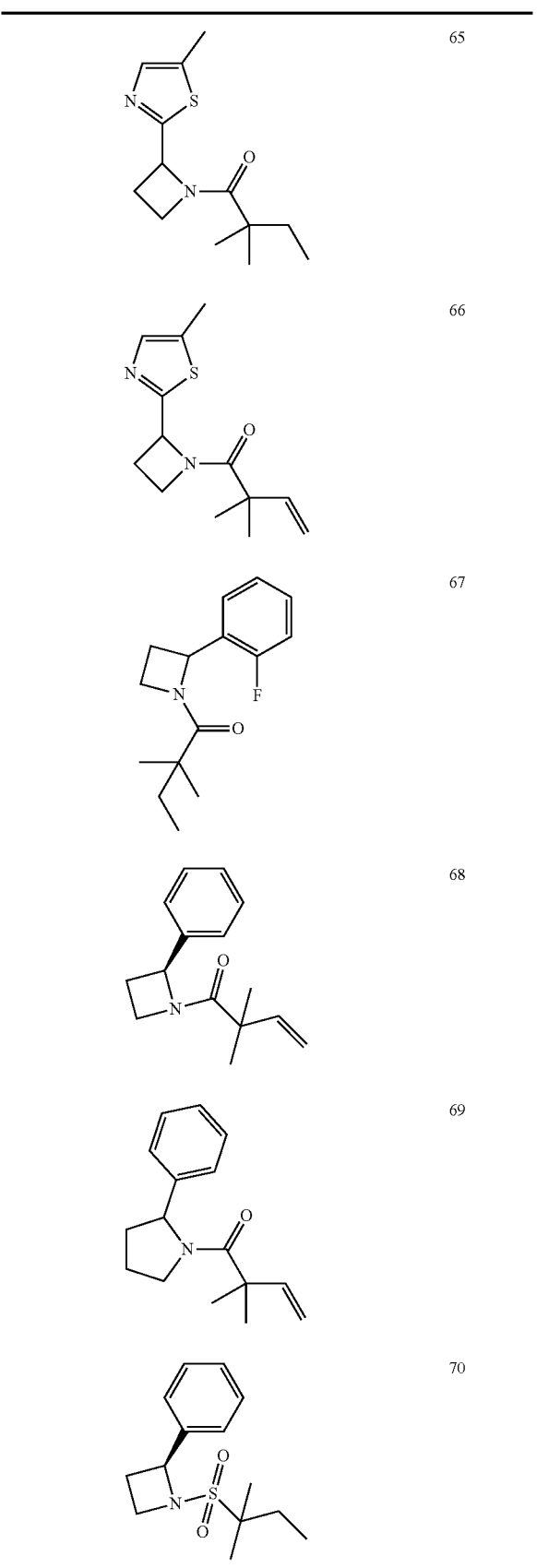
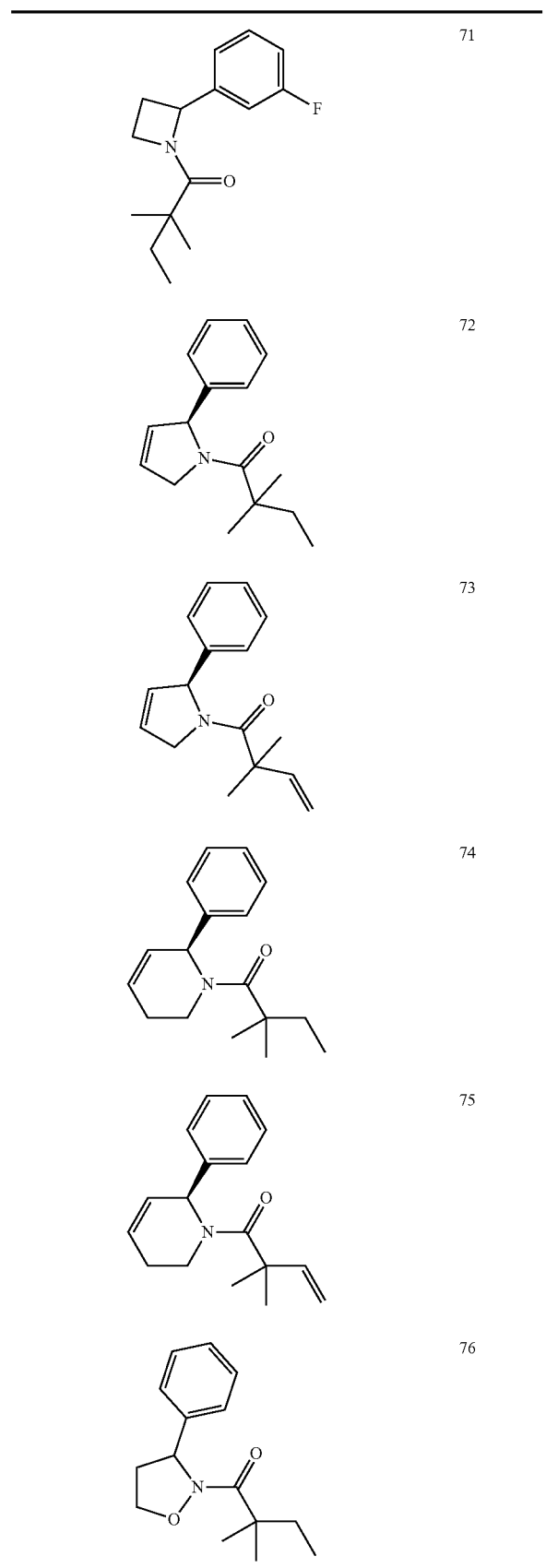

TABLE 3-continued
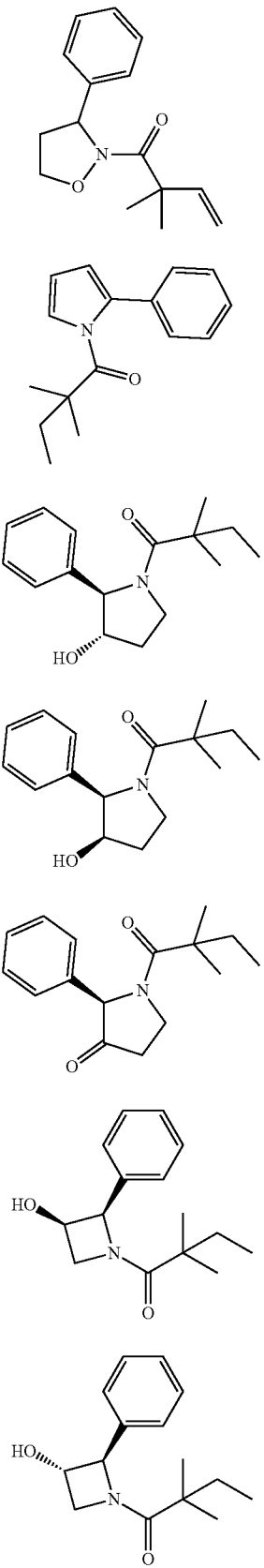
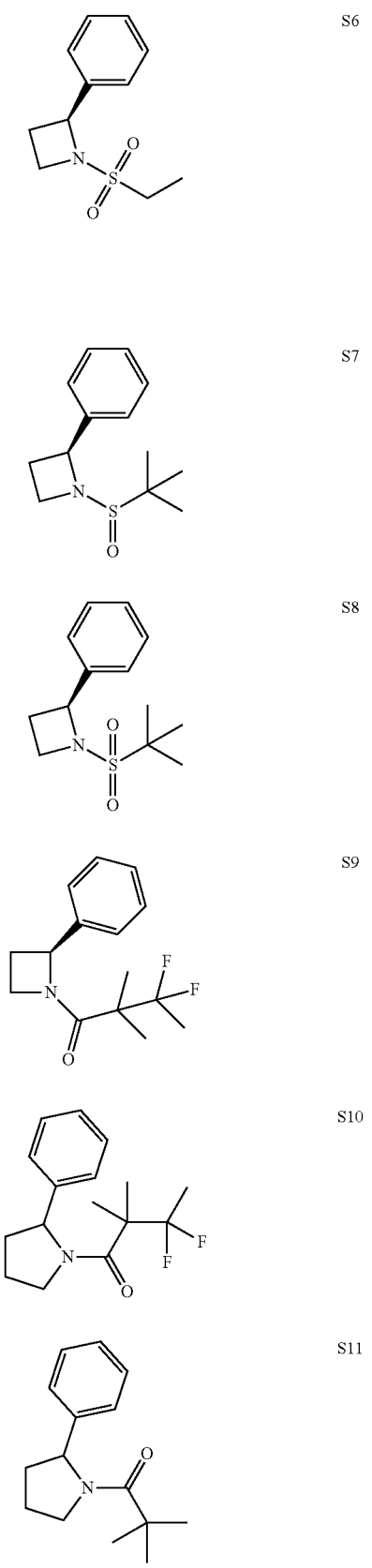

TABLE 3-continued

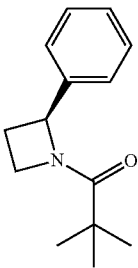 [SMILES: CC(C)(C)C(=O)N1CC[C@H]1c1ccccc1]
S12

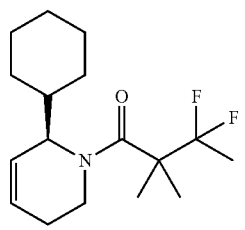 [SMILES: CC(F)(F)C(C)(C)C(=O)N1CCC=C[C@H]1C1CCCCC1]
S13

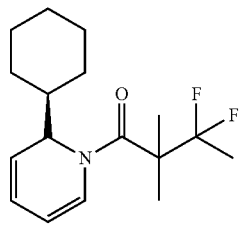
S14

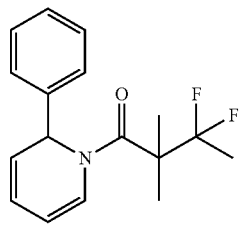 [SMILES: CC(F)(F)C(C)(C)C(=O)N1C=CC=CC1c1ccccc1]
S15

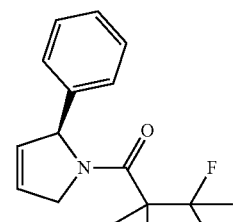
S16

TABLE 3-continued

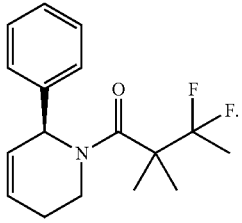 [SMILES: CC(F)(F)C(C)(C)C(=O)N1CCC=C[C@H]1c1ccccc1]
S17

5. The method of claim 1 wherein the necroptosis inhibitor is a RIP3 inhibitor.

6. The method of claim 1 wherein the necroptosis inhibitor is a RIP3 inhibitor selected from a compound of Table 4:

Table 4 tert-butyl 2-(4-(5-(methylcarbamoyl)-1H-benzo[d]imidazol-1-yl)phenyl)acetate (GSK'840)

3-(benzo[d]thiazol-5-yl)-7-(1,3-dimethyl-1H-pyrazol-5-yl)thieno[3,2-c]pyridin-4-amine GSK'843);

N-(6-(isopropylsulfonyl)quinolin-4-yl)benzo[d]thiazol-5-amine (GSK'872);

N-[3-[5-(2-amino-4-pyrimidinyl)-2-(1,1-dimethylethyl)-4-thiazolyl]-2-fluorophenyl]-2,6-difluoro-benzenesulfonamide (Dabrafenib);

3-(2-Imidazo[1,2-b]pyridazin-3-ylethynyl)-4-methyl-N-[4-[4-[(4-methyl-1-piperazinyl)methyl]-3-(trifluoromethyl)phenyl]-benzamide (ponatinib); or 5-[[4-[(2,3-dimethyl-2H-indazol-6-yl)methylamino]-2-pyrimidinyl]amino]-2-methyl-benzenesulfonamide (pazopanib).

7. The method of claim 1 wherein the necroptosis inhibitor is a MLKL inhibitor.

8. The method of claim 1 wherein the necroptosis inhibitor is a MLKL inhibitor selected from a compound of Table 5 or Table 6 or Table 7:

Table 5

(2E)-N-[4-[[(3-Methoxy-2-pyrazinyl)amino]sulfonyl]phenyl]-3-(5-nitro-2-thienyl)-2-propenamide (Necrosulfonamide)

1,3,7-trimethyl-8-(methylsulfonyl)-1H-purine-2,6(3H,7H)-dione (TC13-4)

(2,5-dimethoxybenzylsulfonyl)-1,3,7-trimethyl-1H-purine-2,6(3H,7H)-dione (TC13-58)

7-ethyl-1,3-dimethyl-8-(methylsulfonyl)-1H-purine-2,6 (3H,7H)-dione (TC13-74)

1,7-dimethyl-8-(methylsulfonyl)-3-(prop-2-ynyl)-1H-purine-2,6(3H,7H)-dione (TC13-106)

2-(1,7-dimethyl-8-(methylsulfonyl)-2,6-dioxo-1H-purin-3(2H,6H,7H)-yl)acetonitrile (TC13-107)

3-(3-(3-chlorophenyl)prop-2-yn-1-yl)-8-((cyclopropylmethyl) sulfonyl)-1,7-dimethyl-3,7-dihydro-1H-purine-2,6-dione (TC13-119)

8-((2,5-dimethoxybenzyl)sulfonyl)-1,7-dimethyl-3-(3-(2-(methylamino)pyridin-4-yl)prop-2-yn-1-yl)-3,7-dihydro-1H-purine-2,6-dione (TC13-127)

3-(3-(3-hydroxyphenyl)prop-2-yn-1-yl)-1,7-dimethyl-8-(methylsulfonyl)-3,7-dihydro-1H-purine-2,6-dione (TC13-172)

3-((4-(methyl(4-(3-(4-(trifluoromethoxy)phenyl)ureido) phenyl)amino)pyrimidin-2-yl) amino)benzenesulfonamide (Compound 1)

TABLE 6

TABLE 6-continued
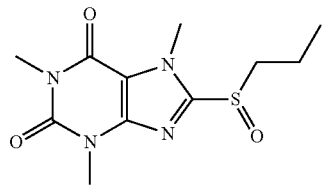 [SMILES: CCCS(=O)c1nc2c(c(=O)n(C)c(=O)n2C)n1C] 9
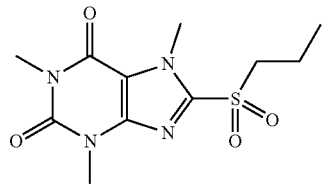 [SMILES: CCCS(=O)(=O)c1nc2c(c(=O)n(C)c(=O)n2C)n1C] 10
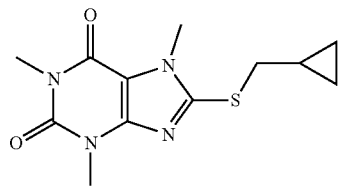 [SMILES: Cn1c(=O)c2c(nc(SCC3CC3)n2C)n(C)c1=O] 11
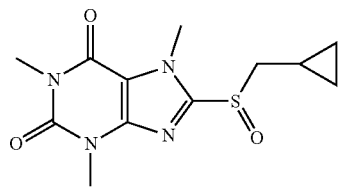 [SMILES: Cn1c(=O)c2c(nc(S(=O)CC3CC3)n2C)n(C)c1=O] 12
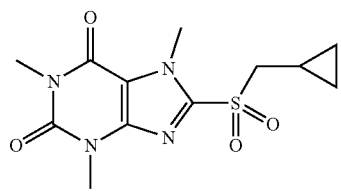 [SMILES: Cn1c(=O)c2c(nc(S(=O)(=O)CC3CC3)n2C)n(C)c1=O] 13
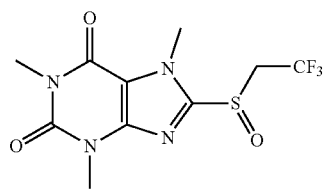 [SMILES: Cn1c(=O)c2c(nc(S(=O)CC(F)(F)F)n2C)n(C)c1=O] 14
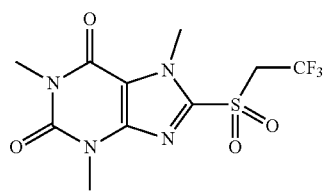 [SMILES: Cn1c(=O)c2c(nc(S(=O)(=O)CC(F)(F)F)n2C)n(C)c1=O] 15

TABLE 6-continued
| | |
|---|---|
| 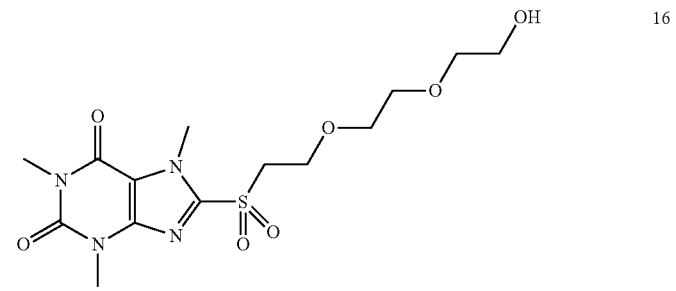 | 16 |
| 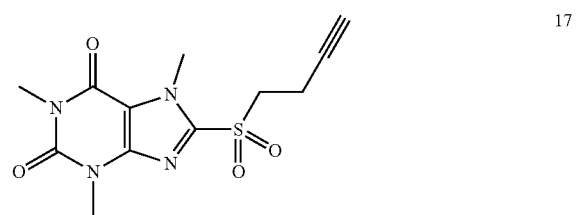 | 17 |
| 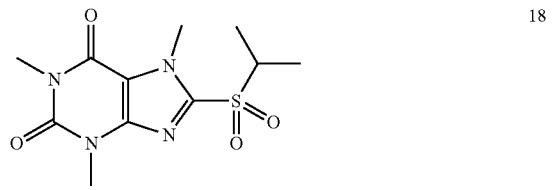 | 18 |
| 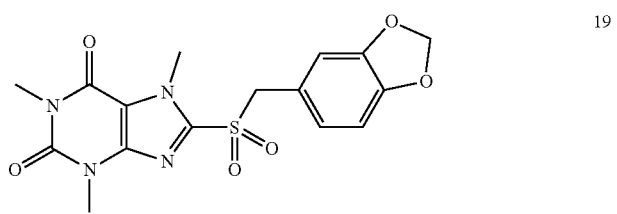 | 19 |
| 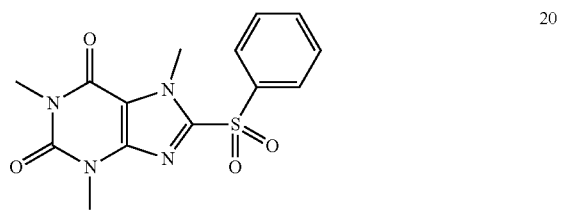 | 20 |
| 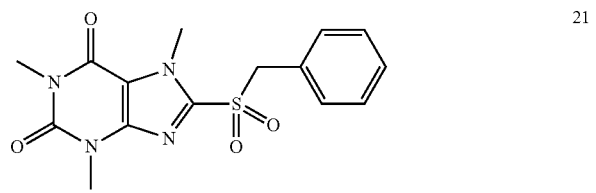 | 21 |
| 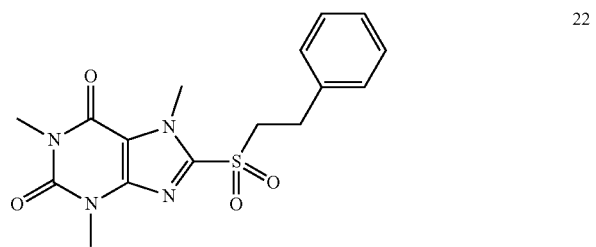 | 22 |

TABLE 6-continued
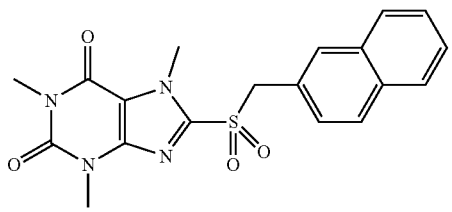 [SMILES: Cn1c(=O)c2c(nc(S(=O)(=O)Cc3ccc4ccccc4c3)n2C)n(C)c1=O] 23
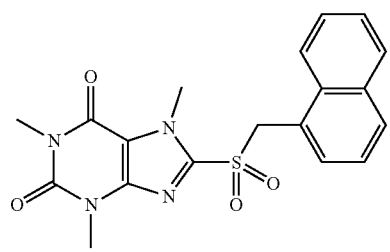 [SMILES: Cn1c(=O)c2c(nc(S(=O)(=O)Cc3cccc4ccccc34)n2C)n(C)c1=O] 24
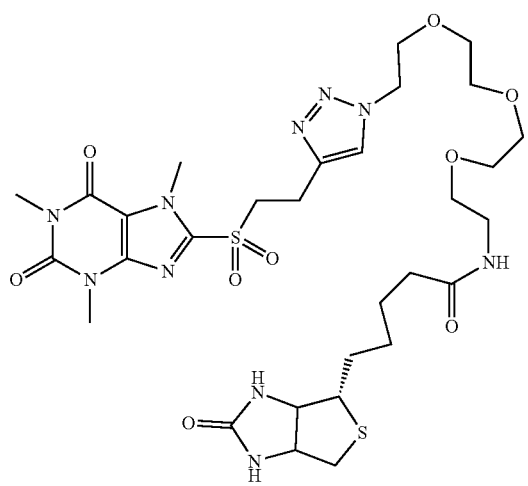 [SMILES: Cn1c(=O)c2c(nc(S(=O)(=O)CCc3cn(CCOCCOCCOCCNC(=O)CCCC[C@@H]4SCC5NC(=O)NC54)nn3)n2C)n(C)c1=O] 25
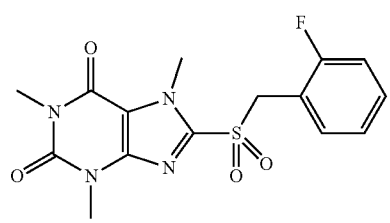 [SMILES: Cn1c(=O)c2c(nc(S(=O)(=O)Cc3ccccc3F)n2C)n(C)c1=O] 26
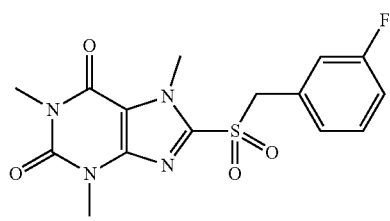 [SMILES: Cn1c(=O)c2c(nc(S(=O)(=O)Cc3cccc(F)c3)n2C)n(C)c1=O] 27
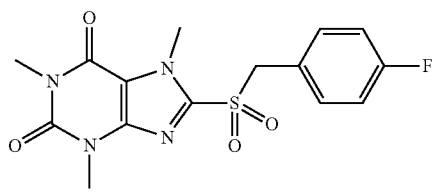 [SMILES: Cn1c(=O)c2c(nc(S(=O)(=O)Cc3ccc(F)cc3)n2C)n(C)c1=O] 28

TABLE 6-continued
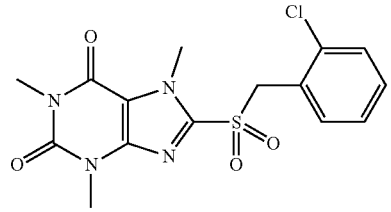 29
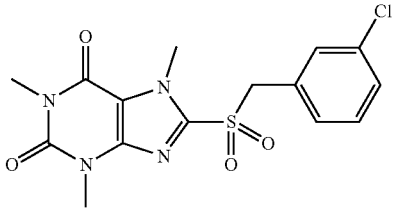 [SMILES: Cn1c(=O)c2c(nc(S(=O)(=O)Cc3cccc(Cl)c3)n2C)n(C)c1=O] 30
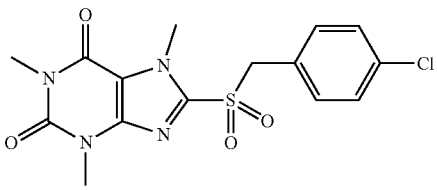 [SMILES: Cn1c(=O)c2c(nc(S(=O)(=O)Cc3ccc(Cl)cc3)n2C)n(C)c1=O] 31
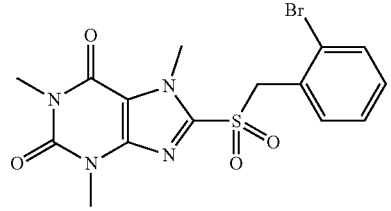 32
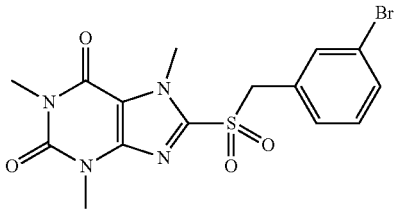 [SMILES: Cn1c(=O)c2c(nc(S(=O)(=O)Cc3cccc(Br)c3)n2C)n(C)c1=O] 33
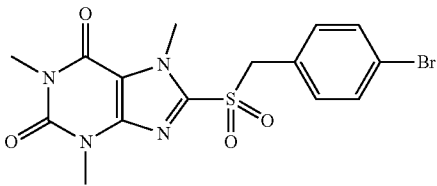 [SMILES: Cn1c(=O)c2c(nc(S(=O)(=O)Cc3ccc(Br)cc3)n2C)n(C)c1=O] 34
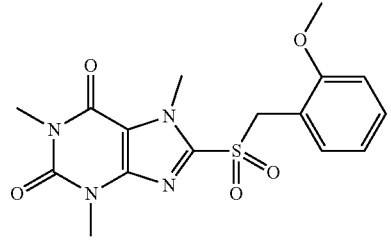 [SMILES: COc1ccccc1CS(=O)(=O)c1nc2c(c(=O)n(C)c(=O)n2C)n1C] 35

TABLE 6-continued
| | |
|---|---|
| 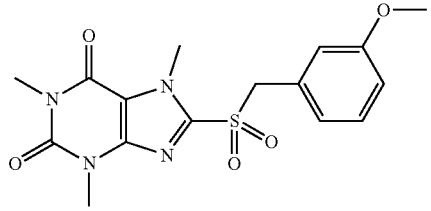 | 36 |
| 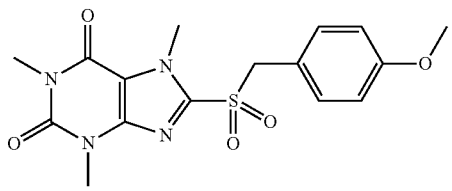 [SMILES: COc1ccc(CS(=O)(=O)c2nc3c(c(=O)n(C)c(=O)n3C)n2C)cc1] | 37 |
| 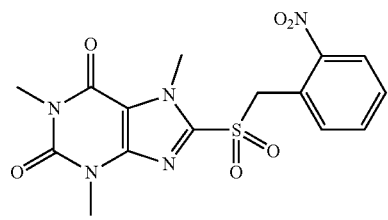 | 38 |
| 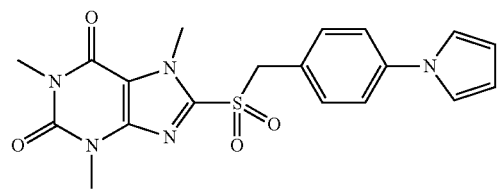 [SMILES: Cn1c(=O)c2c(nc(S(=O)(=O)Cc3ccc(-n4cccc4)cc3)n2C)n(C)c1=O] | 39 |
| 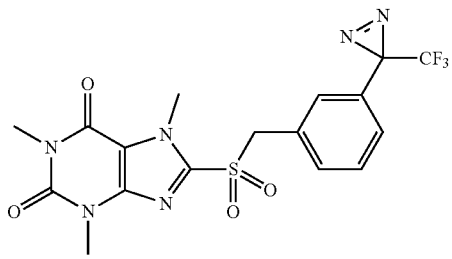 | 40 |
| 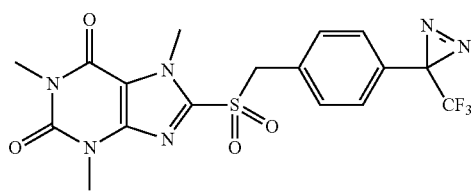 [SMILES: Cn1c(=O)c2c(nc(S(=O)(=O)Cc3ccc(C4(C(F)(F)F)N=N4)cc3)n2C)n(C)c1=O] | 41 |
| 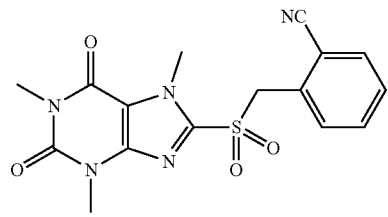 [SMILES: Cn1c(=O)c2c(nc(S(=O)(=O)Cc3ccccc3C#N)n2C)n(C)c1=O] | 42 |

TABLE 6-continued
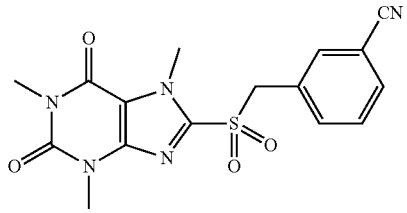 [SMILES: Cn1c(=O)c2c(nc(S(=O)(=O)Cc3cccc(C#N)c3)n2C)n(C)c1=O] 43
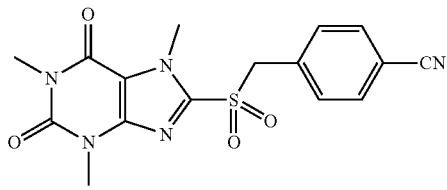 [SMILES: Cn1c(=O)c2c(nc(S(=O)(=O)Cc3ccc(C#N)cc3)n2C)n(C)c1=O] 44
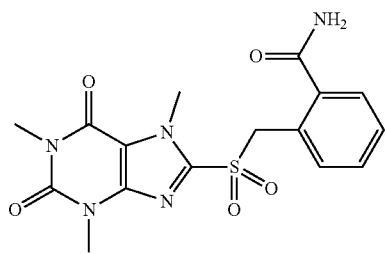 [SMILES: Cn1c(=O)c2c(nc(S(=O)(=O)Cc3ccccc3C(N)=O)n2C)n(C)c1=O] 45
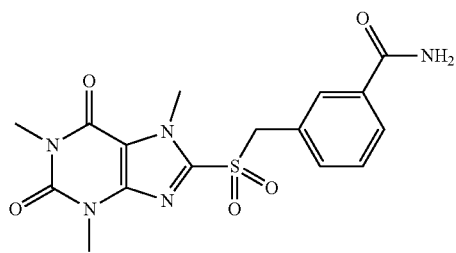 [SMILES: Cn1c(=O)c2c(nc(S(=O)(=O)Cc3cccc(C(N)=O)c3)n2C)n(C)c1=O] 46
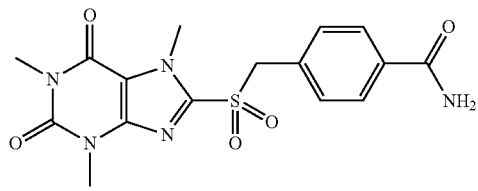 [SMILES: Cn1c(=O)c2c(nc(S(=O)(=O)Cc3ccc(C(N)=O)cc3)n2C)n(C)c1=O] 47
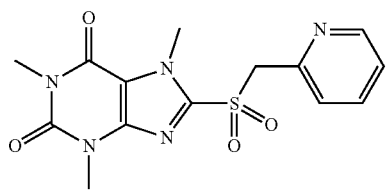 [SMILES: Cn1c(=O)c2c(nc(S(=O)(=O)Cc3ccccn3)n2C)n(C)c1=O] 48
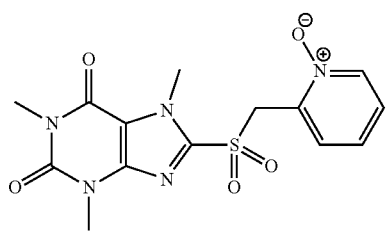 [SMILES: Cn1c(=O)c2c(nc(S(=O)(=O)Cc3cccc[n+]3[O-])n2C)n(C)c1=O] 49

TABLE 6-continued
| | |
|---|---|
| 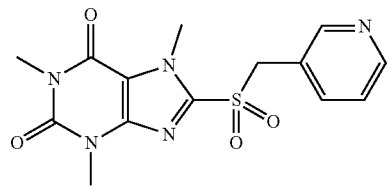 [SMILES: Cn1c(=O)c2c(nc(S(=O)(=O)Cc3cccnc3)n2C)n(C)c1=O] | 50 |
| 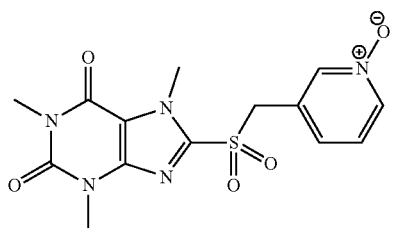 [SMILES: Cn1c(=O)c2c(nc(S(=O)(=O)Cc3ccc[n+]([O-])c3)n2C)n(C)c1=O] | 51 |
| 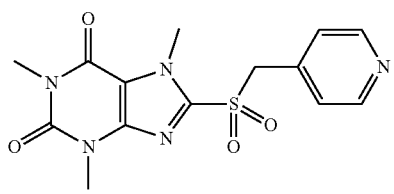 [SMILES: Cn1c(=O)c2c(nc(S(=O)(=O)Cc3ccncc3)n2C)n(C)c1=O] | 52 |
| 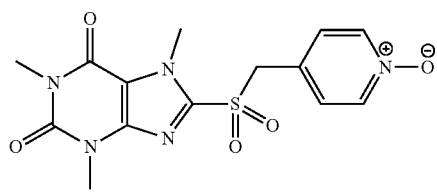 [SMILES: Cn1c(=O)c2c(nc(S(=O)(=O)Cc3cc[n+]([O-])cc3)n2C)n(C)c1=O] | 53 |
| 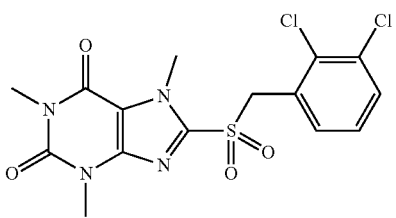 [SMILES: Cn1c(=O)c2c(nc(S(=O)(=O)Cc3cccc(Cl)c3Cl)n2C)n(C)c1=O] | 54 |
| 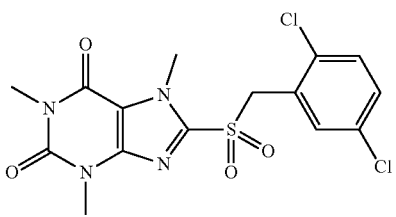 [SMILES: Cn1c(=O)c2c(nc(S(=O)(=O)Cc3cc(Cl)ccc3Cl)n2C)n(C)c1=O] | 55 |
| 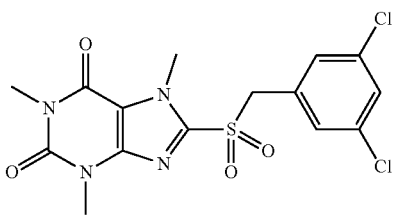 [SMILES: Cn1c(=O)c2c(nc(S(=O)(=O)Cc3cc(Cl)cc(Cl)c3)n2C)n(C)c1=O] | 56 |

TABLE 6-continued
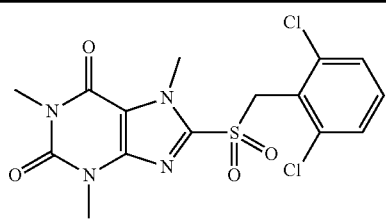 57
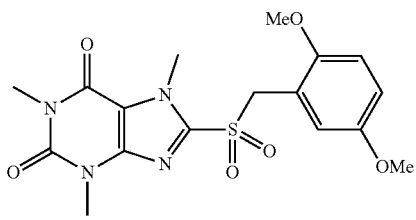 58
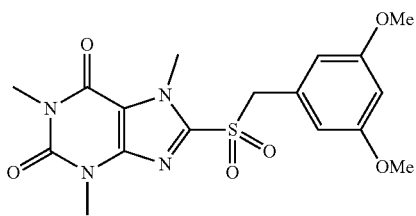 [SMILES: COc1cc(CS(=O)(=O)c2nc3c(c(=O)n(C)c(=O)n3C)n2C)cc(OC)c1] 59
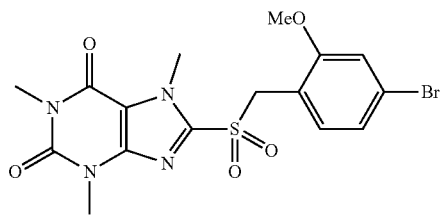 [SMILES: COc1cc(Br)ccc1CS(=O)(=O)c1nc2c(c(=O)n(C)c(=O)n2C)n1C] 60
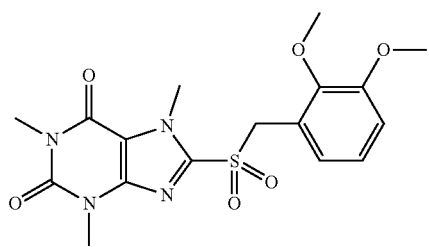 61
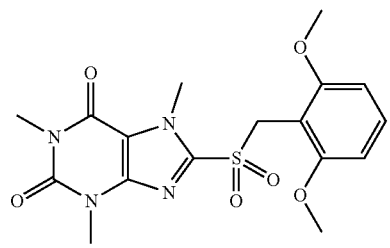 [SMILES: COc1cccc(OC)c1CS(=O)(=O)c1nc2c(c(=O)n(C)c(=O)n2C)n1C] 62
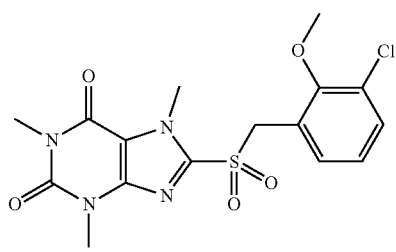 [SMILES: COc1c(Cl)cccc1CS(=O)(=O)c1nc2c(c(=O)n(C)c(=O)n2C)n1C] 63

TABLE 6-continued
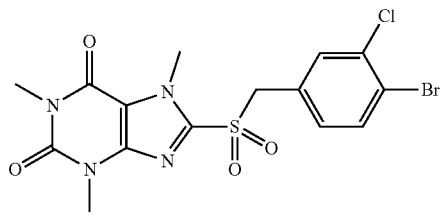 [SMILES: Cn1c(=O)c2c(nc(S(=O)(=O)Cc3ccc(Br)c(Cl)c3)n2C)n(C)c1=O] 64
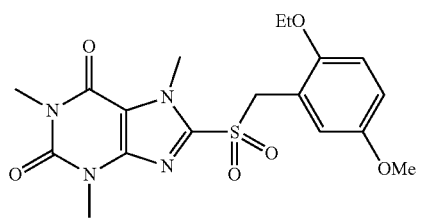 65
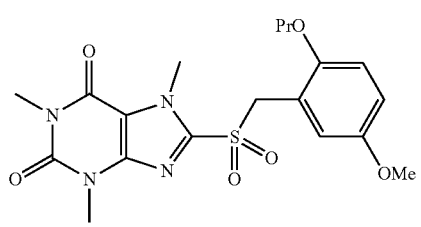 66
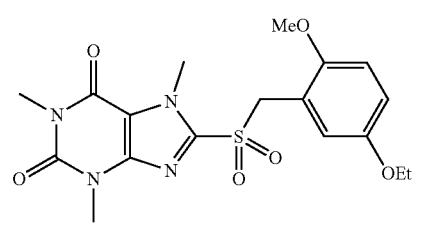 67
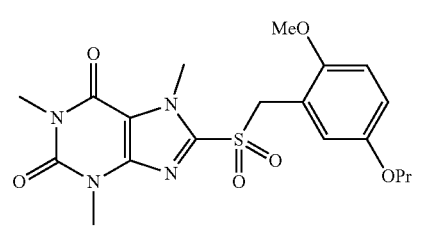 68
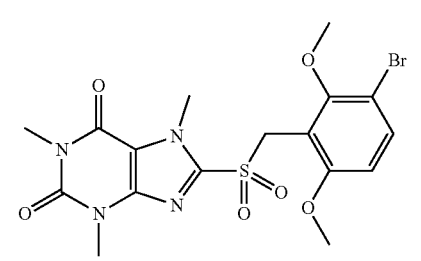 [SMILES: COc1ccc(Br)c(OC)c1CS(=O)(=O)c1nc2c(c(=O)n(C)c(=O)n2C)n1C] 69
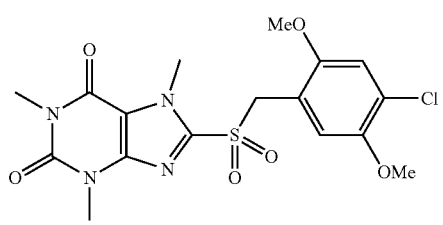 [SMILES: COc1cc(CS(=O)(=O)c2nc3c(c(=O)n(C)c(=O)n3C)n2C)c(OC)cc1Cl] 70

TABLE 6-continued
| | |
|---|---|
| 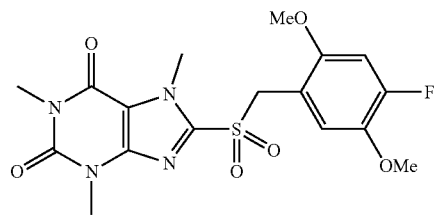 [SMILES: COc1cc(CS(=O)(=O)c2nc3c(c(=O)n(C)c(=O)n3C)n2C)c(OC)cc1F] | 71 |
| 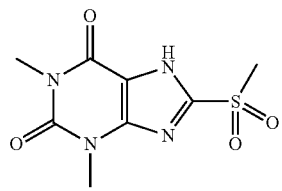 [SMILES: Cn1c(=O)c2[nH]c(S(C)(=O)=O)nc2n(C)c1=O] | 72 |
| 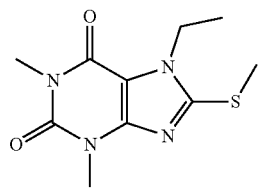 | 73 |
| 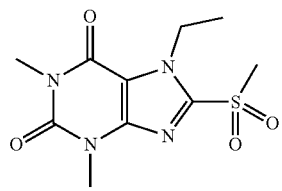 [SMILES: CCn1c(S(C)(=O)=O)nc2c1c(=O)n(C)c(=O)n2C] | 74 |
| 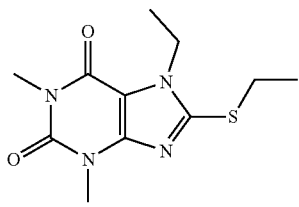 [SMILES: CCSc1nc2c(c(=O)n(C)c(=O)n2C)n1CC] | 75 |
| 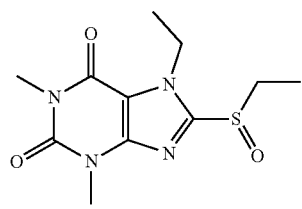 [SMILES: CCn1c(S(=O)CC)nc2c1c(=O)n(C)c(=O)n2C] | 76 |
| 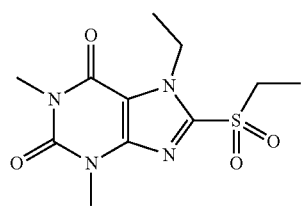 [SMILES: CCn1c(S(=O)(=O)CC)nc2c1c(=O)n(C)c(=O)n2C] | 77 |

TABLE 6-continued
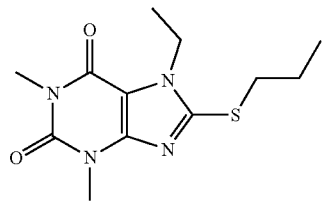 [SMILES: CCCSc1nc2c(c(=O)n(C)c(=O)n2C)n1CC]
78
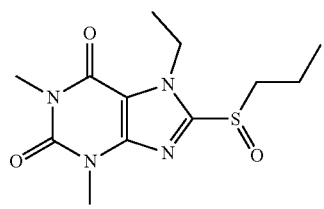 [SMILES: CCCS(=O)c1nc2c(c(=O)n(C)c(=O)n2C)n1CC]
79
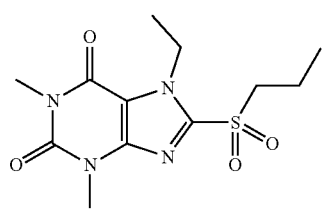 [SMILES: CCCS(=O)(=O)c1nc2c(c(=O)n(C)c(=O)n2C)n1CC]
80
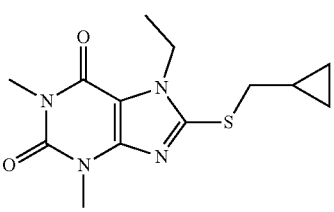 [SMILES: CCn1c(SCC2CC2)nc2c1c(=O)n(C)c(=O)n2C]
81
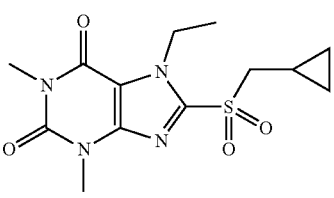 [SMILES: CCn1c(S(=O)(=O)CC2CC2)nc2c1c(=O)n(C)c(=O)n2C]
82
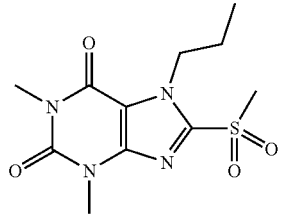 [SMILES: CCCn1c(S(C)(=O)=O)nc2c1c(=O)n(C)c(=O)n2C]
83
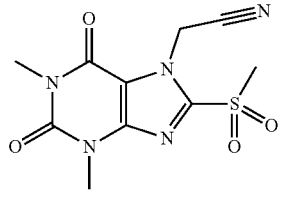 [SMILES: Cn1c(=O)c2c(nc(S(C)(=O)=O)n2CC#N)n(C)c1=O]
84

TABLE 6-continued
| | |
|---|---|
| 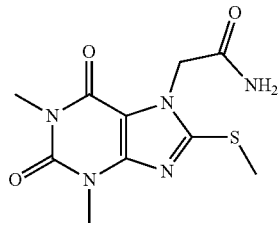 | 85 |
| 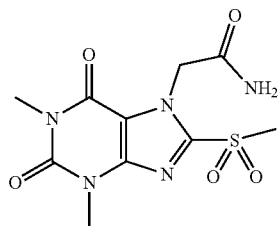 | 86 |
| 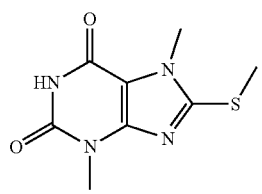 | 87 |
| 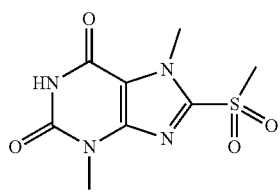 [SMILES: Cn1c(S(C)(=O)=O)nc2c1c(=O)[nH]c(=O)n2C] | 88 |
| 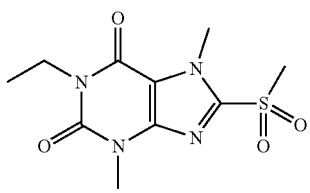 [SMILES: CCn1c(=O)c2c(nc(S(C)(=O)=O)n2C)n(C)c1=O] | 89 |
| 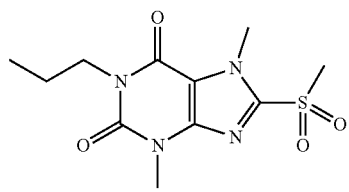 [SMILES: CCCn1c(=O)c2c(nc(S(C)(=O)=O)n2C)n(C)c1=O] | 90 |
| 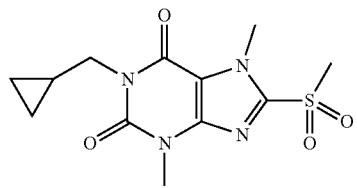 [SMILES: Cn1c(S(C)(=O)=O)nc2c1c(=O)n(CC1CC1)c(=O)n2C] | 91 |

TABLE 6-continued
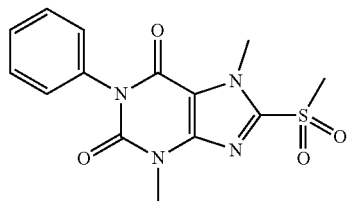 [SMILES: Cn1c(S(C)(=O)=O)nc2c1c(=O)n(-c1ccccc1)c(=O)n2C] 92
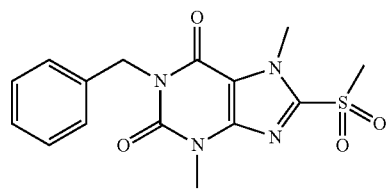 [SMILES: Cn1c(S(C)(=O)=O)nc2c1c(=O)n(Cc1ccccc1)c(=O)n2C] 93
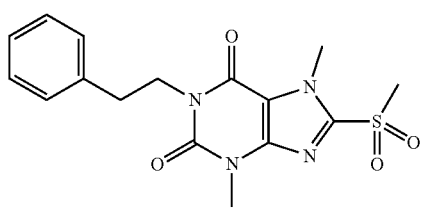 [SMILES: Cn1c(S(C)(=O)=O)nc2c1c(=O)n(CCc1ccccc1)c(=O)n2C] 94
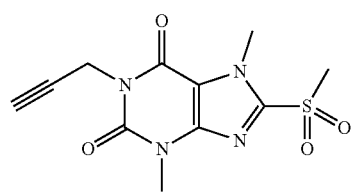 [SMILES: C#CCn1c(=O)c2c(nc(S(C)(=O)=O)n2C)n(C)c1=O] 95
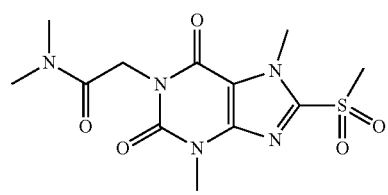 [SMILES: CN(C)C(=O)Cn1c(=O)c2c(nc(S(C)(=O)=O)n2C)n(C)c1=O] 96
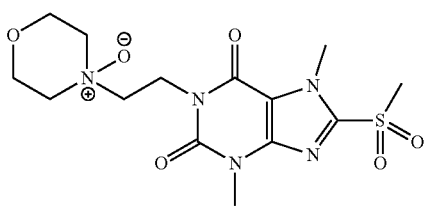 [SMILES: Cn1c(S(C)(=O)=O)nc2c1c(=O)n(CC[N+]1([O-])CCOCC1)c(=O)n2C] 97
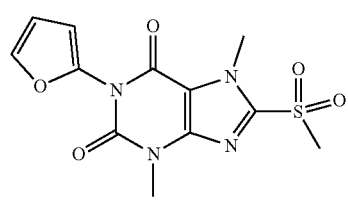 [SMILES: Cn1c(S(C)(=O)=O)nc2c1c(=O)n(-c1ccco1)c(=O)n2C] 98
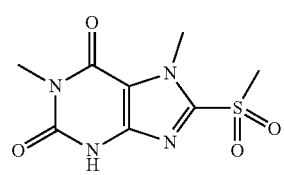 [SMILES: Cn1c(=O)[nH]c2nc(S(C)(=O)=O)n(C)c2c1=O] 99

TABLE 6-continued
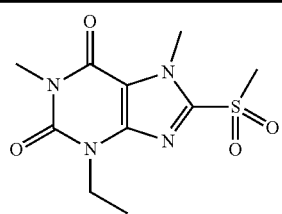
100
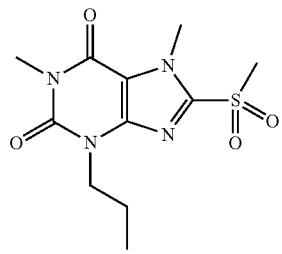 [SMILES: CCCn1c(=O)n(C)c(=O)c2c1nc(S(C)(=O)=O)n2C]
101
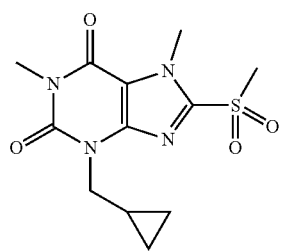 [SMILES: Cn1c(=O)c2c(nc(S(C)(=O)=O)n2C)n(CC2CC2)c1=O]
102
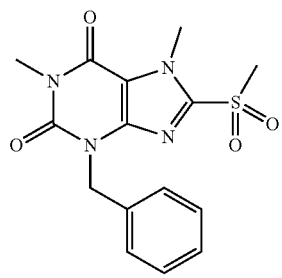 [SMILES: Cn1c(=O)c2c(nc(S(C)(=O)=O)n2C)n(Cc2ccccc2)c1=O]
103
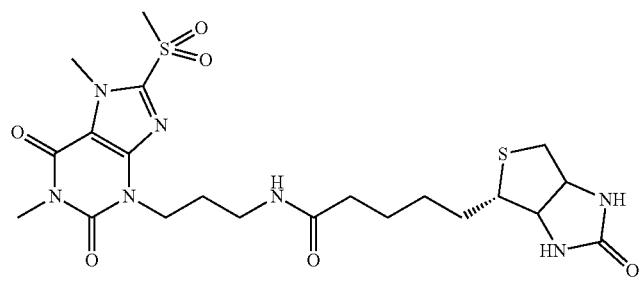 [SMILES: Cn1c(=O)c2c(nc(S(C)(=O)=O)n2C)n(CCCNC(=O)CCCC[C@@H]2SCC3NC(=O)NC32)c1=O]
104
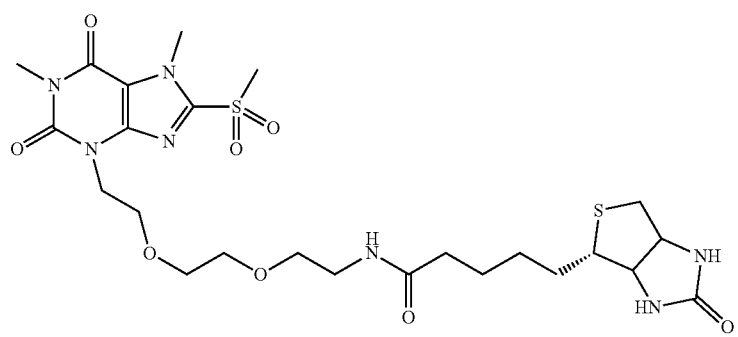 [SMILES: Cn1c(=O)c2c(nc(S(C)(=O)=O)n2C)n(CCOCCOCCNC(=O)CCCC[C@@H]2SCC3NC(=O)NC32)c1=O]
105

TABLE 6-continued
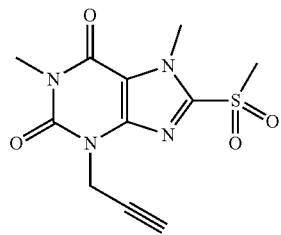 [SMILES: C#CCn1c(=O)n(C)c(=O)c2c1nc(S(C)(=O)=O)n2C]
106
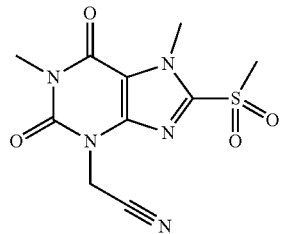 [SMILES: Cn1c(=O)c2c(nc(S(C)(=O)=O)n2C)n(CC#N)c1=O]
107
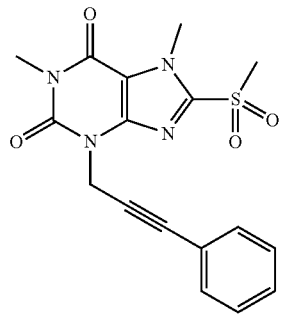 [SMILES: Cn1c(=O)c2c(nc(S(C)(=O)=O)n2C)n(CC#Cc2ccccc2)c1=O]
108
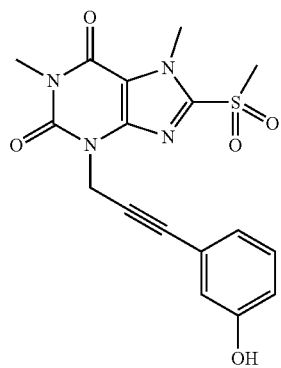 [SMILES: Cn1c(=O)c2c(nc(S(C)(=O)=O)n2C)n(CC#Cc2cccc(O)c2)c1=O]
109
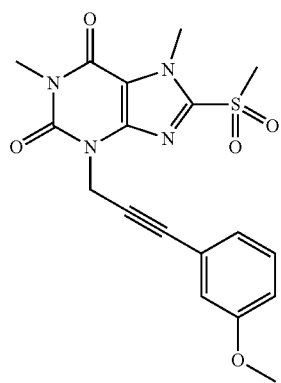
110

TABLE 6-continued
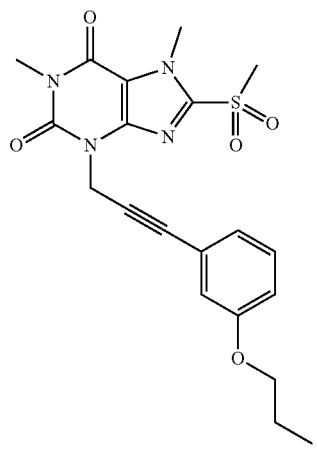 [SMILES: CCCOc1cccc(C#CCn2c(=O)n(C)c(=O)c3c2nc(S(C)(=O)=O)n3C)c1]
111
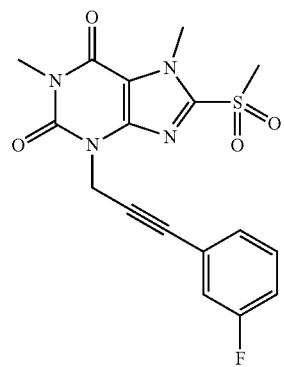 [SMILES: Cn1c(=O)c2c(nc(S(C)(=O)=O)n2C)n(CC#Cc2cccc(F)c2)c1=O]
112
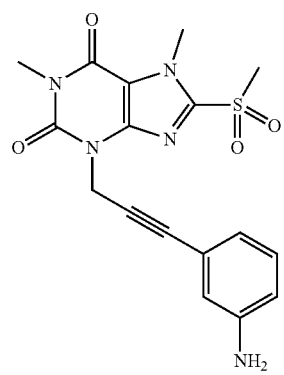 [SMILES: Cn1c(=O)c2c(nc(S(C)(=O)=O)n2C)n(CC#Cc2cccc(N)c2)c1=O]
113
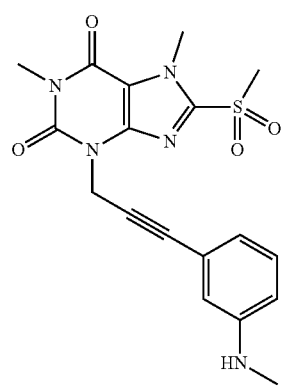
114

TABLE 6-continued
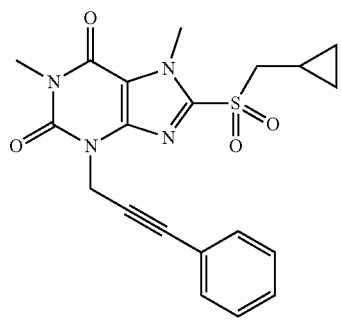 [SMILES: Cn1c(=O)c2c(nc(S(=O)(=O)CC3CC3)n2C)n(CC#Cc2ccccc2)c1=O]
115
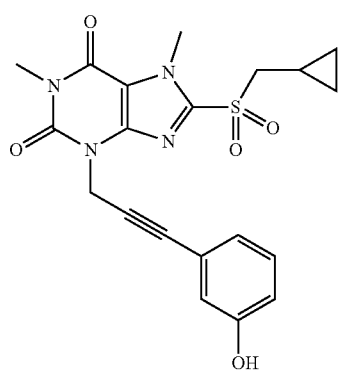
116
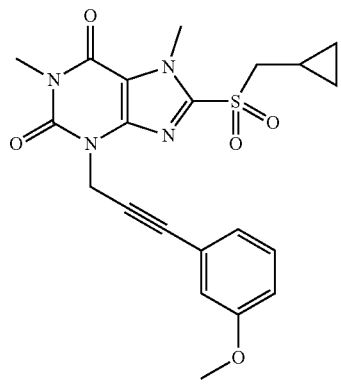 [SMILES: COc1cccc(C#CCn2c(=O)n(C)c(=O)c3c2nc(S(=O)(=O)CC2CC2)n3C)c1]
117
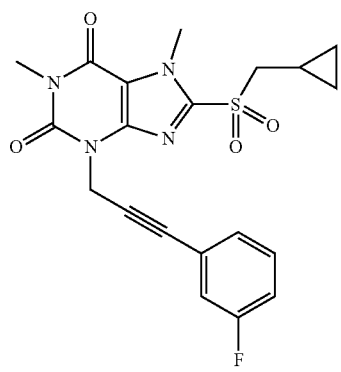 [SMILES: Cn1c(=O)c2c(nc(S(=O)(=O)CC3CC3)n2C)n(CC#Cc2cccc(F)c2)c1=O]
118

TABLE 6-continued
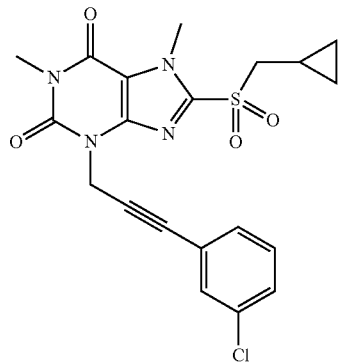 [SMILES: Cn1c(=O)c2c(nc(S(=O)(=O)CC3CC3)n2C)n(CC#Cc2cccc(Cl)c2)c1=O] 119
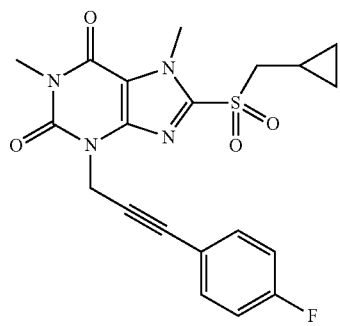 120
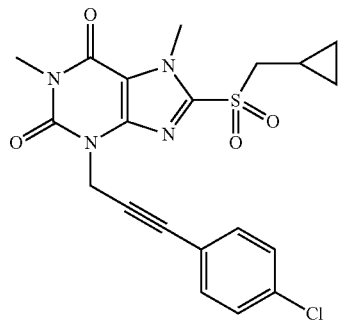 121
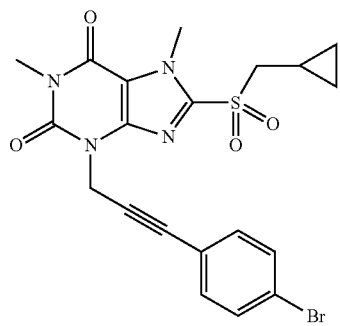 122

TABLE 6-continued
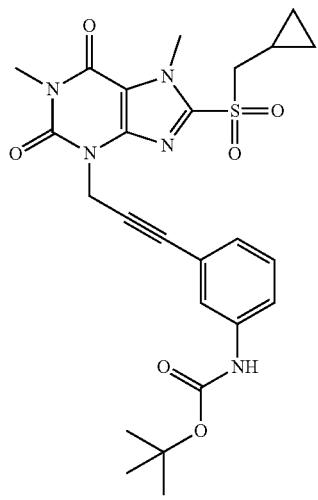 [SMILES: Cn1c(=O)c2c(nc(S(=O)(=O)CC3CC3)n2C)n(CC#Cc2cccc(NC(=O)OC(C)(C)C)c2)c1=O]
123
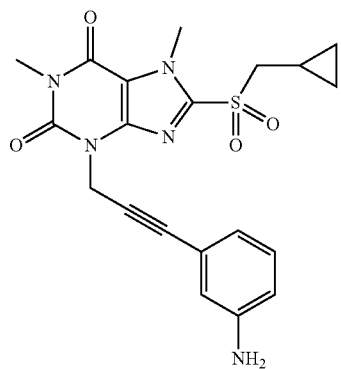
124
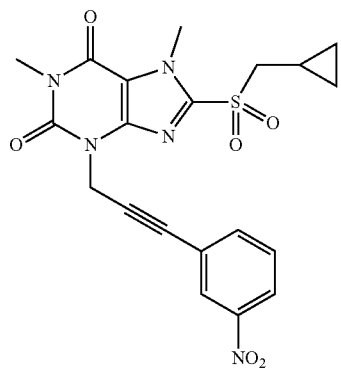
125
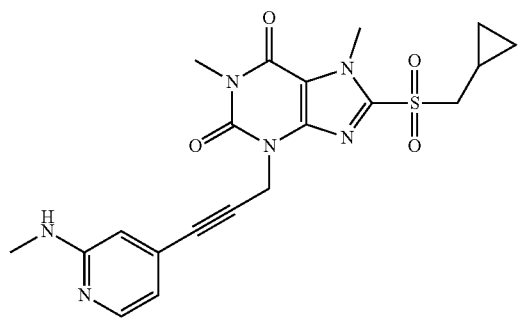 [SMILES: CNc1cc(C#CCn2c(=O)n(C)c(=O)c3c2nc(S(=O)(=O)CC2CC2)n3C)ccn1]
126

TABLE 6-continued
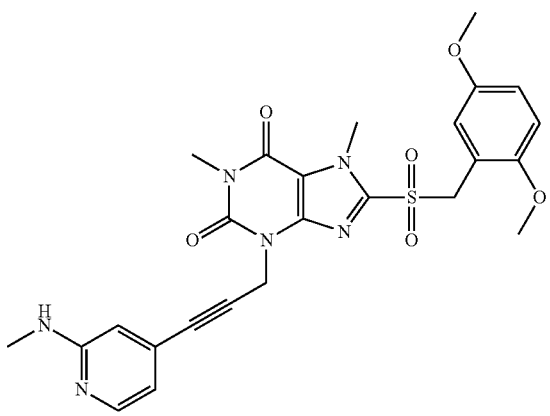 [SMILES: CNc1cc(C#CCn2c(=O)n(C)c(=O)c3c2nc(S(=O)(=O)Cc2cc(OC)ccc2OC)n3C)ccn1]
127
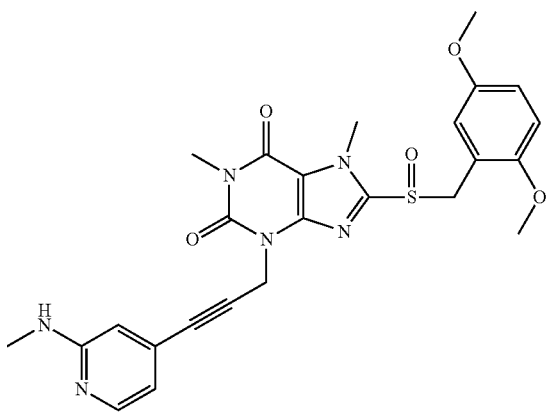 [SMILES: CNc1cc(C#CCn2c(=O)n(C)c(=O)c3c2nc(S(=O)Cc2cc(OC)ccc2OC)n3C)ccn1]
128
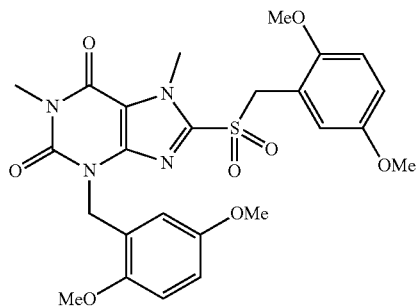 [SMILES: COc1ccc(OC)c(Cn2c(=O)n(C)c(=O)c3c2nc(S(=O)(=O)Cc2cc(OC)ccc2OC)n3C)c1]
129
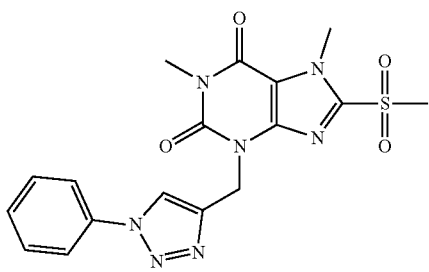 [SMILES: Cn1c(=O)c2c(nc(S(C)(=O)=O)n2C)n(Cc2cn(-c3ccccc3)nn2)c1=O]
130

TABLE 6-continued
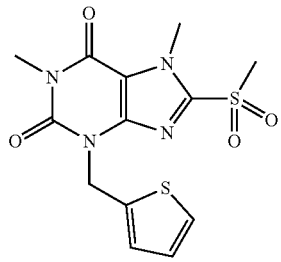 [SMILES: Cn1c(=O)c2c(nc(S(C)(=O)=O)n2C)n(Cc2cccs2)c1=O] 131
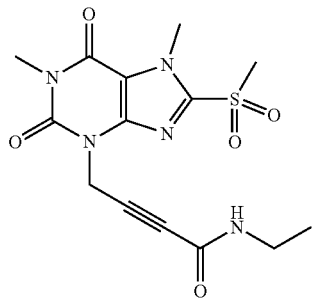 [SMILES: CCNC(=O)C#CCn1c(=O)n(C)c(=O)c2c1nc(S(C)(=O)=O)n2C] 132
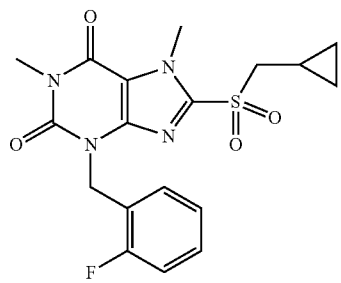 [SMILES: Cn1c(=O)c2c(nc(S(=O)(=O)CC3CC3)n2C)n(Cc2ccccc2F)c1=O] 133
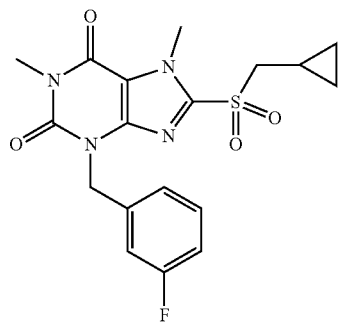 [SMILES: Cn1c(=O)c2c(nc(S(=O)(=O)CC3CC3)n2C)n(Cc2cccc(F)c2)c1=O] 134
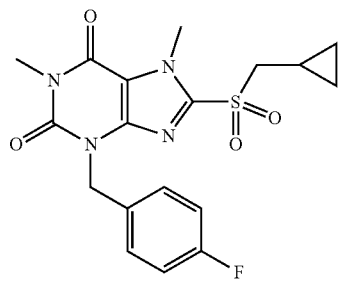 [SMILES: Cn1c(=O)c2c(nc(S(=O)(=O)CC3CC3)n2C)n(Cc2ccc(F)cc2)c1=O] 135

TABLE 6-continued
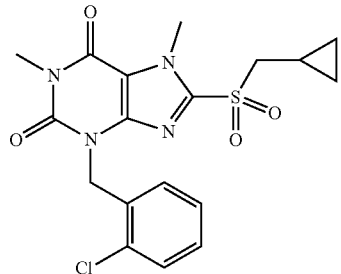 [SMILES: Cn1c(=O)c2c(nc(S(=O)(=O)CC3CC3)n2C)n(Cc2ccccc2Cl)c1=O] 136
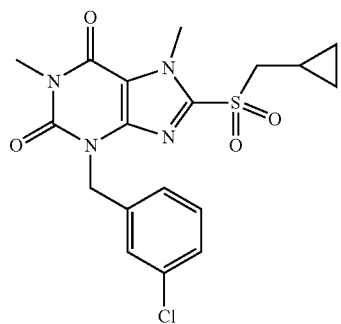 137
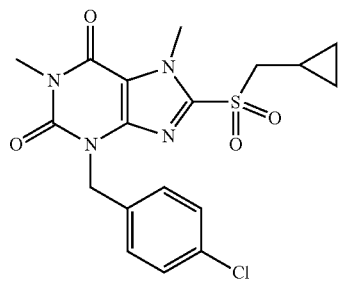 [SMILES: Cn1c(=O)c2c(nc(S(=O)(=O)CC3CC3)n2C)n(Cc2ccc(Cl)cc2)c1=O] 138
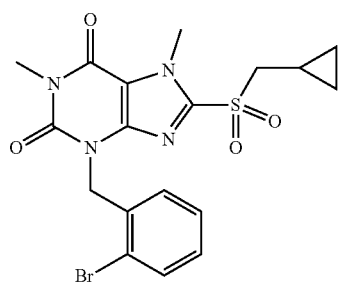 139
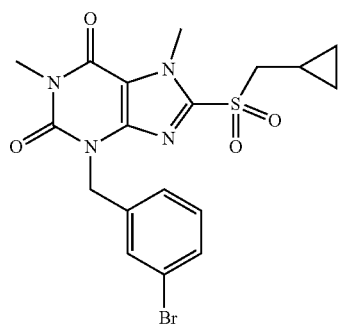 [SMILES: Cn1c(=O)c2c(nc(S(=O)(=O)CC3CC3)n2C)n(Cc2cccc(Br)c2)c1=O] 140

TABLE 6-continued
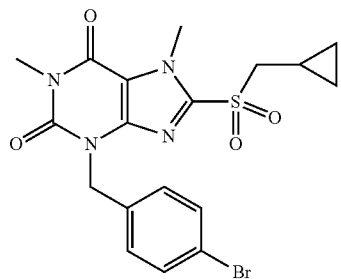 [SMILES: Cn1c(=O)c2c(nc(S(=O)(=O)CC3CC3)n2C)n(Cc2ccc(Br)cc2)c1=O] 141
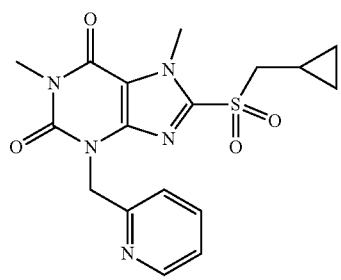 [SMILES: Cn1c(=O)c2c(nc(S(=O)(=O)CC3CC3)n2C)n(Cc2ccccn2)c1=O] 142
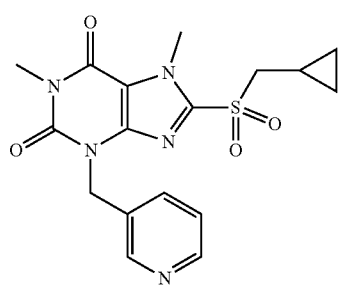 [SMILES: Cn1c(=O)c2c(nc(S(=O)(=O)CC3CC3)n2C)n(Cc2cccnc2)c1=O] 143
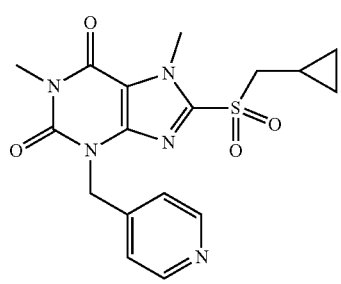 [SMILES: Cn1c(=O)c2c(nc(S(=O)(=O)CC3CC3)n2C)n(Cc2ccncc2)c1=O] 144
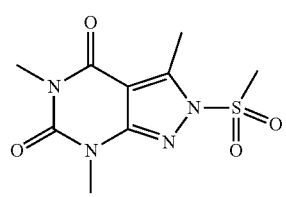 [SMILES: Cc1c2c(=O)n(C)c(=O)n(C)c2nn1S(C)(=O)=O] 145
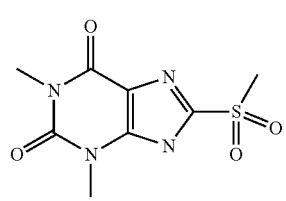 [SMILES: Cn1c(=O)c2nc(S(C)(=O)=O)[nH]c2n(C)c1=O] 146

TABLE 6-continued
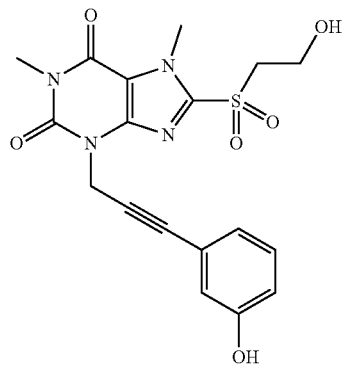 [SMILES: Cn1c(=O)c2c(nc(S(=O)(=O)CCO)n2C)n(CC#Cc2cccc(O)c2)c1=O]
147
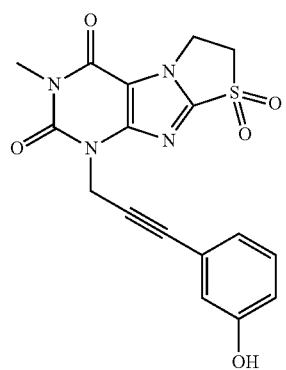 [SMILES: Cn1c(=O)c2c(nc3n2CCS3(=O)=O)n(CC#Cc2cccc(O)c2)c1=O]
148
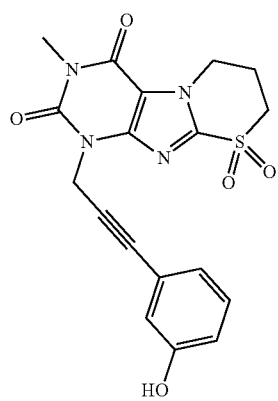 [SMILES: Cn1c(=O)c2c(nc3n2CCCS3(=O)=O)n(CC#Cc2cccc(O)c2)c1=O]
149
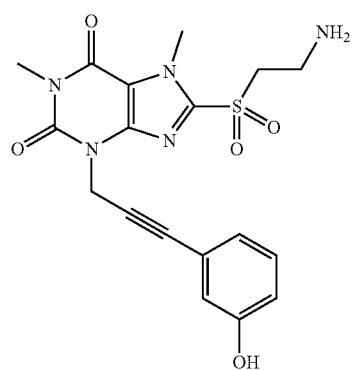 [SMILES: Cn1c(=O)c2c(nc(S(=O)(=O)CCN)n2C)n(CC#Cc2cccc(O)c2)c1=O]
150

TABLE 6-continued
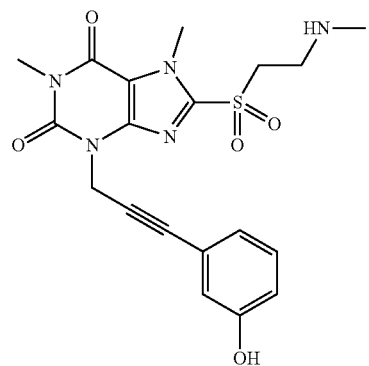
151
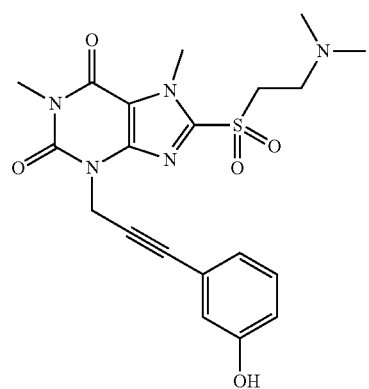
152
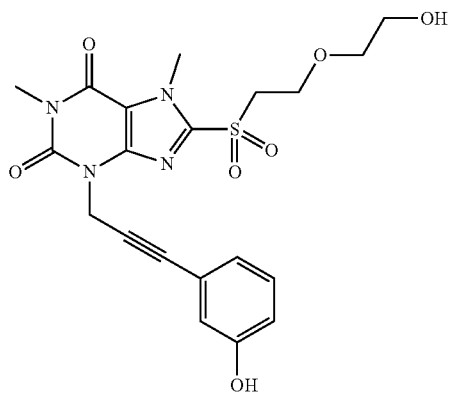 [SMILES: Cn1c(=O)c2c(nc(S(=O)(=O)CCOCCO)n2C)n(CC#Cc2cccc(O)c2)c1=O]
153
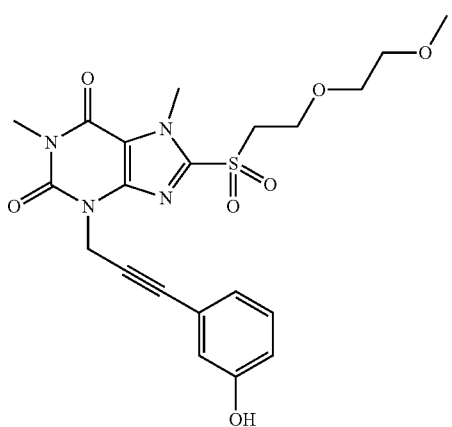
154

TABLE 6-continued
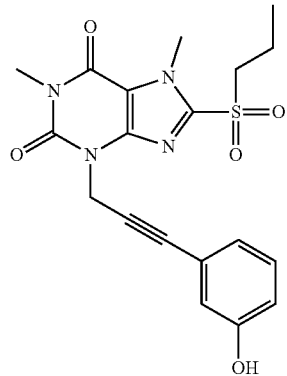 [SMILES: CCCS(=O)(=O)c1nc2c(c(=O)n(C)c(=O)n2CC#Cc2cccc(O)c2)n1C]
155
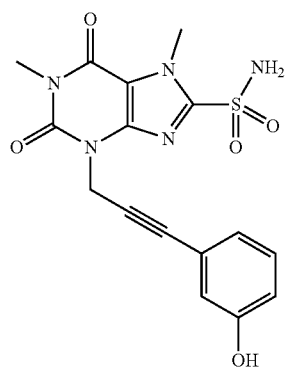 [SMILES: Cn1c(=O)c2c(nc(S(N)(=O)=O)n2C)n(CC#Cc2cccc(O)c2)c1=O]
156
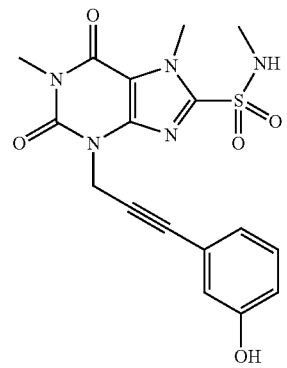 [SMILES: CNS(=O)(=O)c1nc2c(c(=O)n(C)c(=O)n2CC#Cc2cccc(O)c2)n1C]
157
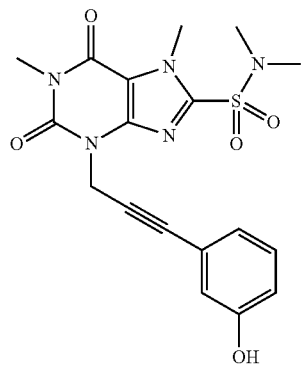 [SMILES: CN(C)S(=O)(=O)c1nc2c(c(=O)n(C)c(=O)n2CC#Cc2cccc(O)c2)n1C]
158

TABLE 6-continued
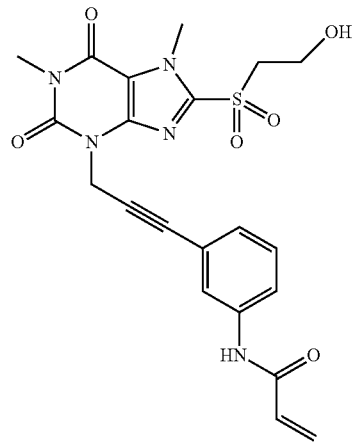 [SMILES: C=CC(=O)Nc1cccc(C#CCn2c(=O)n(C)c(=O)c3c2nc(S(=O)(=O)CCO)n3C)c1]
159
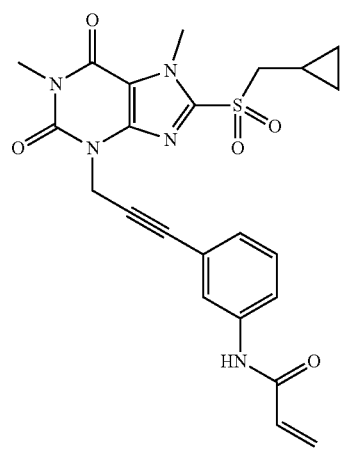 [SMILES: C=CC(=O)Nc1cccc(C#CCn2c(=O)n(C)c(=O)c3c2nc(S(=O)(=O)CC2CC2)n3C)c1]
160
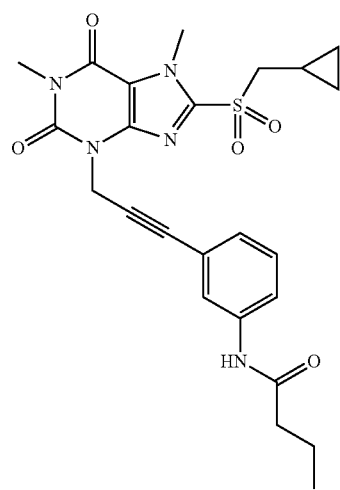 [SMILES: CCCC(=O)Nc1cccc(C#CCn2c(=O)n(C)c(=O)c3c2nc(S(=O)(=O)CC2CC2)n3C)c1]
161

TABLE 6-continued
| | |
|---|---|
| 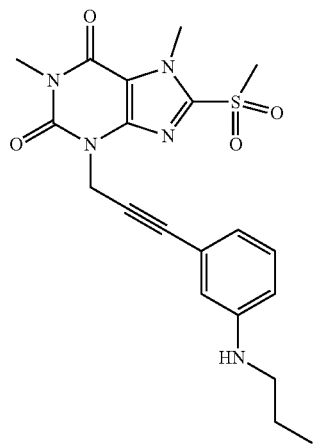 [SMILES: CCCNc1cccc(C#CCn2c(=O)n(C)c(=O)c3c2nc(S(C)(=O)=O)n3C)c1] | 162 |
| 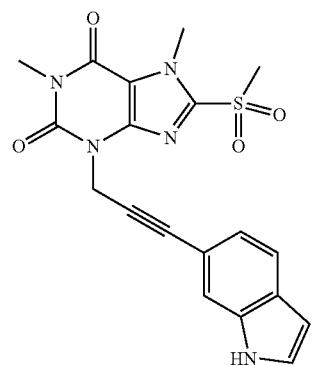 [SMILES: Cn1c(=O)c2c(nc(S(C)(=O)=O)n2C)n(CC#Cc2ccc3cc[nH]c3c2)c1=O] | 163 |
| 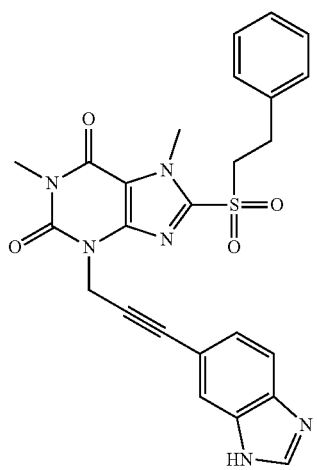 [SMILES: Cn1c(=O)c2c(nc(S(=O)(=O)CCc3ccccc3)n2C)n(CC#Cc2ccc3nc[nH]c3c2)c1=O] | 164 |
| 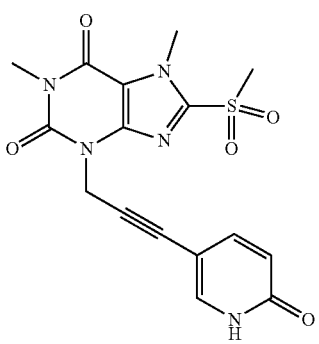 [SMILES: Cn1c(=O)c2c(nc(S(C)(=O)=O)n2C)n(CC#Cc2ccc(=O)[nH]c2)c1=O] | 165 |

TABLE 6-continued
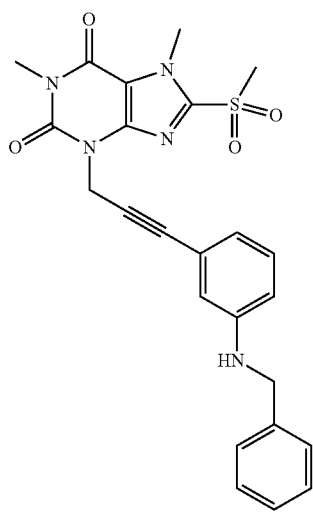 [SMILES: Cn1c(=O)c2c(nc(S(C)(=O)=O)n2C)n(CC#Cc2cccc(NCc3ccccc3)c2)c1=O]
166
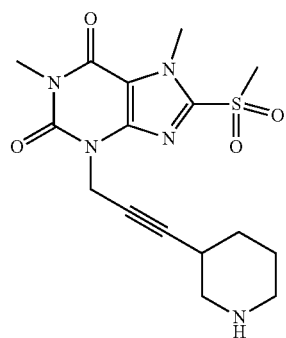 [SMILES: Cn1c(=O)c2c(nc(S(C)(=O)=O)n2C)n(CC#CC2CCCNC2)c1=O]
167
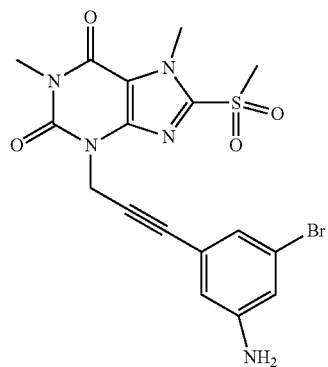 [SMILES: Cn1c(=O)c2c(nc(S(C)(=O)=O)n2C)n(CC#Cc2cc(N)cc(Br)c2)c1=O]
168
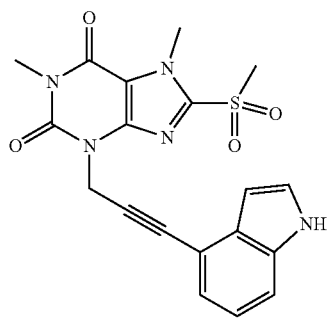 [SMILES: Cn1c(=O)c2c(nc(S(C)(=O)=O)n2C)n(CC#Cc2cccc3[nH]ccc23)c1=O]
169

TABLE 6-continued
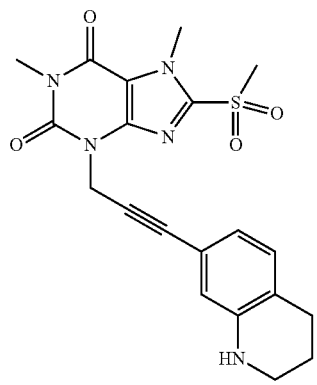 [SMILES: Cn1c(=O)c2c(nc(S(C)(=O)=O)n2C)n(CC#Cc2ccc3c(c2)NCCC3)c1=O]
170
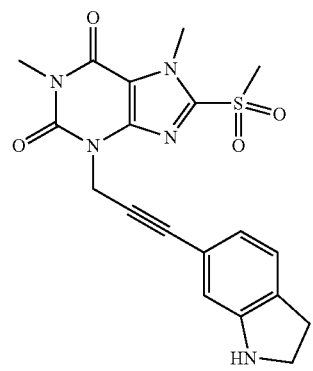 [SMILES: Cn1c(=O)c2c(nc(S(C)(=O)=O)n2C)n(CC#Cc2ccc3c(c2)NCC3)c1=O]
171
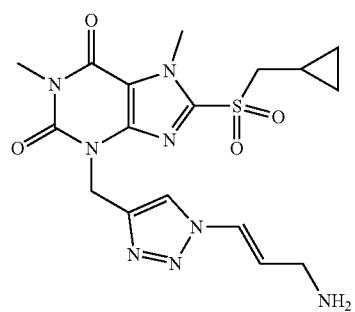 [SMILES: Cn1c(=O)c2c(nc(S(=O)(=O)CC3CC3)n2C)n(Cc2cn(/C=C/CN)nn2)c1=O]
172
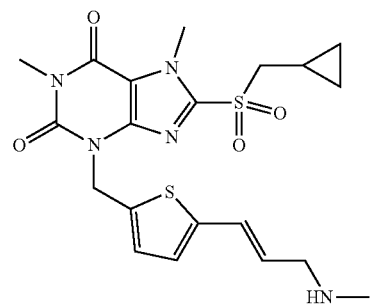
173

TABLE 6-continued
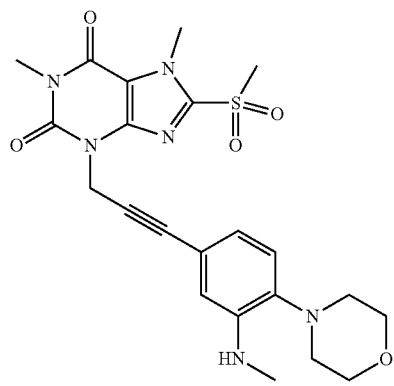 [SMILES: CNc1cc(C#CCn2c(=O)n(C)c(=O)c3c2nc(S(C)(=O)=O)n3C)ccc1N1CCOCC1]
174
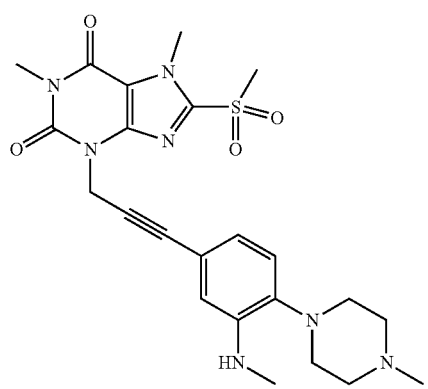
175
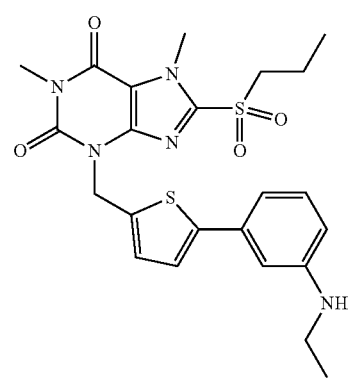 [SMILES: CCCS(=O)(=O)c1nc2c(c(=O)n(C)c(=O)n2Cc2ccc(-c3cccc(NCC)c3)s2)n1C]
176

TABLE 7
| | |
|---|---|
| 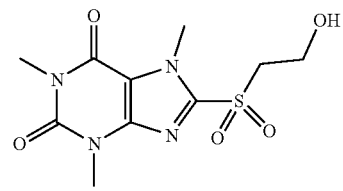 [SMILES: Cn1c(=O)c2c(nc(S(=O)(=O)CCO)n2C)n(C)c1=O] | 1 |
| 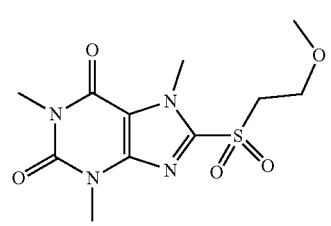 [SMILES: COCCS(=O)(=O)c1nc2c(c(=O)n(C)c(=O)n2C)n1C] | 2 |
| 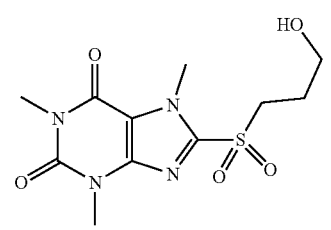 [SMILES: Cn1c(=O)c2c(nc(S(=O)(=O)CCCO)n2C)n(C)c1=O] | 3 |
| 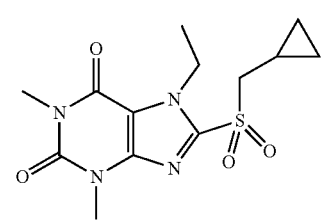 [SMILES: CCn1c(S(=O)(=O)CC2CC2)nc2c1c(=O)n(C)c(=O)n2C] | 4 |
| 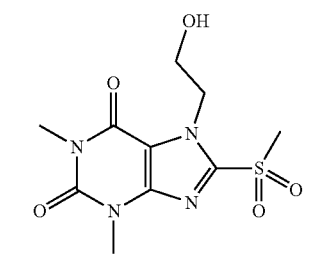 [SMILES: Cn1c(=O)c2c(nc(S(C)(=O)=O)n2CCO)n(C)c1=O] | 5 |
| 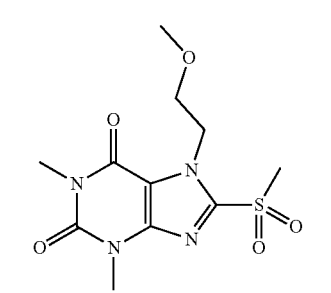 [SMILES: COCCn1c(S(C)(=O)=O)nc2c1c(=O)n(C)c(=O)n2C] | 6 |
TABLE 7-continued
| | |
|---|---|
| 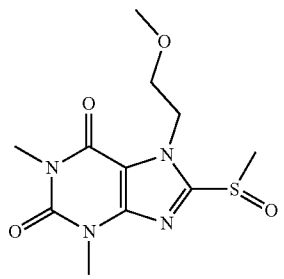 [SMILES: COCCn1c(S(C)=O)nc2c1c(=O)n(C)c(=O)n2C] | 7 |
| 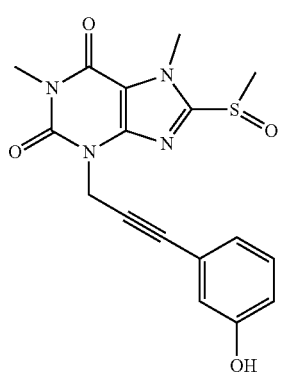 [SMILES: Cn1c(=O)c2c(nc(S(C)=O)n2C)n(CC#Cc2cccc(O)c2)c1=O] | 8 |
| 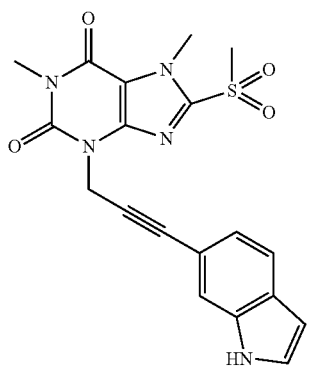 [SMILES: Cn1c(=O)c2c(nc(S(C)(=O)=O)n2C)n(CC#Cc2ccc3cc[nH]c3c2)c1=O] | 9 |
| 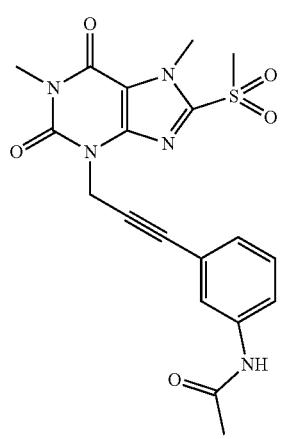 [SMILES: CC(=O)Nc1cccc(C#CCn2c(=O)n(C)c(=O)c3c2nc(S(C)(=O)=O)n3C)c1] | 10 |

TABLE 7-continued
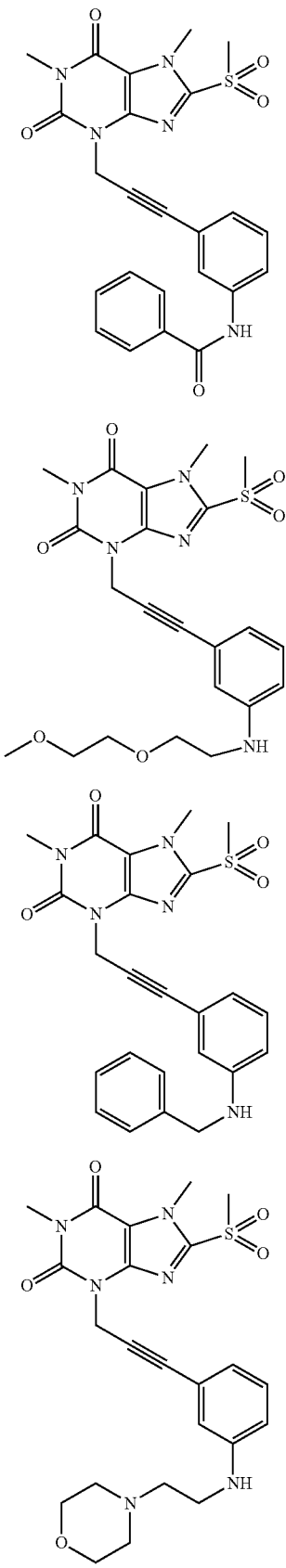
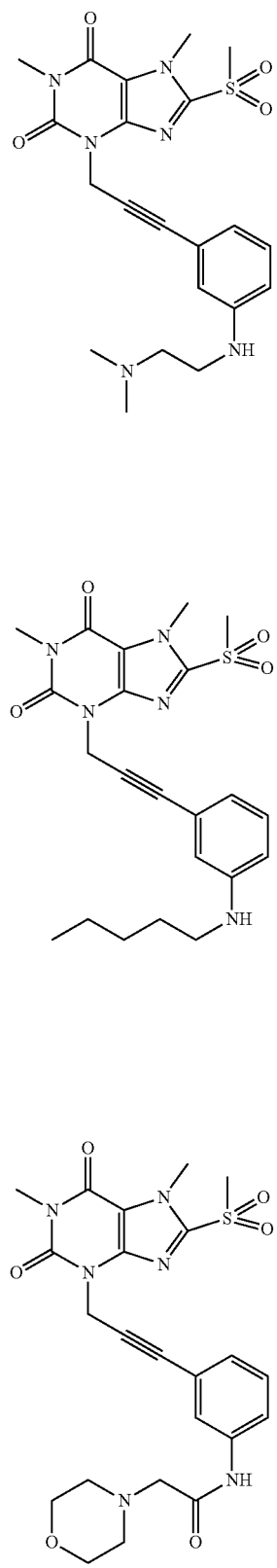

TABLE 7-continued
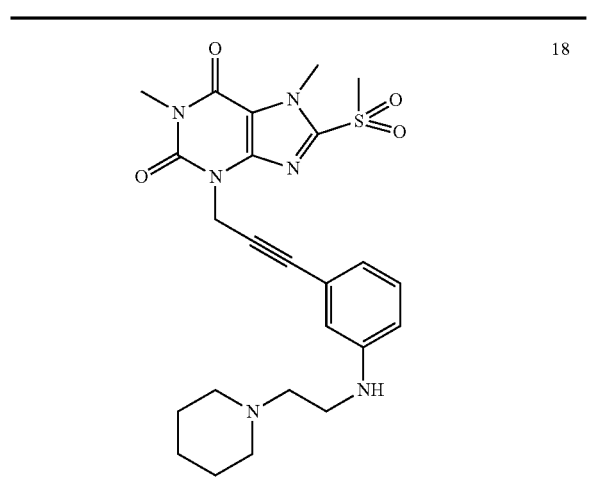
18
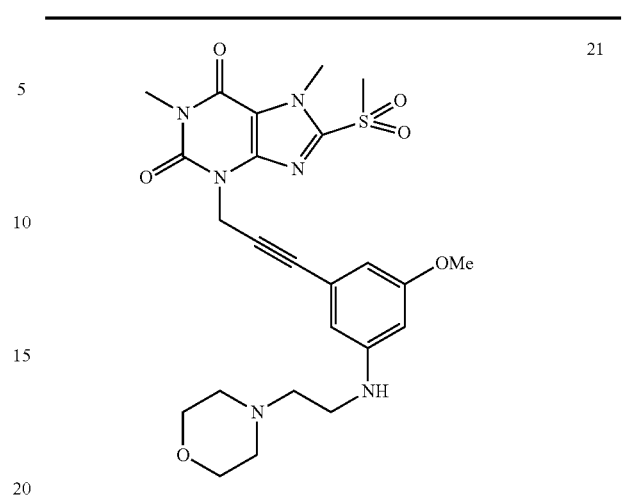
21
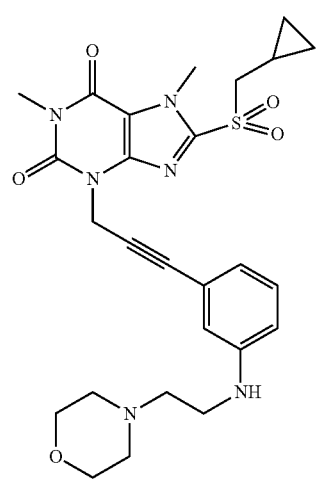 [SMILES: Cn1c(=O)c2c(nc(S(=O)(=O)CC3CC3)n2C)n(CC#Cc2cccc(NCCN3CCOCC3)c2)c1=O]
19
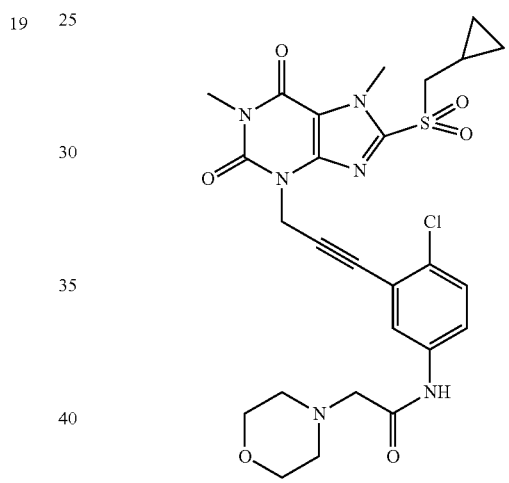
22
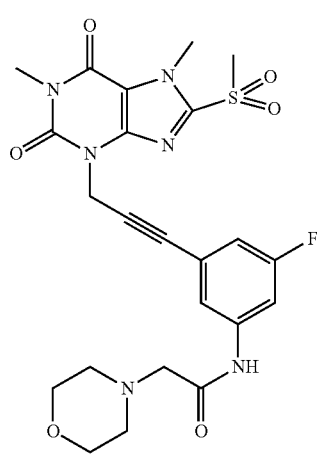 [SMILES: Cn1c(=O)c2c(nc(S(C)(=O)=O)n2C)n(CC#Cc2cc(F)cc(NC(=O)CN3CCOCC3)c2)c1=O]
20
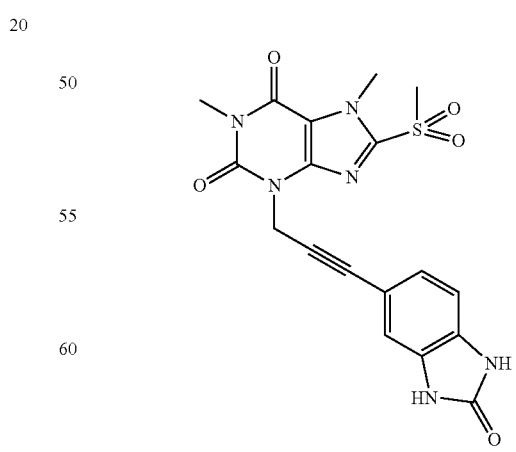
23

TABLE 7-continued
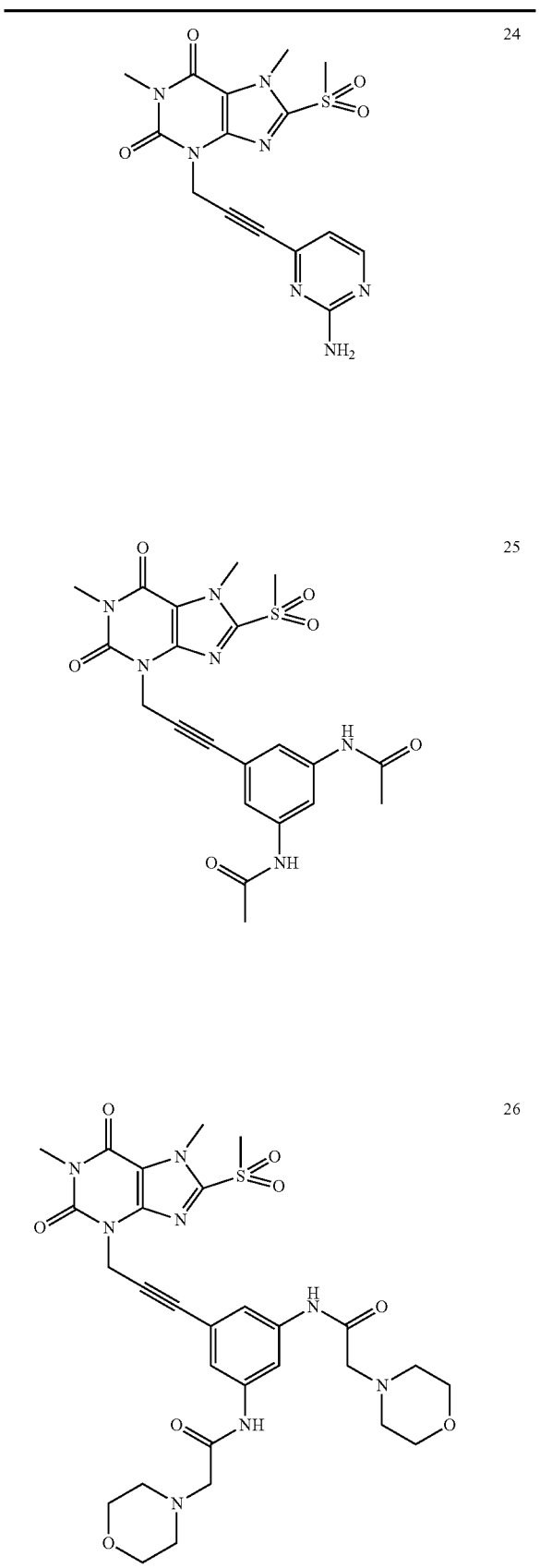
TABLE 7-continued
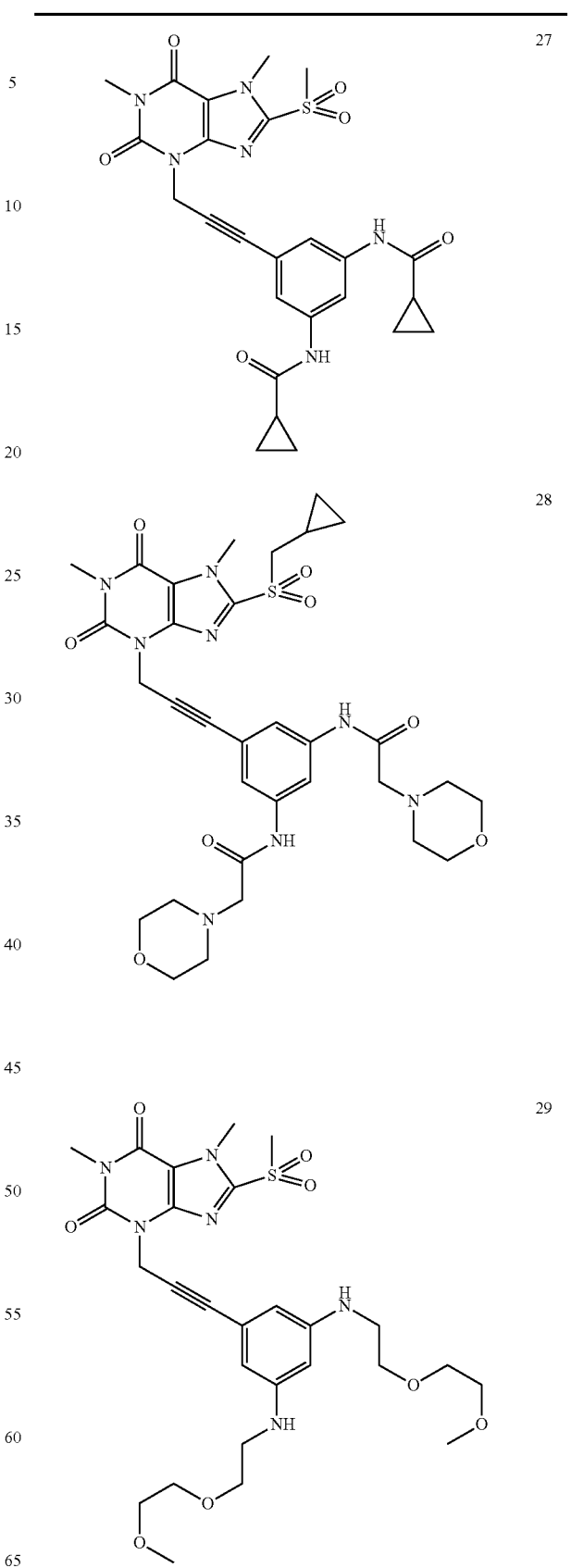

TABLE 7-continued
| | |
|---|---|
| 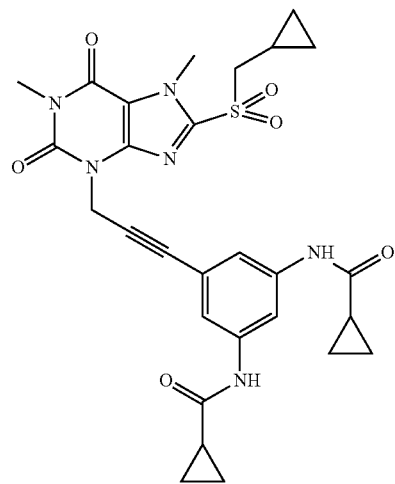 [SMILES: Cn1c(=O)c2c(nc(S(=O)(=O)CC3CC3)n2C)n(CC#Cc2cc(NC(=O)C3CC3)cc(NC(=O)C3CC3)c2)c1=O] 30 | 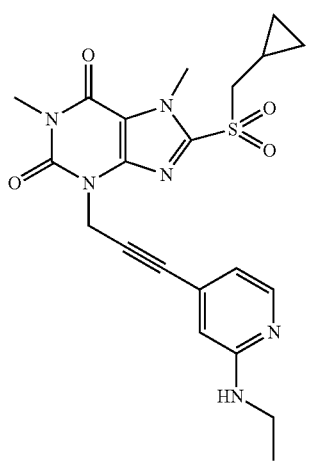 33 |
| 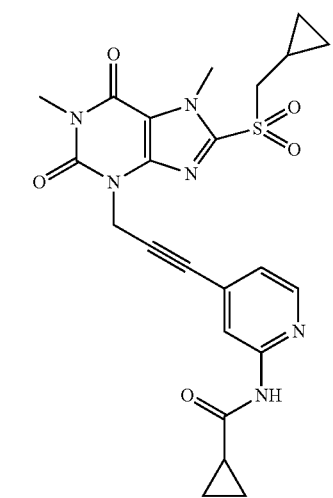 [SMILES: Cn1c(=O)c2c(nc(S(=O)(=O)CC3CC3)n2C)n(CC#Cc2ccnc(NC(=O)C3CC3)c2)c1=O] 31 | 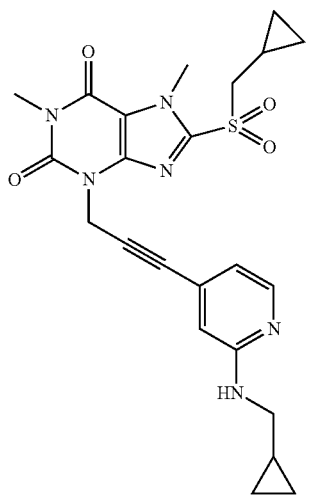 34 |
| 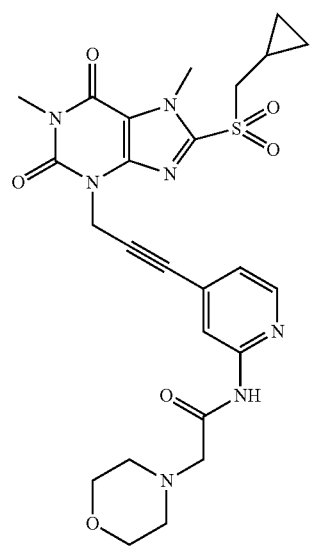 [SMILES: Cn1c(=O)c2c(nc(S(=O)(=O)CC3CC3)n2C)n(CC#Cc2ccnc(NC(=O)CN3CCOCC3)c2)c1=O] 32 | 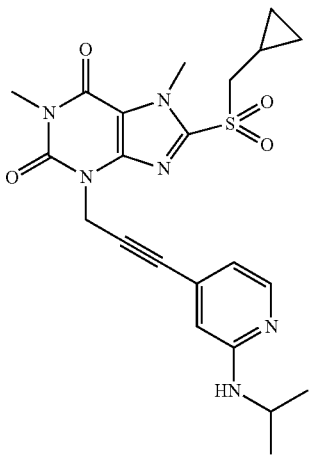 [SMILES: CC(C)Nc1cc(C#CCn2c(=O)n(C)c(=O)c3c2nc(S(=O)(=O)CC2CC2)n3C)ccn1] 35 |

TABLE 7-continued
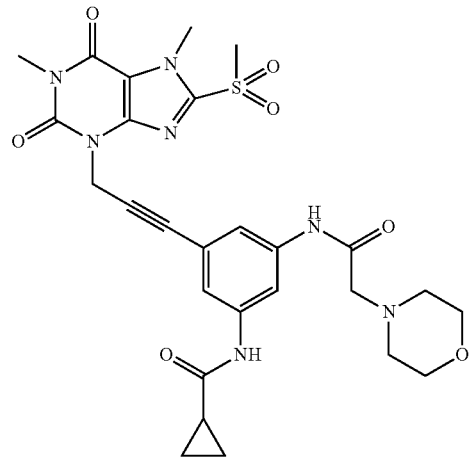 [SMILES: Cn1c(=O)c2c(nc(S(C)(=O)=O)n2C)n(CC#Cc2cc(NC(=O)CN3CCOCC3)cc(NC(=O)C3CC3)c2)c1=O]
36
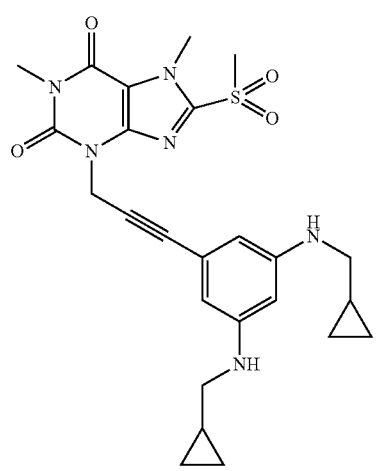 [SMILES: Cn1c(=O)c2c(nc(S(C)(=O)=O)n2C)n(CC#Cc2cc(NCC3CC3)cc(NCC3CC3)c2)c1=O]
37
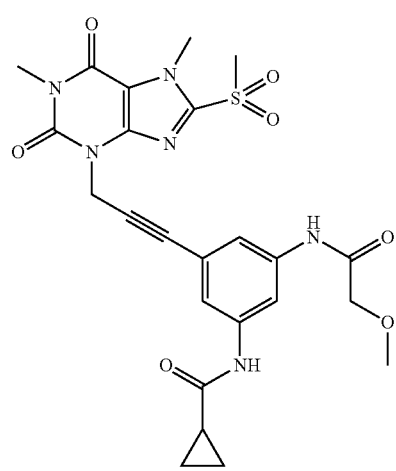
38
TABLE 7-continued
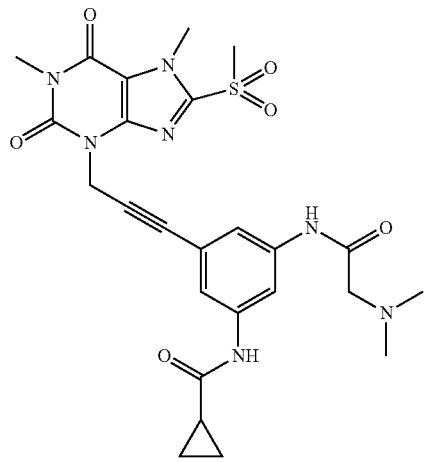
39
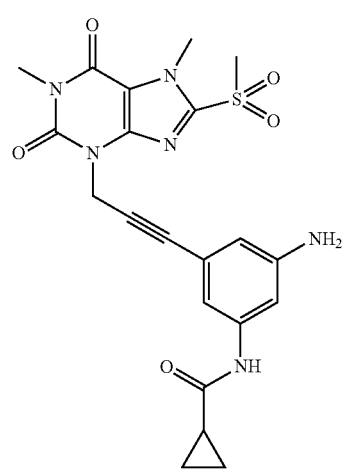 [SMILES: Cn1c(=O)c2c(nc(S(C)(=O)=O)n2C)n(CC#Cc2cc(N)cc(NC(=O)C3CC3)c2)c1=O]
40
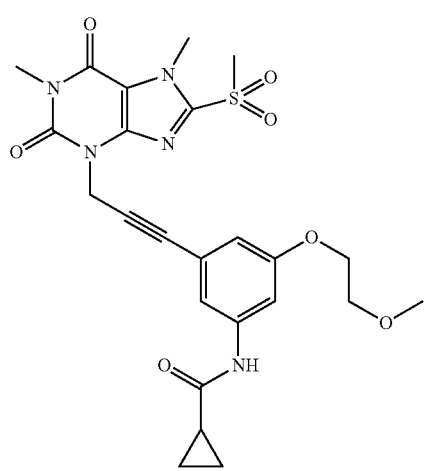
41

TABLE 7-continued
| | |
|---|---|
| 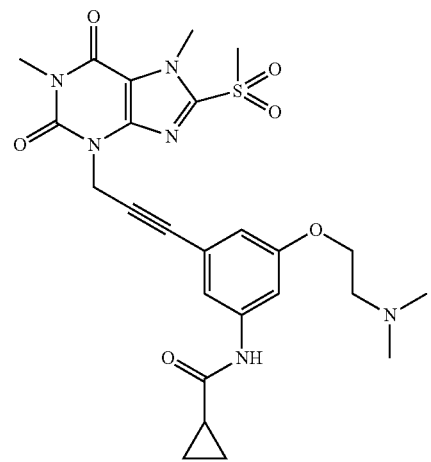 42 | 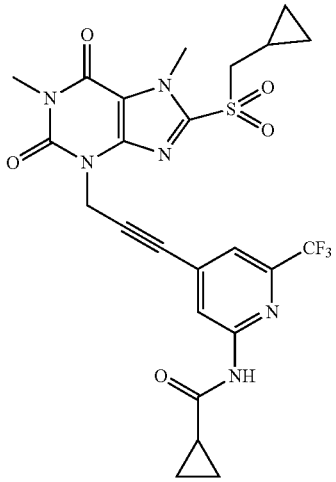 45 |
| 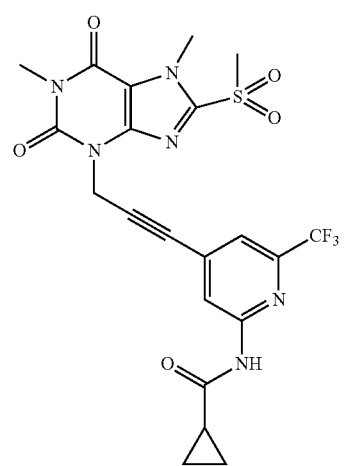 [SMILES: Cn1c(=O)c2c(nc(S(C)(=O)=O)n2C)n(CC#Cc2cc(NC(=O)C3CC3)nc(C(F)(F)F)c2)c1=O] 43 | 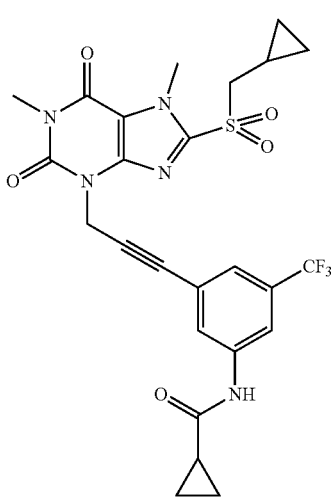 46 |
| 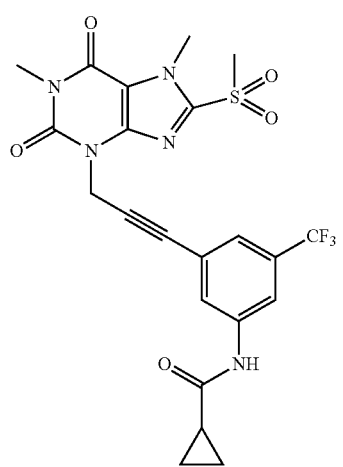 [SMILES: Cn1c(=O)c2c(nc(S(C)(=O)=O)n2C)n(CC#Cc2cc(NC(=O)C3CC3)cc(C(F)(F)F)c2)c1=O] 44 | 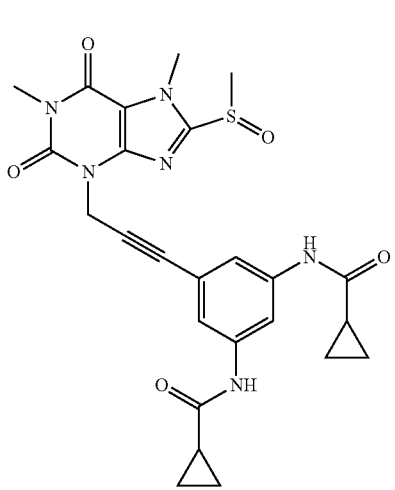 [SMILES: Cn1c(=O)c2c(nc(S(C)=O)n2C)n(CC#Cc2cc(NC(=O)C3CC3)cc(NC(=O)C3CC3)c2)c1=O] 47 |

TABLE 7-continued
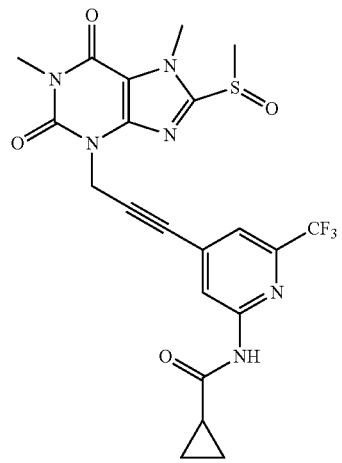 [SMILES: Cn1c(=O)c2c(nc(S(C)=O)n2C)n(CC#Cc2cc(NC(=O)C3CC3)nc(C(F)(F)F)c2)c1=O]
48
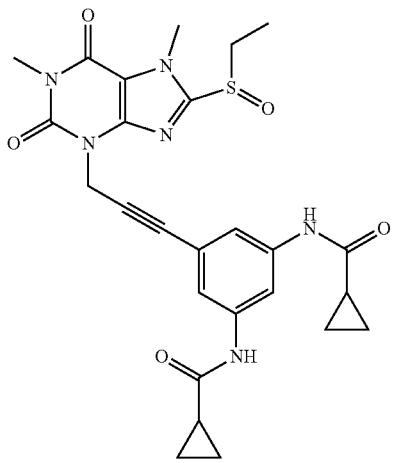
51
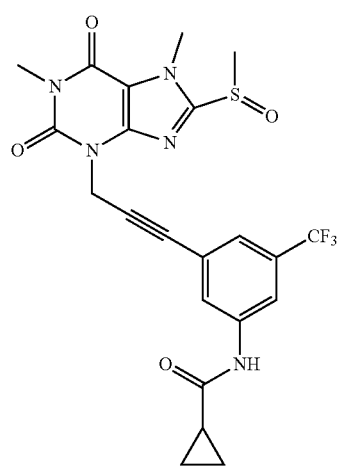 [SMILES: Cn1c(=O)c2c(nc(S(C)=O)n2C)n(CC#Cc2cc(NC(=O)C3CC3)cc(C(F)(F)F)c2)c1=O]
49
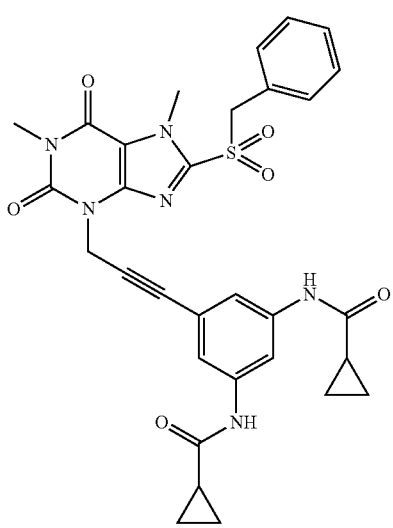
52
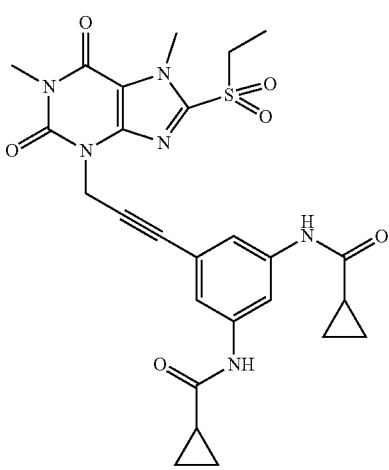 [SMILES: CCS(=O)(=O)c1nc2c(c(=O)n(C)c(=O)n2CC#Cc2cc(NC(=O)C3CC3)cc(NC(=O)C3CC3)c2)n1C]
50
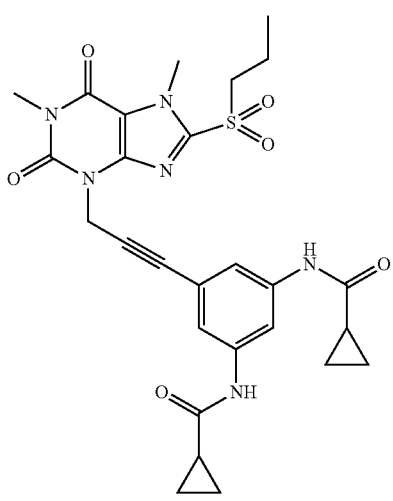 [SMILES: CCCS(=O)(=O)c1nc2c(c(=O)n(C)c(=O)n2CC#Cc2cc(NC(=O)C3CC3)cc(NC(=O)C3CC3)c2)n1C]
53

TABLE 7-continued
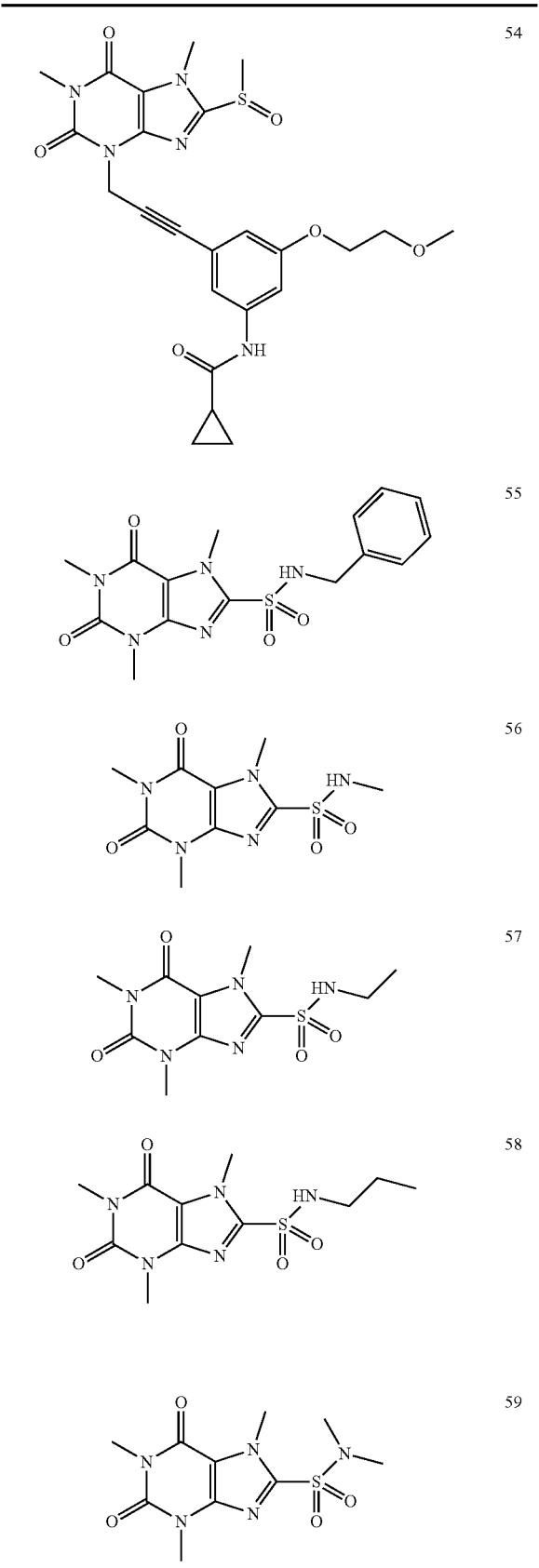
TABLE 7-continued
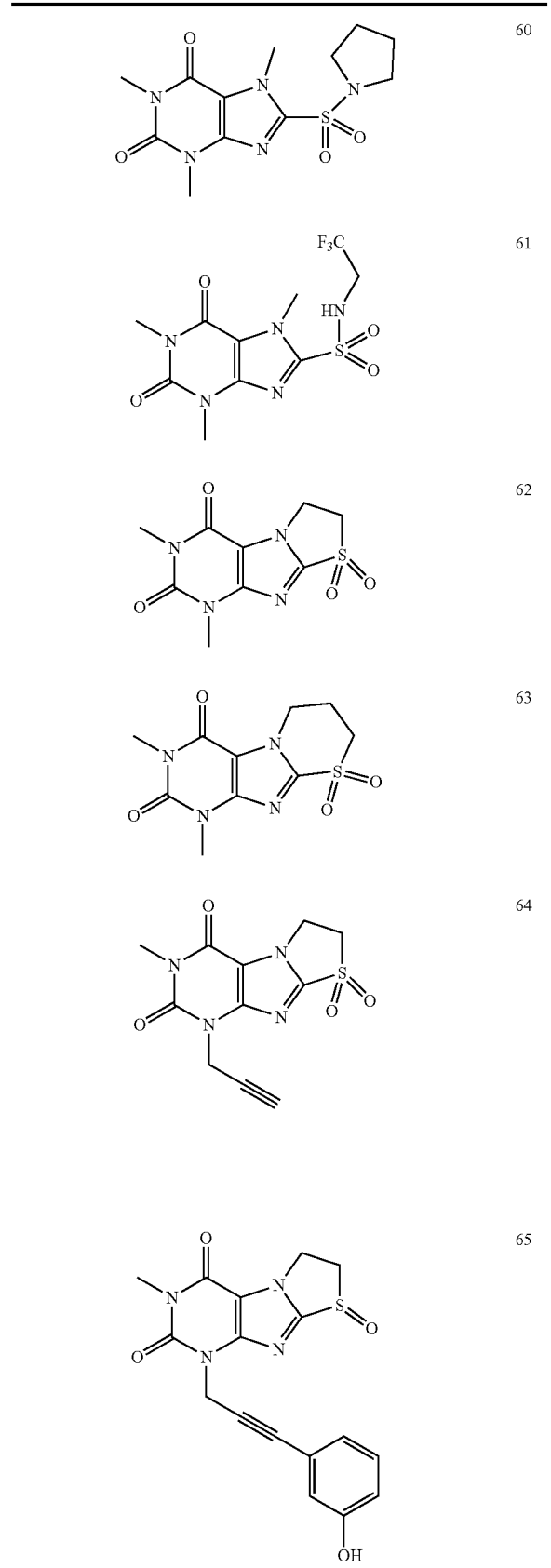

TABLE 7-continued
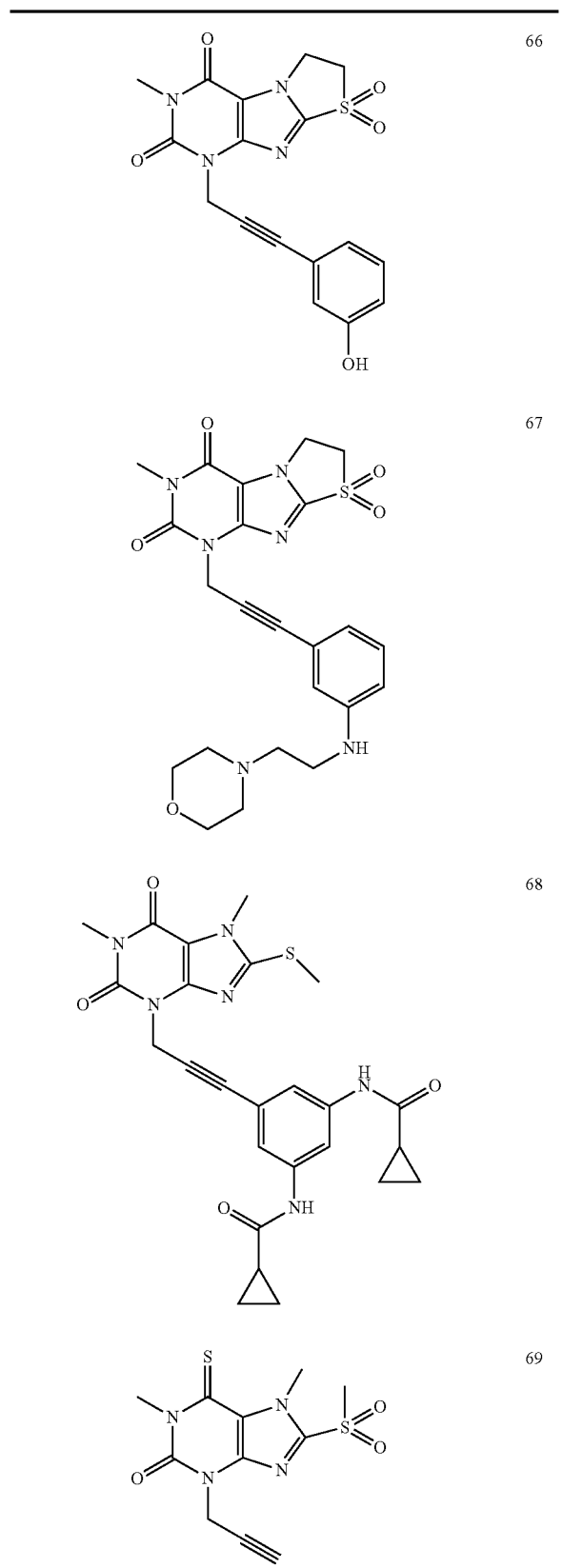
TABLE 7-continued
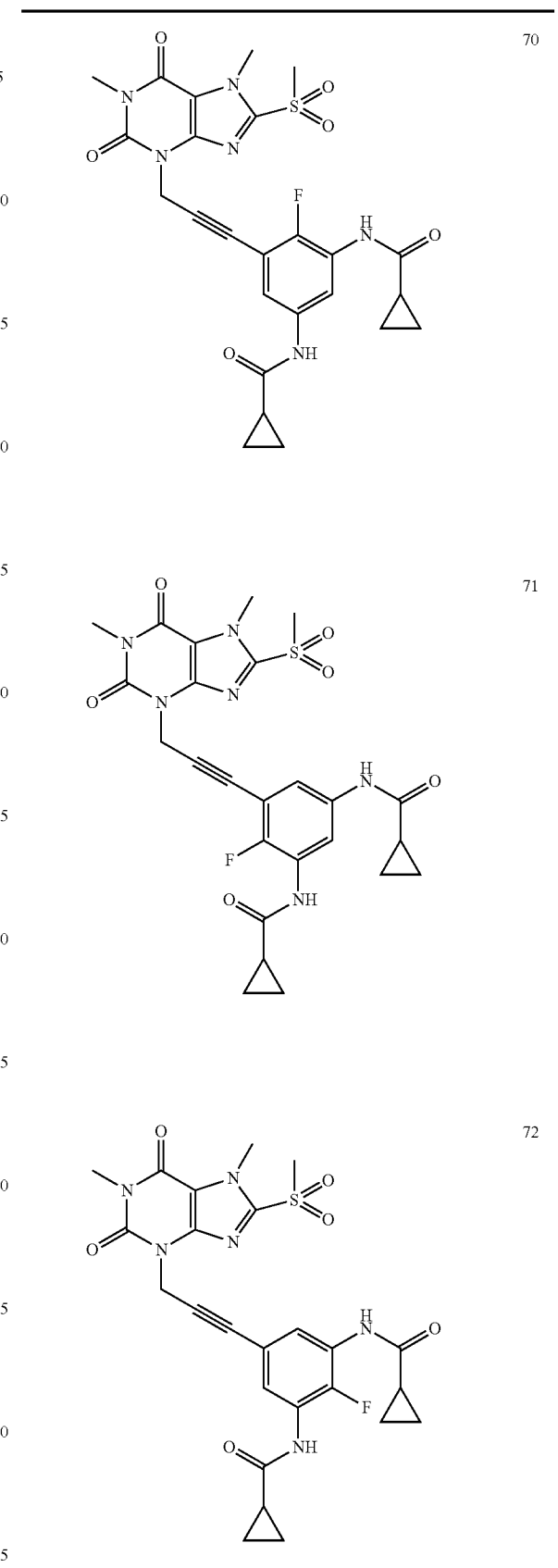

TABLE 7-continued
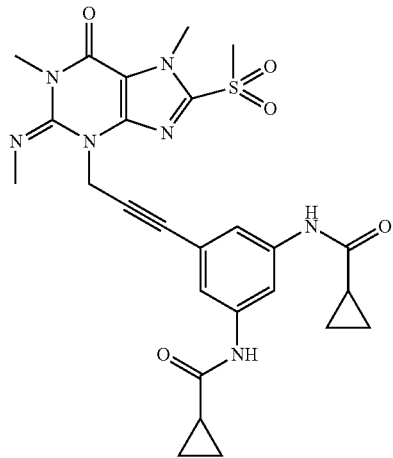 [SMILES: C/N=c1/n(C)c(=O)c2c(nc(S(C)(=O)=O)n2C)n1CC#Cc1cc(NC(=O)C2CC2)cc(NC(=O)C2CC2)c1]
73
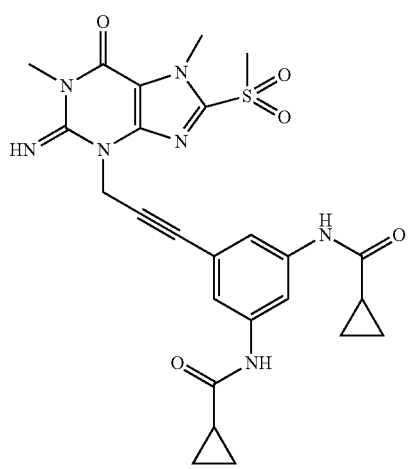 [SMILES: Cn1c(=O)c2c(nc(S(C)(=O)=O)n2C)n(CC#Cc2cc(NC(=O)C3CC3)cc(NC(=O)C3CC3)c2)c1=N]
74
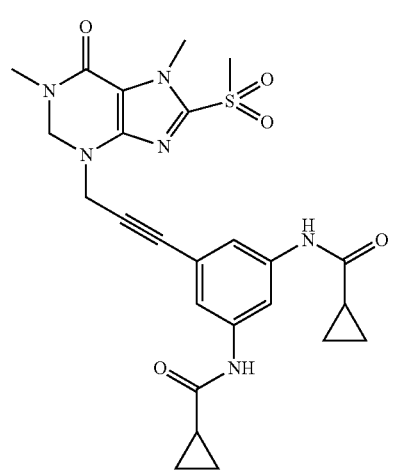 [SMILES: CN1CN(CC#Cc2cc(NC(=O)C3CC3)cc(NC(=O)C3CC3)c2)c2nc(S(C)(=O)=O)n(C)c2C1=O]
75
TABLE 7-continued
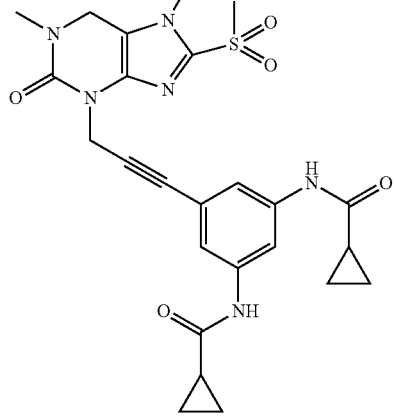
76
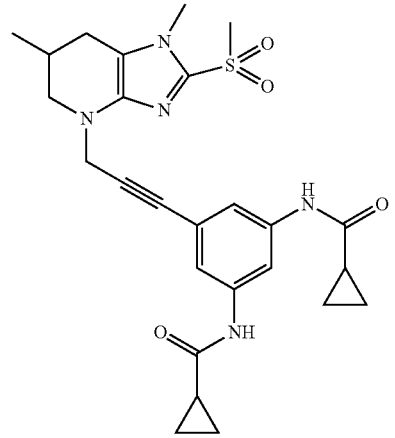 [SMILES: CC1Cc2c(nc(S(C)(=O)=O)n2C)N(CC#Cc2cc(NC(=O)C3CC3)cc(NC(=O)C3CC3)c2)C1]
77
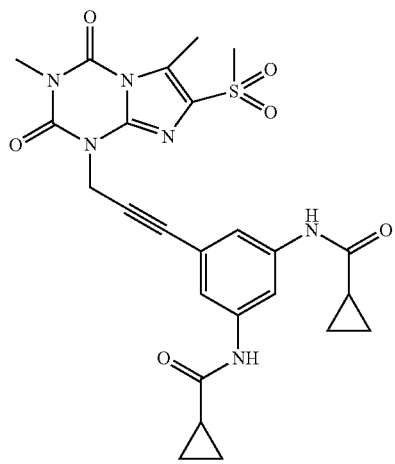 [SMILES: Cc1c(S(C)(=O)=O)nc2n(CC#Cc3cc(NC(=O)C4CC4)cc(NC(=O)C4CC4)c3)c(=O)n(C)c(=O)n12]
78

TABLE 7-continued
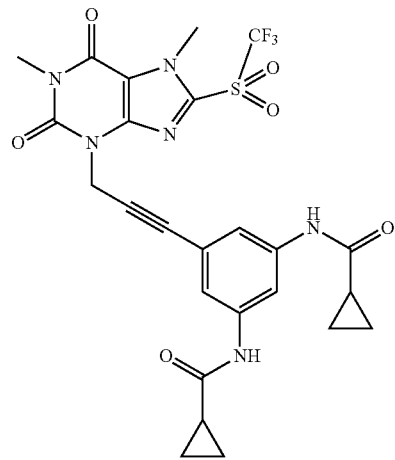 [SMILES: Cn1c(=O)c2c(nc(S(=O)(=O)C(F)(F)F)n2C)n(CC#Cc2cc(NC(=O)C3CC3)cc(NC(=O)C3CC3)c2)c1=O]
79
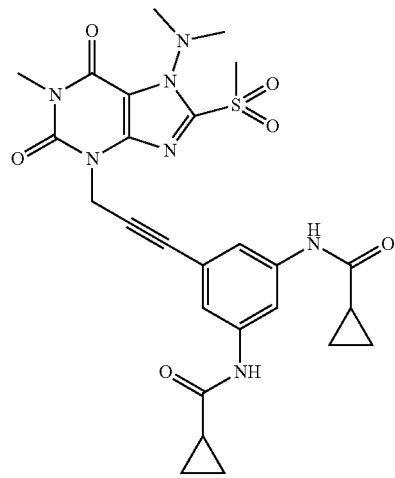
82
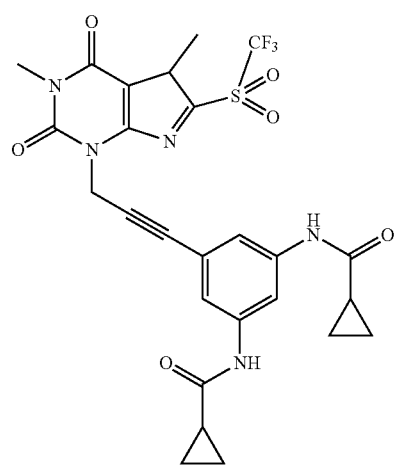 [SMILES: CC1C(S(=O)(=O)C(F)(F)F)=Nc2c1c(=O)n(C)c(=O)n2CC#Cc1cc(NC(=O)C2CC2)cc(NC(=O)C2CC2)c1]
80
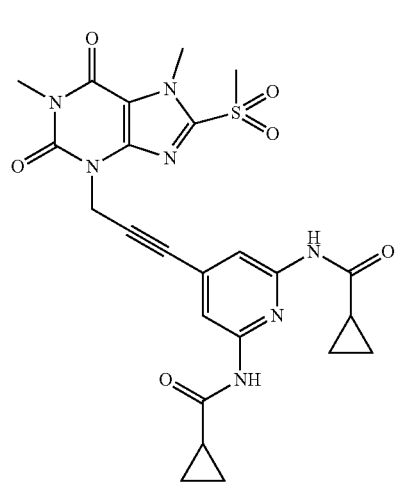
83
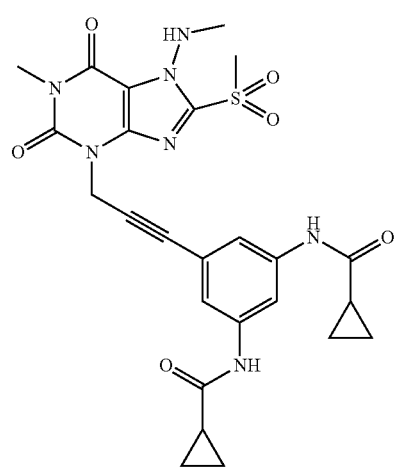 [SMILES: CNn1c(S(C)(=O)=O)nc2c1c(=O)n(C)c(=O)n2CC#Cc1cc(NC(=O)C2CC2)cc(NC(=O)C2CC2)c1]
81
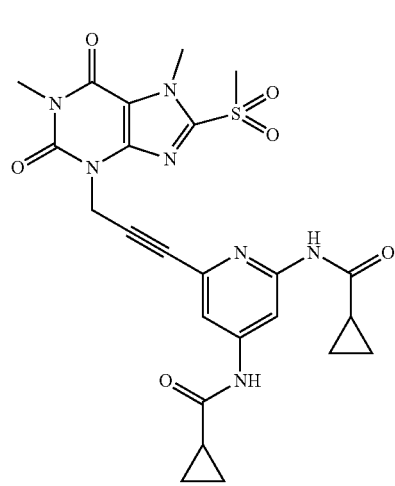 [SMILES: Cn1c(=O)c2c(nc(S(C)(=O)=O)n2C)n(CC#Cc2cc(NC(=O)C3CC3)cc(NC(=O)C3CC3)n2)c1=O]
84

TABLE 7-continued
85
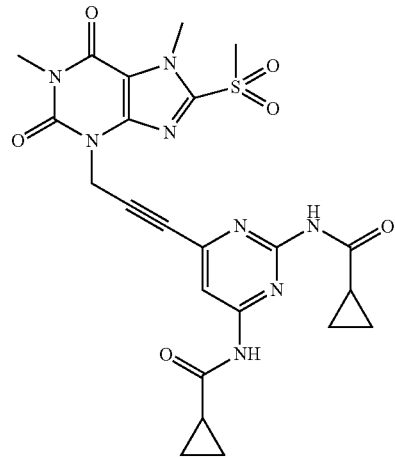
86
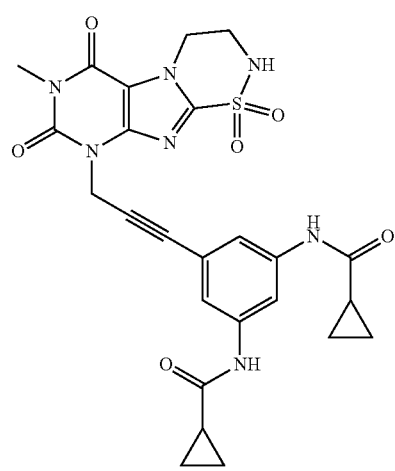
87
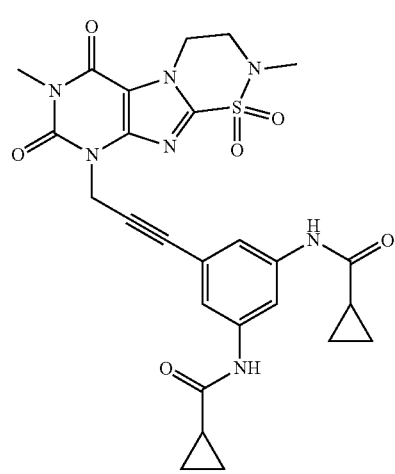 [SMILES: CN1CCn2c(nc3c2c(=O)n(C)c(=O)n3CC#Cc2cc(NC(=O)C3CC3)cc(NC(=O)C3CC3)c2)S1(=O)=O]
TABLE 7-continued
88
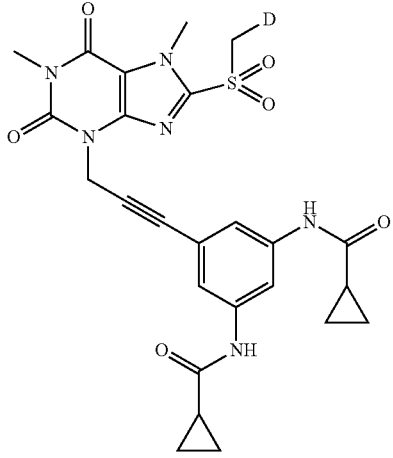
89
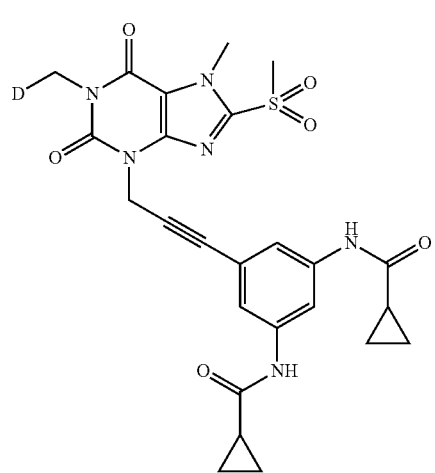 [SMILES: [2H]Cn1c(=O)c2c(nc(S(C)(=O)=O)n2C)n(CC#Cc2cc(NC(=O)C3CC3)cc(NC(=O)C3CC3)c2)c1=O]
90
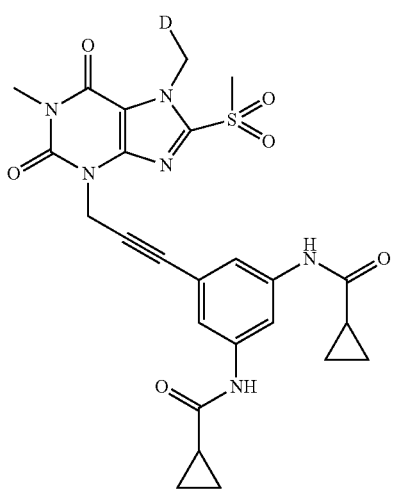 [SMILES: [2H]Cn1c(S(C)(=O)=O)nc2c1c(=O)n(C)c(=O)n2CC#Cc1cc(NC(=O)C2CC2)cc(NC(=O)C2CC2)c1]

TABLE 7-continued
91
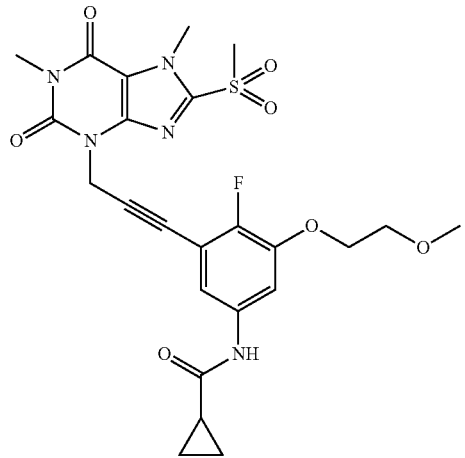
92
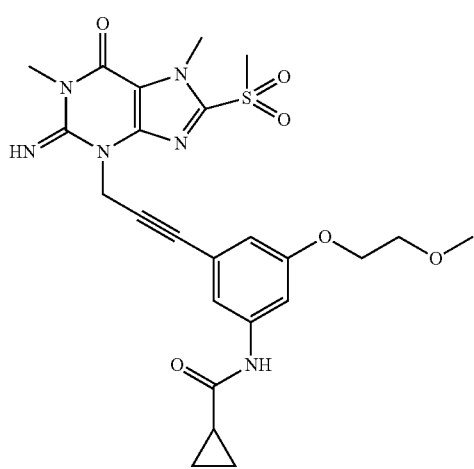
93
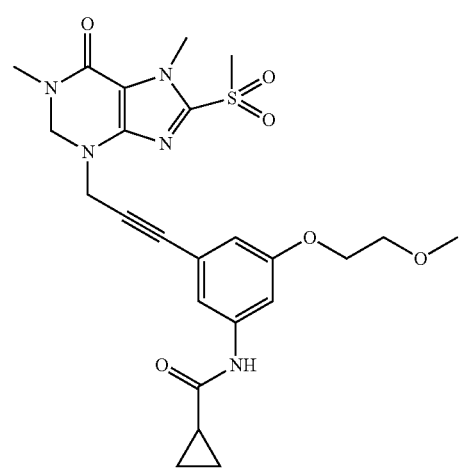
TABLE 7-continued
94
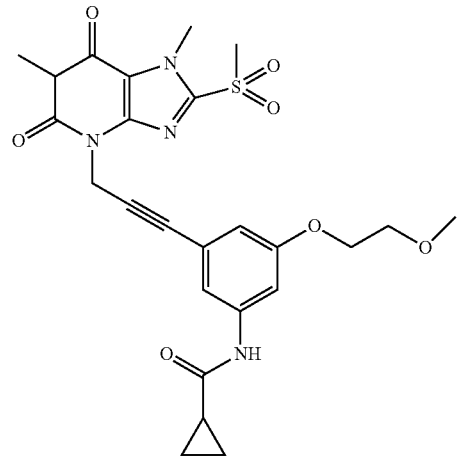
95
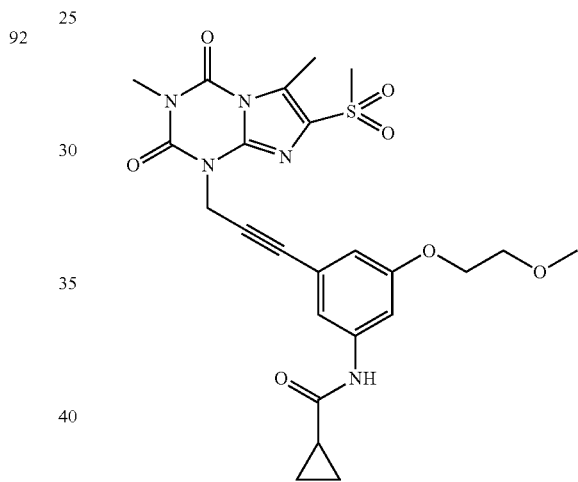
96
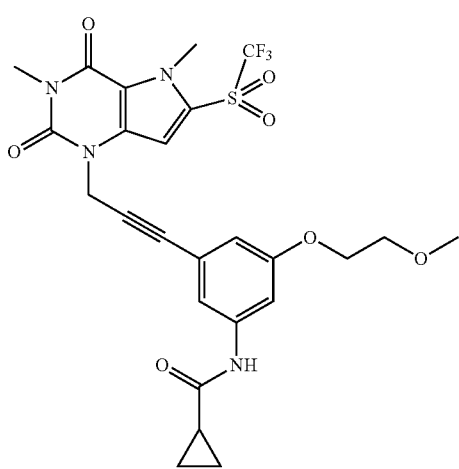

TABLE 7-continued
| | |
|---|---|
| 97 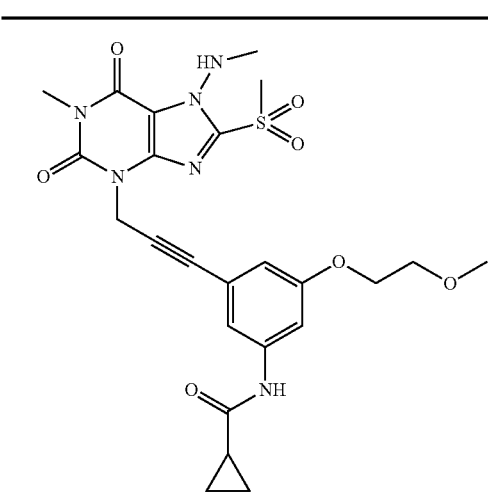 | 100 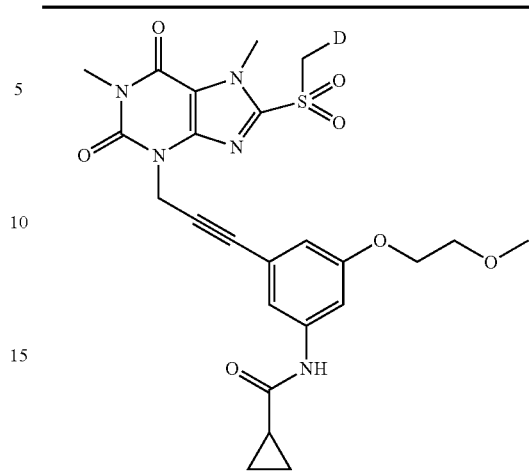 |
| 98 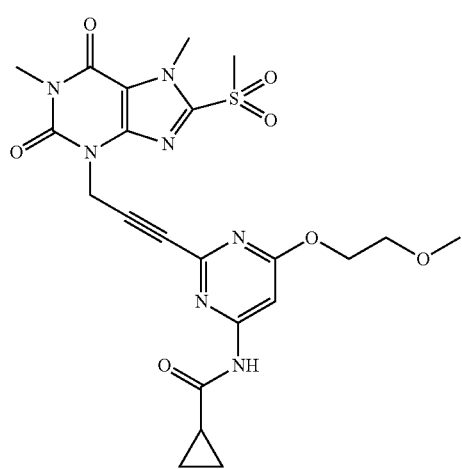 | 101 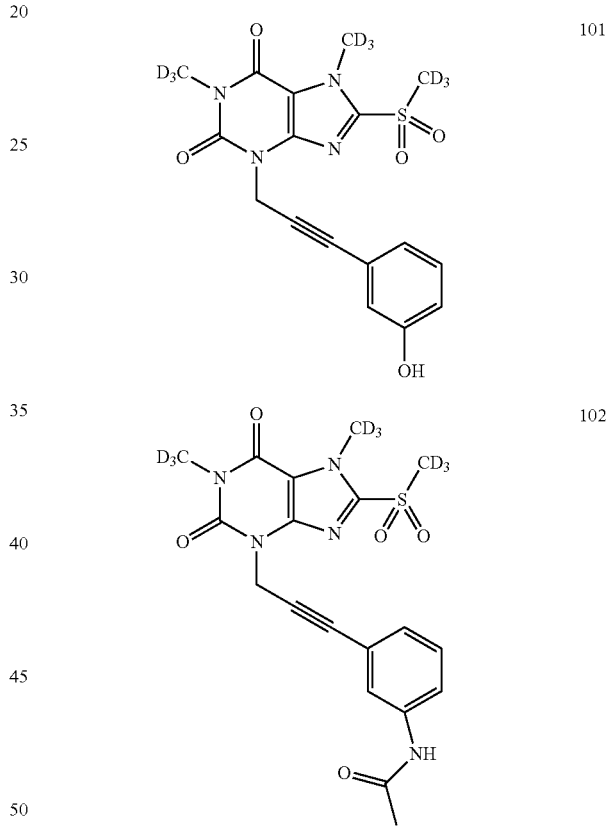 |
| 99 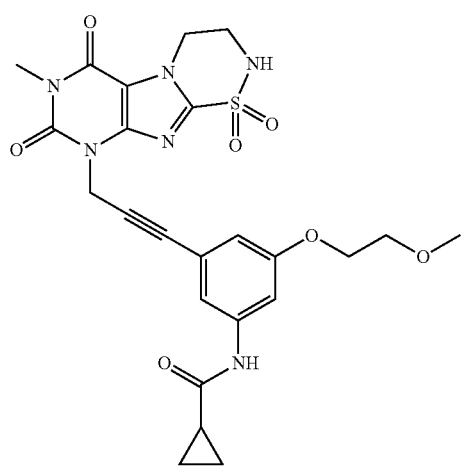 | 102 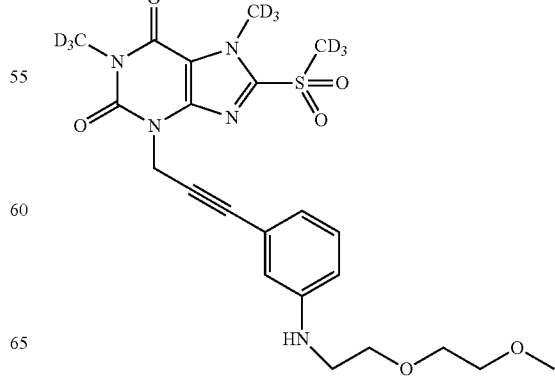 |
| | 103 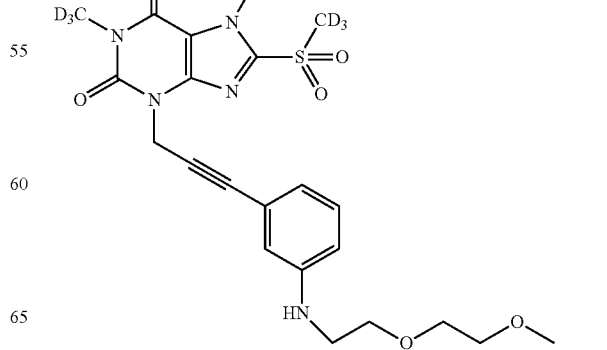 |

TABLE 7-continued
104
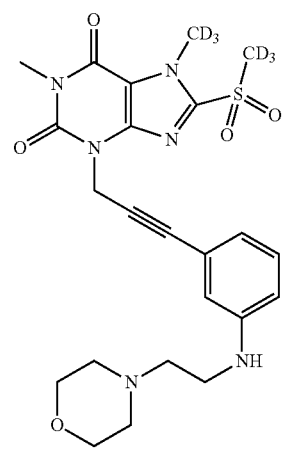 [SMILES: [2H]C([2H])([2H])n1c(S(=O)(=O)C([2H])([2H])[2H])nc2c1c(=O)n(C)c(=O)n2CC#Cc1cccc(NCCN2CCOCC2)c1]
105
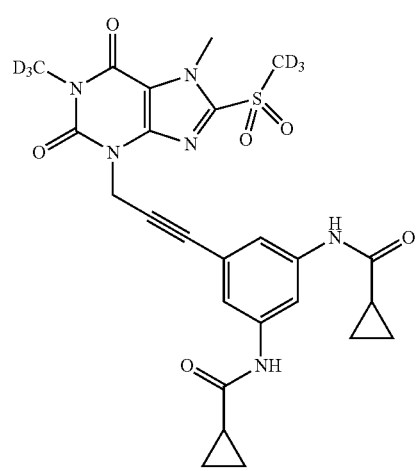 [SMILES: [2H]C([2H])([2H])n1c(=O)c2c(nc(S(=O)(=O)C([2H])([2H])[2H])n2C)n(CC#Cc2cc(NC(=O)C3CC3)cc(NC(=O)C3CC3)c2)c1=O]
106
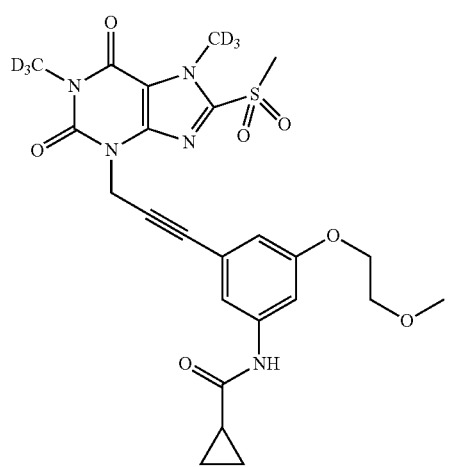 [SMILES: [2H]C([2H])([2H])n1c(=O)c2c(nc(S(C)(=O)=O)n2C([2H])([2H])[2H])n(CC#Cc2cc(NC(=O)C3CC3)cc(OCCOC)c2)c1=O]
TABLE 7-continued
107
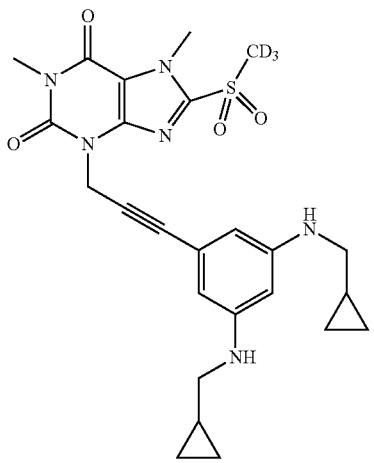 [SMILES: [2H]C([2H])([2H])S(=O)(=O)c1nc2c(c(=O)n(C)c(=O)n2CC#Cc2cc(NCC3CC3)cc(NCC3CC3)c2)n1C]
108
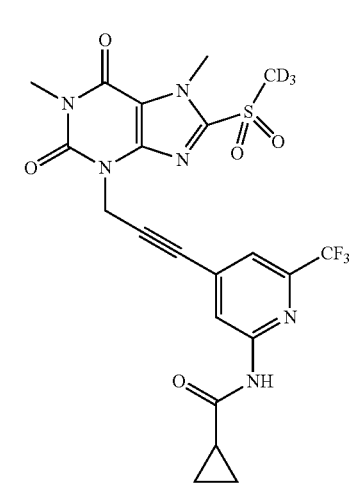 [SMILES: [2H]C([2H])([2H])S(=O)(=O)c1nc2c(c(=O)n(C)c(=O)n2CC#Cc2cc(NC(=O)C3CC3)nc(C(F)(F)F)c2)n1C]
109
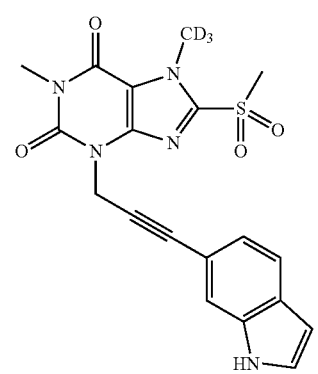 [SMILES: [2H]C([2H])([2H])n1c(S(C)(=O)=O)nc2c1c(=O)n(C)c(=O)n2CC#Cc1ccc2cc[nH]c2c1]

TABLE 7-continued
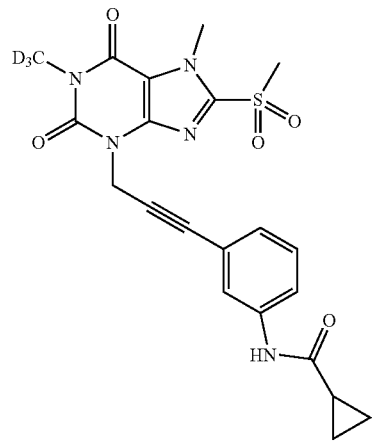 [SMILES: [2H]C([2H])([2H])n1c(=O)c2c(nc(S(C)(=O)=O)n2C)n(CC#Cc2cccc(NC(=O)C3CC3)c2)c1=O]
110
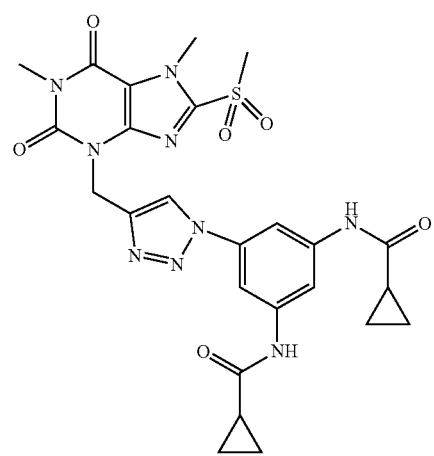 [SMILES: Cn1c(=O)c2c(nc(S(C)(=O)=O)n2C)n(Cc2cn(-c3cc(NC(=O)C4CC4)cc(NC(=O)C4CC4)c3)nn2)c1=O]
111
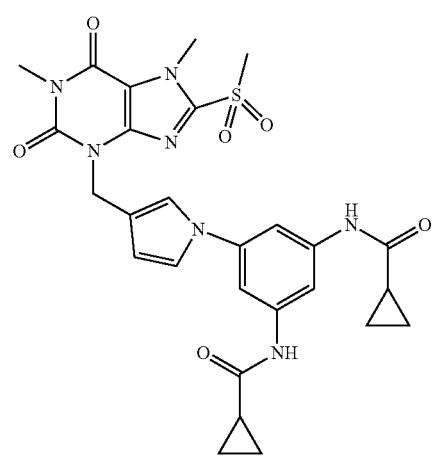 [SMILES: Cn1c(=O)c2c(nc(S(C)(=O)=O)n2C)n(Cc2ccn(-c3cc(NC(=O)C4CC4)cc(NC(=O)C4CC4)c3)c2)c1=O]
112
TABLE 7-continued
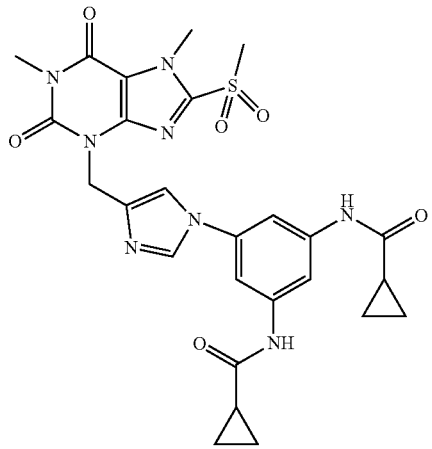 [SMILES: Cn1c(=O)c2c(nc(S(C)(=O)=O)n2C)n(Cc2cn(-c3cc(NC(=O)C4CC4)cc(NC(=O)C4CC4)c3)cn2)c1=O]
113
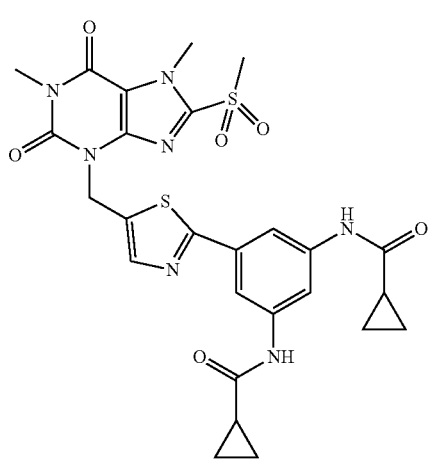 [SMILES: Cn1c(=O)c2c(nc(S(C)(=O)=O)n2C)n(Cc2cnc(-c3cc(NC(=O)C4CC4)cc(NC(=O)C4CC4)c3)s2)c1=O]
114
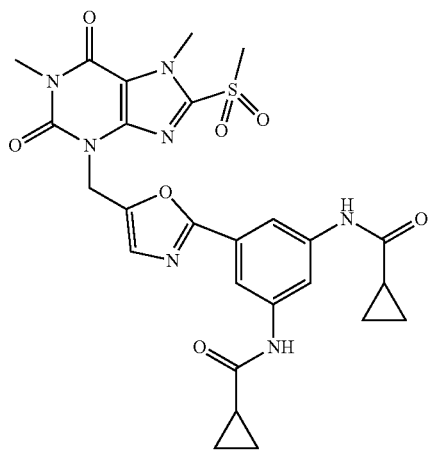 [SMILES: Cn1c(=O)c2c(nc(S(C)(=O)=O)n2C)n(Cc2cnc(-c3cc(NC(=O)C4CC4)cc(NC(=O)C4CC4)c3)o2)c1=O]
115

TABLE 7-continued

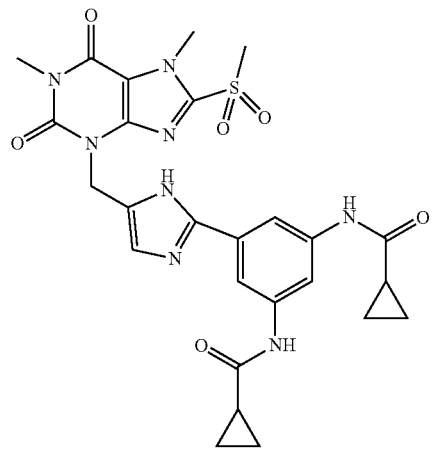 [SMILES: Cn1c(=O)c2c(nc(S(C)(=O)=O)n2C)n(Cc2cnc(-c3cc(NC(=O)C4CC4)cc(NC(=O)C4CC4)c3)[nH]2)c1=O]

116

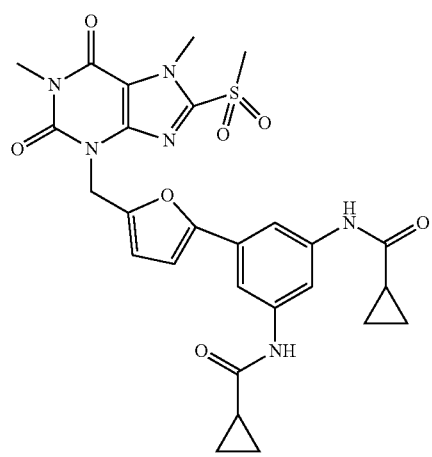 [SMILES: Cn1c(=O)c2c(nc(S(C)(=O)=O)n2C)n(Cc2ccc(-c3cc(NC(=O)C4CC4)cc(NC(=O)C4CC4)c3)o2)c1=O]

117

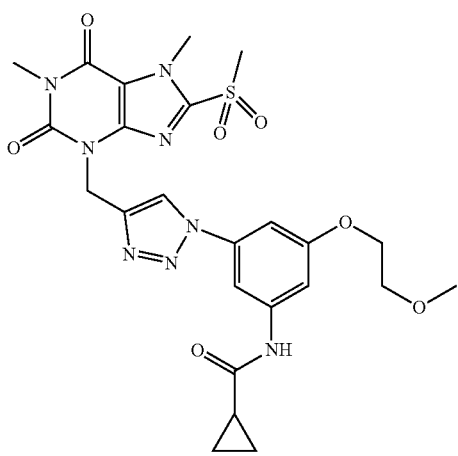 [SMILES: COCCOc1cc(NC(=O)C2CC2)cc(-n2cc(Cn3c(=O)n(C)c(=O)c4c3nc(S(C)(=O)=O)n4C)nn2)c1]

118

TABLE 7-continued

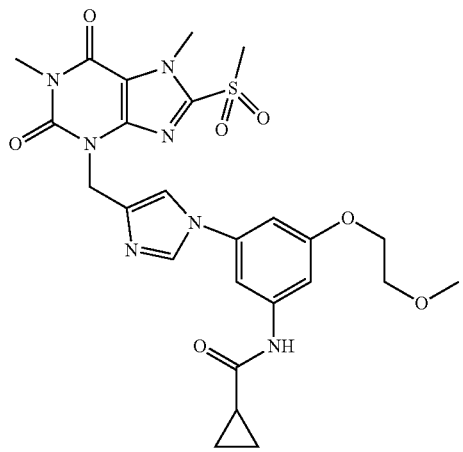 [SMILES: COCCOc1cc(NC(=O)C2CC2)cc(-n2cnc(Cn3c(=O)n(C)c(=O)c4c3nc(S(C)(=O)=O)n4C)c2)c1]

119

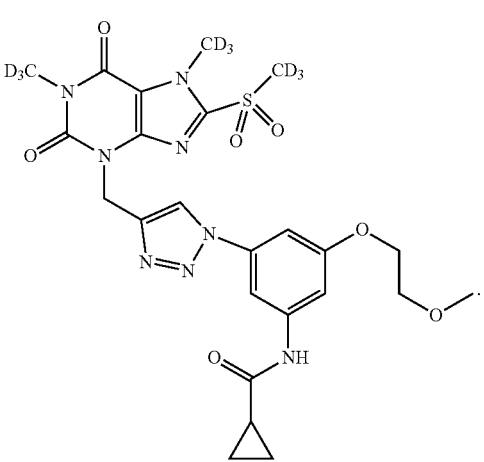 [SMILES: [2H]C([2H])([2H])n1c(=O)c2c(nc(S(=O)(=O)C([2H])([2H])[2H])n2C([2H])([2H])[2H])n(Cc2cn(-c3cc(NC(=O)C4CC4)cc(OCCOC)c3)nn2)c1=O]

120

9. The method of claim 1 wherein the method further comprises administering to the male a second, different drug for treating male senescence.

10. The method of claim 1 wherein the method further comprises administering to the male a second, different drug for treating male senescence, wherein the different drug is selected from an androgen including exogenous and endogenous anabolic androgenic steroids, endogenous androgen stimulators, female hormone inhibitor, growth hormone.

11. The method of claim 1 wherein the method further comprises administering to the male a second, different drug for treating male senescence, wherein the different drug is selected from:

testosterone, prasterone (dehydroepiandrosterone, DHEA), androstenedione (A4), androstenediol (A5), dihydrotestosterone (DHT), 1-Androstenediol, 1-Androstenedione, Bolandiol, Bolasterone, Boldenone, Boldione, Calusterone, Clostebol, Danazol, Dehydrochlormethyltestosterone, Desoxymethyltestosterone, Drostanolone, Ethylestrenol, Fluoxymesterone, Formebolone, Furazabol, Gestrinone, 4-Hydroxytestosterone, Mestanolone, Mesterolone, Metenolone, Methandienone, Methandriol, Methasterone, Methyldienolone, Methyl-1-testosterone, Methylnortestosterone, Methyltestosterone, Metribolone, Mibolerone, Nandrolone, 19-Norandrostenedione, Norboletone, Norclostebol, Norethandrolone, Oxabolone, Oxandrolone, Oxymesterone, Oxymetholone, Prostanozol, Quinbolone, Stanozolol, Stenbolone, 1-Testosterone, Tetrahydrogestrinone, and Trenbolone.

12. The method of claim 1 wherein the male senescence is selected from age-associated low testosterone, low libido, erectile dysfunction, weight gain, reduced muscle mass or tone, and prostate hyperplasia.

13. The method of claim 1 wherein the method further comprises the antecedent step of diagnosis the male senescence.

14. The method of claim 1 wherein the method further comprises the subsequent step of detecting a resultant diminution or reversal of the male senescence.

15. The method of claim 3 wherein the method further comprises the subsequent step of detecting a resultant diminution or reversal of the male senescence.

16. The method of claim 4 wherein the method further comprises the subsequent step of detecting a resultant diminution or reversal of the male senescence.

17. The method of claim 5 wherein the method further comprises the subsequent step of detecting a resultant diminution or reversal of the male senescence.

18. The method of claim 6 wherein the method further comprises the subsequent step of detecting a resultant diminution or reversal of the male senescence.

19. The method of claim 7 wherein the method further comprises the subsequent step of detecting a resultant diminution or reversal of the male senescence.

20. The method of claim 8 wherein the method further comprises the subsequent step of detecting a resultant diminution or reversal of the male senescence.

* * * * *